US011834669B2

(12) United States Patent
Evans et al.

(10) Patent No.: US 11,834,669 B2
(45) Date of Patent: Dec. 5, 2023

(54) RECOMBINANT CYTOMEGALOVIRUS VECTORS AS VACCINES FOR TUBERCULOSIS

(71) Applicants: International AIDS Vaccine Initiative, Inc., New York, NY (US); Oregon Health and Science University, Portland, OR (US)

(72) Inventors: Thomas G. Evans, New York, NY (US); Ravi Anantha, New York, NY (US); Aurelio M. Bonavia, New York, NY (US); Dominick J. Laddy, New York, NY (US); Louis Picker, Beaverton, OR (US); Scott Hansen, Beaverton, OR (US); Guangwu Xu, Beaverton, OR (US)

(73) Assignees: International AIDS Vaccine Initiative, Inc., New York, NY (US); Oregon Health and Science University, Portland, OR (US)

( * ) Notice: Subject to any disclaimer, the term of this patent is extended or adjusted under 35 U.S.C. 154(b) by 0 days.

(21) Appl. No.: 17/365,509

(22) Filed: Jul. 1, 2021

(65) Prior Publication Data

US 2021/0403951 A1    Dec. 30, 2021

Related U.S. Application Data

(63) Continuation of application No. 15/628,921, filed on Jun. 21, 2017, now Pat. No. 11,091,775.

(60) Provisional application No. 62/478,099, filed on Mar. 29, 2017, provisional application No. 62/353,432, filed on Jun. 22, 2016.

(51) Int. Cl.
  *C12N 15/86*   (2006.01)
  *A61K 39/04*   (2006.01)
  *C07K 14/35*   (2006.01)
  *A61K 39/00*   (2006.01)

(52) U.S. Cl.
  CPC .............. *C12N 15/86* (2013.01); *A61K 39/04* (2013.01); *C07K 14/35* (2013.01); *A61K 2039/5256* (2013.01); *A61K 2039/53* (2013.01); *C07K 2319/00* (2013.01); *C12N 2710/16143* (2013.01); *C12N 2710/16151* (2013.01); *C12N 2710/16171* (2013.01); *C12N 2800/204* (2013.01); *C12N 2800/30* (2013.01)

(58) Field of Classification Search
  CPC .. C07K 14/005; C07K 16/088; C07K 14/045; C12N 15/86; C12N 15/869; C12N 7/00; C12N 2710/00011; C12N 2710/16111; C12N 2710/16143; A61K 39/245; A61K 39/12; A61K 35/763; A61K 38/162; A61K 2039/525; A61K 2039/5256; A61K 2039/6075
  See application file for complete search history.

(56) References Cited

U.S. PATENT DOCUMENTS

| | | |
|---|---|---|
| 5,334,498 A | 8/1994 | Roizman et al. |
| 5,593,873 A | 1/1997 | Cochran et al. |
| 5,593,972 A | 1/1997 | Weiner et al. |
| 5,599,544 A | 2/1997 | Cochran et al. |
| 5,676,952 A | 10/1997 | Audonnet et al. |
| 5,720,957 A | 2/1998 | Jones et al. |
| 5,731,188 A | 3/1998 | Cochran et al. |
| 5,741,696 A | 4/1998 | Cochran et al. |
| 5,753,476 A | 5/1998 | Jones et al. |
| 5,804,372 A | 9/1998 | Cochran et al. |
| 5,837,532 A | 11/1998 | Preston et al. |
| 5,843,458 A | 12/1998 | Jones |
| 5,846,806 A | 12/1998 | Jones et al. |
| 5,853,733 A | 12/1998 | Cochran et al. |
| 5,874,279 A | 2/1999 | Cochran et al. |
| 5,906,935 A | 5/1999 | Jones et al. |
| 5,908,780 A | 6/1999 | Jones |
| 5,962,428 A | 10/1999 | Carrano |
| 6,033,671 A | 3/2000 | Frueh et al. |
| 6,103,531 A | 8/2000 | Sedmak et al. |
| 6,140,114 A | 10/2000 | Klatzman et al. |
| 6,410,033 B1 | 6/2002 | Cochran |
| 6,613,892 B2 | 9/2003 | Preston et al. |
| 6,740,324 B2 | 5/2004 | Schall et al. |
| 6,913,751 B2 | 7/2005 | Cochran et al. |
| 6,953,661 B1 | 10/2005 | Diefenbach et al. |

(Continued)

FOREIGN PATENT DOCUMENTS

| | | |
|---|---|---|
| WO | 94016737 | 8/1994 |
| WO | 2007058663 | 5/2007 |

(Continued)

OTHER PUBLICATIONS

Zhang et. al. (Zhang Y, Feng L, Li L, Wang D, Li C, Sun C, Li P, Zheng X, Liu Y, Yang W, Niu X, Zhong N, Chen L. Effects of the fusion design and immunization route on the immunogenicity of Ag85A-Mtb32 in adenoviral vectored tuberculosis vaccine. Hum Vaccin Immunother. 2015;11(7):1803-13. (Year: 2015).*

Bennekov T, Dietrich J, Rosenkrands I, Stryhn A, Doherty TM, Andersen P. Alteration of epitope recognition pattern in Ag85B and ESAT-6 has a profound influence on vaccine-induced protection against *Mycobacterium tuberculosis*. Eur J Immunol. Dec. 2006;36(12):3346-55. (Year: 2006).*

Weinrich Olsen A, van Pinxteren LA, Meng Okkels L, Birk Rasmussen P, Andersen P. Protection of mice with a tuberculosis subunit vaccine based on a fusion protein of antigen 85b and esat-6. Infect Immun. May 2001;69(5):2773-8. (Year: 2001).*

(Continued)

*Primary Examiner* — Rachel B Gill
(74) *Attorney, Agent, or Firm* — Armstrong Teasdale LLP

(57) ABSTRACT

Disclosed herein are cytomegalovirus vectors encoding fusion proteins comprising Mycobacterium tuberculosis (Mtb) antigens, nucleic acid molecules encoding the same, cytomegalovirus vectors comprising nucleic acid molecules, compositions comprising the same, and methods of eliciting an immune response against tuberculosis.

23 Claims, 113 Drawing Sheets

Specification includes a Sequence Listing.

(56) References Cited

U.S. PATENT DOCUMENTS

| | | | |
|---|---|---|---|
| 7,364,893 | B2 | 4/2008 | Wild et al. |
| 7,749,745 | B2 | 7/2010 | Johnson et al. |
| 7,892,564 | B2 | 2/2011 | Wild et al. |
| 8,486,414 | B2 | 7/2013 | Reed et al. |
| 9,249,427 | B2 | 2/2016 | Picker et al. |
| 2009/0304750 | A1 | 12/2009 | Hone et al. |
| 2011/0117133 | A1 | 5/2011 | Shafferman et al. |
| 2013/0136768 | A1 | 5/2013 | Picker et al. |
| 2013/0209500 | A1 | 8/2013 | Reed et al. |
| 2014/0004151 | A1 | 1/2014 | Sette et al. |
| 2014/0141038 | A1 | 5/2014 | Picker et al. |
| 2014/0377300 | A1 | 12/2014 | Ravi et al. |
| 2015/0165014 | A1* | 6/2015 | Tupin .............. C07K 14/35 536/23.4 |
| 2016/0228528 | A1 | 8/2016 | Jungersen et al. |
| 2016/0331823 | A1 | 11/2016 | Marchand et al. |
| 2017/0043003 | A1 | 2/2017 | Aagaard et al. |
| 2017/0362284 | A1 | 12/2017 | Anantha et al. |

FOREIGN PATENT DOCUMENTS

| | | |
|---|---|---|
| WO | 2008124647 | 10/2008 |
| WO | 2014009438 | 1/2014 |
| WO | 2014063704 | 5/2014 |
| WO | 2014140301 | 9/2014 |
| WO | 2014210018 | 12/2014 |
| WO | 20170087921 | 5/2017 |
| WO | 2017218867 | 12/2017 |

OTHER PUBLICATIONS

Velmurugan K, Grode L, Chang R, Fitzpatrick M, Laddy D, Hokey D, Derrick S, Morris S, McCown D, Kidd R, Gengenbacher M, Eisele B, Kaufmann SH, Fulkerson J, Brennan MJ. Nonclinical Development of BCG Replacement Vaccine Candidates. Vaccines (Basel). Apr. 16, 2013;1(2):120-38. (Year: 2013).*

Mu J, Jeyanathan M, Small CL, Zhang X, Roediger E, et al. Immunization with a bivalent adenovirus-vectored tuberculosis vaccine provides markedly improved protection over its monovalent counterpart against pulmonary tuberculosis. Mol Ther. Jun. 2009;17(6):1093-100. Epub Mar. 24, 2009. (Year: 2009).*

Sun R, Skeiky YA, Izzo A, et al. Novel recombinant BCG expressing perfringolysin O and the over-expression of key immunodominant antigens; pre-clinical characterization, safety and protection against challenge with *Mycobacterium tuberculosis*. Vaccine. Jul. 16, 2009;27(33):4412-23. Epub Jun. 2, 2009. (Year: 2009).*

Havenga M, Vogels R, Zuijdgeest D, Radosevic K, Mueller S, Sieuwerts M, Weichold F, Damen I, Kaspers J, Lemckert A, van Meerendonk M, et al. Novel replication-incompetent adenoviral B-group vectors: high vector stability and yield in PER.C6 cells. J Gen Virol. Aug. 2006;87(Pt 8):2135-2143. (Year: 2006).*

Hansen SG, Zak DE, Xu G, Ford JC, Marshall EE, Malouli D, Gilbride RM, Hughes CM, Ventura AB, Ainslie E, Randall KT, Selseth AN, Rundstrom P, Herlache L, et. al. Prevention of tuberculosis in rhesus macaques by a cytomegalovirus-based vaccine. Nat Med. Feb. 2018;24(2):130-143. Epub Jan. 15, 2018. (Year: 2018).*

Advisory Action dated Jan. 14, 2022 in U.S. Appl. No. 16/756,206.
Non-Final Office Action dated Mar. 3, 2022 in U.S. Appl. No. 16/756,206.

Angulo et al., "The Major Immediate-Early Gene ie3 of Mouse Cytomegalovirus Is Essential for Viral Growth", J. Virol., 2000, 74, 11129-11136.

Asanuma, H., et al., "Frequencies of memory T cells specific for varicella-zoster virus, herpes simplex virus, and cytomegalovirus by intracellular detection of cytokine expression", J Infect Dis, 2000, 181, p. 859-866.

Barnes et al., "Harnessing Endogenous miRNAs to Control Virus Tissue Tropism as a Strategy for Developing Attenuated Virus VaccinesCell Host Microbe", 2008, 4, 239-248.

Brown et al., "Endogenous microRNA can be broadly exploited to regulate transgene expression according to tissue, lineage and differentiation state", Nat. Biotechnol., 2007, 25, 1457-1467.

Dankner, W. M., et al., "Localization of human cytomegalovirus in peripheral blood leukocytes by in situ hybridization", J Infect Dis, 1990, 161, p. 31-36.

Einhorn, L., et al., "Cytomegalovirus infection of human blood cells", J Infect Dis, 1984, 149, p. 207-214.

Gerna, G., et al., "Dendritic-cell infection by human cytomegalovirus is restricted to strains carrying functional UL131-128 genes and mediates efficient viral antigen presentation to CD8+ T cells", J Gen Virol, 2005, 86, p. 275-284.

Gnann, J. W. Jr., et al., "Inflammatory cells in transplanted kidneys are infected by human cytomegalovirus", Am J Pathol, 1988, 132, p. 239-248.

Hahn, G., et al., "Human cytomegalovirus UL131-128 genes are indispensable for virus growth in endothelial cells and virus transfer to leukocytes", J Virol, 2004, 78, p. 10023-10033.

Hansen et al., "Effector memory T cell responses are associated with protection of rhesus monkeys from mucosal simian immunodeficiency virus challenge", Nat. Med., 2009, 15, 293-299.

Hansen, S. G., et al., "Evasion of CD8+ T cells is critical for superinfection by cytomegalovirus", Science, 2010, 328, p. 102-106.

Hansen et al., "Profound early control of highly pathogenic SIV by an effector memory T-cell vaccine", Nature, 2011, 473, 523-527.

Hansen et al., "Immune clearance of highly pathogenic SIV infection", Nature, 2013, 502, 100-104.

Hansen et al., "Cytomegalovirus Vectors Violate CD8+ T Cell Epitope Recognition Paradigms", Science, 2013, 340, 1237874.

Hansen et al., "Broadly targeted CD8+ T cell responses restricted by major histocompatibility complex E", Science, 2016, 351, 714-720.

Harari, A., et al., "Functional heterogeneity of memory CD4+ T cell responses in different conditions of antigen exposure and persistence", J Immunol, 2005, 174, p. 1037-1045.

Harari, A., et al., "Distinct profiles of cytotoxic granules in memory CD8+ T cells correlate with function, differentiation stage, and antigen exposure", J Virol, 2009, 83, p. 2862-2871.

Howell, C. L., et al., "Comparison of rates of virus isolation from leukocyte populations separated from blood by conventional and Ficoll-Paque/Macrodex methods", J Clin Microbiol, 1979, 10, p. 533-537.

Jarvis, M. A., et al., "Mechanisms of human cytomegalovirus persistence and latency", Front Biosci., 2002, 7, d1575-1582.

Lee et al., "MicroRNA Regulation of Oncolytic Herpes Simplex Virus-1 for Selective Killing of Prostate Cancer Cells", Clin. Cancer Res., 2009, 15, 5126-5135.

Lilja, et al., "Efficient replication of rhesus cytomegalovirus variants in multiple rhesus and human cell types", Proc Natl Acad Sci USA, 2008, 105, p. 19950-19955.

Lilja, A. E., et al., "Functional genetic analysis of rhesus cytomegalovirus: Rh-1 is an epithelial cell tropism factor", J Virol, 2008, 82, p. 2170-2181.

Myerson, D., et al., "Widespread presence of histologically occult cytomegalovirus", Hum Pathol, 1984, 15, p. 430-439.

Perez et al., "MicroRNA-mediated species-specific attenuation of influenza A virus", Nat. Biotechnol., 2009, 27, 572-576.

Rue, C. A., et al., "A cyclooxygenase-2 homologue encoded by rhesus cytomegalovirus is a determinant for endothelial cell tropism", Journal of Virology, 2004, 78, p. 12529-12536.

Ryckman, B. J., et al., "Human cytomegalovirus entry into epithelial and endothelial cells depends on genes UL128 to UL150 and occurs by endocytosis and low-pH fusion", J Virol, 2006, 80, p. 710-722.

Ryckman, B. J., et al., "Characterization of the human cytomegalovirus gH/gL/UL128-131 complex that mediates entry into epithelial and endothelial cells", J Virol, 2008, 82, p. 60-70.

Schrier, R. D., et al., "Detection of human cytomegalovirus in peripheral blood lymphocytes in a natural infection", Science, 1985, 230, p. 1048-1051.

Sinzger, C., et al., "Fibroblasts, epithelial cells, endothelial cells and smooth muscle cells are major targets of human cytomegalovirus infection in lung and gastrointestinal tissues", J Gen Virol, 1995, 76, p. 741-750.

(56) References Cited

OTHER PUBLICATIONS

Snyder et al., "Cross-presentation of a spread-defective MCMV is sufficient to prime the majority of virus-specific CD8+ T cells", PLoS One, 2010, 5:e9681, doi:10.1371/journal.pone.0009681.

Sylwester, A. W., et al., "Broadly targeted human cytomegalovirus-specific CD4+ and CD8+ T cells dominate the memory compartments of exposed subjects", J Exp Med, 2005, 202, p. 673-685.

Wang, D., et al., "Human cytomegalovirus UL131 open reading frame is required for epithelial cell tropism", J Virol, 2005, 79, p. 10330-10338.

Wang, D., et al., "Human cytomegalovirus virion protein complex required for epithelial and endothelial cell tropism", Proc Natl Acad Sci USA, 2005, 102, p. 18153-18158.

Leung-Theung-Long et al., "A Novel MVA-Based Multiphasic Vaccine for Prevention or Treatment of Tuberculosis Induces Broad and Multifunctional Cell-Mediated Immunity in Mice and Primates", PLoS One, 2015, 10(11), e0143552.

Leung-Theung-Long, "MVA Technology in the Development of Highly Complexed TB Vaccine Candidates", TBVI Symposium, Les Diablerets, Feb. 3, 2016.

De Sousa et al., "Immunogenicity of a Fusion Protein Containing Immunodominant Epitopes of Ag85C, MPT51, and HspX from *Mycobacterium tuberculosis* in Mice and Active TB Infection", Plos ONE, 2012, 7(10), e47781.

Langermans et al.,"Protection of macaques against *Mycobacterium tuberculosis* infection by a subunit vaccine based on a fusion protein of antigen 85B and ESAT-6", Vaccine, 2005, 23, pp. 2740-2750.

Luo et al., "Fusion Protein Ag85B-MPT64(190-198)-Mtb8.4 Has Higher Immunogenicity Than Ag85B With Capacity to Boost BCG-primed Immunity Against *Mycobacterium tuberculosis* in Mice", Vaccine, 2009, 27, pp. 6179-6185.

Non-Final Office Action dated Mar. 11, 2021 for U.S. Appl. No. 16/756,206.

Graves et al., "Tuberculosis Vaccines: Review of Current Development Trends and Future Challenges", J Bioterr Biodef, 2011, S1-009.

Da Costa et al., "Tuberculosis vaccines-state of the art, and novel approaches to vaccine development", Int J Infect Dis, 2015, 32, pp. 5-12.

Zvi et al., "Whole genome identification of *Mycobacterium tuberculosis* vaccine candidates by comprehensive data mining and bioinformatic analyses", BMC Med Genomics, 2008, 1(18), pp. 1-25.

Hoft et al., "Safety and Immunogenicity of the Recombinant BCG Vaccine AERAS-422 in Healthy BCG-naive Adults: A Randomized, Active-controlled, First-in-human Phase 1 Trail", EBioMedicine, 2016, 7, pp. 278-286.

Velmurugan et al., "Nonclinical Development of BCG Replacement Vaccine Candidates", Vaccines, 2013, 1(2), pp. 120-138.

Singh et al., "*Mycobacterium tuberculosis* controls microRNA-99b (miR-99b) expression in infected murine dendritic cells to modulate host immunity", J Biol Chem, 2012, 288(7), pp. 5056-5061.

McGregor et al., "Expression of the human cytomegalovirus UL97 gene in a chimeric guinea pig cytomegalovirus (GPCMV) results in viable virus with increased susceptibility to ganciclovir and maribavir", Antiviral Res, 2008, 78(3), pp. 250-259.

Brennan, "The Enigmatic PE/PPE Multigene Family of Mycobacteria and Tuberculosis Vaccination", Infection and Immunity, 2017, 85(6), pp. 1-8.

Final Office Action dated Nov. 1, 2021 for U.S. Appl. No. 16/756,206.

Notice of Allowance dated Dec. 19, 2022 in related U.S. Appl. No. 16/756,206.

Notice of Allowance dated Jan. 5, 2023 in related U.S. Appl. No. 16/756,206.

\* cited by examiner

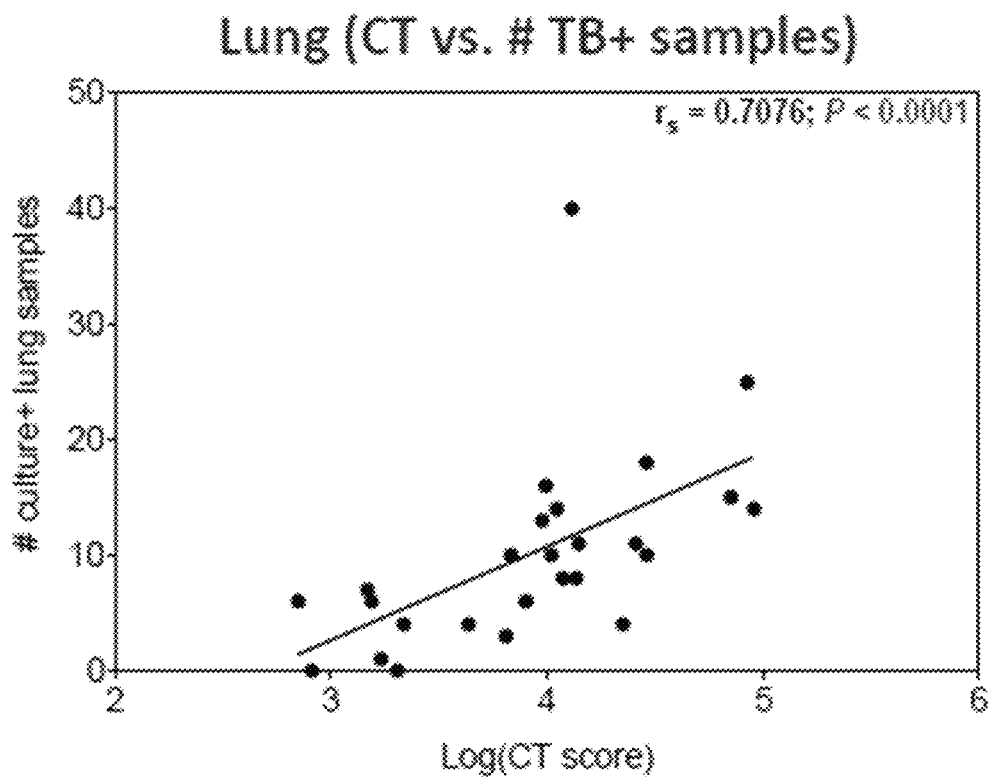
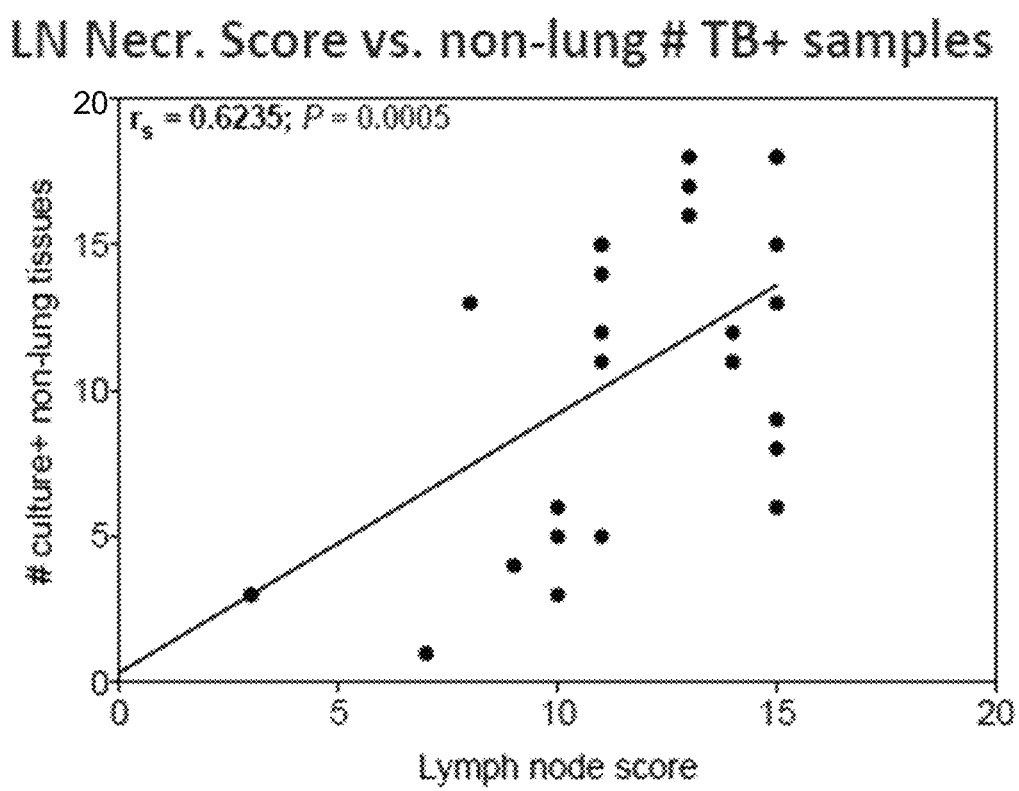
Figure 13 (cont.)

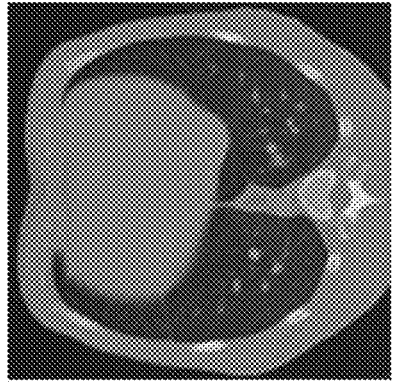
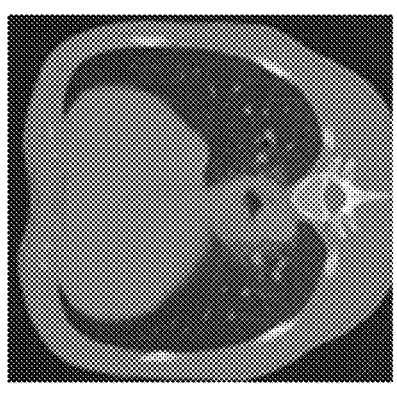
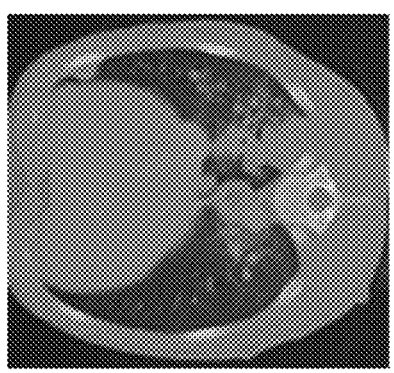
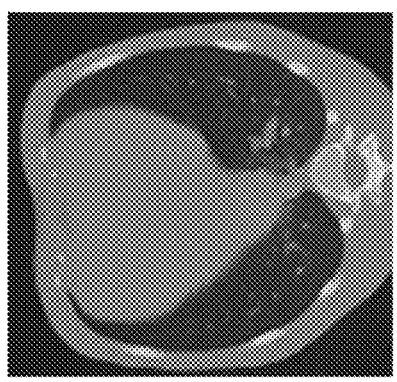
Figure 14

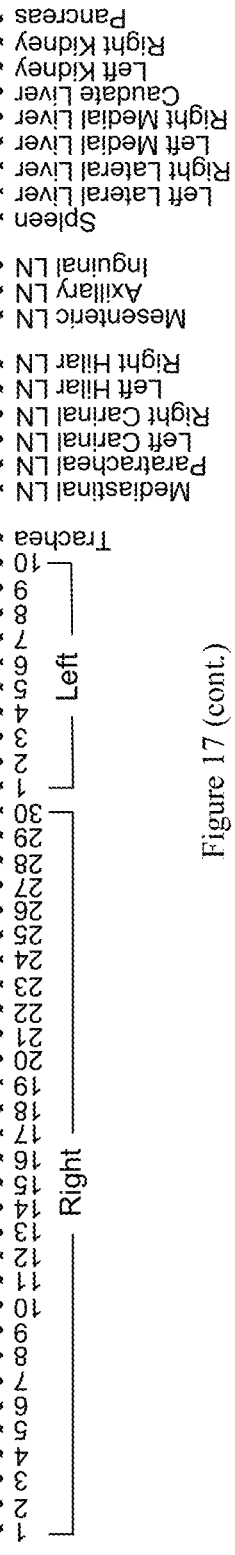
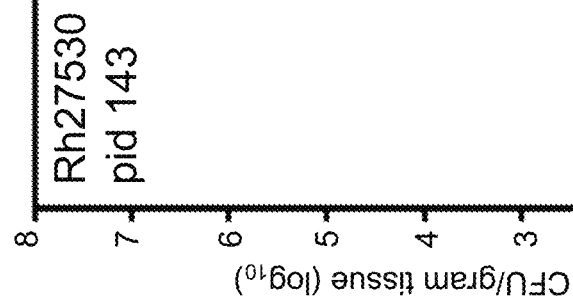
Figure 17 (cont.)

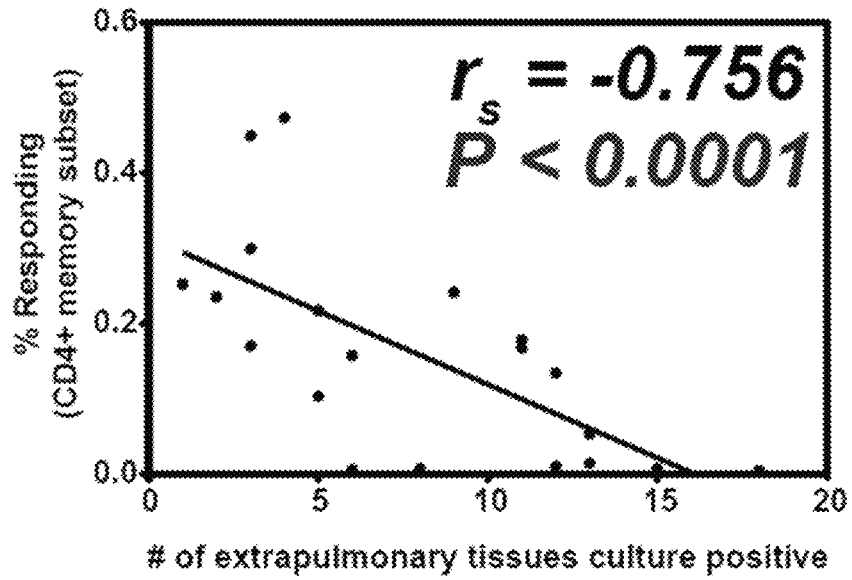
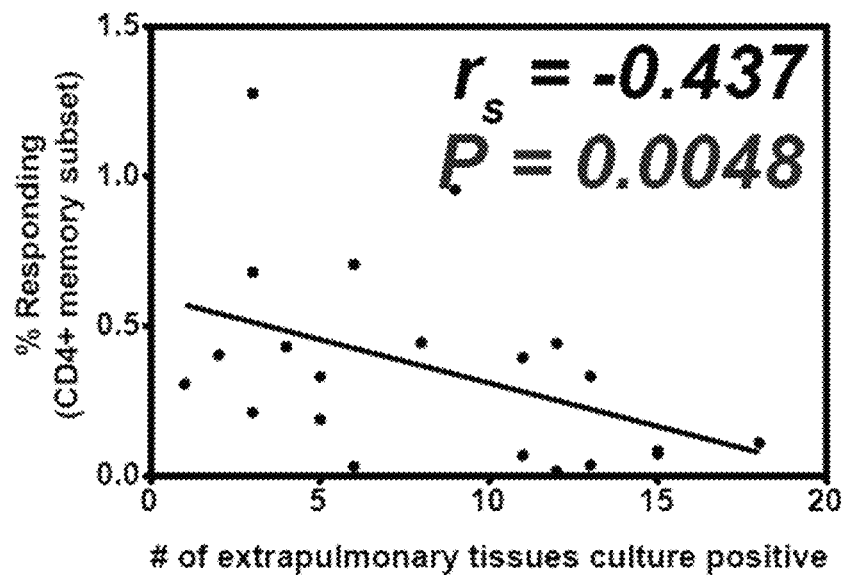
Figure 22

CD4+
Day 63
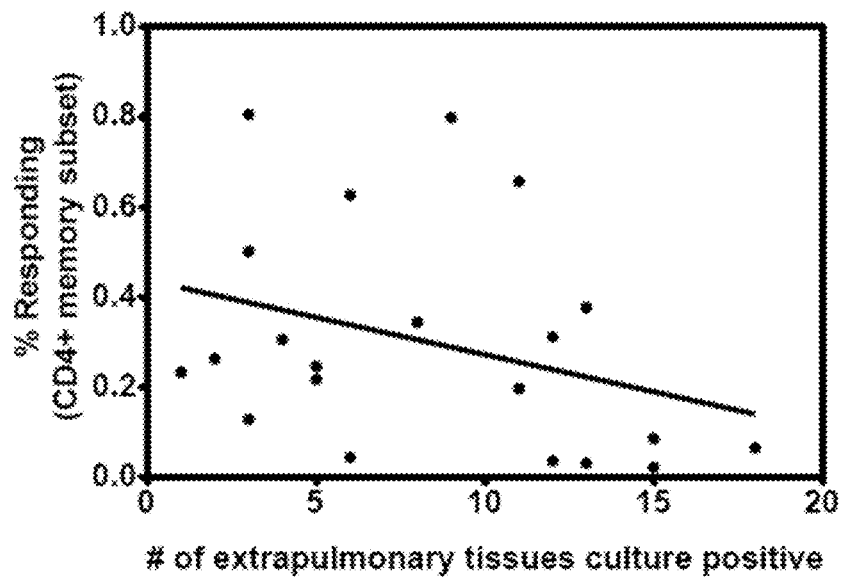
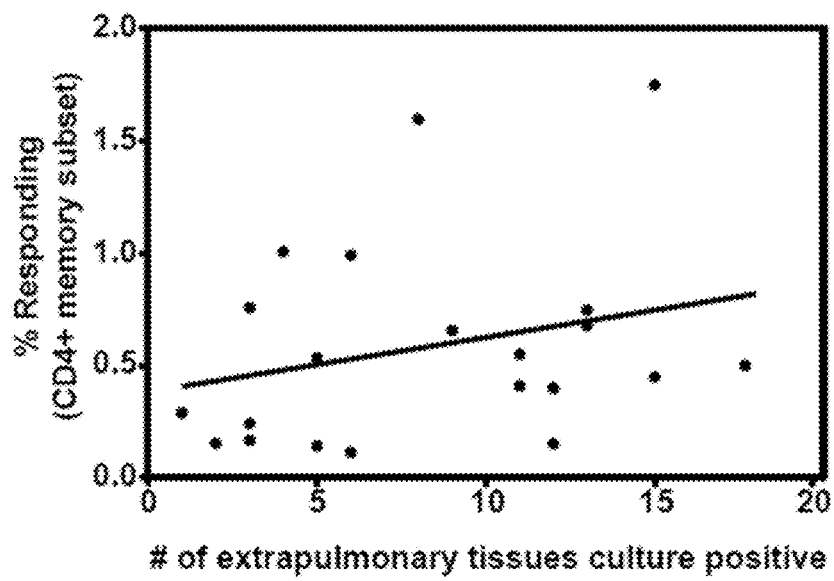
Figure 22 (cont.)

CD4+
Day 63
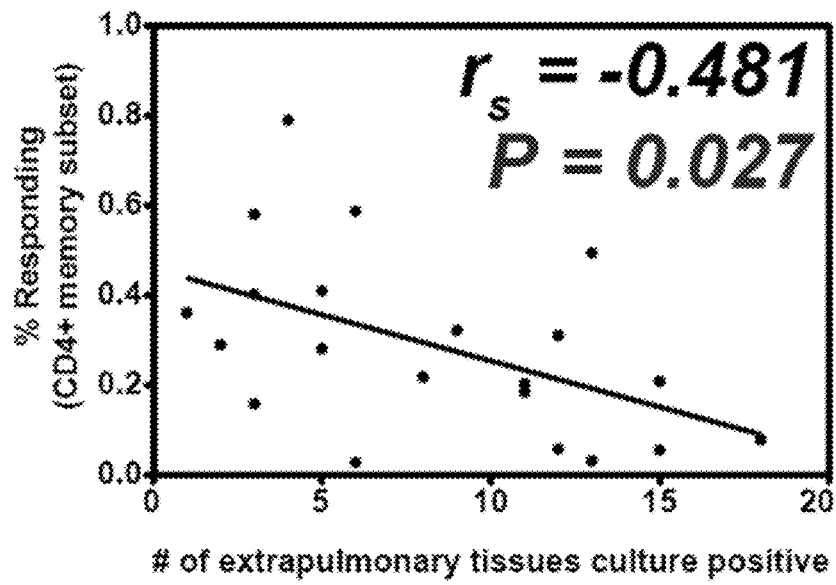
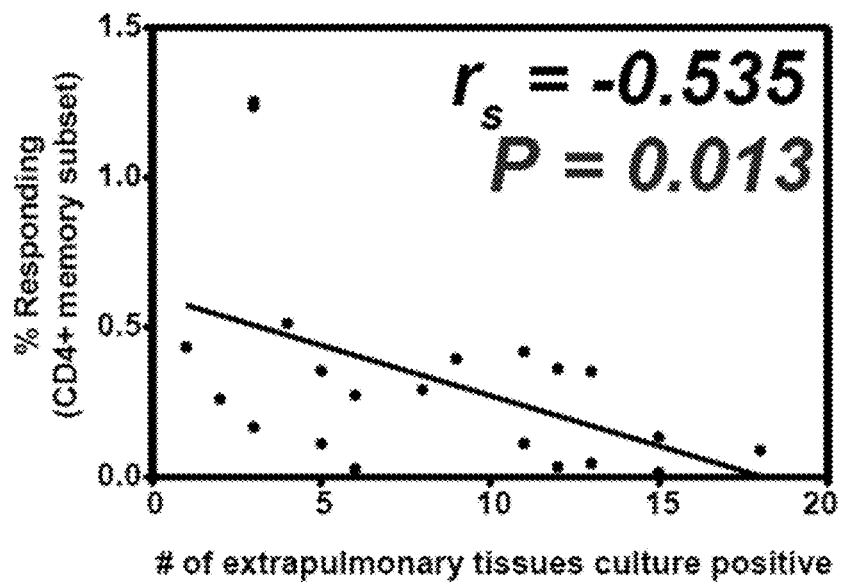
Figure 22 (cont.)

CD4+
Day 63
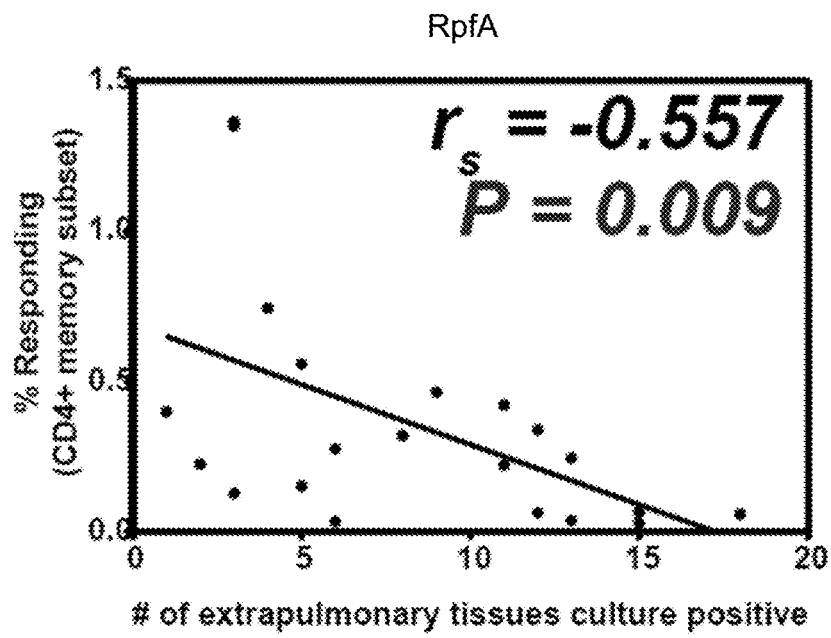
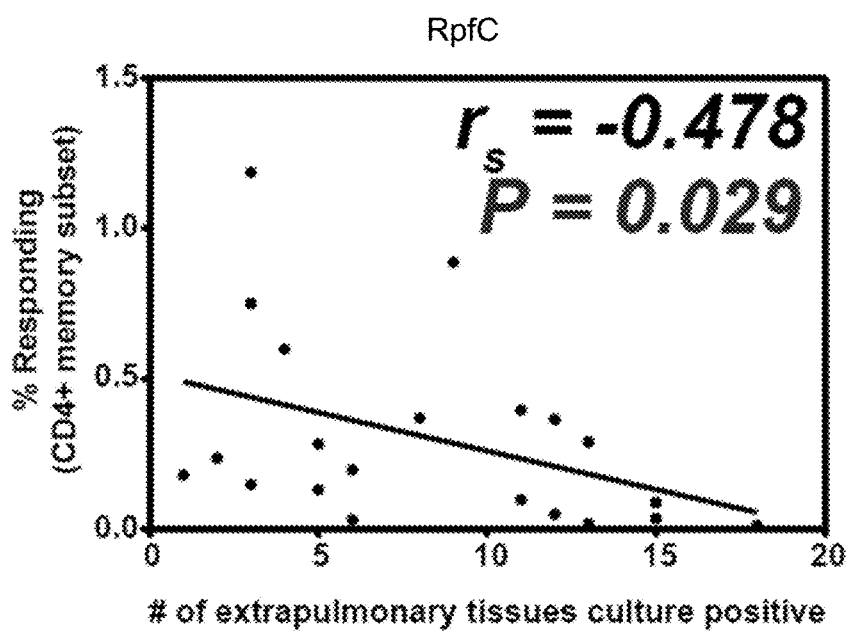
Figure 22 (cont.)

CD4+
Day 168
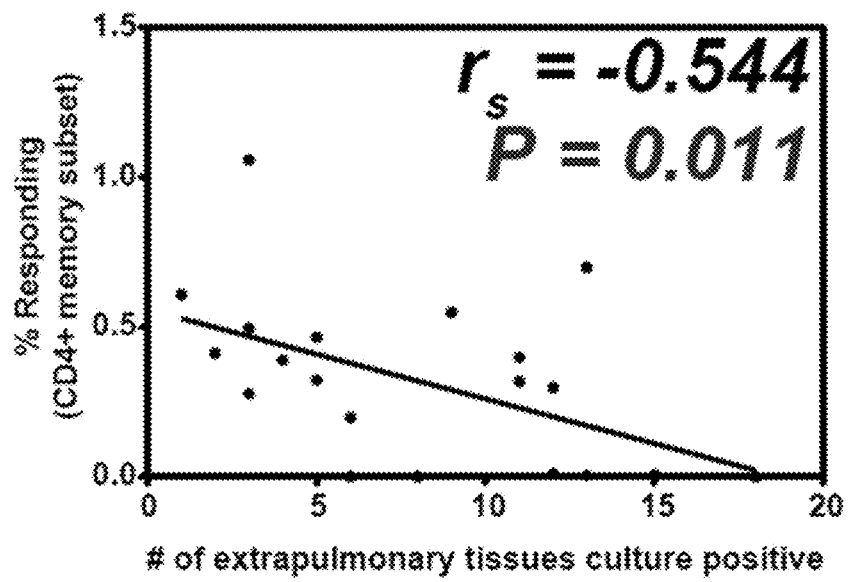
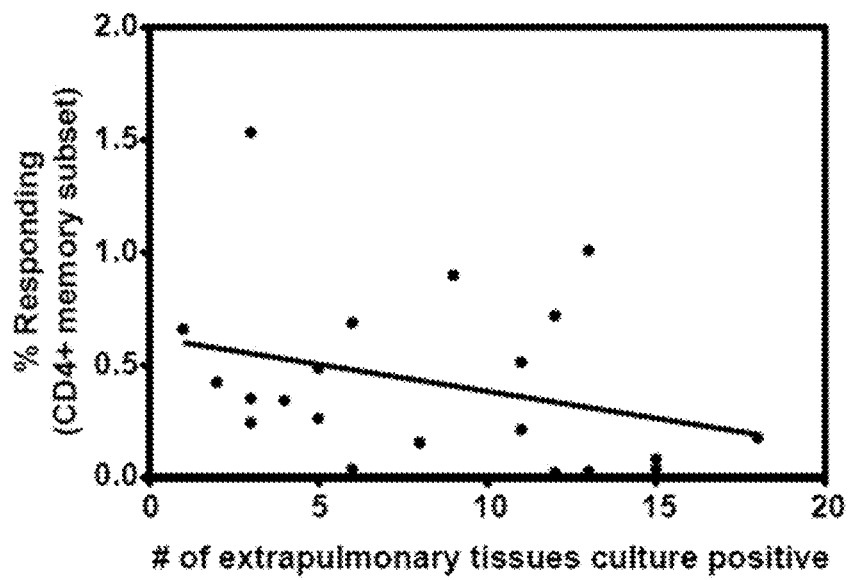
Figure 22 (cont.)

CD4+
Day 168
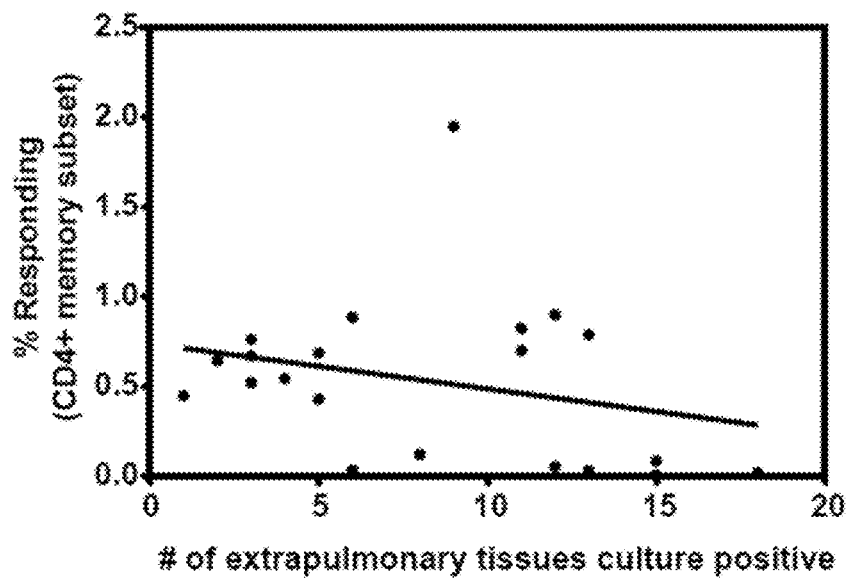
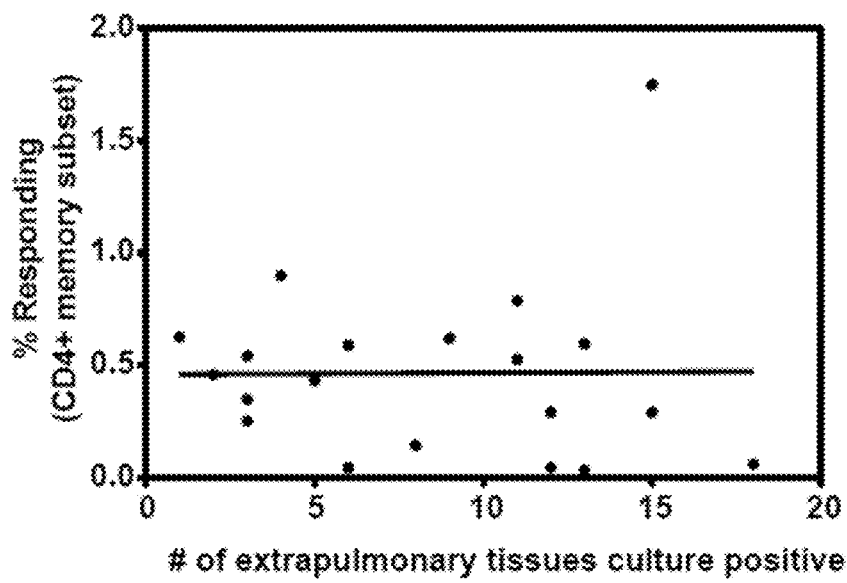
Figure 22 (cont.)

CD4+
Day 168
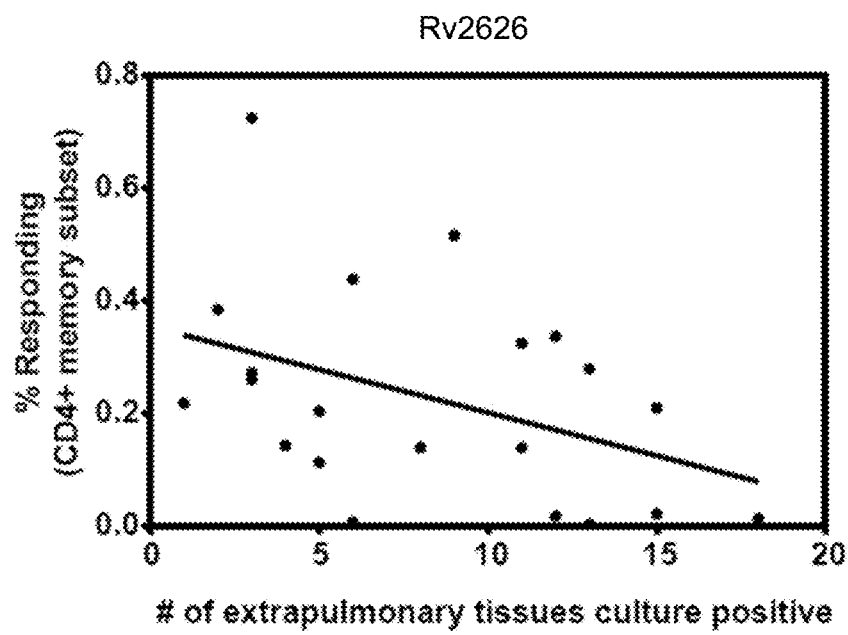
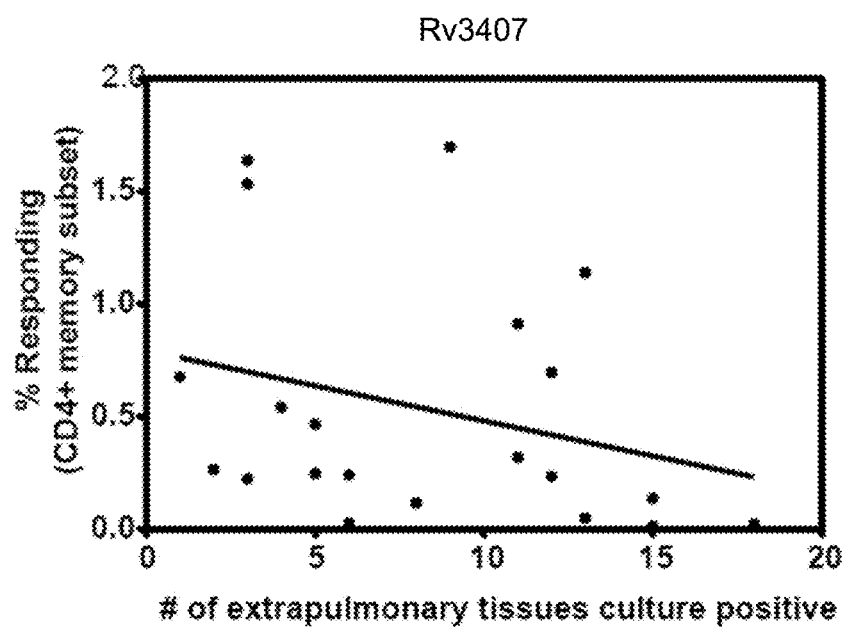
Figure 22 (cont.)

CD4+
Day 168
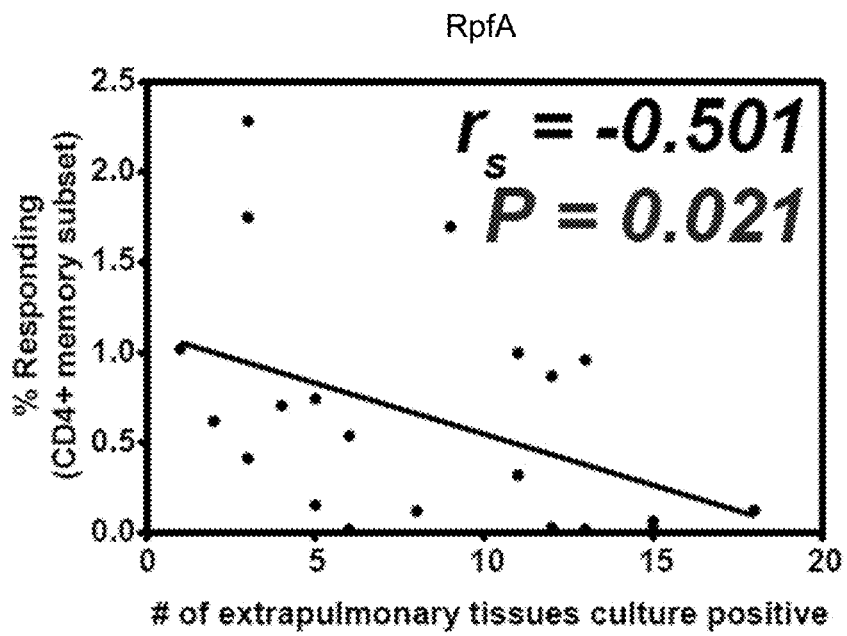
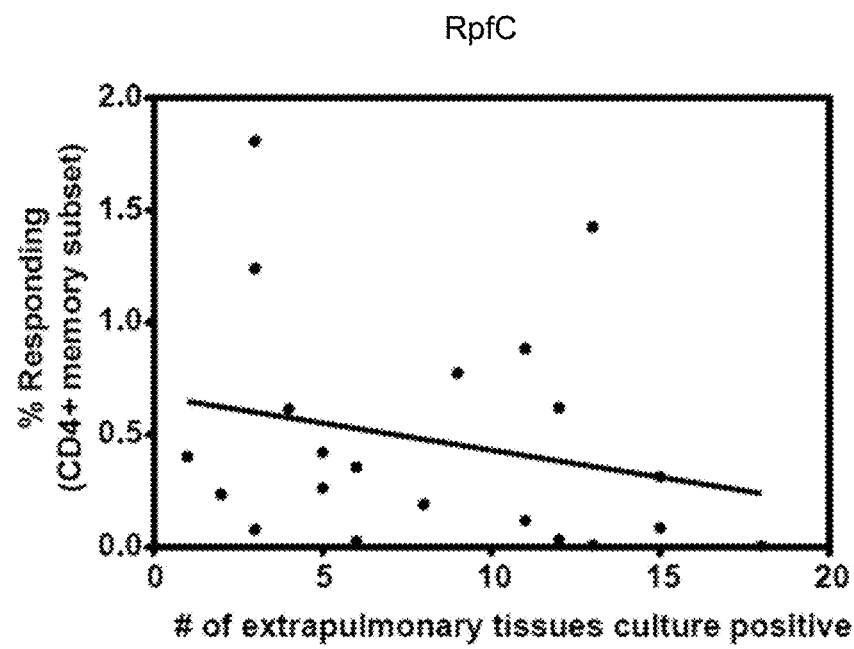
Figure 22 (cont.)

CD4+
Day 344
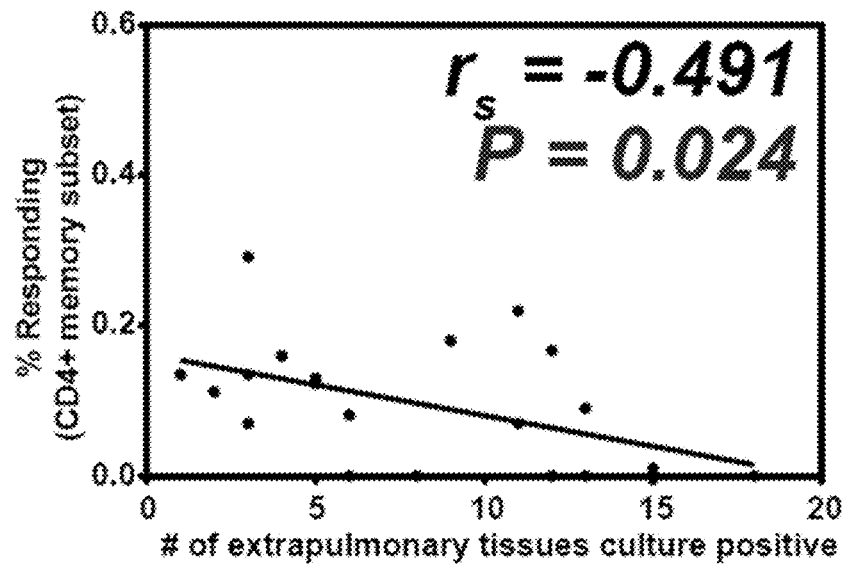
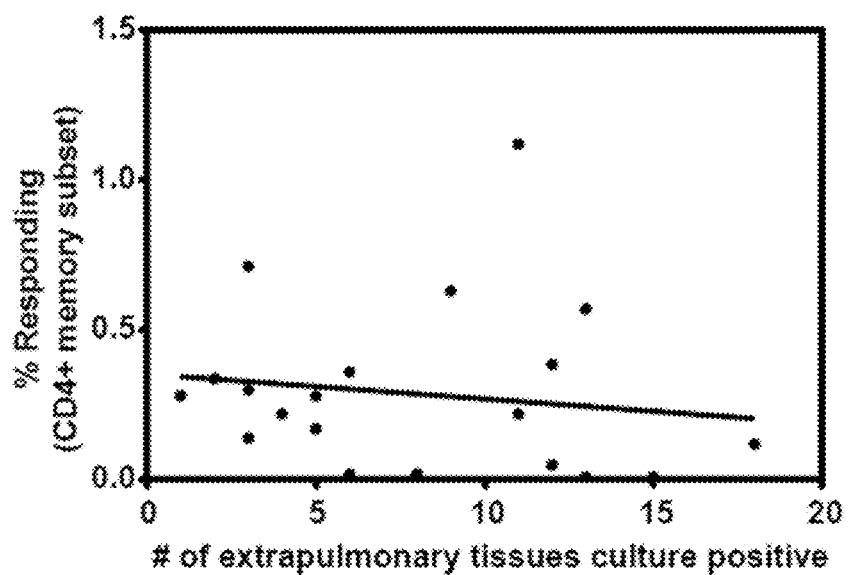
Figure 22 (cont.)

CD4+
Day 344
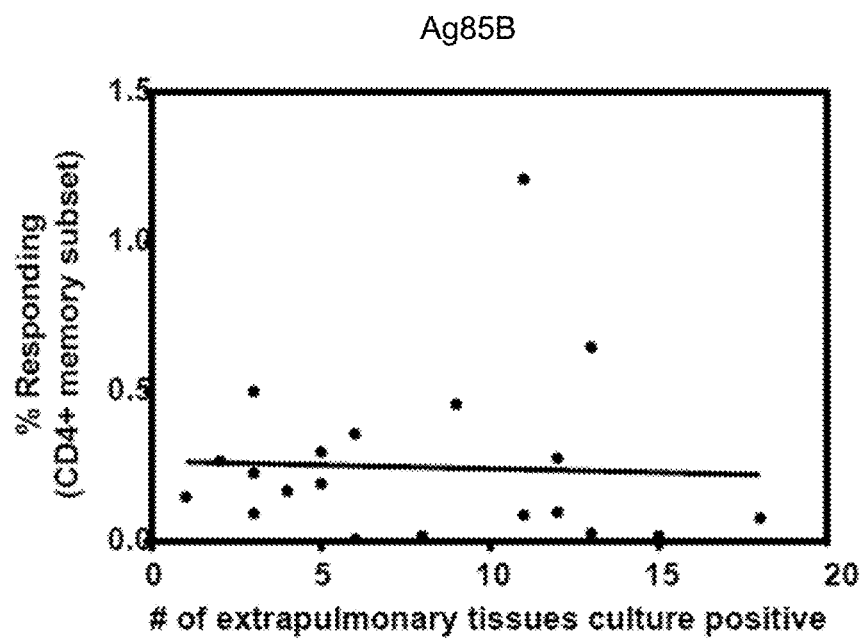
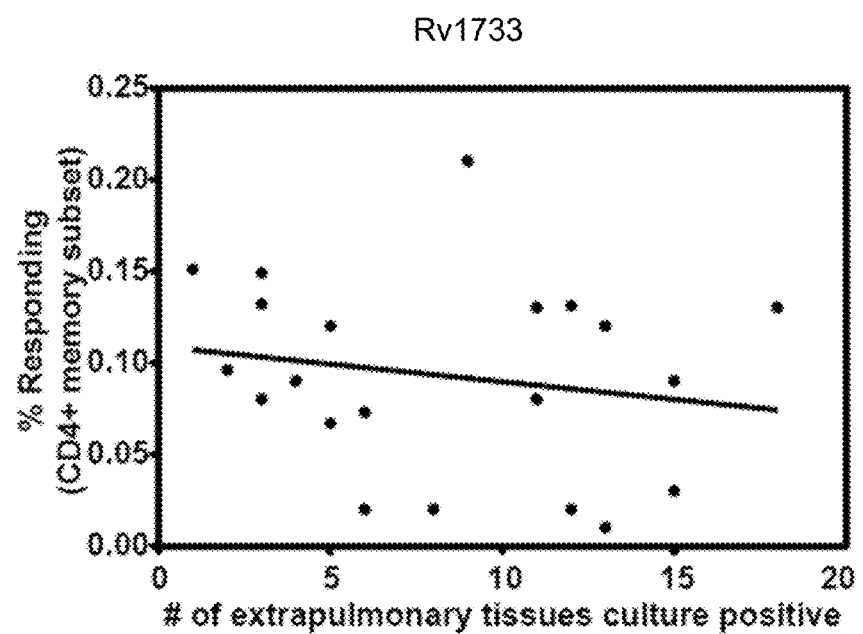
Figure 22 (cont.)

CD4+
Day 344
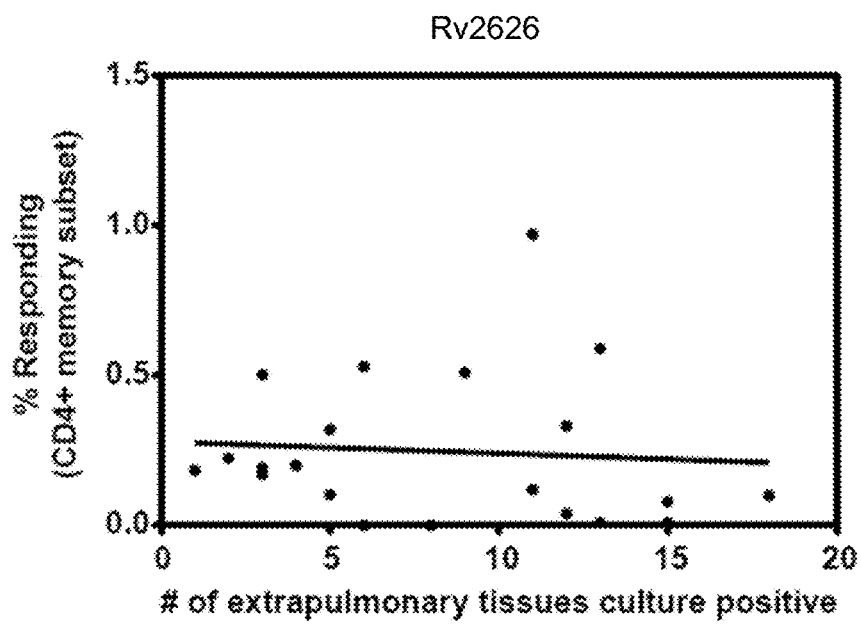
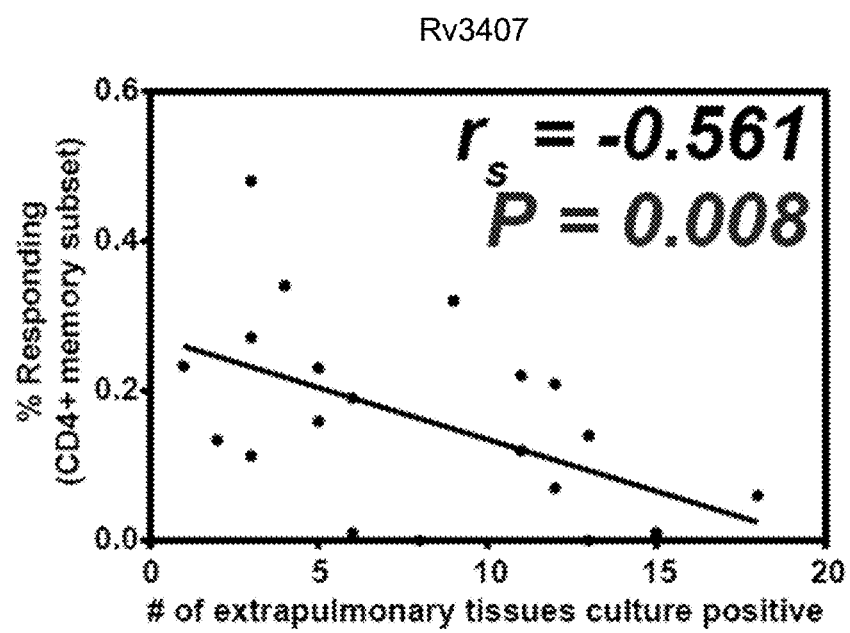
Figure 22 (cont.)

CD4+
Day 344
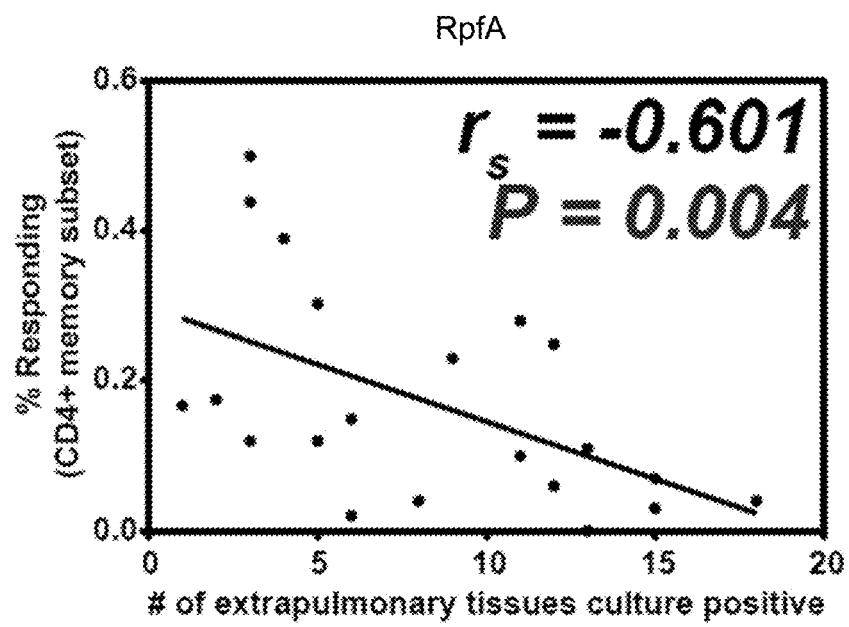
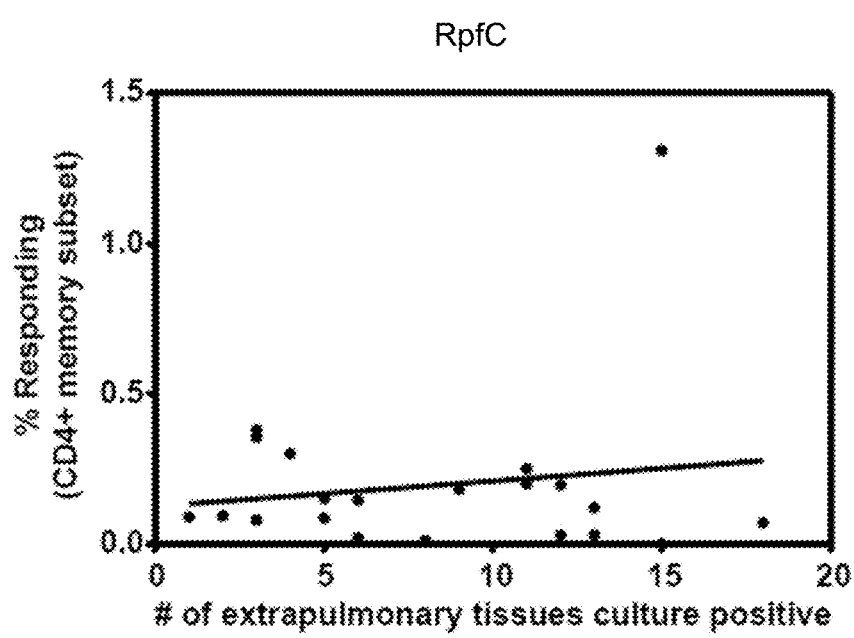
Figure 22 (cont.)

CD8+
Day 63
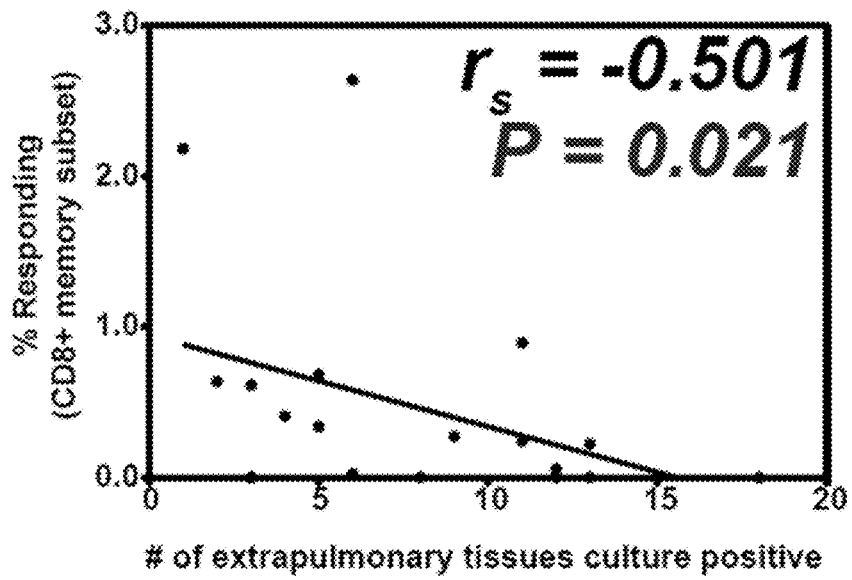
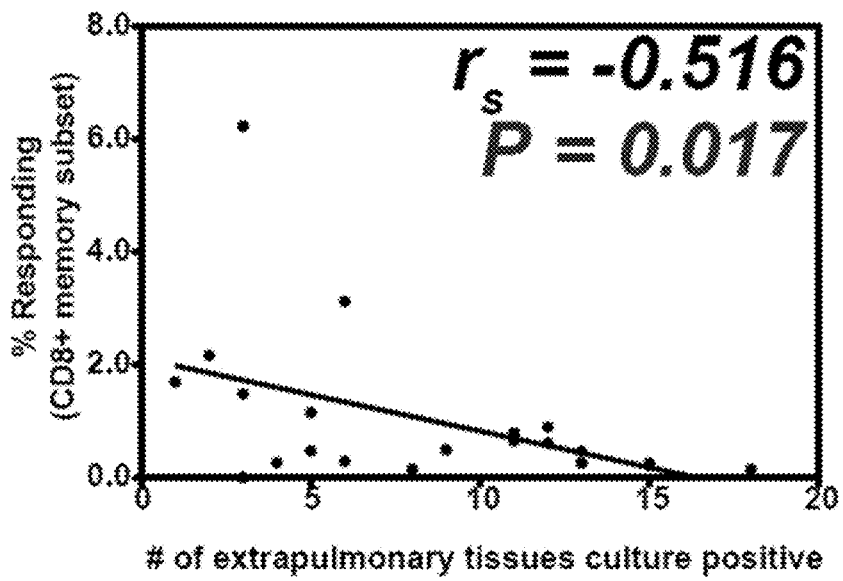
Figure 23

CD8+
Day 63
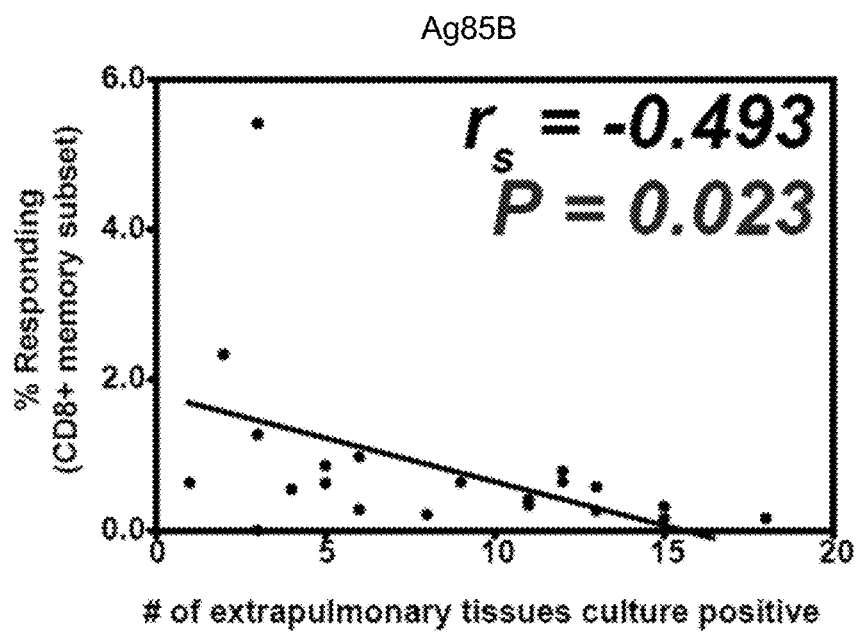
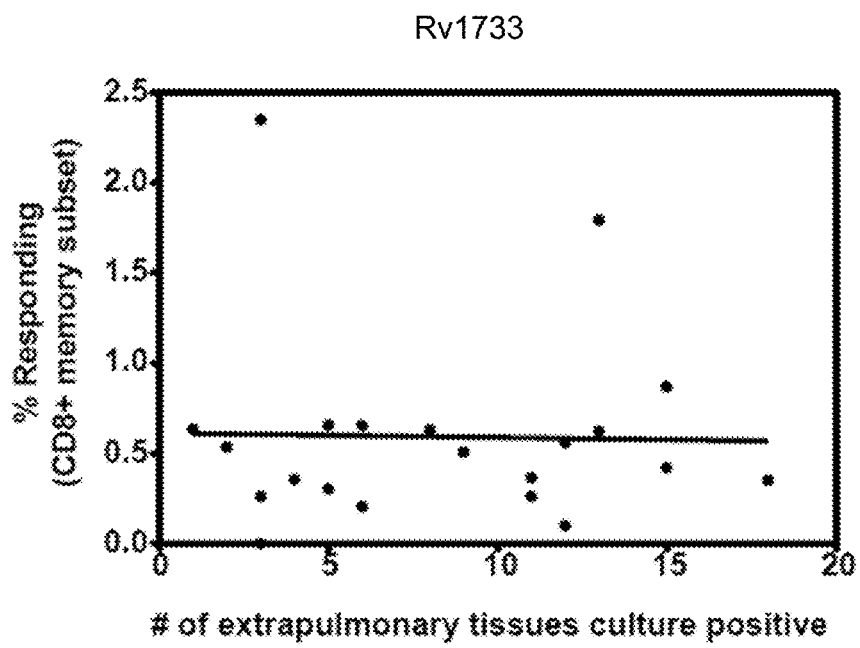
Figure 23 (cont.)

CD8+
Day 63
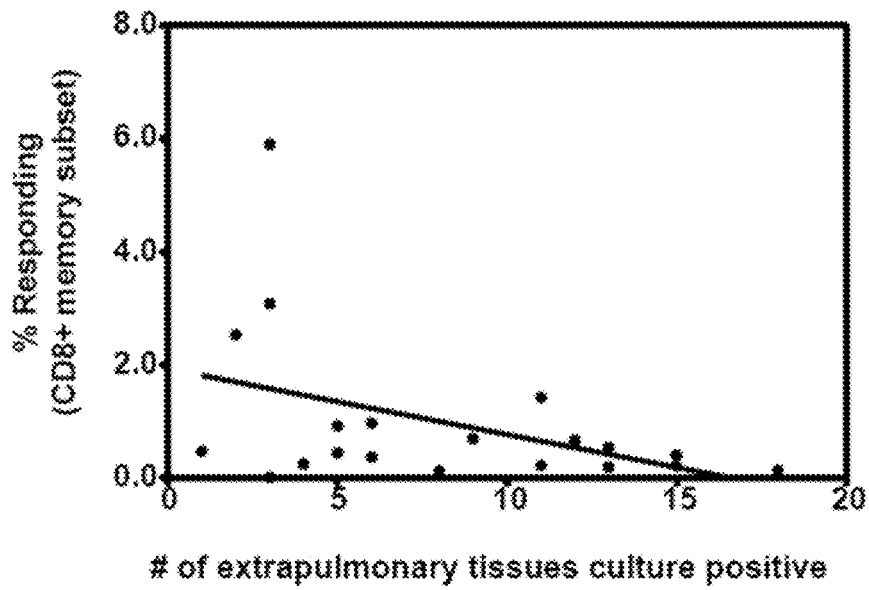
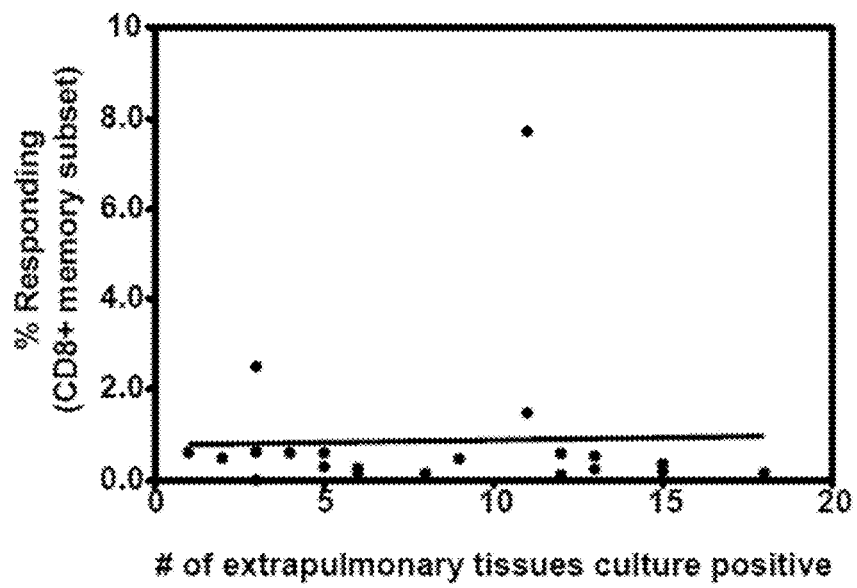
Figure 23 (cont.)

CD8+
Day 63
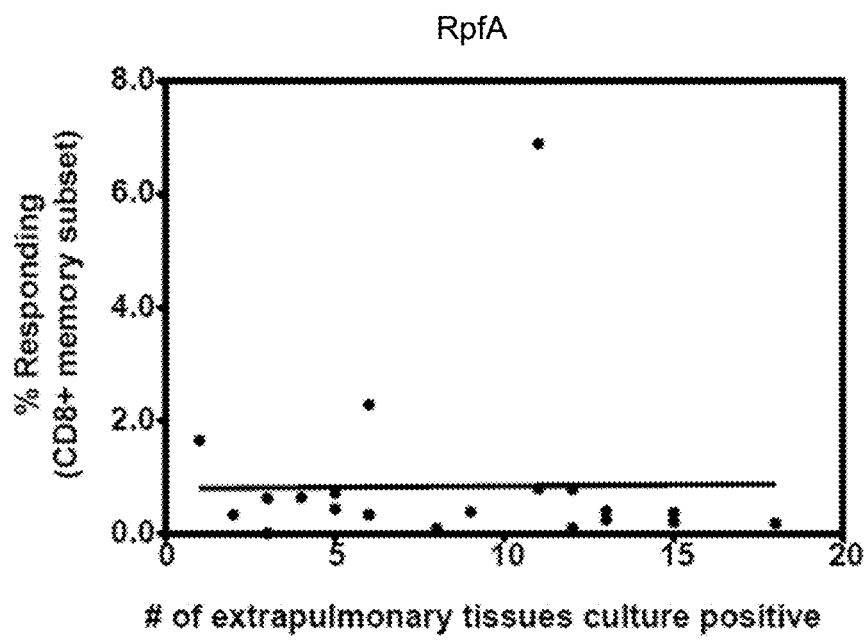
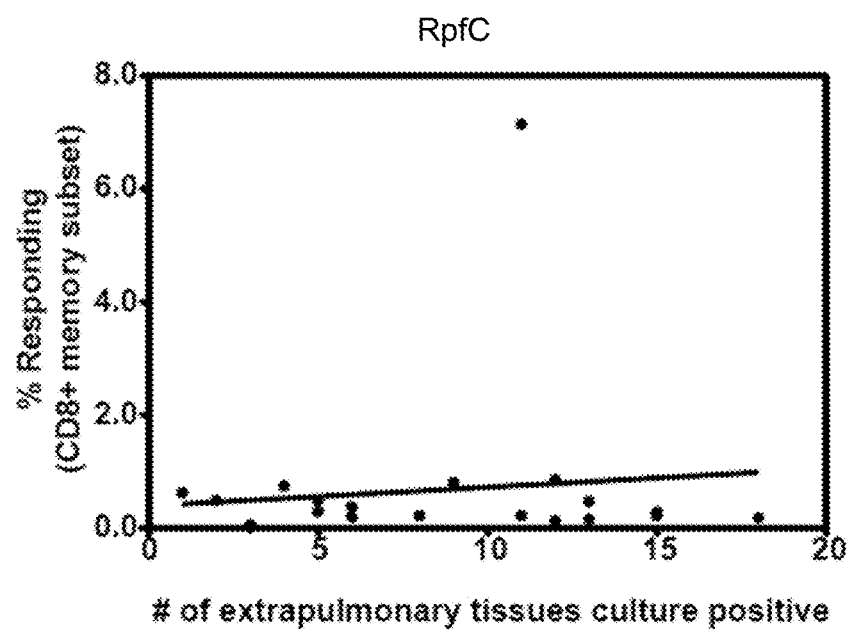
Figure 23 (cont.)

CD8+
Day 168
ESAT-6
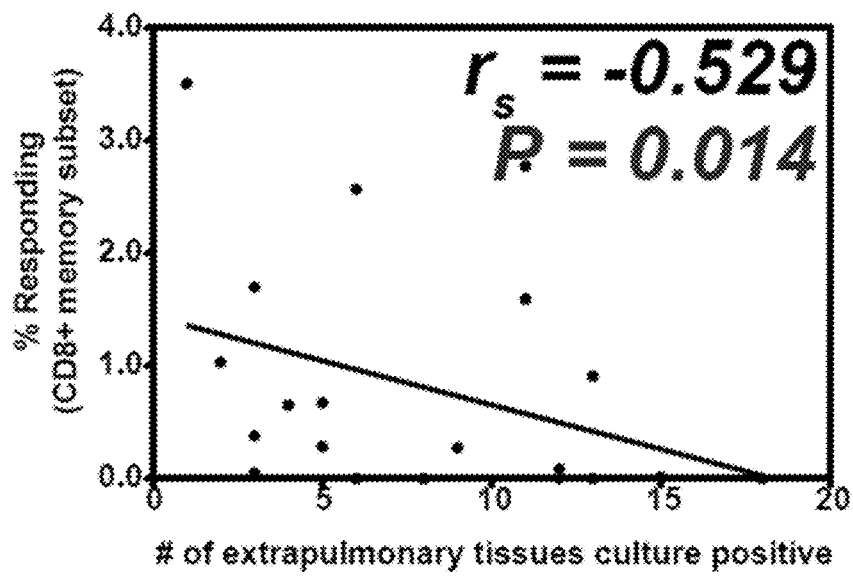
Ag85A
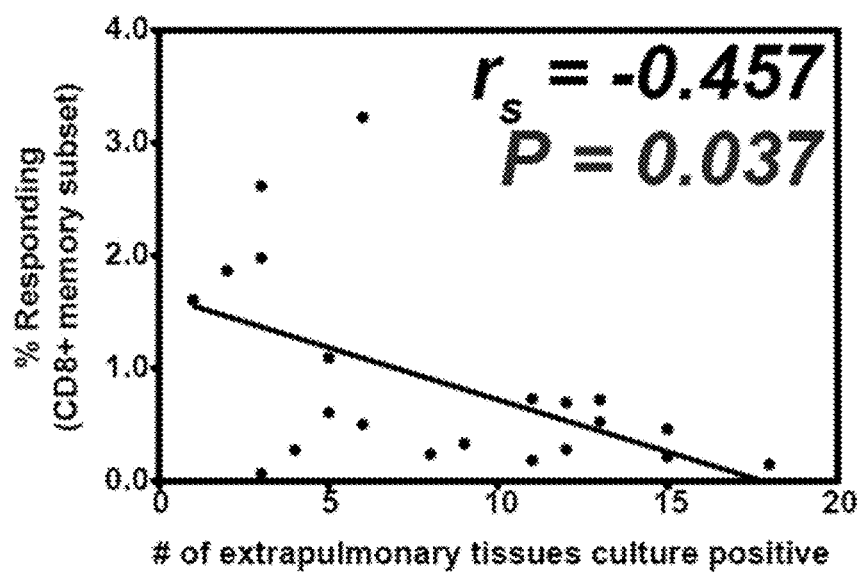
Figure 23 (cont.)

CD8+
Day 168
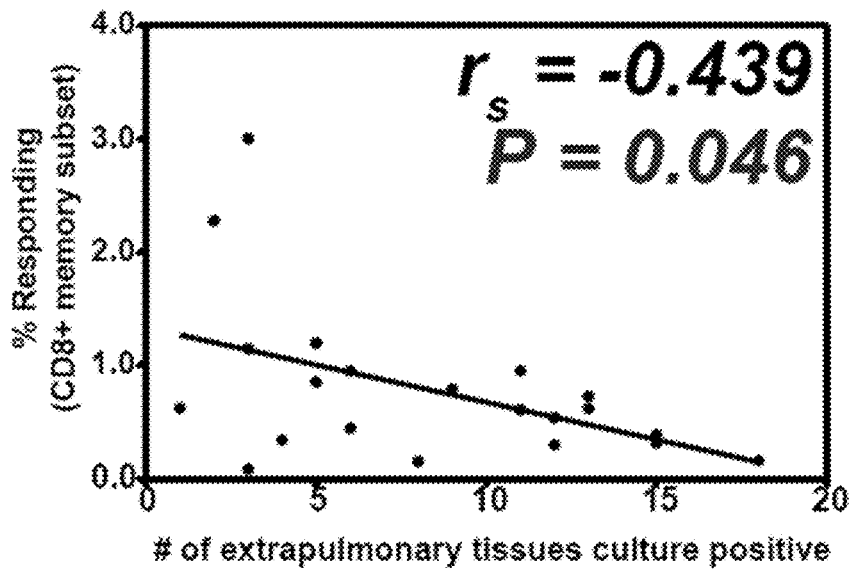
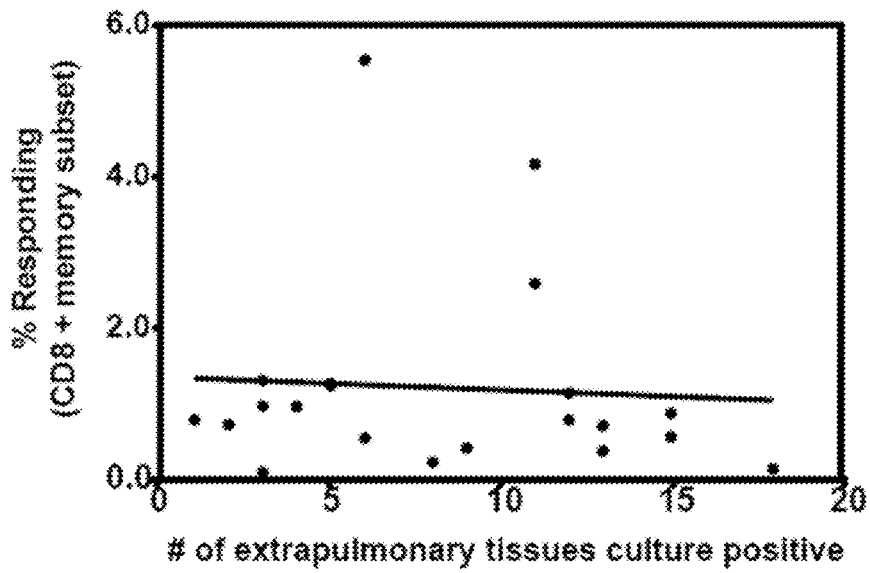
Figure 23 (cont.)

CD8+
Day 168
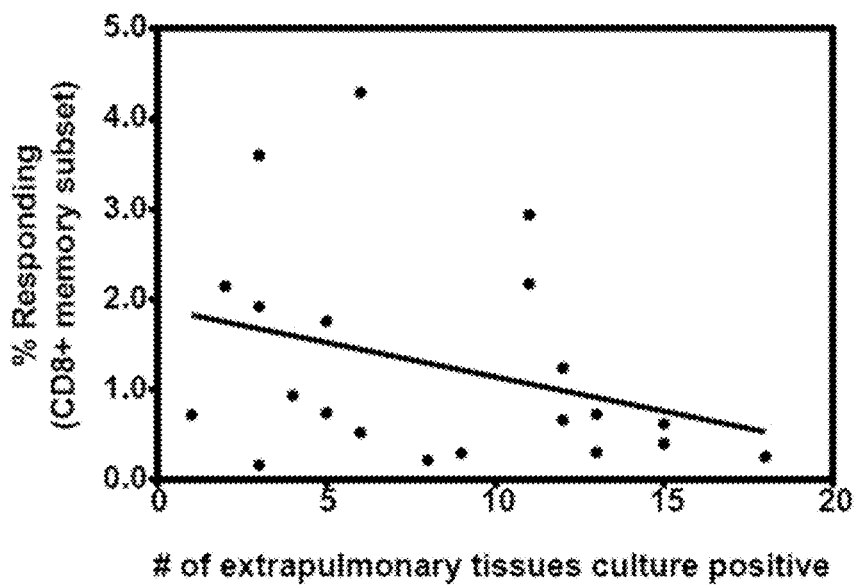
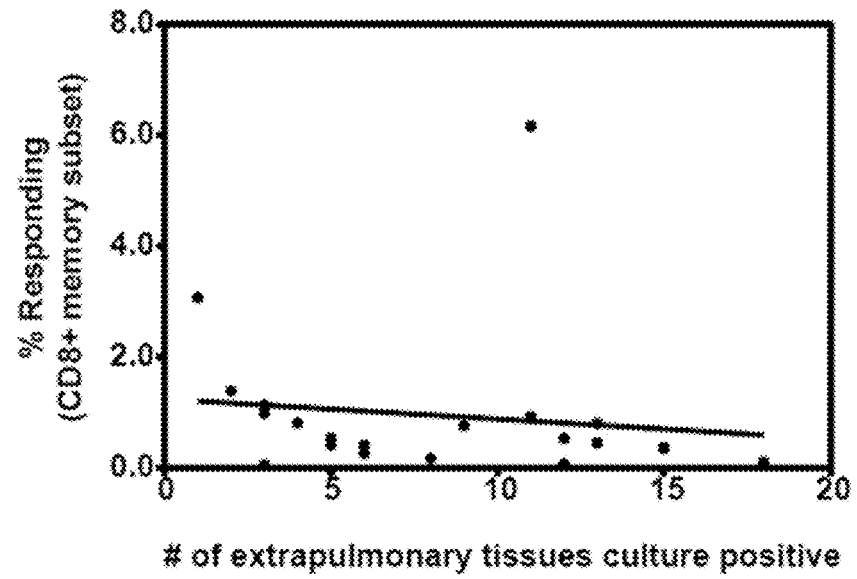
Figure 23 (cont.)

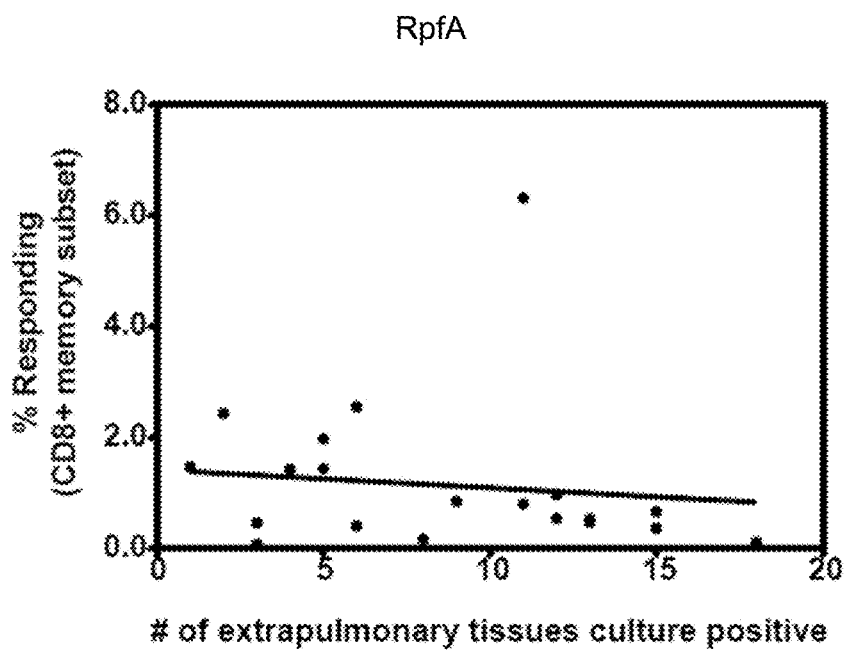
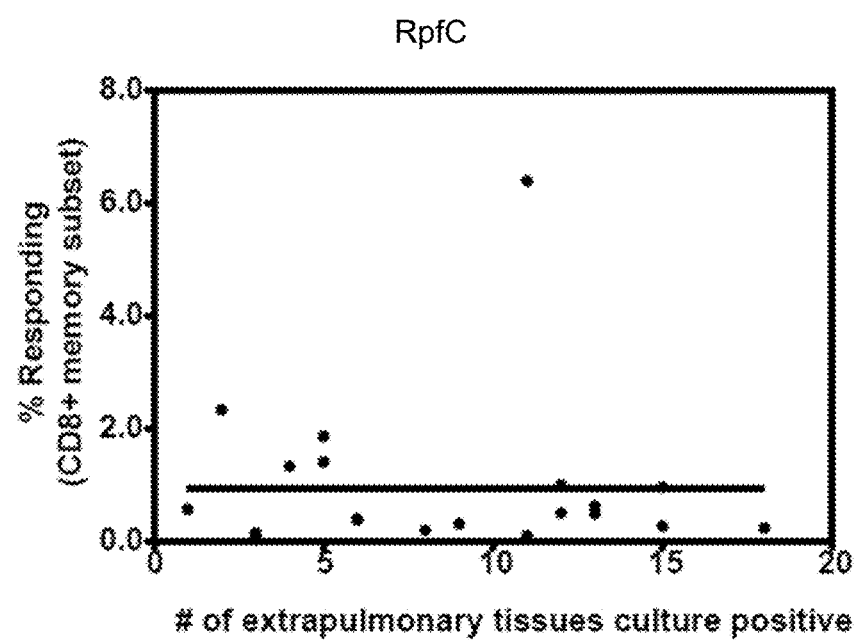
Figure 23 (cont.)

CD8+
Day 344
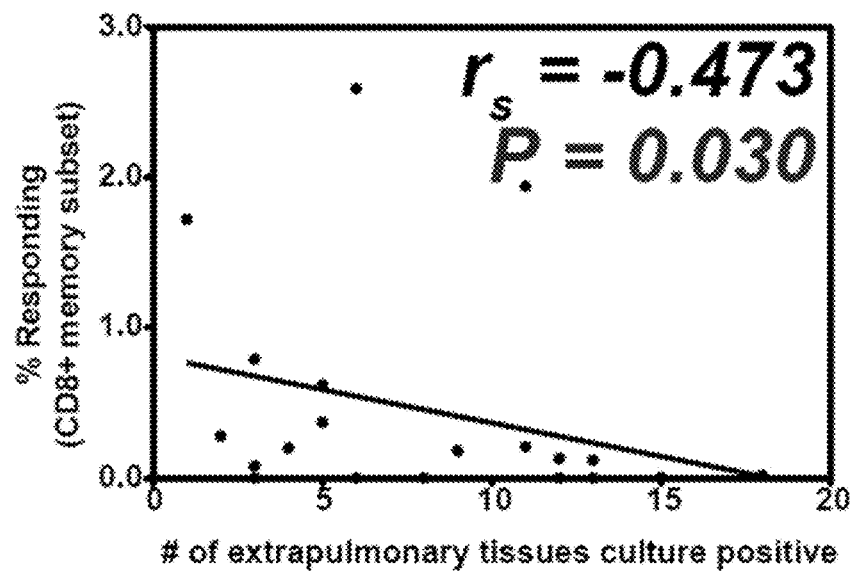
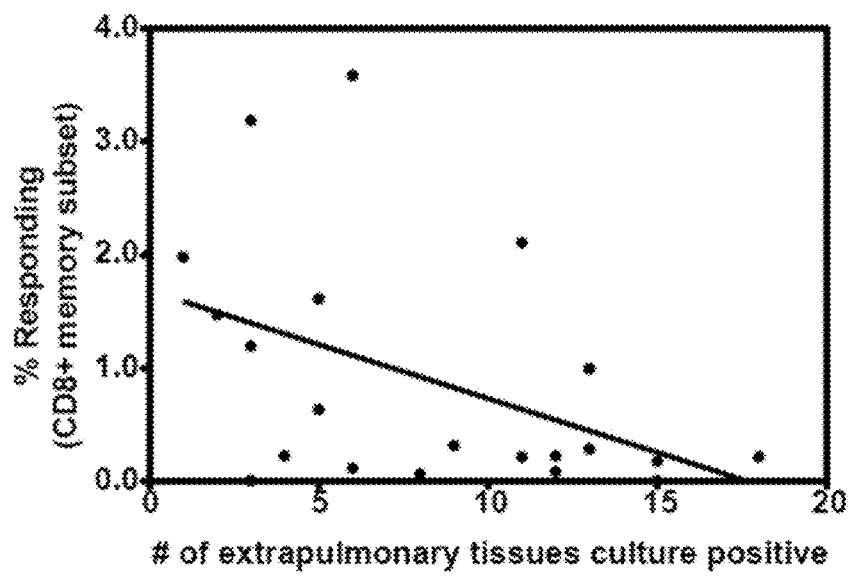
Figure 23 (cont.)

CD8+
Day 344
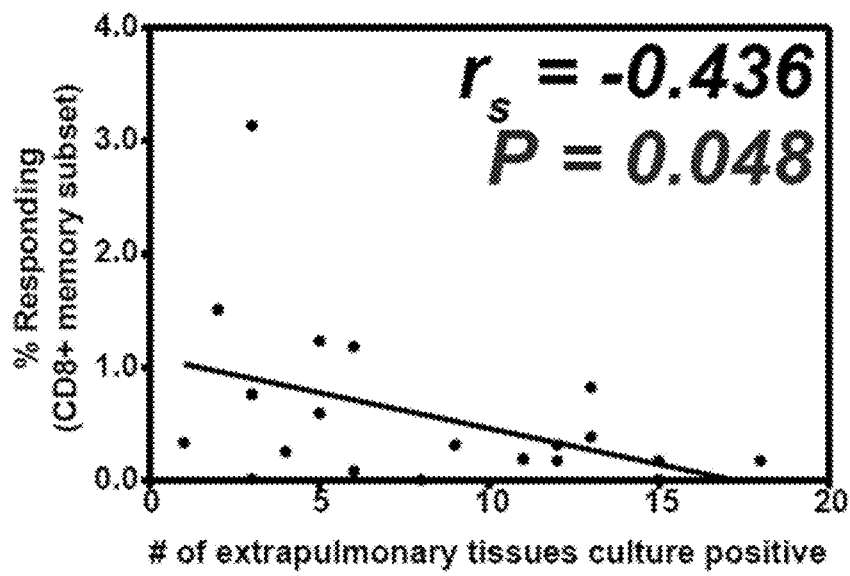
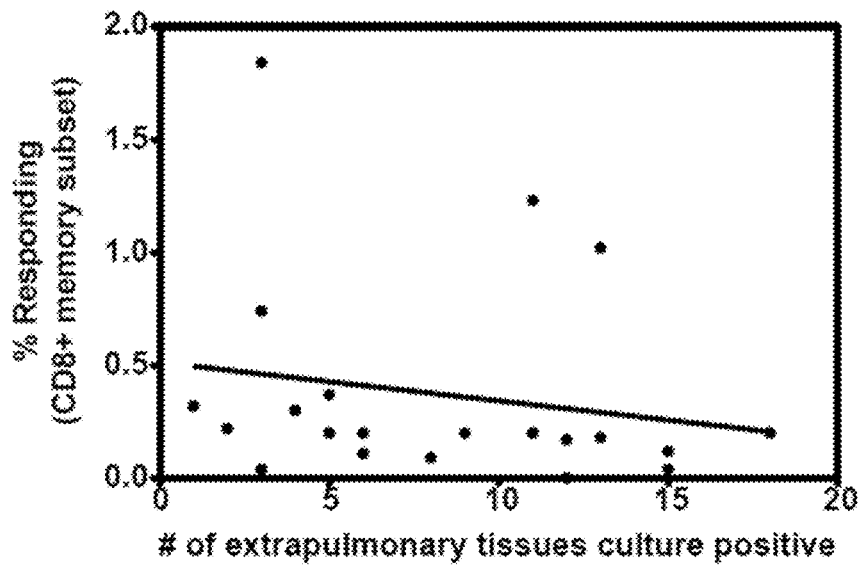
Figure 23 (cont.)

CD8+
Day 344
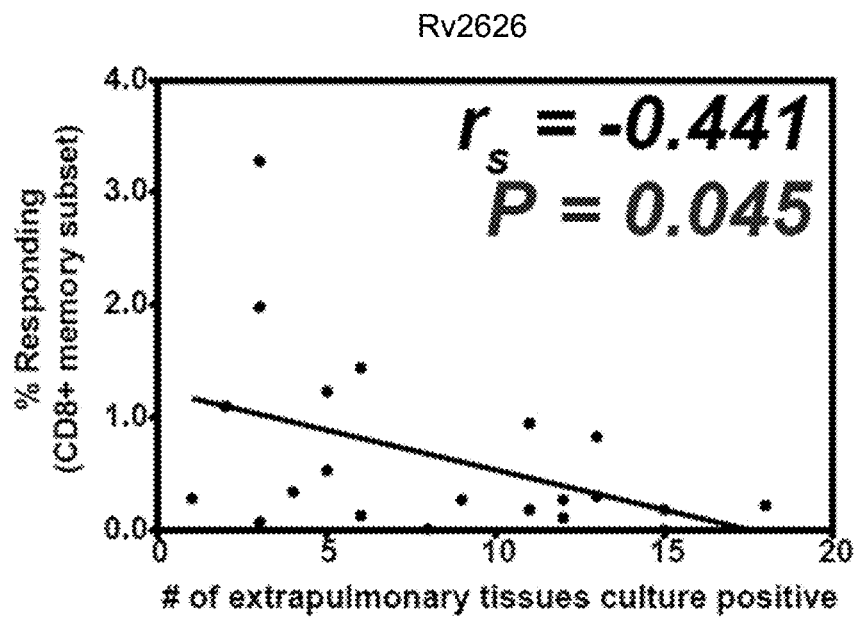
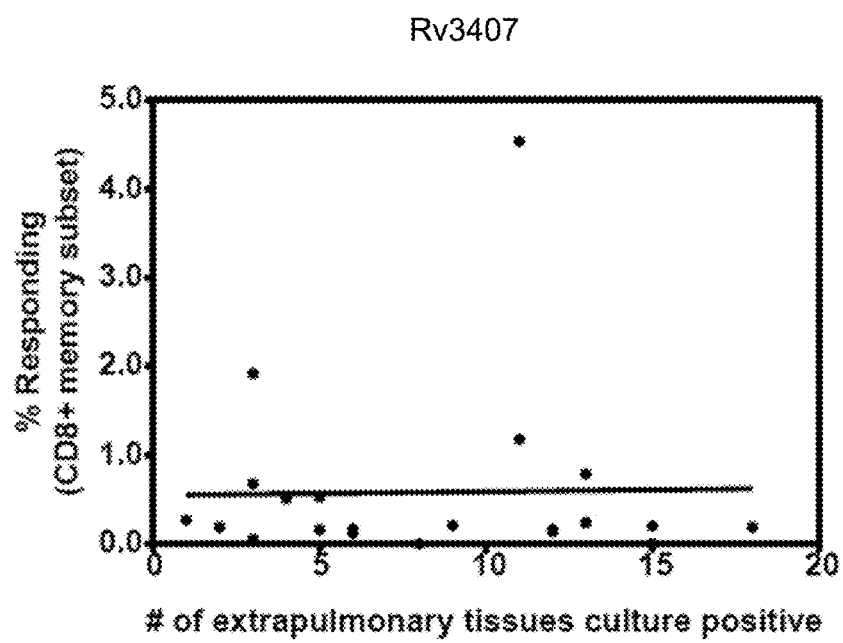
Figure 23 (cont.)

CD8+
Day 344
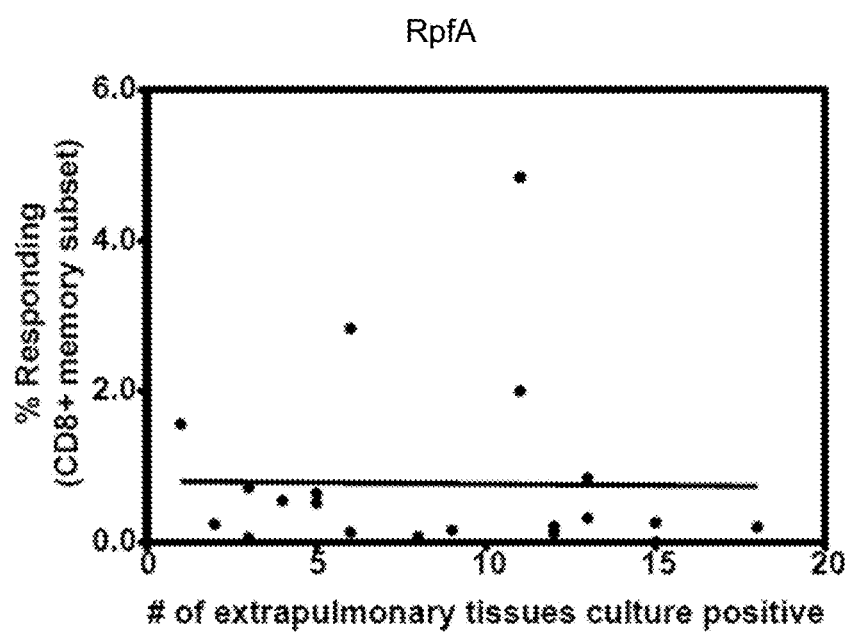
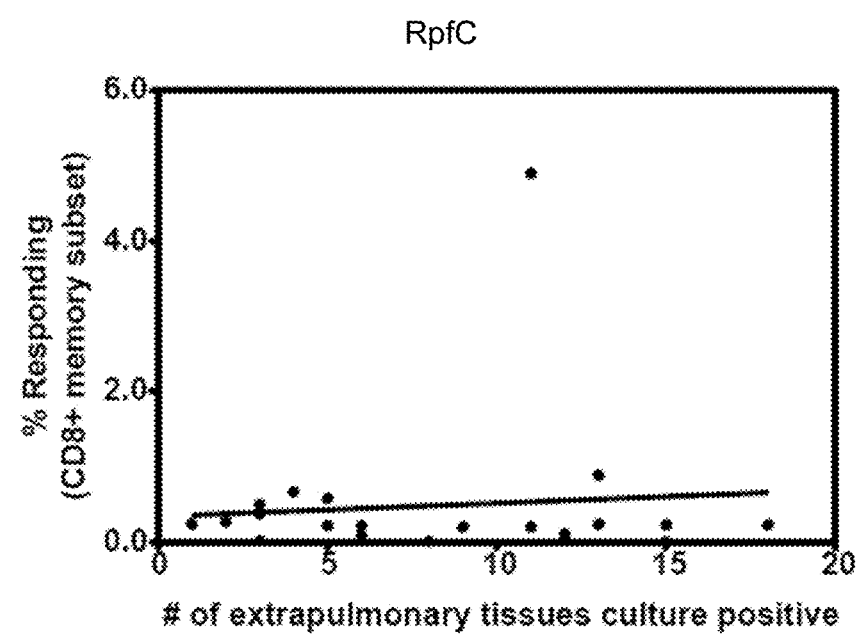
Figure 23 (cont.)

**Pulmonary Parenchymal Disease (each lobe\* scored separately and summed)**

| Granuloma Presence\*\* | |
|---|---|
| No granulomas | 0 |
| 1-3 granulomas | 1 |
| 4-10 granulomas | 2 |
| 11-15 granulomas | 3 |
| 16-20 granulomas | 4 |
| >20 granulomas | 5 |
| Miliary <50% of lobe | 6 |
| Miliary >50% of lobe | 7 |

| Granuloma Size | |
|---|---|
| No granulomas | 0 |
| <1-2 mm | 1 |
| 3-4 mm | 2 |
| 5-10 mm | 3 |
| 11-20 mm | 4 |
| >20mm, not miliary or confluent | 5 |
| Confluent or miliary lesions involving <50% of lobe | 6 |
| Confluent or miliary lesions involving >50% of lobe | 7 |

\*Left Upper, Left Middle, Left Lower, Right Upper, Right Middle; Right Lower; Right Accessory
\*\*an additional point is scored for each of the following: 1) cavitation of 1 or more granulomas, 2) granulomatous involvement of the trachea or large bronchi resulting in perforation. 3) pleura thickening, and 4) pleural adhesions (max 1 point per RM for each).

Chest Wall Disease

| | |
|---|---|
| Granulomatous disease not present | 0 |
| Granulomatous disease present; all lesions <1cm | 1 |
| Granulomatous disease present; one or more lesions >1cm | 2 |

Liver Disease

| Granuloma Number | |
|---|---|
| No granulomas | 0 |
| 1-3 granulomas | 1 |
| 4-10 granulomas | 2 |
| 11-20 granulomas | 3 |
| 20-50 granulomas | 4 |
| >50 granulomas-miliary | 5 |

| Granuloma Size | |
|---|---|
| No granulomas | 0 |
| <1-2 mm | 1 |
| 3-4 mm | 2 |
| >4 mm | 3 |

**Lymph Node Disease (each node group\* scored separately and summed)**

| Granuloma Size | |
|---|---|
| No granulomas | 0 |
| Focal or Multifocal, <2mm, not miliary or confluent | 1 |
| Coalescing involving <50% of lobe | 2 |
| Coalescing involving >50% of lobe (but without effacement) | 3 |
| Complete granulomatous effacement | 4 |

| Lymph Node Size | |
|---|---|
| no granulomatous involvement | 0 |
| Nodes visibly enlarged (5-10 mm) unilateral | 1 |
| Nodes visibly enlarged (5-10 mm) bilateral | 2 |
| Nodes visibly enlarged\*\* (>1 cm) unilateral/bilateral | 3 |

\*Hilar, Carinal; Paratracheal; Internal Mammary; Other Mediastinal, Mesenteric or Peripheral
\*\*Scored only if LN was enlarged due to granulomatous inflammation.

Spleen Disease

| Granuloma Number | |
|---|---|
| No granulomas | 0 |
| 1-3 granulomas | 1 |
| 4-10 granulomas | 2 |
| 11-20 granulomas | 3 |
| >20 granulomas-miliary | 4 |

| Granuloma Size | |
|---|---|
| No granulomas | 0 |
| <1-2 mm | 1 |
| 3-4 mm | 2 |
| >4 mm | 3 |

**Other Organ Disease (each organ type\* scored separately and summed)**

| Granuloma Number | |
|---|---|
| No granulomas | 0 |
| 1-3 granulomas | 1 |
| 4-10 granulomas | 2 |
| >10 granulomas | 3 |
| Miliary pattern | 4 |

| Granuloma Size | |
|---|---|
| No granulomas | 0 |
| <1-2 mm | 1 |
| 3-4 mm | 2 |
| >4 mm | 3 |

\*kidney, bladder, pancreas, small bowel, large bowel

Figure 48 a Study 1 Efficacy by Group*:

| Group A | Group B | CT AUC | Nx Culture Lung | Nx Score Lung | Nx Culture Non-lung | Nx Score Non-lung | Nx Culture Overall | Nx Score Overall |
|---|---|---|---|---|---|---|---|---|
| Unvaccinated | BCG | 0.5358 | 0.0818 | 0.0919 | 0.4491 | 0.1473 | 0.1046 | 0.1206 |
| | | 0.5619 | 0.0818 | 0.1447 | 0.4491 | 0.2946 | 0.1046 | 0.2412 |
| | 68-1 RhCMV/TB | 0.0093 | 0.0031 | 0.0148 | 0.0064 | 0.0045 | 0.0026 | 0.0065 |
| | | *0.0280* | *0.0092* | *0.0445* | *0.0192* | *0.0136* | *0.0077* | *0.0195* |
| | BCG + 68-1 RhCMV/TB | 0.2810 | 0.0317 | 0.0723 | 0.0314 | 0.2950 | 0.0077 | 0.1893 |
| | | 0.5619 | *0.0633* | 0.1447 | *0.0627* | 0.2950 | *0.0153* | 0.2412 |
| BCG | 68-1 RhCMV/TB | 0.0728 | 0.1223 | 0.2475 | 0.0083 | 0.0103 | 0.0247 | 0.0250 |
| | | 0.1457 | 0.2446 | 0.4951 | *0.0166* | *0.0207* | *0.0494* | *0.0501* |
| | BCG + 68-1 RhCMV/TB | 0.6200 | 0.7961 | 1.0000 | 0.0628 | 0.8979 | 0.2003 | 0.7104 |
| | | 0.6200 | 0.7961 | 1.0000 | 0.0628 | 0.8979 | 0.2003 | 0.7104 |
| 68-1 RhCMV/TB | BCG + 68-1 RhCMV/TB | 0.2593 | 0.2433 | 0.1589 | 0.1773 | 0.0545 | 0.1240 | 0.0839 | b Study 1 estimated Vaccine Efficacy (VE) to reduce the rate of each outcome measure, using a negative binomial (Poisson) model:

| Group A | Group B | Outcome | Estimated VE | 2.50% | 97.50% | P value |
|---|---|---|---|---|---|---|
| Unvaccinated | 68-1 RhCMV/TB | Necropsy Culture - Overall | 68.71% | 49.58% | 80.61% | <0.0001 |
| | | Necropsy Score - Overall | 67.32% | 44.22% | 80.76% | <0.0001 |
| BCG | 68-1 RhCMV/TB | Necropsy Culture - Overall | 57.67% | 30.52% | 74.30% | 0.0007 |
| | | Necropsy Score - Overall | 51.44% | 15.68% | 72.05% | 0.0100 |

Figure 49 c Study 2 Efficacy by Group*:

| Group A | Group B | CT AUC | Nx Culture Lung | Nx Score Lung | Nx Culture Non-lung | Nx Score Non-lung | Nx Culture Overall | Nx Score Overall |
|---|---|---|---|---|---|---|---|---|
| Unvaccinated | 68-1 RhCMV/TB-9Ag | 0.2116 / 0.2116 | 0.0524 / 0.0551 | 0.0727 / 0.0727 | 0.0032 / 0.0065 | 0.0074 / 0.0169 | 0.0162 / 0.0162 | 0.0321 / 0.0643 |
| | 68-1.2 RhCMV/TB-9Ag** | 0.0214 / 0.0428 | 0.0009 / 0.0027 | 0.0098 / 0.0295 | 0.0118 / 0.0118 | 0.1435 / 0.1435 | 0.0031 / 0.0077 | 0.1011 / 0.1011 |
| | 68-1 RhCMV/TB-6Ag | 0.0057 / 0.0170 | 0.0276 / 0.0551 | 0.0173 / 0.0347 | 0.0022 / 0.0065 | 0.0056 / 0.0169 | 0.0026 / 0.0077 | 0.0064 / 0.0193 |
| 68-1 RhCMV/TB-9Ag | 68-1.2 RhCMV/TB-9Ag** | 1.0000 / 1.0000 | 0.5110 / 1.0000 | 0.9259 / 1.0000 | 0.5812 / 1.0000 | 0.3798 / 0.7596 | 0.8810 / 1.0000 | 0.5479 / 1.0000 |
| | 68-1 RhCMV/TB-6Ag | 0.5939 / 1.0000 | 1.0000 / 1.0000 | 0.8842 / 1.0000 | 0.9261 / 1.0000 | 0.8462 / 0.8462 | 0.9271 / 1.0000 | 0.8844 / 1.0000 |
| Unvaccinated | All RhCMV/TB Vaccinated | 0.0071 | 0.0012 | 0.0041 | 0.0003 | 0.0033 | 0.0004 | 0.0056 | d Study 2 estimated Vaccine Efficacy (VE) to reduce the rate of each outcome measure, using a negative binomial (Poisson) model:

| Group A | Group B | Outcome | Estimated VE | 2.50% | 97.50% | P value |
|---|---|---|---|---|---|---|
| Unvaccinated | All RhCMV/TB Vaccinated | Necropsy Culture - Overall | 74.48% | 40.74% | 90.11% | 0.0024 |
| | | Necropsy Score - Overall | 61.42% | 31.51% | 78.27% | 0.0011 | e Overall (Study 1 + Study 2) estimated Vaccine Efficacy (VE) to reduce the rate of the scaled, combined outcome measure using a negative binomial (Poisson) model

| Group A | Group B | Outcome | Estimated VE | 2.50% | 97.50% | P value |
|---|---|---|---|---|---|---|
| All Unvaccinated | All RhCMV/TB Vaccinated | Scaled, Combined Outcome Measure | 68.24% | 35.89% | 85.14% | 0.0019 |

Figure 49 (cont.)

RECOMBINANT CYTOMEGALOVIRUS VECTORS AS VACCINES FOR TUBERCULOSIS

CROSS-REFERENCE TO RELATED APPLICATIONS

This application claims priority to U.S. Provisional Application Ser. No. 62/353,432 filed Jun. 22, 2016 and U.S. Provisional Application Ser. No. 62/478,099 filed Mar. 29, 2017, each of which is incorporated herein by reference in its entirety.

FIELD

The present disclosure is directed, in part, to cytomegalovirus vectors encoding fusion proteins comprising *Mycobacterium tuberculosis* (Mtb) antigens, nucleic acid molecules encoding the same, cytomegalovirus vectors comprising nucleic acid molecules, compositions comprising the same, and methods of eliciting an immune response against tuberculosis.

BACKGROUND

Tuberculosis (TB) is a global health problem resulting in 8 million new cases and 2 million deaths each year. The emergence of multi-drug and totally-drug resistant strains of TB only makes this problem more severe. The life cycle of Mtb has 3 stages. In the acute phase following initial infection the bacteria replicate in the host and virulence factors are expressed, leading to the generation of an immune response by the host. As the immune response begins to control the infection, the Mtb enters a latent, asymptomatic state in which the bacteria become non-replicating and are encased in granulomas. The bacterium can persist in this latent state in infected individuals for many years, making diagnosis and treatment of disease difficult. In some cases, the bacteria are reactivated and begin replicating again, leading back to the disease state. Reactivation can occur for numerous reasons, including immune suppression caused by diseases such as HIV, treatments such as chemotherapy, or the weakening of the immune system due to aging. An estimated 2 billion people are latently infected with Mtb worldwide, and reactivation of latent Mtb accounts for most new cases of active TB disease. Reactivation is associated with inflammation, necrosis and cavitation of the lung, a process that results in draining of the lesions into the bronchus. Aerosols generated when individuals with bronchial lesions cough causes dissemination of the Mtb organism to uninfected, susceptible persons, and the transmission cycle is thus maintained.

The only currently available vaccine against TB, *Mycobacterium bovis* (Bacille Calmette-Guérin) (BCG), was first introduced in 1921. BCG has been widely utilized and while studies show that for some purposes BCG is effective (e.g. against disseminated TB in infants), it is known to be ineffective with respect to preventing the development, persistence and reactivation of latent TB in adults. There is an ongoing need to develop improved, more effective vaccines against TB.

Use of cytomegalovirus (CMV) vectors (e.g., Rhesus CMV (RhCMV) and human CMV (HCMV)) has particular advantages. First, CMV elicits an astoundingly high frequency (steady-state) T cell response, at least an order of magnitude higher than that of most non-persistent virus (it is not uncommon for CMV-specific T cells to encompass >20% of the circulating memory repertoire), and the representation of CMV-specific T cells (as it relates to CMV-driven non-CMV antigens) is even higher in tissues such as the lung and liver. In addition, the above responses persist indefinitely. CMV is also capable of re-infecting already chronically infected individuals, even in the face of pre-existing immune responses, and such re-infection with recombinant CMVs is also capable of inducing new responses to distinct CMV-encoded foreign proteins. CMV also engenders pathogenicity only in very specific situations of immune deficiency, immaturity, or seronegative pregnant women (its potential for disease is among the best documented among potential human pathogens). Finally, CMV infection is ubiquitous in most of humanity.

While vaccines are often effective to immunize individuals prophylactically or therapeutically against pathogen infection or human diseases, there is a need for improved vaccines and vectors. There is also a need for compositions and methods that produce an enhanced immune response. Likewise, while some immunotherapeutics are useful to modulate immune response in a patient, there remains a need for improved immunotherapeutic compositions and methods.

SUMMARY

The present disclosure provides recombinant RhCMV or HCMV vectors comprising a nucleic acid sequence encoding an expressible Mtb antigen selected from Ag85A-Ag85B-Rv3407, Rv1733-Rv2626c, RpfA-RpfC-RpfD, Ag85B-ESAT6, and Ag85A-ESAT6-Rv3407-Rv2626c-RpfA-RpfD.

The present disclosure also provides pharmaceutical compositions comprising the recombinant RhCMV or HCMV vaccine vectors described herein and a pharmaceutically acceptable carrier.

The present disclosure also provides methods for treatment or prevention of tuberculosis comprising administering to a subject in need thereof at least one recombinant RhCMV or HCMV vaccine vector described herein.

The present disclosure also provides methods for eliciting an immune response to a Mtb antigen comprising administering to a subject in need thereof at least one recombinant RhCMV or HCMV vaccine vector described herein.

The present disclosure also provides methods for eliciting a CD8+ or CD4+ T cell response to a Mtb antigen comprising administering to a subject in need thereof at least one recombinant RhCMV or HCMV vaccine vector described herein.

The present disclosure also provides Mtb antigens selected from Ag85B-ESAT6 and Ag85A-ESAT6-Rv3407-Rv2626c-RpfA-RpfD.

BRIEF DESCRIPTION OF THE DRAWINGS

FIG. 14 shows representative CT scans from NHP in the unvaccinated and RhCMV/TB groups.

FIG. 48 shows pathologic scoring of TB disease at necropsy.

FIG. 49 (panels a, b, c, d, and e) shows a summary of outcome statistics.

DESCRIPTION OF EMBODIMENTS

Figure 1:
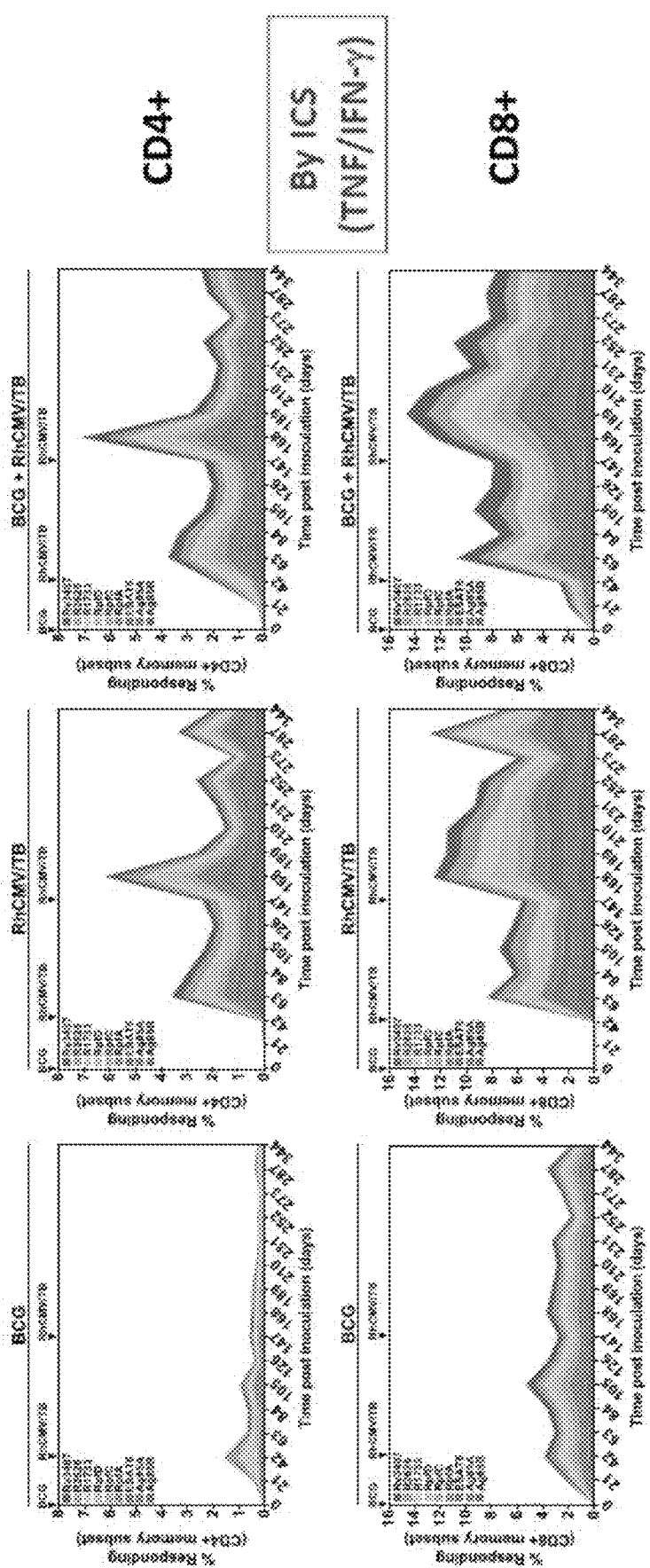
FIG. 1 shows immunogenicity of BCG and Rhesus CMV vectors containing various TB constructs; immune responses induced by vaccination were analyzed by intracellular cytokine staining throughout the vaccination period; shown is the percentage of memory cells expressing either IFNγ or TNF; CD4+ T cells are shown in the upper panel and CD8+ T cells are shown in the lower panels.
Figure 2:
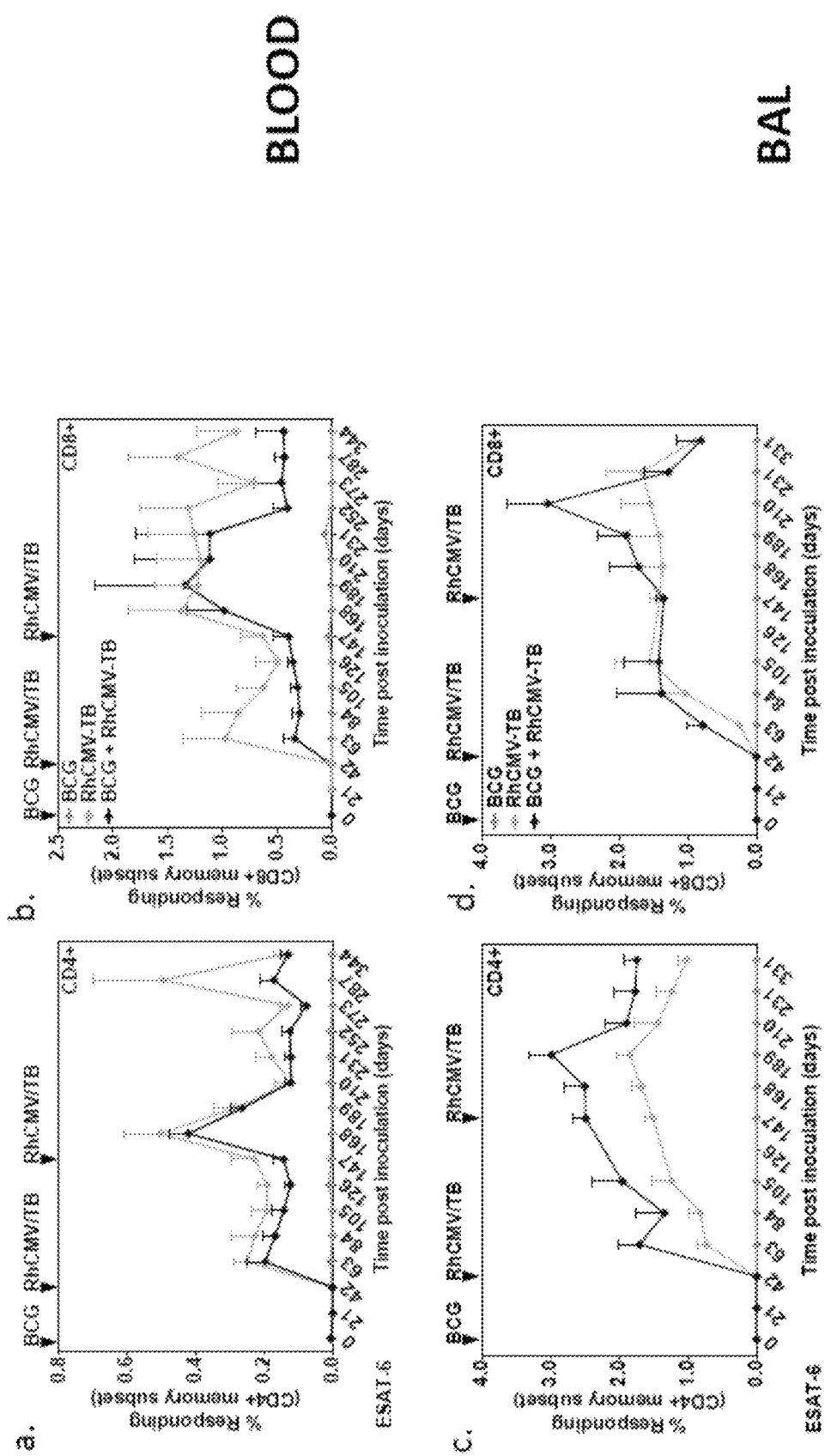
FIG. 2 (panels a, b, c, and d) shows ESAT-6-specific responses analyzed by intracellular cytokine staining throughout the vaccination period; shown above are the percentages of memory cells expressing either IFNγ or TNF; included are responses from peripheral blood mononuclear cells (PBMCs; shown in panels a and b) and bronchoalevolar lavage cells (BAL; shown in panels c and d); CD4+ T cells are shown in panels a and c, and CD8+ T cells are shown in panels b and d.

The terminology used herein is for the purpose of describing particular embodiments only and is not intended to be limiting.

As used herein, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "adjuvant" means any molecule added to any composition described herein to enhance the immunogenicity of the Mtb antigens.

As used herein, "coding sequence" or "encoding nucleic acid" means the nucleic acids (RNA or DNA molecule) that comprise a nucleotide sequence which encodes an Mtb antigen. The coding sequence can further include initiation and termination signals operably linked to regulatory elements including a promoter and polyadenylation signal capable of directing expression in the cells of an individual or mammal to which the nucleic acid is administered.

As used herein, "consensus" or "consensus sequence" means a polypeptide sequence based on analysis of an alignment of multiple subtypes of a particular Mtb antigen. Nucleic acid sequences that encode a consensus polypeptide sequence can be prepared. Vaccines comprising Mtb antigens that comprise consensus sequences and/or nucleic acid molecules that encode such antigens can be used to induce broad immunity against multiple subtypes or serotypes of a particular antigen. I some embodiments, the consensus sequence may be the most common sequence.

As used herein, "electroporation" means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, "fragment" with respect to nucleic acid sequences, means a nucleic acid sequence or a portion thereof, that encodes a portion of an Mtb antigen capable of eliciting an immune response in a mammal that cross reacts with a full length wild type Mtb antigen. The fragments can be DNA fragments selected from at least one of the various nucleotide sequences that encode protein fragments set forth below. For example, polynucleotides may comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200 to 500; 500 to 1,000, and the like.

As used herein, "fragment" or "immunogenic fragment" with respect to polypeptide sequences, means a portion of an MTB antigen capable of eliciting an immune response in a mammal that cross reacts with a full length wild type strain Mtb antigen. Fragments of consensus or wild type Mtb antigens can comprise at least 10%, at least 20%, at least 30%, at least 40%, at least 50%, at least 60%, at least 70%, at least 80%, at least 90% or at least 95% of a consensus or wild type Mtb antigen. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a consensus or wild type protein.

As used herein, "genetic construct" refers to the DNA or RNA molecules that comprise a nucleotide sequence which encodes an Mtb antigen. The coding sequence includes initiation and termination signals operably linked to regulatory elements including a promoter and polyadenylation signal capable of directing expression in the cells of the individual to whom the nucleic acid molecule is administered.

As used herein, "expressible form" refers to gene constructs that contain the necessary regulatory elements operable linked to a coding sequence that encodes an Mtb antigen such that when present in the cell of the individual, the coding sequence will be expressed.

As used herein, "homology" refers to a degree of complementarity for nucleic acid molecules. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous" refers to a probe that can hybridize to a strand of the double-stranded nucleic acid sequence under conditions of low stringency. When used in reference to a single-stranded nucleic acid sequence, the term "substantially homologous" refers to a probe that can hybridize to (i.e., is the complement of) the single-stranded nucleic acid template sequence under conditions of low stringency.

As used herein, "identical" or "identity" in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) residues can be considered equivalent. Identity and/or homology can be performed manually or by using a computer sequence algorithm such as BLAST or BLAST 2.0.

As used herein, "immune response" means the activation of a host's immune system, e.g., that of a mammal, in response to the introduction of an Mtb antigen. The immune response can be in the form of a cellular or humoral response, or both.

As used herein, "isolated" means that a polynucleotide is substantially away from other coding sequences, and that the nucleic acid segment does not contain large portions of unrelated coding DNA, such as large chromosomal fragments or other functional genes or polypeptide coding regions. Of course, this refers to the nucleic acid segment as originally isolated, and does not exclude genes or coding regions later added to the segment by the hand of man.

As used herein, "Mtb antigen" means an antigen from *Mycobacterium tuberculosis*, which may be an isolated antigen, or an antigen that forms part of a fusion protein with other antigen(s).

As used herein, "Mycobacteria" means a genus of aerobic intracellular bacterial organisms. Upon invasion of a host, these organisms survive within endosomal compartments of monocytes and macrophages. Human mycobacterial diseases include tuberculosis (caused by *M. tuberculosis* (Mtb)), Leprosy (caused by *M. leprae*), Bairnsdale ulcers (caused by *M. ulcerans*), and other infections that can be caused by *M. marinum, M. kansasii, M. scrofulaceum, M. szulgai, M. xenopi, M. fortuitum, M. haemophilum, M. chelonei*, and *M. intracelluare*. Mycobacterium strains that were previously considered to be nonpathogenic (such as *M. avium*) are also now known to be major killers of immunosuppressed AIDS patients. The major response to mycobacteria involves cell mediated hypersensitivity (DTH) reactions with T cells and macrophages playing major roles in the intracellular killing and walling off (or containing) of the organism (granuloma formation). A major T cell response involves $CD4^+$ lymphocytes that recognize mycobacterial heat shock proteins and immunodominant antigens.

As used herein, "nucleic acid" or "oligonucleotide" or "polynucleotide" means at least two nucleotides covalently linked together, which has been isolated free of total genomic DNA of a particular species. Included within these terms are nucleic acid segments and smaller fragments of such segments, and also recombinant CMV vectors. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods. As will be understood by those skilled in the art, the nucleic acid molecules can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As used herein, "operably linked" means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

As used herein, "promoter" means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

As used herein, "signal peptide" and "leader sequence", used interchangeably, refer to an amino acid sequence that can be linked at the amino terminus of an Mtb antigenic protein set forth herein. Signal peptides/leader sequences typically direct localization of a protein. Signal peptides/leader sequences used herein can facilitate secretion of the protein from the cell in which it is produced or anchor it in the membrane. Signal peptides/leader sequences are often cleaved from the remainder of the protein, often referred to as the mature protein, upon secretion from the cell. Signal peptides/leader sequences are linked at the N terminus of the protein.

As used herein, "stringent hybridization conditions" means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5 to 10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01 to 1.0 M sodium ion concentration (or other salts) at pH 7.0 to 8.3 and the temperature is at least about 30° C. for short probes (e.g., about 10 to 50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, "substantially complementary" means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used herein, "substantially identical" means that a first and second sequence are at least 50%, 55%, 60%, 65%, 70%, 75%, 80%, 85%, 90%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used herein, "tuberculosis" means a disease that is generally caused by *Mycobacterium tuberculosis* that usually infects the lungs. However, other "atypical" mycobacteria such as *M. kansasii* may produce a similar clinical and pathologic appearance of disease. Transmission of *M. tuberculosis* occurs by the airborne route in confined areas with poor ventilation. In more than 90% of cases, following infection with *M. tuberculosis*, the immune system prevents development of disease from *M. tuberculosis*, often called, active tuberculosis. However, not all of the *M. tuberculosis* is killed and, thus tiny, hard capsules are formed. "Primary tuberculosis" is seen as disease that develops following an initial infection, usually in children. The initial focus of infection is a small subpleural granuloma accompanied by granulomatous hilar lymph node infection. Together, these make up the Ghon complex. In nearly all cases, these granulomas resolve and there is no further spread of the infection. "Secondary tuberculosis" is seen mostly in adults as a reactivation of previous infection (or reinfection), particularly when health status declines. The granulomatous inflammation is much more florid and widespread. Typically, the upper lung lobes are most affected, and cavitation can occur. Dissemination of tuberculosis outside of the lungs can lead to the appearance of a number of uncommon findings with characteristic patterns that include skeletal tuberculosis, genital tract tuberculosis, urinary tract tuberculosis, central nervous system (CNS) tuberculosis, gastrointestinal tuberculosis, adrenal tuberculosis, scrofula, and cardiac tuberculosis. "Latent" tuberculosis is an Mtb infection in an individual that can be detected by a diagnostic assay, such as, but not limited to a tuberculin skin test (TST) wherein the infection does not produce symptoms in that individual. "Active" tuberculosis is a symptomatic Mtb infection in a subject. Microscopically, the inflammation produced with TB infection is granulomatous, with epithelioid macrophages and Langhans giant cells along with lymphocytes, plasma cells, maybe a few polymorphonuclear cells, fibroblasts with collagen, and characteristic caseous necrosis in the center. The inflammatory response is mediated by a type IV hypersensitivity reaction, and skin testing is based on this reaction. In some examples, tuberculosis can be diagnosed by a skin test, an acid fast stain, an auramine stain, or a combination thereof. The most common specimen screened is sputum, but the histologic stains can also be performed on tissues or other body fluids.

As used herein, "variant" with respect to a nucleic acid means: i) a portion or fragment of a referenced nucleotide sequence; ii) the complement of a referenced nucleotide sequence or portion thereof; iii) a nucleic acid that is substantially identical to a referenced nucleic acid or the complement thereof; or iv) a nucleic acid that hybridizes under stringent conditions to the referenced nucleic acid, complement thereof, or a sequences substantially identical thereto.

As used herein, "variant" with respect to a peptide or polypeptide means that it differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change Amino acid substitutions that are compatible with biological function are understood to depend on the relative similarity of the amino acids, and particularly the side chains of those amino acids, as revealed by the hydrophobicity, hydrophilicity, charge, size, and other properties. The term "variant" also encompasses homologous genes of xenogeneic origin.

As used herein, "CMV vector" means a CMV nucleic acid molecule as introduced into a host cell, thereby producing a transformed host cell. A CMV vector may include nucleic acid sequences that permit it to replicate in a host cell, such as an origin of replication. A CMV vector may also include one or more selectable marker gene and other genetic elements known in the art.

The present disclosure provides recombinant RhCMV or HCMV vectors comprising a nucleic acid molecule encoding an expressible Mtb antigen selected from Ag85A-Ag85B-Rv3407, Rv1733-Rv2626c, RpfA-RpfC-RpfD, Ag85B-ESAT6, and Ag85A-ESAT6-Rv3407-Rv2626c-RpfA-RpfD. In some embodiments, the nucleic acid molecule encoding any particular Mtb antigen can be a mycobacterial sequence, a bacterial codon optimized sequence (such as an *E. coli* optimized sequence), or a mammalian optimized sequence (such as a human optimized sequence). Methods of codon optimization (whether for bacterial or mammalian) are well known to the skilled artisan.

In any of the embodiments of the nucleic acid molecules set forth herein, the individual Mtb nucleic acid sequences can be present in any order. For example, for a fusion protein comprising Ag85A, Ag85B, and Rv3407 antigens, the first (or N-terminal) nucleic acid molecule may encode Ag85A, Ag85B, or Rv3407; the second nucleic acid molecule may encode Ag85A, Ag85B, or Rv3407 (whichever one is not the first Mtb antigen); and the third nucleic acid molecule may encode Ag85A, Ag85B, or Rv3407 (whichever one is not the first or second Mtb antigen). Likewise for every nucleic acid molecule disclosed herein.

Additional coding or non-coding sequences may, but need not, be present within a polynucleotide of the present invention, and a polynucleotide may, but need not, be linked to other molecules and/or support materials.

Polynucleotides may comprise a native sequence (e.g., an endogenous sequence that encodes a CMV or TB protein or a portion thereof) or may comprise a variant, or a biological or antigenic functional equivalent of such a sequence.

A nucleotide sequence encoding Ag85A is shown in Table 1 as SEQ ID NO:1, and an amino acid sequence of Ag85A is shown in Table 1 as SEQ ID NO:2.

A nucleotide sequence encoding Ag85B is shown in Table 1 as SEQ ID NO:3, and an amino acid sequence of Ag85B is shown in Table 1 as SEQ ID NO:4.

A nucleotide sequence encoding Rv3407 is shown in Table 1 as SEQ ID NO:5, and an amino acid sequence of Rv3407 is shown in Table 1 as SEQ ID NO:6.

A nucleotide sequence encoding Rv1733 is shown in Table 1 as SEQ ID NO:7, and an amino acid sequence of Rv1733 is shown in Table 1 as SEQ ID NO:8.

A nucleotide sequence encoding Rv2626c is shown in Table 1 as SEQ ID NO:9, and an amino acid sequence of Rv2626c is shown in Table 1 as SEQ ID NO:10.

A nucleotide sequence encoding RpfA is shown in Table 1 as SEQ ID NO:11, and an amino acid sequence of RpfA is shown in Table 1 as SEQ ID NO:12.

A nucleotide sequence encoding RpfC is shown in Table 1 as SEQ ID NO:13, and an amino acid sequence of RpfC is shown in Table 1 as SEQ ID NO:14.

A nucleotide sequence encoding RpfD is shown in Table 1 as SEQ ID NO:15, and an amino acid sequence of RpfD is shown in Table 1 as SEQ ID NO:16.

A nucleotide sequence encoding ESAT-6 is shown in Table 1 as SEQ ID NO:17, and an amino acid sequence of ESAT-6 is shown in Table 1 as SEQ ID NO:18.

TABLE 1

| Construct | nucleotide sequence<br>amino acid sequence |
|---|---|
| Ag85A | atgcagcttgagacagggttcgtggcgccgtcacgggtatgtcgcgtcgactcgtggtcggggccgtcggc<br>gcggccctagtgtcggtctggtcggcgccgtcggtggcacggcgaccgcggggggcattacccggccgg<br>gcttgccggtggagtacctgcaggtgccgtcgccgtcgatgggccgtgacatcaaggtccaattccaagtg<br>gtggtgccaactcgcccgccctgtacctgctcgacggcctgcgcgcgcaggacgacttcagcggctgggac<br>atcaacaccccggcgttcgagtggtacgaccagtcgggcctgtcggtggtcatgccggtgggtggccagtca<br>agatctactccgactggtaccagccgcctgcggcaaggccggagccagacttacaagtgggagaccttc<br>ctgaccagcgagctgccggggtggctgcaggccaacaggcacgtcaagcccaccggaagcgccgtcgtc<br>ggtattcgatggctgatatcggcgctgacgctggcgatctatcacccccagcagttcgtctacgcgggagc<br>gatgtcgggcctgaggacccctccaggcgatgggtcccaccctgatcggcctggcgatgggtgacgctg<br>gcggctacaaggcctccgacatgtgggggcccgaaggaggacccgtggcagcgcaacgacccgctgt<br>tgaacgtcgggaagctgatcgccaacaacacccgcgtctgggtgtactgcggcaacggcaagccgtcggat<br>ctgggtggcaacaacctgccggccaagaccctgagggcttcgtgcggaccagcaacatcaagttccaagac<br>gcctacaacgccggtggcggccacaacggcgtgacgacttcccgacagcggtacgcacagctgggagt<br>actggggcgcagctcaacgctatgaagcccgacctgcaacgggcactgggtgccacgcccaacaccgg<br>gcccgcgccccaggcgcctag (SEQ ID NO: 1)<br>MQLVDRVRGAVTGMSRRLVVGAVGAALVSGLVGAVGGTATAGAF<br>SRPGLPVEYLQVPSPSMGRDIKVQFQSGGANSPALYLLDGLRAQDDF<br>SGWDINTPAFEWYDQSGLSVVMPVGGQSSFYSDWYQPACGKAGCQ<br>TYKWETFLTSELPGWLQANRHVKPTGSAVVGLSMAASSALTLAIYH<br>PQQFVYAGAMSGLLDPSQAMGPTLIGLAMGDAGGYKASDMWGPKE<br>DPAWQRNDPLLNVGKLIANNTRVWVYCGNGKPSDLGGNNLPAKFL<br>EGFVRTSNIKFQDAYNAGGGHNGVFDFPDSGTHSWEYWGAQLNAM<br>KPDLQRALGATPNTGPAPQGA (SEQ ID NO: 2) |
| Ag85B | atgacagacgtgagccgaaagattcgagcaggggacgccgattgatgatcggcacggcagcggctgtagt<br>ccttccgggcctggtggggcttgccggcggagcggcaacgcgggcgcgttctcccggccggggctgcc<br>ggtcgagtacctgcaggtgccgtcgccgtcgatgggccgcgacatcaaggttcagttccagaggcggtggga<br>acaactcacctgcggtttatctgctcgacggcctgcgcgcccaagacgactacaacggctgggatatcaaca<br>ccccggcgttcgagtggtactaccagtcgggactgtcgatagtcatgccggtcggcgggcagtccagcttcta<br>cagcgactggtacagcccggcctgcggtaaggctggctgccagacttacaagtggggaaaccttcctgacca<br>gcgagctgccgcaatggagtccgccaacagggccgtgaagcccaccggcagcgctgcaatcggcttgtcg<br>atggccggctcgtcggcaatgatcttggccgcctaccacccccagcagttcatctacgccggctcgctgtcgg<br>ccctgctggaccccctctcagggggatggggcctagcctgatcggcctcgcgatgggtgacgccggcggttac<br>aaggccgcagacatgtggggtccctcgagtgacccggcatgggagcgcaacgaccctacgcagcagatcc<br>ccaagctggtcgcaaacaacacccggctatgggatattgcggaacggcacccgaacgagagggcggt<br>gccaacataccgccgagttcaggagaacttcgttcgtagcagcaacctgaagttccaggatcgtacaacg<br>ccgcgggcgggcacaacgccgtgacaacttcccgcccaacggcacgcacagctgggagtactggggcgc<br>tcagctcaacgccatgaagggtgacctgcagagttcgttaggcgccggctga (SEQ ID NO: 3)<br>MTDVSRKIRAWGRRLMIGTAAAVVLPGLVGLAGGAATAGAFSRPGL<br>PVEYLQVPSPSMGRDIKVQFQSGGNNSPAVYLLDGLRAQDDYNGWD<br>INTPAFEWYYQSGLSIVMPVGGQSSFYSDWYSPACGKAGCQTYKWE<br>TFLTSELPQWLSANRAVKPTGSAAIGLSMAGSSAMILAAYHPQQFIY<br>AGSLSALLDPSQGMGPSLIGLAMGDAGGYKAADMWGPSSDPAWER<br>NDPTQQIPKLVANNTRLWVYCGNGTPNELGGANIPAEFLENFVRSSN<br>LKFQDAYNAAGGHNAVFNFPPNGTHSWEYWGAQLNAMKGDLQSSL<br>GAG (SEQ ID NO: 4) |
| Rv3407 | atgcgtgctaccgagggcagtggaggcaatcggaatccgagaactaagacagcacgcatcgcgataccctc<br>gcccgggagaagccggcgaggaacttggcgtcaccaacaaaggaagacttgtggcccgactcatcccggt<br>gcaggccgcggagcgactcgcgaagccctgattgaatcaggtgtcctgattccggctcgtcgtccacaaaac<br>cttctcgacgtcaccgccgaaccggcgcgcggccgcaagcgcaccctgtccgatgttctcaacgaaatgcg<br>cgacgagcagtga (SEQ ID NO: 5)<br>MRATVGLVEAIGIRELRQHASRYLARVEAGEELGVTNKGRLVARLIP<br>VQAAERSREALIESGVLIPARRPQNLLDVTAEPARGRKRTLSDVLNE<br>MRDEQ (SEQ ID NO: 6) |
| Rv1733 | atgatcgccacaacccgcgatcgtgaaggagccaccatgatcacgataggctgcgcttgccgtgccggacg<br>atactcgcgggtgacagccgcaatccgctggtgcgtgggacggatcgactcgaggcggtcgtcatgctgctg<br>gccgtcacggtctcgctgctgactatcccgttcgccgccgcggccggcaccgcagtccaggattcccgcagc<br>cacgtctatgcccaccaggcccagacccgcacatccgcaaccgcgaccgtgatcgatcacgaggggtgat<br>cgacagcaacacgaccgccacgtcagccgccgcgcacgaagatcaccgtgcctgcccgatgggtcgtg<br>aacgaatagaacgcagccgtgaggtcaacgcgaagccgggaaccaaatccggtgaccgcgtcggcattt<br>gggtcgacagtgccggtcagctggtcgatgaaccagctccgccgcccgtgccattgcggatgcggccctg<br>gccgcctgggactcttggttgagcgtcgccgcggttgcgggcgccctgctggcgctcactcgggcgattctg<br>atccgcgttcgcaacgccagaggcaacacgacatcgacgcctgactgcacgcagcggtga (SEQ ID<br>NO: 7)<br>MIATTRDREGATMITFRLRLPCRTILRVFSRNPLVRGTDRLEAVVMLL<br>AVTVSLLTIPFAAAAGTAVQDSRSHVYAHQAQTRHPATATVIDHEGV<br>IDSNTTATSAPPRTKITYPARWYVNGIERSGEVNAKPGTKSGDRVGIW<br>VDSAGQLVDEPAPPARAIADAALAALGLWLSVAAVAGALLALTRAI<br>LIRVRNASWQHDIDSLFCTQR (SEQ ID NO: 8) |
| Rv2626c | atgaccaccgcacgcgacatcatgaacgcaggtgtgacctgtgttggcgaacacgagacgctaaccgctgc<br>cgctcaatacatgcgtgagcacagcatcggcgcgttgccgatctgcggggacgacgaccggctgcacggc<br>atgctcaccgaccgcgacattgtgatcaaaggcctggctgcgggcctagaccccgaataccgccacggctgg<br>cgagaggcccggacagcatctactacgtcgatgcgaacgcaagcatccaggagatgctcaacgtcatggaa<br>gaacatcaggtccgccgtgaccggtcatcctcagagcaccgcaggtcggaatcgtcaccgaagccgacatc |

TABLE 1-continued

| Construct | nucleotide sequence<br>amino acid sequence |
|---|---|
| | gcccgacacctgcccgagcacgccattgtgcagttcgtcaaggcaatctgctcgcccatggccctcgccagc<br>tag (SEQ ID NO: 9)<br>MTTARDIMNAGVTCVGEHETLTAAAQYMREHDIGALPICGDDDRLH<br>GMLTDRDIVIKGLAAGLDPNTATAGELARDSIYYVDANASIQEMLNV<br>MEEHQVRRVPVISEHRLVGIVTEADIARHLPEHAIVQFVKAICSPMAL<br>AS (SEQ ID NO: 10) |
| RpfA | atgagtggacgccaccgtaagcccaccacatccaacgtcagcgtcgccaagatcgcattaccggcgcagta<br>ctcggtggcggcggcatcgccatggccgctcaggcgaccgcggccaccgacggggaatgggatcaggtg<br>gcccgctgcgagtcgggcggcaactggtcgatcaacaccggcaacggttacctcggtggcttgcagttcact<br>caaagcacctgggccgcacatggtggcggcgagttcgccccgtcggctcagctggccagccgggagcag<br>cagattgccgtcggtgagcgggtgctggccacccagggtcgcggcgctggccggtgtgcggccgcgggt<br>tatcgaacgcaacacccgcgaagtgatcccgcttcggcagcgatggacgctccgaggacgcggccgcg<br>gtcaacggcgaaccagcaccgctgccccgccgccgccgacccggcgccaccgtggaacttgccgct<br>aacgacctgcccgcaccgctgggtgaaccctcccggcagctcccgccgacccggcaccacccgccgac<br>ctggcaccacccgcgcccgccgacgtcgcgccacccgtggaacttgccgtaaacgacctgcccgcaccgc<br>tgggtgaaccctcccggcagctcccgccgacccggcaccacccgccgacctggcaccacccgcgcccg<br>ccgacctggcgccacccgcgcccgccgacctggcgccacccgccgacctggcaccacccgtgg<br>aacttgccgtaaacgacctgcccgcgccgctgggtgaaccctcccggcagctcccgccgaactggcgcca<br>cccgccgatctggcacccgcgtccgccgacctggcgccacccgcgcccgccgacctggcgccacccgcg<br>cccgccgaactggcgccacccgcgcccgccgacctggcaccacccgctgcggtgaacgagcaaaccgcg<br>ccgggcgatcagccgccacagctccaggcggcccggaggcagccaccgataggaactcccccgagcc<br>cgaccccaaccagctgacgcaccgccgcccggcgacgtcaccgaggcgcccgccgaaacgcccaagt<br>ctcgaacatcgcctatacgaagaagctgtggcaggcgattcgggcccaggacgtctgcggcaacgatgcgc<br>tggactcgctcgcacagccgtacgtcatcggctga (SEQ ID NO: 11)<br>MSGRHRKPTTSNVSVAKIAFTGAVLGGGGIAMAAQATAATDGEWD<br>QVARCESGGNWSINTGNGYLGGLQFTQSTWAAHGGGEFAPSAQLAS<br>REQQIAVGERVLATQGRGAWPVCGRGLSNATPREVLPASAAMDAPL<br>DAAAVNGEPAPLAPPPADPAPPVELAANDLPAPLGEPLPAAPADPAPP<br>ADLAPPAPADVAPPVELAVNDLPAPLGEPLPAAPADPAPPADLAPPAP<br>ADLAPPAPADLAPPAPADLAPPVELAVNDLPAPLGEPLPAAPAELAPP<br>ADLAPASADLAPPAPADLAPPAPAELAPPAPADLAPPAAVNEQTAPG<br>DQPATAPGGPVGLATDLELPEPDPQPADAPPPGDVTEAPAETPQVSNI<br>AYTKKLWQAIRAQDVCGNDALDSLAQPYVIG (SEQ ID NO: 12) |
| RpfC | gtgcatcattgccggccgaccacggccggtcgcggtgcaatagacacccgatctcaccactctctctaatcg<br>gtaacgcttcggccacttccggcgatatgtcgagcatgacaagaatcgccaagccgctcatcaagtccgccat<br>ggccgcaggactcgtcacggcatccatgtcgctctccaccgccgttgcccacgccggtcccagcccgaact<br>gggacgccgtcgcgcagtgcgaatccgggggcaactgggcggccaacaccggaaacggcaaatacggc<br>ggactgcagttcaagccggccacctgggccgcattcggcggtgtcggcaacccagcagctgcctctcggga<br>acaacaaatcgcagagccaatcgggactcgccgaacagggattggacgcgtggccgacgtgcggcgccg<br>cctctggccaccgatcgcactgtggtcgaaacccgcgcagggcatcaagcaaatcatcaacgagatcatttg<br>ggcaggcattcaggcaagtattccgcgctga (SEQ ID NO: 13)<br>VHPLPADHGRSRCNRHPISPLSLIGNASATSGDMSSMTRIAKPLIKSA<br>MAAGLVTASMSLSTAVAHAGPSPNWDAVAQCESGGNWAANTGNG<br>KYGGLQFKPATWAAFGGVGNPAAASREQQIAVANRVLAEQGLDAW<br>PTCGAASGLPIALWSKPAQGIKQIINEIIWAGIQASIPR (SEQ ID NO: 14) |
| RpfD | atgacaccgggtttgcttactactgcgggtgctggccgaccacgtgacaggtgcgccaggatcgtatgcacg<br>gtgacatcgaaaccgccgagtcgcgaccatgatgtcgcgttgagggtctgtccaccatcagctcgaaagcc<br>gacgacatcgattgggacgccatcgcgcaatgcgaatccggcggcaattgggcggccaacaccggtaacg<br>ggttatacggtggtctgcagatcagccaggcgacgtgggattccaacggtggtgtcggtcggctcgccggcc<br>gcgagtccccagcaacagatcgaggtcgcagacaacattatgaaaacccaaggcccgggtgcgtggccga<br>aatgtagacttgtagtcagggagacgcaccgctgggctgctcacccacatcctgacgacctcgcggccga<br>gactggaggttgttcggggagcagggacgattga (SEQ ID NO: 15)<br>MTPGLLTTAGAGRPRDRCARIVCTVFIETAVVATMFVALLGLSTISSK<br>ADDIDWDAIAQCESGGNWAANTGNGLYGGLQISQATWDSNGGVGS<br>PAAASPQQQIEVADNIMKTQGPGAWPKCSSCSQGDAPLGSLTHILTFL<br>AAETGGCSGSRDD (SEQ ID NO: 16) |
| ESAT-6 | atgacagagcagcagtggaatttcgcgggtatcgaggccgcggcaagcgcaatccagggaaatgtcacgtc<br>cattcattccctccttgacgaggggaagcagtccctgaccaagctcgcagcggcctgggcggtagcggttc<br>ggaggcgtaccagggtgtccagcaaaaatgggacgccacggctaccgagctgaacaacgcgctgcagaa<br>cctggcgcggacgatcagcgaagccggtcaggcaatggcttcgaccgaaggcaacgtcactgggatgttcg<br>catag (SEQ ID NO: 17)<br>MTEQQWNFAGIEAAASAIQGNVTSIHSLLDEGKQSLTKLAAAWGGS<br>GSEAYQGVQQKWDATATELNNALQNLARTISEAGQAMASTEGNVT<br>GMFA (SEQ ID NO: 18) |

All sequences shown in Table 1 are derived from HCMV.

In some embodiments, the fusion protein comprises Ag85A, Ag85B, and Rv3407 antigens. In some embodiments, the fusion protein comprises Rv1733 and Rv2626c antigens. In some embodiments, the fusion protein comprises RpfA, RpfC, and Rpm antigens. In some embodiments, the fusion protein comprises Ag85B and ESAT6 antigens. In some embodiments, the fusion protein comprises Ag85A, ESAT6, Rv3407, Rv2626c, RpfA, and Rpm antigens.

In any of the embodiments of fusion proteins set forth herein, the individual Mtb antigens can be present in any order. For example, for a fusion protein comprising Ag85A, Ag85B, and Rv3407 antigens, the first (or N-terminal) antigen may be Ag85A, Ag85B, or Rv3407; the second antigen may be Ag85A, Ag85B, or Rv3407 (whichever one is not the first Mtb antigen); and the third antigen may be Ag85A, Ag85B, or Rv3407 (whichever one is not the first or second Mtb antigen). Likewise for every fusion protein disclosed herein.

Individual Mtb antigens may be linked together in a C-terminus to N-terminus or N-terminus to C-terminus manner without any linker. Alternately, a linker may be present between any two Mtb antigens within any of the fusion proteins disclosed herein. In some embodiments, the linker is a segment of DNA optionally containing one or more restrictions sites, wherein the linker is inserted between nucleic acid molecules encoding two Mtb antigens of any of the fusion proteins disclosed herein.

In some embodiments, the fusion protein comprises Ag85A-Ag85B-Rv3407 (Construct A; see Table 2). The nucleotide sequence is SEQ ID NO:19, and the corresponding amino acid sequence is SEQ ID NO:20.

In some embodiments, the fusion protein comprises Rv1733-Rv2626c (Construct B; see Table 2). The nucleotide sequence is SEQ ID NO:21, and the corresponding amino acid sequence is SEQ ID NO:22.

In some embodiments, the fusion protein comprises RpfA-RpfC-RpfD (Construct C; see Table 2). The nucleotide sequence is SEQ ID NO:23, and the corresponding amino acid sequence is SEQ ID NO:24.

In some embodiments, the fusion protein comprises Ag85B-ESAT6 (Construct D; see Table 2). The nucleotide sequence is SEQ ID NO:25, and the corresponding amino acid sequence is SEQ ID NO:26.

In some embodiments, the fusion protein comprises Ag85A-ESAT6-Rv3407-Rv2626c-RpfA-RpfD (Construct E; see Table 2). The nucleotide sequence is SEQ ID NO:27 or SEQ ID NO:28, and the corresponding amino acid sequence is SEQ ID NO:29 or SEQ ID NO:30.

TABLE 2

| Construct | nucleotide sequence<br>amino acid sequence |
|---|---|
| A | atggcattacccggccgggcttgccggtggagtacctgcaggtgccgtcgccgtcgatgggccgtgacatc<br>aaggtccaattccaaagtggtggtgccaactcgcccgccctgtacctgctcgacggcctgcgcgcgcaggac<br>gacttcagcggctgggacatcaacacccggcgttcgagtggtacgaccagtcgggcctgtcggtggtcatg<br>ccggtgggtggccagtcaagcttctactccgactggtaccagcccgcctgcggcaaggccggttgccagact<br>tacaagtgggagaccttcctgaccagcgagctgccggggtggctgcaggccaacaggcacgtcaagccca<br>ccggaagcgccgtcgtcggtattcgatggctgatatcggcgctgacgctggcgatctatcaccccagca<br>gttcgtctacgcgggagcgatgtcgggcctgttggaccccctcccaggcgatgggtcccaccctgatcggcct<br>ggcgatgggtgacgctggcggctacaaggcctccgacatgtggggcccgaaggaggaccggcgtggca<br>gcgcaacgaccgctgttgaacgtcgggaagctgatcgccaacaacaccgcgtctgggtgtactgcggca<br>acggcaagccgtcggatctgggtggcaacaacctgccggccaagacctcgagggcttcgtgcggaccagc<br>aacatcaagttccaagacgcctacaacgccggtggcggccacaacggcgtgacgacttcccggacagcgg<br>tacgcacagctgggagtactgggggcgcgcagctcaacgctatgaagcccgacctgcaacgggcactgggt<br>gccacgcccaacaccgggcccgcgcccagggcgccatgactcccggccggggctgccggtcgagtac<br>ctgcaggtgccgtcgccgtcgatgggccgcgacatcaaggttcagttccagagcggtgggaacaactcacct<br>gcggatatctgctcgacggcctgcgcgcccaagacgactacaacggctgggatatcaacacccggcgttc<br>gagtggtactaccagtcgggactgtcgatagtcatgccggtcggcgggcagtccagatctacagcgactgg<br>tacgcccggcctgcggtaaggctggctgccagacttacaagtgggaaaccacctgaccagcgagctgcc<br>gcaatggagtccgccaacagggccgtgaagccaccggcagcgctgcaatcggcttgtcgatggccggct<br>cgtcggcaatgatcaggccgcctaccaccccagcagttcatctacgccggctcgctgtcggccctgctgga<br>ccctctcagggatgggctagcctgatcggcctcgcgatgggtgacgccggcggttacaaggccgca<br>gacatgtgggtccctcgagtgacccggcatgggagcgcaacgaccctacgcagcagatccccaagctggt<br>cgcaaacaacacccggctatgggatattgcgggaacggcaccccgaacgagagggcggtgccaacatac<br>ccgccgagttcaggagaacttcgttcgtagcagcaacctgaagaccaggatgcgtacaacgccgcgggcg<br>ggcacaacgccgtgacaacttcccgcccaacggcacgcacagctgggagtactggggcgctcagctcaac<br>gccatgaagggtgacctgcagagttcgttaggcgccggcatgcgtgctaccgagggcttgtggaggcaatc<br>ggaatccgagaactaagacagcacgcatcgcgatacctcgcccgggagaagccggcgaggaacttggcgt<br>caccaacaaggaagacttgtggcccgactcatcccggtgcaggccgcggagcgttctcgcgaagccctga<br>ttgaatcaggtgtcctgattccggctcgtcgtccacaaaaccactcgacgtcaccgccgaaccggcgcgcgg<br>ccgcaagcgcaccctgtccgatgttctcaacgaaatgcgcgacgagcagtga (SEQ ID NO: 19)<br>MAFSRPGLPVEYLQVPSPSMGRDIKVQFQSGGANSPALYLLDGLRAQ<br>DDFSGWDINTPAFEWYDQSGLSVVMPVGGQSSFYSDWYQPACGKA<br>GCQTYKWETFLTSELPGWLQANRHVKPTGSAVVGLSMAASSALTLA<br>IYHPQQFVYAGAMSGLLDPSQAMGPTLIGLAMGDAGGYKASDMWG<br>PKEDPAWQRNDPLLNVGKLIANNTRVWVYCGNGKPSDLGGNNLPA<br>KFLEGFVRTSNIKFQDAYNAGGGHNGVFDFPDSGTHSWEYWGAQLN<br>AMKPDLQRALGATPNTGPAPQGAFSRPGLPVEYLQVPSPSMGRDIKV<br>QFQSGGNNSPAVYLLDGLRAQDDYNGWDINTPAFEWYYQSGLSIVM<br>PVGGQSSFYSDWYSPACGKAGCQTYKWETFLTSELPQWLSANRAVK<br>PTGSAAIGLSMAGSSAMILAAYHPQQFIYAGSLSALLDPSQGMGPSLI<br>GLAMGDAGGYKAADMWGPSSDPAWERNDPTQQIPKLVANNTRLW<br>VYCGNGTPNELGGANIPAEFLENFVRSSNLKFQDAYNAAGGHNAVF<br>NFPPNGTHSWEYWGAQLNAMKGDLQSSLGAGAAARATVGLVEAIGI<br>RELRQHASRYLARVEAGEELGVTNKGRLVARLIPVQAAERSREALIE<br>SGVLIPARRPQNLLDVTAEPARGRKRTLSDVLNEMRDEQ (SEQ ID<br>NO: 20) |
| B | atgaccaccgcacgcgacatcatgaacgcaggtgtgacctgtgaggcgaacacgagacgctaaccgctgc<br>cgctcaatacatgcgtgagcacgacatcggcgcgttgccgatctgcggggacgacgaccggctgcacggc<br>atgctcaccgaccgcgacattgtgatcaaaggcctggctgcgggcctagacccgaataccgccacggctgg<br>cgagaggcccgggacagcatctactacgtcgatgcgaacgcaagcatccaggagatgctcaacgtcatgga<br>agaacatcaggtccgccgtgaccggtcatctcagagcaccgcaggtcggaatcgtcaccgaagccgacatc<br>gcccgacacctgcccgagcacgccattgtgcagttcgtcaaggcaatctgctcgcccatggccctcgccagc |

TABLE 2-continued

| Construct | nucleotide sequence<br>amino acid sequence |
|---|---|
| | atgatcgccacaacccgcgatcgtgaaggagccaccatgatcacgataggctgcgcttgccgtgccggacg<br>atactgcgggtgacagccgcaatccgctggtgcgtgggacggatcgactcgaggcggtcgtcatgctgctg<br>gccgtcacggtctcgctgctgactatcccgttcgccgccgcggccggcaccgcagtccaggattcccgcagc<br>cacgtctatgcccaccaggcccagacccgccatcccgcaaccgcgaccgtgatcgatcacgaggggtgat<br>cgacagcaacacgaccgccacgtcagcgccgccgcgcacgaagatcaccgtgcctgcccgatgggtcgtg<br>aacggaatagaacgcagcggtgaggtcaacgcgaagcgggaaccaaatccggtgaccgcgtcggcattt<br>gggtcgacagtgccggtcagctggtcgatgaaccagctccgccggcccgtgccattgcggatgcggccctg<br>gccgccttgggactctggttgagcgtcgccgcggttgcgggcgccctgctggcgctcactcgggcgattct<br>atccgcgttcgcaacgccagaggcaacacgacatcgacagcctgactgcacgcagcggtga (SEQ ID<br>NO: 21)<br>MTTARDIMNAGVTCVGEHETLTAAAQYMREHDIGALPICGDDDRLH<br>GMLTDRDIVIKGLAAGLDPNTATAGELARDSIYYVDANASIQEMLNV<br>MEEHQVRRVPVISEHRLVGIVTEADIARHLPEHAIVQFVKAICSPMAL<br>ASMIATTRDREGATMITFRLRLPCRTILRVFSRNPLVRGTDRLEAVVM<br>LLAVTVSLLTIPFAAAAGTAVQDSRSHVYAHQAQTRHPATATVIDHE<br>GVIDSNTTATSAPPRTKITVPARWVVNGIERSGEVNAKPGTKSGDRV<br>GIWVDSAGQLVDEPAPPARAIADAALAALGLWLSVAAVAGALLALT<br>RAILIRVRNASWQHDIDSLFCTQR (SEQ ID NO: 22) |
| C | atggcgtcagggaggcatcggaaaccaactacaagcaatgtatctgagccaagattgattcaccggcgcag<br>ttcttggaggtggcggaattgccatggctgcccaggcaacagccgctacagatggagagtgggatcaggtg<br>gctcgatgtgagtctggtggcaactggtctatcaacactgggaacgggtatcaggcggcttgcaatttactcag<br>agcacttgggctgcccacgagggggtgaatttgctcctagcgcgcagctggcctcccgcgagcagcagat<br>cgctgtgggagagagggtgaggccacacagggaagaggtgcctggcctgtctgtggccgcggactcagta<br>atgctaccccctaggaggtgctgcccgcctcagccgctatggacgctccactggatgctgccgccgtgaatg<br>gcgagccagctccgctggcaccccacctgcagacccccgctccccagtcgagctggcggcaaacgacct<br>gcccgcacctctcggagaaccacttcctgcagcgcctgccgatccacctgctgtgataggctccccc<br>gctcccgccgatgtagcccctccggtcgagaggctgtgaatgacctgccggcacctctgggcgagcccctc<br>ccagccgctccggccgaccctgccctcctgctgatctggcaccacccgctcctgccgacctcgccccaccc<br>gccccagcagacctggctccaccagcgcctgcggatcttgccccgcctgagagctggctgtcaacgatcttc<br>ctgcgcctcaggagagcccctgcccgctgctccagccgaactgcaccaccggcagatctggctcccgcct<br>ctgccgatcttgcacctcccgcaccggcggacttggcacctccagcaccagcagaactggctcccctgcgc<br>cggctgacctggcccctccagcagccgttaatgagcaaaccgcaccaggggaccagccggctacggcacc<br>aggtggaccggtggggctggccaccgacctggagctgcctgagccggatcccaaccagctgatgctccc<br>ccacctggcgacgtaactgaggccccagctgaaacgcccagtcagtaacatcgcttacacaaagaaact<br>gtggcaggcaatttagggctcaggacgtgtgtgggaacgacgccctggacagcaggcccaaccgtacgga<br>tcggtatgcaccccctccccgctgatcatggtcgcagtcgctgtaaccgccaccccatttcacctctcagcctta<br>ttgggaatgcgtctgctacaagtggcgacatgtctagtatgacaaggattgctaagcccctcatcaaaagtgcg<br>atggctgccggtctggtaacagcatccatgagcttgtccaccgcagtggctcacgctgggccaccccgaac<br>tgggatgccgtcgcccagtgcgagtcaggcggcaattgggccgcaaataccggtaacggtaagtatgagg<br>actgcagataaacctgcaacttgggccgcctaggaggagtgggtaatcctgcagctgatctagagaacagc<br>agattgccgtggctaaccgcgttctcgcggagcagggtctggacgcctgccgacctgtggccgccatca<br>ggtttgccgatcgcgttggtcaaagcccgcccagggaatcaagcagattatcaatgagatcatctgggccg<br>gaatacaggcaagcatccctagaatgactcctgggcactgacaaccgctggcgctggggaggcccagggat<br>aggtgcgcccggatcgtagtaccgtattcatagagaccgccgtggtcgcgacaatgacgtggctctcttggg<br>cttgagcaccattagctctaaggccgatgatatagattgggatgctattgctcaatgcgaatccggtgggaact<br>gggccgctaataccggaaatgggctctacggcggactgcagatcagccaggctacatgggatagcaacgg<br>aggagtcgggtccccctgccgctgcatccccgcaacagcaaatcgaggtggccgataacatcatgaaaaccc<br>agggaccccggagcctggcccaaatgtagctcatgtagccaaggagatgcgcccctcggacactgacgcac<br>atcctcaccacctcgccgcggaaaccggagggtgctctggcagccgggacgactga (SEQ ID<br>NO: 23)<br>MSGRHRKPTTSNVSVAKIAFTGAVLGGGGIAMAAQATAATDGEWD<br>QVARCESGGNWSINTGNGYLGGLQFTQSTWAAHGGGEFAPSAQLAS<br>REQQIAVGERVLATQGRGAWPVCGRGLSNATPREVLPASAAMDAPL<br>DAAAVNGEPAPLAPPPADPAPPVELAANDLPAPLGEPLPAAPADPAPP<br>ADLAPPAPADVAPPVELAVNDLPAPLGEPLPAAPADPAPPADLAPPAP<br>ADLAPPAPADLAPPAPADLAPPVELAVNDLPAPLGEPLPAAPAELAPP<br>ADLAPASADLAPPAPADLAPPAPAELAPPAPADLAPPAAVNEQTAPG<br>DQPATAPGGPVGLATDLELPEPDPQPADAPPPGDVTEAPAETPQVSNI<br>AYTKKLWQAIRAQDVCGNDALDSLAQPYVIGVHPLPADHGRSRCNR<br>HPISPLSLIGNASATSGDMSSMTRIAKPLIKSAMAAGLVTASMSLSTA<br>VAHAGPSPNWDAVAQCESGGNWAANTGNGKYGGLQFKPATWAAF<br>GGVGNPAAASREQQIAVANRVLAEQGLDAWPTCGAASGLPIALWSK<br>PAQGIKQIINEIIWAGIQASIPRMTPGLLTTAGAGRPRDRCARIVCTVFI<br>ETAVVATMFVALLGLSTISSKADDIDWDAIAQCESGGNWAANTGNG<br>LYGGLQISQATWDSNGGVGSPAAASPQQQIEVADNIMKTQGPGAWP<br>KCSSCSQGDAPLGSLTHILTFLAAETGGCSGSRDD (SEQ ID NO: 24) |
| D | atgactcccggccggggctgccggtcgagtacctgcaggtgcctgccgtcgatgggccgcgacatcaa<br>ggttcagttccagagcggtgggaacaactcacctgcggtttatctgctcgacggcctgcgcgcccaagacga<br>ctacaacggctgggatatcaacaccccggcgttcgagtggtactaccagtcgggactgtcgatagtcatgccg<br>gtcggcgggcagtccagatctctacgacgactggtacagcccggcctgcctgtaaggctggctgccagactta<br>caagtgggaaaccacctgaccagcgagctgccgcaatggatccgccaacagggcgtgaagcccaccg<br>gcagcgctgcaatcggcttgtcgatgccggctcgtcggcaatgatcaggccgcctaccaccccagcagtt<br>catctacgccggctcgctgtcggccctgctggaccccctcaggggatggggcctagcctgatcggcctcgc<br>gatgggtgacgccgcggttacaaggccgcagacatgtgggtccctcgagtgacccggcatgggagcgc<br>aacgaccctacgcagcagatccccaagctggtcgcaaacaacacccggctatgggatattgcgggaacgg |

TABLE 2-continued

| Construct | nucleotide sequence<br>amino acid sequence |
|---|---|
| | caccccgaacgagagggcggtgccaacataccccgccgagttcaggagaacttcgttcgtagcagcaacct<br>gaagaccaggatgcgtacaacgccgcgggcgggcacaacgccgtgacaacttcccgcccaacggcacg<br>cacagctgggagtactgggggcgctcagctcaacgccatgaagggtgacctgcagagttcgttaggcgccgg<br>catgacagagcagcagtggaatttcgcgggtatcgaggccgcggcaagcgcaatccaggaaatgtcacgt<br>ccattcattccctccttgacgaggggaagcagtccctgaccaagctcgcagcggcctggggcggtagcggtt<br>cggaggcgtaccagggtgtccagcaaaaatgggacgccacggctaccgagctgaacaacgcgctgcaga<br>acctggcgcggacgatcagcgaagccggtcaggcaatggcttcgaccgaaggcaacgtcactgggatgttc<br>gcatag (SEQ ID NO: 25)<br>MFSRPGLPVEYLQVPSPSMGRDIKVQFQSGGNNSPAVYLLDGLRAQD<br>DYNGWDINTPAFEWYYQSGLSIVMPVGGQSSFYSDWYSPACGKAGC<br>QTYKWETFLTSELPQWLSANRAVKPTGSAAIGLSMAGSSAMILAAY<br>HPQQFIYAGSLSALLDPSQGMGPSLIGLAMGDAGGYKAADMWGPSS<br>DPAWERNDPTQQIPKLVANNTRLWVYCGNGTPNELGGANIPAEFLE<br>NFVRSSNLKFQDAYNAAGGHNAVFNFPPNGTHSWEYWGAQLNAMK<br>GDLQSSLGAGMTEQQWNFAGIEAAASAIQGNVTSIHSLLDEGKQSLT<br>KLAAAWGGSGSEAYQGVQQKWDATATELNNALQNLARTISEAGQA<br>MASTEGNVTGMFA (SEQ ID NO: 26) |
| E | atggcgttcagcagacccggcctgcccgtggagtacctgcaggtgcccagccccagcatgggccgggaca<br>tcaaagtgcagttccagagcggcggagccaacagccctgccctgtacctgctggacggcctgcgggcccag<br>gacgacttcagcggctgggacatcaacacccccgccacgagtggtacgaccagagcggcctgagcgtggt<br>gatgcccgtgggcggccagagcagatctacagcgactggtatcagcccgcctgcggcaaggccggctgc<br>cagacctacaagtgggagaccacctgaccagcgagctgccccggctggctgcaggccaaccggcacgtga<br>agcccaccggcagcgccgtggtgggcctgagcatggccgccagcagcgccctgaccctggccatctacca<br>cccccagcagttcgtgtacgccggagccatgagcggcctgctggaccccagccaggccatgggccccacc<br>ctgatcggcctggccatgggcgacgccggaggctacaaggccagcgacatgtggggccccaaggaggac<br>cccgcctggcagcggaacgacccccctgctgaacgtgggcaagctgatcgccaacaacacccgcgtgtggg<br>tgtactgcggcaacggcaagcccagcgacctgggcggcaacaacctgcccgccaagacctggagggcttc<br>gtgcggaccagcaacatcaagttccaggacgcctacaacgccggaggcggccacaacggcgtgacgactt<br>ccccgacagcggcacccacagctgggagtactggggagcccagctgaacgccatgaagcccgacctgca<br>gcgggccctgggcgccaccccaacaccggccctgccccccaggggcgctaccgagcagcagtggaactt<br>cgccggcatcgaagctgccgcgagcgccatccaaggcaacgtgaccagcatccacagcctgctggacgag<br>ggcaagcagagcctgaccaagctggctgctgcttggggcggatccggaagcgaagcctaccagggcgtgc<br>agcagaagtgggacgccacagccaccgagctgaacaacgccctgcagaacctcgccagaaccatcagcg<br>aggccggacaggctatggccagcacagagggcaatgtgaccggcatgaccgcgggccacagtgggcct<br>ggtggaggccattggcatcagggagctgaggcagcacgccagcaggtacctggccagagtggaggctgg<br>agaggagctgggcgtgaccaacaagggcaggctggtggccagactgatccccgtgcaggctgccgagag<br>gagcagagaggccctgatcgagagcggcgtgctgatccctgccagaaggcctcagaacctgctggacgtg<br>accgctgagcctgccagaggcaggaagaggaccctgagcgacgtgctgaacgagatgagggacgag<br>acaacagccagggacatcatgaacgccggcgtgacctgcgtgggagagcatgaaaccctcaccgccgccg<br>cccaatacatgagggagcacgacatcggcgccctgcccatctgtggagacgacgacaggctgcacggcat<br>gctgaccgacagggacatcgtgatcaagggcctggctgccggcctcgatcctaacaccgctacagccggcg<br>agctggccagagacagcatctactacgtggacgccaacgccagcatccaggagatgctcaacgtgatggag<br>gagcaccaggtgagaagggtgcctgtgatcagcgagcacaggctggtgggcatcgtgaccgaggccgata<br>tcgctaggcacctgcccgagcacgccatcgtgcagttcgtgaaggccatctgcagcccatggctctggcca<br>gctcaggaggcatcggaaaccaactacaagcaatgtatctgagccaagattgattcaccggcgcagttctt<br>ggaggtggcggaattgccatggctgcccaggcaacagccgctacagatggagagtgggatcaggtggctc<br>gatgtgagtctggtggcaactggtctatcaacactgggaacgggtatcaggcggcttgcaatttactcagagc<br>acttgggctgcccacgaggggggtgaatttgctcctagcgcgcagctggcctcccgcgagcagcagatcgc<br>tgtgggagagagggtgttggccacacagggaagaggtgcctggcctgtctgtggccgcggactcagtaatg<br>ctacccctagggaggtgctgcccgcctcagccgctatggacgctccactggatgctgccgccgtgaattggcg<br>agccagctccgctggcacccccacctgcagacccccgctccccsagtcgagctggcggcaaacgacctgcc<br>cgcacctctcggagaaccacttcctgcagcgcctgccgatccagctccacctgctgataggctcccccgct<br>cccgccgatgtagcccctccggtcgagaggctgtgaatgacctgccggcacctctgggcgagcccctccca<br>gccgctccggccgaccctgcccctcctgctgatctggcaccaccgctcctgccgacctcgcccacccgcc<br>ccagcagacctggctccaccagcgctcggatcttgcccgcctgagagctggctgtcaacgatcacctg<br>cgcctcttggagagccctgcccgctgctccagccgaactcgcaccaccggcagatctggctcccgcctctg<br>ccgatcttgcacctcccgcaccggcggacttggcacctcagcaccagcagaactggctcccccctgcgccg<br>gctgacctggcccctccagcagccgttaatgagcaaaccgcaccaggggaccagccggctacggcaccag<br>gtggaccggtggggctggccaccgacctggagctgcctggcggatccccaaccagctgatgctcccccca<br>cctggcgacgtaactgaggcccagctgaaacgcccaggtcagtaacatcgcttacacaaagaaactgtgg<br>caggcaattagggctcaggacgtgtgtgggaacgacgccctggacagcaggcccaaccgtacgtgatcgg<br>taccccggactcctcaccacagctggagctggcaggcccagagacagatgcgccaggatcgtgtgcacc<br>gtgacatcgagaccgccgtggtggctaccatgacgtggccctgcctgagcaccatcagcagcaag<br>gccgacgacatcgactgggacgccatcgcccagtgtgaatccggcggaaactggccgccaataccggca<br>atggcctgtacggcggcctgcagatcagccaggctacctgggactccaacgggaggagtgggaagccctgc<br>cgctgcttcccctcagcagcagatcgaggtggccgacaacatcatgaagacccaaggccctggcgcctggc<br>ctaagtgttccagctgtgtagccaggggcggtgctcctctgggcccacatcctgacctttctcgccgcc<br>gagacaggcggatgtagccggaagcagggacgac (SEQ ID NO: 27)<br>gctagcaccatggcgttcagcagacccggcctgcccgtggagtacctgcaggtgcccagccccagcatggg<br>ccgggacatcaaagtgcagaccagagcggcggagccaacagccctgccctgtacctgctggacggcctgc<br>gggcccaggacgacttcagcggctgggacatcaacacccccgccacgagtggtacgaccagagcggcct<br>gagcgtggtgatgcccgtgggcggccagagcagatctacagcgactggtatcagcccgcctgcggcaag<br>gccggctgccagacctacaagtgggagaccttcctgaccagcgagctgccccggctggctgcaggccaacc<br>ggcacgtgaagcccaccggcagcgccgtggtgggcctgagcatggccgccagcagcgccctgaccctgg<br>ccatctaccaccccagcagttcgtgtacgccggagccatgagcggcctgctggaccccagccaggccatg<br>ggccccaccctgatcggcctggccatgggcgacgccggaggctacaaggccagcgacatgtggggcccc |

TABLE 2-continued

| Construct | nucleotide sequence<br>amino acid sequence |
|---|---|
| | aaggaggaccccgcctggcagcggaacgacccctgctgaacgtgggcaagctgatcgccaacaacacc<br>cgcgtgtgggtgtactgcggcaacggcaagcccagcgacctgggcggcaacaacctgcccgccaagttcct<br>ggagggcttcgtgcggaccagcaacatcaagttccaggacgcctacaacgccggaggcggccacaacgg<br>cgtgacgacttccccgacagcggcacccacagctgggagtactggggagcccagctgaacgccatgaagc<br>ccgacctgcagcgggccctgggcgccacccccaacaccggccctgcccccagggcgctaccgagcagc<br>agtggaacttcgccggcatcgaagctgccgcgagcgccatccaaggcaacgtgaccagcatccacagcctg<br>ctggacgagggcaagcagagcctgaccaagctggctgctgcaggggcggatccggaagcgaagcctacc<br>agggcgtgcagcagaagtgggacgccacagccaccgagctgaacaacgccctgcagaacctcgccagaa<br>ccatcagcgaggccggacaggctatggccagcacagagggcaatgtgaccggcatgacgccagggccac<br>agtgggcctggtggaggccattggcatcagggagctgaggcagcacgccagcaggtacctggccagagtg<br>gaggctggagaggagctgggcgtgaccaacaagggcaggctggtggccagactgatcccgtgcaggct<br>gccgagaggagcagagaggccctgatcgagagcggcgtgctgatccctgccagaaggcctcagaacctgc<br>tggacgtgaccgctgagcctgccagaggcaggaagaggaccctgagcgacgtgctgaacgagatgaggg<br>acgagcagacaacagccagggacatcatgaacgccggcgtgacctgcgtggagagcatgaaaccctcac<br>cgccgccgcccaatacatgagggagcacgacatcggcgcctgcccatctgtggagacgacgacaggctg<br>cacggcatgctgaccgacagggacatcgtgatcaagggcctggctgccggcctcgatcctaacaccgctac<br>agccggcgagctggccagagacagcatctactacgtggacgccaacgccagcatccaggagatgctcaac<br>gtgatggaggagcaccaggtgagaagggtgcctgtgatcagcgagcacaggctggtgggcatcgtgaccg<br>aggccgatatcgctaggcacctgcccgagcacgccatcgtgcagttcgtgaaggccatctgcagcccatgg<br>ctctggccagctcagggaggcatcggaaaccaactacaagcaatgtatctgagccaagattgattcaccgg<br>cgcagttcaggaggtggcggaattgccatggctgcccaggcaacagccgctacgatggagagtgggatc<br>aggtggctcgatgtgaagtctggtggcaactggtctatcaacactgggaacgggtatcaggcggcttgcaatttt<br>actcagagcacttgggctgcccacggaggggggtgaatttgctcctagcgcgcagctggcctcccgcgagca<br>gcagatcgctgtgggagagagggtgttggccacacagggaagaggtgcctggcctgtctgtggccgcgga<br>ctcagtaatgctaccccctagggaggtgctgcccgcctcagccgctatggacgctccactggatgctgccgcc<br>gtgaatggcgagccagctccgctggcaccccccacctgcagaccccgctcccccagtcgagctggcggcaa<br>acgacctgcccgcaccctctcggagaaccacttcctgcagcgcctgccgatccagctccacctgctgataggc<br>tccccccgctcccgccgatgtagccctccggtcgagaggctgtgaatgacctgccggcacctctgggcga<br>gcccctcccagccgctccggccgaccctgcccctcctgctgatctggcaccaccgctcctgccgacctcgc<br>cccacccgcccagcagacctggctccaccagcgcctgcggatcttgccccgcctgagagctggctgtcaa<br>cgatcttcctgcgcctcttggagagccctgcccgctgctccagccgaactcgcaccaccggcagatctggct<br>cccgcctctgccgatcttgcacctcccgcaccggcggacttggcacctccagcaccagcagaactggctccc<br>cctcgccggctgacctggcccctccagcagccgttaatgagcaaaccgcaccaggggaccagccggcta<br>cggcaccaggtggaccggtggggctggccaccgacctggagctgcctgagccggatcccaaccagctga<br>tgctccccacctggcgacgtaactggggcccagctgaaacgccccaggtcagtaacatcgcttacacaaa<br>gaaactgtggcaggcaattagggctcaggacgtgtgtgggaacgacgccctggacagcaggcccaaccgt<br>acgtgatcggtaccccggactcctcaccacagctggagctggcaggcccagagacagatgcgccaggat<br>cgtgtgcaccgtgacatcgagaccgccgtggtggctaccatgacgtggccctgctgggcctgagcaccatc<br>agcagcaaggccgacgacatcgactgggacgccatcgccagtgtgaatccggcggaaactgggccgcc<br>aataccggcaatggcctgtacggcggcctgcagatcagccaggctacctgggactccaacggaggagtgg<br>gaagccctgccgctgcttcccctcagcagcagatcgaggtggccgacaacatcatgaagacccaaggccct<br>ggcgcctggcctaagtgaccagctgtagccagggcgatgctcctctgggcagcctgacccacatcctgacct<br>ttctcgccgccgagacaggcggatgtagcggaagcagggacgactacccctacgacgtgcccgactacgc<br>cgattagtctaga (SEQ ID NO: 28)<br>MAFSRPGLPVEYLQVPSPSMGRDIKVQFQSGGANSPALYLLDGLRAQ<br>DDFSGWDINTPAFEWYDQSGLSVVMPVGGQSSFYSDWYQPACGKA<br>GCQTYKWETFLTSELPGWLQANRHVKPTGSAVVGLSMAASSALTLA<br>IYHPQQFVYAGAMSGLLDPSQAMGPTLIGLAMGDAGGYKASDMWG<br>PKEDPAWQRNDPLLNVGKLIANNTRVWVYCGNGKPSDLGGNNLPA<br>KFLEGFVRTSNIKFQDAYNAGGGHNGVFDFPDSGTHSWEYWGAQLN<br>AMKPDLQRALGATPNTGPAPQGATEQQWNFAGIEAAASAIQGNVTSI<br>HSLLDEGKQSLTKLAAAWGGSGSEAYQGVQQKWDATATELNNALQ<br>NLARTISEAGQAMASTEGNVTGMFARATVGLVEAIGIRELRQHASRY<br>LARVEAGEELGVTNKGRLVARLIPVQAAERSREALIESGVLIPARRPQ<br>NLLDVTAEPARGRKRTLSDVLNEMRDEQTTARDIMNAGVTCVGEHE<br>TLTAAAQYMREHDIGALPICGDDDRLHGMLTDRDIVIKGLAAGLDPN<br>TATAGELARDSIYYVDANASIQEMLNVMEEHQVRRVPVISEHRLVGI<br>VTEADIARHLPEHAIVQFVKAICSPMALASSGRHRKPTTSNVSVAKIA<br>FTGAVLGGGGIAMAAQATAATDGEWDQVARCESGGNWSINTGNY<br>LGGLQFTQSTWAAHGGGEFAPSAQLASREQQIAVGERVLATQGRGA<br>WPVCGRGLSNATPREVLPASAAMDAPLDAAAVNGEPAPLAPPPADP<br>APPVELAANDLPAPLGEPLPAAPADPAPPADLAPPAPADVAPPVELA<br>VNDLPAPLGEPLPAAPADPAPPADLAPPAPADLAPPAPADLAPPAPAD<br>LAPPVELAVNDLPAPLGEPLPAAPAELAPPADLAPASADLAPPAPADL<br>APPPAPAELAPPAPADLAPPAAVNEQTAPGDQPATAPGGPVGLATDLE<br>LPEPDPQPADAPPPGDVTEAPAETPQVSNIAYTKKLWQAIRAQDVCG<br>NDALDSLAQPYVIGTPGLLTTAGAGRPRDRCARIVCTVFIETAVVAT<br>MFVALLGLSTISSKADDIDWDAIAQCESGGNWAANTGNGLYGGLQIS<br>QATWDSNGGVGSPAAASPQQQIEVADNIMKTQGPGAWPKCSSCSQG<br>DAPLGSLTHILTFLAAETGGCSGSRDD (SEQ ID NO: 29)<br>MAFSRPGLPVEYLQVPSPSMGRDIKVQFQSGGANSPALYLLDGLRAQ<br>DDFSGWDINTPAFEWYDQSGLSVVMPVGGQSSFYSDWYQPACGKA<br>GCQTYKWETFLTSELPGWLQANRHVKPTGSAVVGLSMAASSALTLA<br>IYHPQQFVYAGAMSGLLDPSQAMGPTLIGLAMGDAGGYKASDMWG<br>PKEDPAWQRNDPLLNVGKLIANNTRVWVYCGNGKPSDLGGNNLPA<br>KFLEGFVRTSNIKFQDAYNAGGGHNGVFDFPDSGTHSWEYWGAQLN<br>AMKPDLQRALGATPNTGPAPQGATEQQWNFAGIEAAASAIQGNVTSI |

TABLE 2-continued

| Construct | nucleotide sequence<br>amino acid sequence |
|---|---|
| | HSLLDEGKQSLTKLAAAWGGSGSEAYQGVQQKWDATATELNNALQ<br>NLARTISEAGQAMASTEGNVTGMFARATVGLVEAIGIRELRQHASRY<br>LARVEAGEELGVTNKGRLVARLIPVQAAERSREALIESGVLIPARRPQ<br>NLLDVTAEPARGRKRTLSDVLNEMRDEQTTARDIMNAGVTCVGEHE<br>TLTAAAQYMREHDIGALPICGDDDRLHGMLTDRDIVIKGLAAGLDPN<br>TATAGELARDSIYYVDANASIQEMLNVMEEHQVRRVPVISEHRLVGI<br>VTEADIARHLPEHAIVQFVKAICSPMALASSGRHRKPTTSNVSVAKIA<br>FTGAVLGGGGIAMAAQATAATDGEWDQVARCESGGNWSINTGNGY<br>LGGLQFTQSTWAAHGGGEFAPSAQLASREQQIAVGERVLATQGRGA<br>WPVCGRGLSNATPREVLPASAAMDAPLDAAAVNGEPAPLAPPPADP<br>APPVELAANDLPAPLGEPLPAAPADPAPPADLAPPAPADVAPPVELA<br>VNDLPAPLGEPLPAAPADPAPPADLAPPAPADLAPPAPADLAPPAPAD<br>LAPPVELAVNDLPAPLGEPLPAAPAELAPPADLAPASADLAPPAPADL<br>APPAPAELAPPAPADLAPPAAVNEQTAPGDQPATAPGGPVGLATDLE<br>LPEPDPQPADAPPPGDVTEAPAETPQVSNIAYTKKLWQAIRAQDVCG<br>NDALDSLAQPYVIGTPGLLTTAGAGRPRDRCARIVCTVFIETAVVAT<br>MFVALLGLSTISSKADDIDWDAIAQCESGGNWAANTGNGLYGGLQIS<br>QATWDSNGGVGSPAAASPQQQIEVADNIMKTQGPGAWPKCSSCSQG<br>DAPLGSLTHILTFLAAETGGCSGSRDDYPYDVPDYAD (SEQ ID<br>NO: 30) |

Any Mtb antigen, including any Mtb antigen within any of the fusion proteins described herein, can have an amino acid sequence that is 100%, or from 70% to 99.9%, identical to the particular amino acid sequence listed in Tables 1 and 2. The amino acid sequence of any individual Mtb antigen, including any Mtb antigen within any of the fusion proteins described herein, can be at least 70%, at least 75%, at least 80%, at least 85%, at least 90%, at least 95%, at least 96%, at least 97%, at least 98%, or at least 99% identical to the particular amino acid sequence listed in Tables 1 and 2. Identity or similarity with respect to an amino acid or nucleotide sequence is defined herein as the percentage of amino acid residues (or nucleotide residues as the case may be) in the particular Mtb antigen that are identical (i.e., same residue) with the amino acid or nucleotide sequence for the Mtb antigen shown in Tables 1 and 2, after aligning the sequences and introducing gaps, if necessary, to achieve the maximum percent sequence identity. Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Any amino acid number calculated as a % identity can be rounded up or down, as the case may be, to the closest whole number.

Optimal alignment of sequences for comparison can also be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternately, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

Suitable examples of algorithms for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

In some embodiments, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Any Mtb antigen, including any Mtb antigen within any of the fusion proteins described herein, can be fragments of the particular amino acid sequence listed in Table 1. The amino acid sequence of any individual Mtb antigen, including any Mtb antigen within any of the fusion proteins described herein, can be missing consecutive amino acids constituting at least 20%, at least 15%, at least 10%, at least 5%, at least 4%, at least 3%, at least 2%, or at least 1%, of the particular amino acid sequence listed in Table 1. The omitted consecutive amino acids may be from the C-terminus or N-terminus portion of the antigen. Alternately, the omitted consecutive amino acids may be from the internal portion of the antigen, thus retaining at least its C-terminus and N-terminus amino acids of the antigen.

Any Mtb antigen, including any Mtb antigen within any of the fusion proteins described herein, can have one or more amino acid additions, deletions, or substitutions compared to the particular amino acid sequence listed in Table 1. Any individual Mtb antigen, including any Mtb antigen within any of the fusion proteins described herein, can have at least one, at least two, at least three, at least four, at least five, at least six, at least seven, at least eight, at least nine, at least ten, at least eleven, or at least twelve amino acid additions, deletions, or substitutions compared to the particular amino acid sequence listed in Table 1. The amino acid additions, deletions, or substitutions can take place at any amino acid position within the Mtb antigen.

Where a particular Mtb antigen, including any Mtb antigen within any of the fusion proteins described herein, comprises at least one or more substitutions, the substituted amino acid(s) can each be, independently, any naturally occurring amino acid or any non-naturally occurring amino acid. Thus, a particular Mtb antigen may comprise one or more amino acid substitutions that are naturally occurring amino acids and/or one or more amino acid substitutions that are non-naturally occurring amino acids. Individual amino acid substitutions are selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe. Substitutions of a member of one class with another member of the same class are contemplated herein. Naturally occurring amino acids include, for example, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Non-naturally occurring amino acids include, for example, norleucine, ornithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

The Mtb antigens, including any Mtb antigen within any of the fusion proteins described herein, which are modified as described herein retain their ability to elicit an immune response against *Mycobacterium tuberculosis*. That is, modification of a particular Mtb antigen, including any Mtb antigen within any of the fusion proteins described herein, will still allow the resultant Mtb antigen, or fusion protein comprising the same, to elicit an immune response against *Mycobacterium tuberculosis*.

The present disclosure also provides nucleic acid molecules encoding any of the fusion proteins described herein that comprise at least three *Mycobacterium tuberculosis* (Mtb) antigens. The nucleic acid molecules described herein and in Tables 1 and 2 are representative. The specific sequences recited in Table 1 are simply one example of a nucleic acid molecule that can encode a particular Mtb antigen within a fusion protein. One skilled in the art having knowledge of the genetic code can routinely prepare and design a plethora of nucleic acid molecules encoding the same Mtb antigen. The length and nucleotide content of any particular nucleic acid molecule is dictated by the desired amino acid sequence of the encoded Mtb antigen. The nucleic acid molecule sequences shown in Tables 1 and 2 are DNA, although RNA nucleic acid molecules are also contemplated.

In some embodiments, the CMV vaccines are attenuated CMV vaccines which are unable or impaired in their ability to replicate or assemble in cells and tissues associated with CMV transmission and disease. In addition, the present disclosure includes embodiments that relate to the unique ability of RhCMV to re-infect sero-positive Rhesus Macaques (or HCMV to re-infect sero-positive humans) in spite of the presence of a significant anti-RhCMV immune response (or anti-HCMV immune response). This inherent property of CMV vectors can be attributed to the extensive repertoire of immune evasion genes encoded by this virus (Hansen, S. G., Powers, C. J., Richards, R., Ventura, A. B., Ford, J. C., Siess, D., Axthelm, M. K., Nelson, J. A., Jarvis, M. A., Picker, L. J., et al. 2010. Evasion of CD8+ T cells is critical for superinfection by cytomegalovirus. Science 328: 102-106).

Some embodiments address issues of virus shedding and pathogenesis and relate to two potentially complementary approaches to generate a safe and effective vaccines using the CMV vectors. One approach focuses on development of CMV vectors that are either completely or conditionally spread defective or severely restricted in their replication, but that remain capable of inducing a protective immune response against a heterologous antigen. The second approach focuses on the generation of replication competent CMV vectors that are unable to infect cells, such as epithelial cells, which are a major cell type, along with fibroblasts, in the lung associated with CMV pneumonia. Some embodiments may relate to additional safety features into these vectors, including a block in replication in neural and myeloid cells.

In some embodiments, the HCMV and RhCMV recombinant vectors encode heterologous antigens that may elicit and maintain high level cellular and/or humoral immune responses specific for the encoded antigen.

Further provided are recombinant RhCMV or HCMV vectors including a deletion in one or more RhCMV or HCMV genes that are important for replication. In some embodiments, at least one essential or augmenting gene is UL82, UL94, UL32, UL99, UL115 or UL44, or a homolog thereof. In some embodiments, the recombinant RhCMV or HCMV vectors further include a heterologous antigen, such as a pathogen-specific antigen or a tumor antigen.

For a human CMV (HCMV)/TB vaccine to be safe for all potential subjects in a general population, including individuals with unsuspected immune compromise, the CMV vaccine vector needs to be attenuated without losing the ability to induce protective immunity. CMV can replicate in a wide variety of cells and tissues in the host, including: neurons in the central nervous system (CNS), epithelial cells, hepatocytes, lung and kidney. Myeloid and endothelial cells are considered persistent sites for CMV in the host. During overt CMV disease in immunocompromised individuals, direct infection resulting in destruction of epithelial and endothelial cells in the lung, liver and retina is responsible for disease in these target organs. During congenital infection, direct CMV infection of neuronal cells is believed to account for the associated hearing deficits and mental retardation. Embodiments of the invention relate to modulating the ability of CMV to replicate in these critical cell types in order to increase vector safety without compromising vaccine efficacy, said attenuated viruses and their use as vaccines.

Some embodiments relate to HCMV as a vector for inducing protective immunity to TB, which is based on the highly innovative hypothesis that a high frequency, effector memory-biased T cell response has distinct advantages over conventional vaccine generated memory, combined with the recognition that HCMV provides just such a response. This characteristic of HCMV is unique to this virus, even when compared to other persistent viruses such as herpes simplex virus (HSV) and Epstein-Barr virus (Asanuma, H., Sharp, M., Maecker, H. T., Maino, V. C., and Arvin, A. M. 2000. Frequencies of memory T cells specific for varicella-zoster virus, herpes simplex virus, and cytomegalovirus by intracellular detection of cytokine expression. J Infect Dis 181: 859-866; Harari, A., Vallelian, F., Meylan, P. R., and Pantaleo, G. 2005. Functional heterogeneity of memory CD4+ T cell responses in different conditions of antigen exposure and persistence. J Immunol 174:1037-1045; Harari, A., Enders, F. B., Cellerai, C., Bart, P. A., and Pantaleo, G. 2009. Distinct profiles of cytotoxic granules in memory CD8+ T cells correlate with function, differentiation stage, and antigen exposure. J Virol 83:2862-2871; Sylwester, A. W., Mitchell, B. L., Edgar, J. B., Taormina, C, Pelte, C., Ruchti, F., Sleath, P. R., Grabstein, K. H., Hosken, N. A., Kern, F., et al. 2005. Broadly targeted human cytomegalovirus-specific CD4+ and CD8+ T cells dominate the memory compartments of exposed subjects. J Exp Med 202:673-685).

While the HCMV vaccine may be considered safe, concerns still remain regarding both pathogenicity as well as the ability of the virus to spread to unvaccinated sero-negative individuals. The ability to rationally design an HCMV vaccine that is less pathogenic and not shed into the environment is now available with the advent of technological breakthroughs to clone and genetically manipulate CMV. With a long-term goal of generating a CMV vaccine vector encoding TB antigens that is safe and unable to spread to other individuals. Embodiments of this invention relate to the rational design and use of the latest reverse genetic techniques to generate a CMV-based vector that has a restricted tropism for cells involved in shedding as well as an altered ability to replicate in tissues associated with both adult and immunosuppressed populations.

In some embodiments, the recombinant RhCMV or HCMV vaccine vector is a tropism-restricted vector. In some embodiments, the tropism-restrictive vector lacks genes required for optimal growth in certain cell types or contains targets for tissue-specific micro-RNAs in genes essential for viral replication or wherein the tropism-restrictive vector has an epithelial, central nervous system (CNS), or macrophage deficient tropism, or a combination thereof.

Some embodiments relate to alteration of the cell-tropism of the CMV vector so as to prevent infection of specific cell types involved in potential tissue damage and/or shedding into urine or secretions. CMV is capable of infecting a wide variety of cells in the host, including: epithelial cells in gut, kidney, lung and retina, neuronal cells in the CNS, hepatocytes, as well as endothelial cells and myeloid lineage cells that are considered persistent sites of the virus (Dankner, W. M., McCutchan, J. A., Richman, D. D., Hirata, K., and Spector, S. A. 1990. Localization of human cytomegalovirus in peripheral blood leukocytes by in situ hybridization. J Infect Dis 161:31-36; Einhorn, L., and Ost, A. 1984. Cytomegalovirus infection of human blood cells. J Infect Dis 149:207-214; Gnann, J. W., Jr., Ahlmen, J., Svalander, C., Olding, L., Oldstone, M. B., and Nelson, J. A. 1988. Inflammatory cells in transplanted kidneys are infected by human cytomegalovirus. Am J Pathol 132:239-248; Howell, C. L., Miller, M. J., and Martin, W. J. 1979. Comparison of rates of virus isolation from leukocyte populations separated from blood by conventional and Ficoll-Paque/Macrodex methods. J Clin Microbiol 10:533-537; Myerson, D., Hackman, R. C., Nelson, J. A., Ward, D. C., and McDougall, J. K. 1984. Widespread presence of histologically occult cytomegalovirus. Hum Pathol 15:430-439; Schrier, R. D., Nelson, J. A., and Oldstone, M. B. 1985. Detection of human cytomegalovirus in peripheral blood lymphocytes in a natural infection. Science 230:1048-1051; Sinzger, C., Grefte, A., Plachter, B., Gouw, A. S., The, T. H., and Jahn, G. 1995. Fibroblasts, epithelial cells, endothelial cells and smooth muscle cells are major targets of human cytomegalovirus infection in lung and gastrointestinal tissues. J Gen Virol 76:741-750).

HCMV encodes >200 genes and several of the genes that are dispensable for basic virus replication have been identified as tropism determinants that enable the virus to enter and replicate in macrophages, endothelial cells, and epithelial cells. One locus of HCMV genes, UL128-131A, has been shown to be essential for entry into endothelial and epithelial cells (Gerna, G., Percivalle, E., Lilleri, D., Lozza, L., Fornara, C., Hahn, G., Baldanti, F., and Revello, M. G. 2005. Dendritic-cell infection by human cytomegalovirus is restricted to strains carrying functional UL131-128 genes and mediates efficient viral antigen presentation to CD8+ T cells. J Gen Virol 86:275-284; Hahn, G., Revello, M. G., Patrone, M., Percivalle, E., Campanini, G., Sarasini, A., Wagner, M., Gallina, A., Milanesi, G., Koszinowski, U., et al. 2004. Human cytomegalovirus UL131-128 genes are indispensable for virus growth in endothelial cells and virus transfer to leukocytes. J Virol 78:10023-10033; Wang, D., and Shenk, T. 2005. Human cytomegalovirus UL131 open reading frame is required for epithelial cell tropism. J Virol 79:10330-10338; Wang, D., and Shenk, T. 2005. Human cytomegalovirus virion protein complex required for epithelial and endothelial cell tropism. Proc Natl Acad Sci USA 102:18153-18158; Ryckman, B. J., Rainish, B. L., Chase, M. C., Borton, J. A., Nelson, J. A., Jarvis, M. A., and Johnson, D. C. 2008. Characterization of the human cytomegalovirus gH/gL/UL128-131 complex that mediates entry into epithelial and endothelial cells. J Virol 82:60-70; Ryckman, B. J., Jarvis, M. A., Drummond, D. D., Nelson, J. A., and Johnson, D. C. 2006. Human cytomegalovirus entry into epithelial and endothelial cells depends on genes UL128 to UL150 and occurs by endocytosis and low-pH fusion. J Virol 80:710-722).

The RhCMV homologues for HCMV UL128 and 130 are inactivated in the RhCMV strain 68-1. Efficient replication of rhesus cytomegalovirus variants in multiple rhesus and human cell types. Proc Natl Acad Sci USA 105:19950-19955. Interestingly, RhCMV 68-1 still grows in epithelial and endothelial cells (albeit at a reduced rate compared to low passage RhCMV virus with intact UL128/130) (Lilja, A. E., Chang, W. L., Barry, P. A., Becerra, S. P., and Shenk, T. E. 2008. Functional genetic analysis of rhesus cytomegalovirus: Rh-1 is an epithelial cell tropism factor. J Virol 82:2170-2181; Rue, C. A., Jarvis, M. A., Knoche, A. J., Meyers, H. L., DeFilippis, V. R., Hansen, S. G., Wagner, M., Fruh, K., Anders, D. G., Wong, S. W., et al. 2004. A cyclooxygenase-2 homologue encoded by rhesus cytomegalovirus is a determinant for endothelial cell tropism. Journal of Virology 78:12529-12536). Mutational analysis of RhCMV 68-1 has identified 4 other RhCMV genes (Rh01 (HCMV TLR1), Rh159 (HCMV UL148), Rh160 (UL132) and Rh203 (HCMVUS22)) that are also required for epithelial cell tropism (Lilja et al., J Virol, 2008, 82, 2170-2181). Some embodiments relate to the mutation of the remainder of these epithelial cell tropism genes to highly reduce, if not abrogate, the ability of CMV to infect epithelial cells, thereby preventing its ability to be shed into urine or glandular secretions (i.e., saliva and breast milk), yet likely not compromise the ability of a CMV vector to induce a protective immune response to TB.

Moreover, since CMV infection of epithelial cells in the lung and retina results in pneumonia and retinitis, respectively, elimination of all the CMV epithelial cell tropism genes may significantly reduce the resultant vector's pathogenic potential. Aspects of the invention relate to this highly targeted and innovative approach that will significantly enhance both the safety of the RhCMV/HCMV vector for use as a TB vaccine, as well as prevent shedding and the potential spread of the vaccine vector into the unvaccinated population.

Further embodiments relate to exploiting the tissue-specific expression of cellular microRNAs (miRNAs) to attenuate the virus in tissues associated with disease in adult and congenital infection. Endogenous microRNA can be broadly exploited to regulate transgene expression according to tissue, lineage and differentiation state. (Barnes et al., Cell Host Microbe, 2008, 4, 239-248; Lee et al., Clin. Cancer Res., 2009, 15, 5126-5135; Perez et al., Nat. Biotechnol., 2009, 27, 572-576).

Tissue specific expression of miRNAs has been exploited to generate an attenuated polio vaccine through the introduction of multiple miRNA target sequences of miR-124 that is specifically expressed in the CNS into the 3'UTR of the poliovirus genome (Barnes et al., supra). Addition of the miR-124 target sequences to the poliovirus genome was observed to significantly attenuate virus infection in mice. Similarly, multiple target sequences of miR-93 that is ubiquitously expressed in all mammalian but not avian tissues were added to the nucleoprotein gene of influenza resulting in a species-restricted influenza mutant that was able to grow in chicken eggs but not in mice (Perez et al., supra).

Some embodiments relate to this attenuation approach being effective for larger viruses, such as murine CMV (MCMV). Unlike the small RNA viruses, CMV encodes over 200 genes of which approximately 50% are essential and necessary for replication or encode structural proteins of the virus. One of these essential MCMV genes is the immediate early (IE) 3 gene (the mouse correlate of IE2 in HCMV or RhCMV) that encodes a transcriptional regulatory protein necessary for subsequent activation of early and late genes in the virus. Deletion of this gene completely blocks viral replication in cells and mouse tissues (Angulo et al., J. Virol., 2000, 74, 11129-11136). It is described herein that introduction of target sequences of tissue-specific miRNAs into the 3'UTR of this gene would attenuate viral replication in these cells.

In further embodiments, the CMV vector may comprise one or more microRNA recognition elements (MREs). A mature microRNA (interchangeably termed an miRNA or miR) is typically an 18-25 nucleotide non-coding RNA that regulates expression of an mRNA operably linked to an MRE with specificity for the miRNA. An MRE can be any sequence that base pairs with and interacts with the miRNA somewhere on the mRNA transcript. Often, the MRE is present in the 3' untranslated region (UTR) of the mRNA, but it can also be present in the coding sequence or in the 5'-UTR. MRE's are not necessarily perfect complements to miRNAs, usually having only a few bases of complementarity to the miRNA and often containing one or more mismatches within those bases of complementarity. An MRE, therefore, can be any sequence capable of being bound by an miRNA sufficiently that the translation of a gene to which the MRE is operably linked (such as a CMV gene that is essential or augmenting for growth in vivo) is repressed by an miRNA silencing mechanism such as the RISC.

In some examples, a microRNA recognition element (MRE) is operably linked to a CMV gene that is essential or augmenting for growth in vivo. In other examples, the MRE silences expression in the presence of a miRNA that is expressed in cells of the myeloid lineage. Such miRNA include, but are not limited to, miR-142-3p, miR-223, miR-27a, miR-652, miR-155, miR146a, miR-132, miR-21, or miR-125 (Brown et al., Nat. Biotechnol., 2007, 25, 1457-1467). Myeloid lineage cells have been shown to represent a reservoir of latent virus, and are thought to harbor and disseminate virus throughout the host (Jarvis and Nelson, Front Biosci., 2002, 7, d1575-1582).

Further studies with MCMV (Snyder et al., C. M., Allan, J. E., Bonnett, E. L., Doom, C. M., and Hill, A. B. Cross-presentation of a spread-defective MCMV is sufficient to prime the majority of virus-specific CD8+ T cells. PLoS One 5:e9681) indicate that cross-priming is the primary mechanism by which CMV-encoded proteins prime the immune response, replication in myeloid dendritic cells may have a surprisingly minimal impact on CMV immunogenicity.

Bacterial artificial chromosome (BAC)-based technology is used to generate a recombinant MCMV virus that contained four repeated target sequences (four 21mers) with exact complementarity to the cellular miRNA, miR-142-3p, within the 3'UTR of the essential viral gene IE3 (IE3-142). To confirm the extent to which miR-142-3p expression could repress IE3-142 replication, virus growth assays are performed in the macrophage cell line, IC-21. RT-PCR analysis confirmed that IC-21 cells express high levels of miR-142-3p making the cell line suitable to test the effectiveness of the strategy. Preliminary experiments confirmed the utility of the approach for cell-type specific attenuation of CMV. Although IE3-142 replicated to wild type levels in fibroblasts, growth was completely blocked in IC-21 macrophage cells. A control virus, IE3-015, which contains only vector sequence within the IE3 insertion site, replicates to wild-type levels in IC-21 cells. RT-PCR analysis indicates that IE3 expression was completely abrogated following infection of IC-21 cells, but not following infection of fibroblast cells (lacking miR-142-3p expression) indicating that disruption of IE3 expression is not due to insertion of the target sequence.

Some embodiments relate to strategy to attenuate CMV based on the showing that viruses can be attenuated for tissue-specific growth by using miRNA target sequences and the attenuation of MCMV in myeloid cells through the targeting of cell specific miRNAs to essential viral genes. Since the CNS is a major target for CMV pathogenesis in both congenital and adult disease, HCMV/TB vaccines are generated that contain target sequences of highly conserved miRNAs specifically expressed by neurons fused to essential CMV genes to prevent replication in the CNS. Target sequences of the myeloid miRNA miR-124 to prevent replication and dissemination of the CMV vector in this cell type are also used. Together, these attenuated viruses will provide a further level of safety that will enable the use of this vaccine in all human target populations.

Also disclosed herein are recombinant CMV vectors, such as RhCMV and HCMV vectors, having a deletion in one or more genes that are essential for or augment CMV replication, dissemination or spreading. Thus, these vectors are referred to as "replication-deficient" CMV vectors. As used herein, "replication-deficient" encompasses CMV vectors that are unable to undergo any replication in a host cell, or have a significantly reduced ability to undergo viral replication. In some examples, the replication-deficient CMV vectors are able to replicate, but are unable to disseminate since they are incapable of infection neighboring cells. In some examples, the replication-deficient CMV vectors are able to replicate, but are unable to spread since they are not released from infected hosts.

CMV essential and augmenting genes are well known in the art (see, for example, Dunn et al., Proc. Natl. Acad. Sci. USA, 2003, 100, 14223-14228; and Dong et al., Proc. Natl. Acad. Sci. USA, 2003, 100, 12396-12401), and are described herein. In some embodiments, the recombinant RhCMV or HCMV vector includes a deletion in one gene that is essential for or augments virus replication, dissemination or spreading. In other embodiments, the recombinant RhCMV or HCMV vector includes a deletion in multiple (such as, but not limited to, two, three or four) genes essential for or augmenting CMV replication, dissemination or spreading. The deletion need not be a deletion of the entire open reading frame of the gene, but includes any deletion that eliminates expression of functional protein.

In some embodiments, the recombinant RhCMV or HCMV vaccine vector comprises a deletion in a RhCMV or HCMV gene that is essential for replication within a host, dissemination within a host, or spreading from host to host. In some embodiments, the essential gene is UL82 (encoding pp71), UL94 (encoding the UL94 protein), UL32 (encoding pp150), UL99 (encoding pp28), UL115 (encoding gL) and UL44 (encoding p52), or a homolog thereof.

Replication-deficient RhCMV and HCMV vectors disclosed herein can include a nucleic acid sequence encoding a heterologous antigen, such as a pathogen-specific antigen. As disclosed for other recombinant RhCMV and HCMV vectors described herein, replication-deficient RhCMV and HCMV vectors can be used to elicit an immune response in a subject against the encoded heterologous antigen.

A recombinant RhCMV vector having a deletion in gene UL82 (which encodes the pp71 protein) is severely impaired in its ability to grow in vitro and to spread in vivo, but still elicits a robust T cell immune response against CMV (U.S. Pat. No. 9,249,427). Thus, it is contemplated herein to use such a replication-deficient vector as a vaccine against CMV itself.

In some embodiments, the recombinant RhCMV or HCMV vaccine vector has a deletion in a gene region non-essential for growth in vivo. In some embodiments, the gene region is selected from the group consisting of the RL11 family, the pp65 family, the US12 family, and the US28 family. In some embodiments, the RhCMV gene region is selected from the group consisting of Rh13-Rh29, Rh111-Rh112, Rh191-Rh202, and Rh214-Rh220. In some embodiments, the RhCMV gene region is selected from the group consisting of Rh13.1, Rh19, Rh20, Rh23, Rh24, Rh112, Rh190, Rh192, Rh196, Rh198, Rh199, Rh200, Rh201, Rh202, and Rh220. In some embodiments, the HCMV gene region is selected from the group consisting of RL11, UL6, UL7, UL9, UL11, UL83 (pp65), US12, US13, US14, US17, US18, US19, US20, US21, and UL28.

In some embodiments, the recombinant RhCMV or HCMV vector comprises a deletion in a RhCMV or HCMV gene that is essential for or augments replication. CMV essential genes and augmenting have been well described in the art (see, for example, Dunn et al., supra; and Dong et al., supra). Essential CMV genes include, but are not limited to, UL32, UL34, UL37, UL44, UL46, UL48, UL48.5, UL49, UL50, UL51, UL52, UL53, UL54, UL55, UL56, UL57, UL60, UL61, UL70, UL71, UL73, UL75, UL76, UL77, UL79, UL80, UL82, UL84, UL85, UL86, UL87, UL89, UL90, UL91, UL92, UL93, UL94, UL95, UL96, UL98, UL99, UL100, UL102, UL104, UL105, UL115 and UL122. In some embodiments, the CMV essential or augmenting gene is UL82, UL94, UL32, UL99, UL115 or UL44, or a homolog thereof (i.e., the homologous gene in RhCMV). Other essential or augmenting genes are known in the art and are described herein. In particular examples, the essential gene is UL82, or a homolog thereof. In some embodiments, the recombinant RhCMV and HCMV vectors do not include a heterologous antigen. In other embodiments, the recombinant RhCMV or HCMV vector having a deletion in an essential or augmenting gene includes a nucleic acid sequence encoding a heterologous antigen, such as a pathogen-specific antigen or a tumor antigen. Compositions comprising recombinant RhCMV or HCMV vectors and a pharmaceutically acceptable carrier also are provided. Such vectors and compositions can be used, for example, in a method of treating a subject with an infectious disease, or at risk of becoming infected with an infectious disease. CMV vectors having a deletion of at least one important gene are generally attenuated and thus can be used as vaccines for the treatment or prevention of CMV (in which case, the recombinant vector does not encode a heterologous antigen).

In some embodiments, the recombinant RhCMV or HCMV vectors comprise a suicide or safety means to prevent further replication of the virus. For example, the recombinant CMV vectors can include LoxP sites flanking an essential gene or region of the RhCMV or HCMV genome (essential CMV genes are listed above and are known in the art), as well as the coding sequence for Cre-recombinase. Cre-recombinase is generally under the control of an inducible promoter to regulate expression of Cre, thereby controlling removal of the essential gene and inhibition of viral replication. In particular examples, Cre is a Tet-regulated Cre and expression of Cre is controlled by the presence of Dox.

The present disclosure also relates to a method of a CMV vector capable of repeatedly infecting an organism which may comprise (a) constructing a vector containing and over-expressing at least one cytomegalovirus (CMV) glycoprotein, wherein the glycoprotein is US2, US3, US6 or US11, and (b) administering the vector repeatedly into the animal or human. Where superinfectivity is desired, any CMV vector, may express one or more of the HCMV glycoproteins US2, US3, US6 and US11 (or the RhCMV homologues Rh182, Rh184, Rh185, Rh189).

In some embodiments, the recombinant RhCMV or HCMV vaccine vector further comprises a second nucleic acid sequence encoding US2, US3, or US6, or a homolog thereof, wherein the vector does not encode a functional US11. In some embodiments, the second nucleic acid sequence encodes US2, US3, and US6. In some embodiments, the nucleic acid encoding a US11 open reading frame is deleted. In some embodiments, the recombinant RhCMV or HCMV vaccine vector further comprises a third nucleic acid sequence encoding US11, and wherein the nucleic acid sequence encoding US11 comprises a point mutation, a frameshift mutation, and/or a deletion of one or more nucleotides of the nucleic acid sequence encoding US11.

In some embodiments, the glycoproteins within the US2 to US11 region of RhCMV or HCMV are deleted from the vector. In some embodiments, the recombinant RhCMV or HCMV vaccine vector lacks the transactivator pp71. In some embodiments, the recombinant RhCMV or HCMV vaccine vector lacks the tegument protein pp65.

In some embodiments, the recombinant RhCMV or HCMV vaccine vector further comprises a nucleic acid sequence that encodes UL128 or an ortholog thereof, and another nucleic acid sequence that encodes UL131 or an ortholog thereof, wherein the vector does not express an active UL130 protein.

In some embodiments, the recombinant RhCMV or HCMV vaccine vector further comprises a nucleic acid sequence that encodes UL130 or an ortholog thereof, and another nucleic acid sequence that encodes UL131 or an ortholog thereof, wherein the vector does not express an active UL128 protein.

In some embodiments, the recombinant RhCMV or HCMV vaccine vector comprises a mutation in UL128 or UL130 selected from a point mutation, a frameshift mutation, and a deletion of all or less than all of UL128 or UL130.

In some embodiments, the recombinant RhCMV or HCMV vaccine vector further comprises an antisense sequence or an RNAi sequence that inhibits the expression of UL128 or UL130 or both.

In some embodiments, the recombinant RhCMV or HCMV vaccine vector comprises a deletion or modification of US2, US3, US4, US5, US6, US11, or UL97, or a homolog thereof.

In some embodiments, the recombinant RhCMV or HCMV vaccine vector comprises a deletion of Rh158-166 or a homolog thereof.

In some embodiments where repeated infection of a CMV vector is desired, the CMV vector may express one or more of the glycoproteins US2, US3, US6 and US11. In a particularly advantageous embodiment, the vector expresses glycoproteins US2, US3, US6 and US11. More advantageously, the vector contains and expresses all of the glycoproteins within the US2 to US11 region of CMV. In an advantageous embodiment, the one or more of the glycoproteins US2, US3, US6 and US11 may include, but not limited to, the glycoproteins of U.S. Pat. Nos. 7,892,564; 7,749,745; 7,364,893; 6,953,661; 6,913,751; 6,740,324; 6,613,892; 6,410,033; 6,140,114; 6,103,531; 6,033,671; 5,908,780; 5,906,935; 5,874,279; 5,853,733; 5,846,806; 5,843,458; 5,837,532; 5,804,372; 5,753,476; 5,741,696; 5,731,188; 5,720,957; 5,676,952; 5,599,544; 5,593,873 and 5,334,498.

Disclosed herein are human or animal CMV vectors comprising a nucleic acid sequence that encodes a heterologous protein antigen and a nucleic acid sequence that encodes an active UL131 protein. In one example, the CMV vector comprises a nucleic acid sequence that expresses an active UL128 protein but does not express an active UL130 protein. In another example, the CMV vector encodes an active UL130 protein but does not express an active UL128 protein.

In some examples, the CMV vector does not express an active UL128 or UL130 protein due to the presence of a deleterious mutation in the nucleic acid sequence encoding UL128 or UL130 or their orthologous genes in animal CMVs. The mutation may be any deleterious mutation that results in a lack of expression of active UL128 or UL130 protein. Such mutations can include point mutations, frameshift mutations, deletions of less than all of the sequence that encodes the protein (truncation mutations), or deletions of all of the nucleic acid sequence that encodes the protein, or any other mutations.

In further examples, the CMV vector does not express an active UL128 or UL130 protein due to the presence of a nucleic acid sequence in the vector that comprises an antisense or RNAi sequence (siRNA or miRNA) that inhibits the expression of the UL128 or UL130 protein.

Also disclosed herein are methods of generating CD8+ T cell responses to heterologous antigens in a subject. The methods involve administering an effective amount of a CMV vector to the subject. The CMV vector is characterized by having a nucleic acid sequence that encodes a heterologous antigen and a nucleic acid sequence that encodes an active UL131 protein. The CMV vector is further characterized by not encoding an active UL128 protein or an active UL130 protein or neither an active UL128 or active UL130 protein. The CD8+ T cell response is further characterized by having at least 10% of the CD8+ T cells directed against epitopes presented by MHC class II. In further examples, at least 20%, at least 30%, at least 40%, at least 50%, at least 60%, or more than 60% of the CD8+ T cells are directed against epitopes presented by MHC class II.

In further examples, the methods involve administering an effective amount of a second CMV vector, the second CMV vector comprising a nucleic acid sequence that encodes a heterologous antigen to the subject. This second vector can be any CMV vector, including a CMV vector with an active UL128 and an active UL130 protein. The second CMV vector may comprise additional deletions known in the art to provide different immune responses such as a US11 deletion or any other deletion. The second heterologous antigen can be any heterologous antigen, including a heterologous antigen identical to the heterologous antigen in the first CMV vector. The second CMV vector can be administered at any time relative to the administration of the first CMV vector including before, concurrently with, or after the administration of the first CMV vector. This includes administration of the second vector any number of months, days, hours, minutes or seconds before or after the first vector. In preferred embodiments of the present invention viral vectors are used. Advantageously, the vector is a CMV vector, lacking at least the glycoprotein UL128 or a CMV vector lacking at least the glycoprotein UL130. Each CMV vector also expresses the glycoprotein UL131.

Suitable dosages of the CMV vectors in the immunogenic compositions can be readily determined by those of skill in the art. For example, the dosage of the CMV vectors can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-.gamma. ELISPOT assays, IL-2 ELISPOT assays, intracellular cytokine assays, and other immunological detection assays, e.g., as detailed in the text "Antibodies: A Laboratory Manual" by Ed Harlow and David Lane.

In some embodiments, the recombinant RhCMV vaccine vector is Rh68-1 or Rh68-1.2. During in vitro culture on fibroblasts, the Rh68-1 CMV vector lost the ability to express gene products from the Rh13, Rh60, Rh157.5, and Rh157.6 open reading frames. The HCMV orthologs of these genes are RL11, UL36, UL128, and UL130, respectively. The Rh68-1.2 vector had expression of Rh60, Rh157.5, and Rh157.6 restored through recombinant DNA techniques (Lilja and Shenk, Proc. Natl. Acad. Sci. USA, 2008, 105, 19950-19955). The Rh68-1 CMV vector, but not the Rh68-1.2 CMV vector, primes surprisingly high number of $CD8^+$ T cells restricted by MHC-E.

In some embodiments, the CMV vectors can comprise regulatory elements for gene expression of the coding sequences of the nucleic acid. The regulatory elements can be a promoter, an enhancer an initiation codon, a stop codon, a polyadenylation signal, additional restriction enzyme sites, multiple cloning sites, or other coding segments, and the like. In some embodiments, the CMV vector can comprise heterologous nucleic acid encoding an Mtb antigen and can further comprise an initiation codon, which is upstream of the antigen coding sequence, and a stop codon, which is downstream of the antigen coding sequence. The initiation and termination codon are in frame with the antigen coding sequence.

In some embodiments, expression of the Mtb antigen is driven by an antigen-coding sequence in operable association with a promoter selected from the group consisting of a constitutive CMV promoter, an immediate early CMV promoter, an early CMV promoter, and a late CMV promoter. In some embodiments, the promoter is selected from the group consisting of EF1-alpha, UL82, MIE, pp65, and gH.

The CMV vector can also comprise a polyadenylation signal, which can be downstream of the antigen coding sequence. The polyadenylation signal can be a SV40 polyadenylation signal, LTR polyadenylation signal, CMV polyadeylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The CMV vector can also comprise an enhancer. In some embodiments, the enhancer can be necessary for DNA expression. The enhancer can be human actin, human myosin, human hemoglobin, human muscle creatine or a viral enhancer such as one from CMV, RSV or EBV. Polynucleotide function enhances are described in U.S. Pat. Nos. 5,593,972, 5,962,428, and WO94/016737, the contents of each are incorporated herein by reference.

The CMV vector can also comprise a mammalian origin of replication to maintain the vector extrachromosomally and produce multiple copies of the vector in a cell. The CMV vector can comprise the Epstein Barr virus origin of replication and nuclear antigen EBNA-1 coding region, which can produce high copy episomal replication without integration. The CMV vector can contain certain elements of the pVAX1 or a pVax1 variant. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The CMV vector can also comprise a regulatory sequence, which can be well suited for gene expression in a mammalian or human cell into which the vector is administered. The consensus coding sequence can comprise a codon, which can allow more efficient transcription of the coding sequence in the host cell.

The present disclosure also provides host cells comprising any of the nucleic acid molecules or CMV vectors disclosed herein. The host cells can be used, for example, to express the Mtb antigens, or fragments of thereof. The Mtb antigens, or fragments thereof, can also be expressed in cells in vivo. The host cell that is transformed (for example, transfected) to produce the Mtb antigens, or fragments of thereof can be an immortalised mammalian cell line, such as those of lymphoid origin (for example, a myeloma, hybridoma, trioma or quadroma cell line). The host cell can also include normal lymphoid cells, such as B-cells, that have been immortalized by transformation with a virus (for example, the Epstein-Barr virus).

In some embodiments, the host cells include, but are not limited to: bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda* (for example, Sf9 and Sf21 cell lines, and expresSF™ cells (Protein Sciences Corp., Meriden, Conn., USA)), *Drosophila* S2 cells, and *Trichoplusia* in High Five® Cells (Invitrogen, Carlsbad, Calif., USA); and mammalian cells, such as COS1 and COS7 cells, Chinese hamster ovary (CHO) cells, NS0 myeloma cells, NIH 3T3 cells, 293 cells, Procell92S, perC6, HEPG2 cells, HeLa cells, L cells, HeLa, MDCK, HEK293, WI38, murine ES cell lines (for example, from strains 129/SV, C57/BL6, DBA-1, 129/SVJ), K562, Jurkat cells, and BW5147. Other useful mammalian cell lines are well known and readily available from the American Type Culture Collection ("ATCC") (Manassas, Va., USA) and the National Institute of General Medical Sciences (NIGMS) Human Genetic Cell Repository at the Coriell Cell Repositories (Camden, N.J., USA). In some embodiments, the cell is a recombinant BCG. These cell types are only representative and are not meant to be an exhaustive list.

Among other considerations, some of which are described above, a host cell strain may be chosen for its ability to process the expressed Mtb antigens, or fragment thereof, in the desired fashion. Post-translational modifications of the polypeptide include, but are not limited to, glycosylation, acetylation, carboxylation, phosphorylation, lipidation, and acylation, and it is an aspect of the present disclosure to provide Mtb antigens thereof with one or more of these post-translational modifications.

In some embodiments, the recombinant BCG has been genetically engineered to express a functional endosomalytic protein that is bioactive at pH values near neutrality (e.g. about pH 6-8 or about 6.5 to 7.5). The endosomalytic protein is active within Mycobacteria-containing endosomes, which typically have an internal pH near neutrality. The activity of the endosomalytic protein produced by the rBCG results in disruption of the endosome, permitting the rBCG to escape from the endosome and into the cytoplasm of the cell. In some embodiments, the endosomalytic protein that is introduced into the rBCG by genetic engineering is Perfringolysin O (PfoA) from *Clostridium perfringens* or a mutant thereof, such as $PfoA_{G137Q}$, as described in WO 2007/058663, which is incorporated herein by reference in its entirety.

In some embodiments, the Mycobacteria are attenuated, as exemplified by BCG. However, those of skill in the art will recognize that other attenuated and nonattenuated Mycobacteria exist which would also be suitable for use herein. Examples of additional types of Mycobacteria include, but are not limited to, *M. tuberculosis* strain CDC1551, *M. tuberculosis* strain Beijing, *M. tuberculosis* strain H37Ra (ATCC #:25177), *M. tuberculosis* strain H37Rv (ATCC #:25618), *M. bovis* (ATCC #:19211 and 27291), *M. fortuitum* (ATCC #:15073), *M. smegmatis* (ATCC #:12051 and 12549), *M. intracellulare* (ATCC #:35772 and 13209), *M. kansasii* (ATCC #:21982 and 35775) *M. avium* (ATCC #:19421 and 25291), *M. gallinarum* (ATCC #:19711), M vaccae (ATCC #:15483 and 23024), *M. leprae* (ATCC #:), *M. marinarum* (ATCC #:11566 and 11567), and *M. microtti* (ATCC #:11152).

Examples of attenuated *Mycobacterium* strains include, but are not restricted To, *M. tuberculosis* pantothenate auxotroph strain, *M. tuberculosis* rpoV mutant strain, *M. tuberculosis* leucine auxotroph strain, BCG Danish strain (ATCC #35733), BCG Japanese strain (ATCC #35737), BCG Chicago strain (ATCC #27289), BCG Copenhagen strain (ATCC #: 27290), BCG Pasteur strain (ATCC #: 35734), BCG Glaxo strain (ATCC #: 35741), BCG Connaught strain (ATCC #35745), BCG Montreal (ATCC #35746), BCG1331 strain, BCG Tokyo strain, BCG Moreau strain, BCG-Pasteur Aeras, and BCG Moscow strain.

The present disclosure also provides pharmaceutical compositions comprising any one or more of the recombinant RhCMV or HCMV vaccine vectors described herein and a pharmaceutically acceptable carrier.

In some embodiments, the Mtb antigen, or fragment thereof, is labeled with a detectable marker. Detectable markers include, but are not limited to, radioactive isotopes (such as $P^{32}$ and $S^{35}$), enzymes (such as horseradish peroxidase, chloramphenicol acetyltransferase (CAT), β-galactosidase (β-gal), and the like), fluorochromes, chromophores, colloidal gold, dyes, and biotin. The labeled Mtb antigens, or fragments thereof, can be used to carry out diagnostic procedures in a variety of cell or tissue types. For imaging procedures, in vitro or in vivo, the Mtb antigens can be labeled with additional agents, such as NMR contrasting agents, X-ray contrasting agents, or quantum dots. Methods for attaching a detectable agent to polypeptides are known in the art. The Mtb antigens can also be attached to an insoluble support (such as a bead, a glass or plastic slide, or the like).

In some embodiments, the Mtb antigens, or fragment thereof, can be conjugated to a therapeutic agent including, but not limited to, radioisotopes (such as $^{111}In$ or $^{90}Y$), toxins (such as tetanus toxoid or ricin), toxoids, and chemotherapeutic agents.

In some embodiments, the Mtb antigens, or fragments thereof, can be conjugated to an imaging agent. Imaging agents include, for example, a labeling moiety (such as biotin, fluorescent moieties, radioactive moieties, histidine tag or other peptide tags) for easy isolation or detection.

The present disclosure also provides compositions comprising any one or more of the fusion proteins, Mtb antigens, nucleic acid molecules encoding Mtb antigens, including fusion proteins thereof, cells, and/or CMV vectors and a pharmaceutically acceptable carrier useful in, for example, vaccines.

In some embodiments, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In some embodiments, liquid formulations of a pharmaceutical composition for injection can comprise various carriers such as vegetable oils, dimethylacetamide, dimethylformamide, ethyl lactate, ethyl carbonate, isopropyl myristate, ethanol, polyols such as, for example, glycerol, propylene glycol, liquid polyethylene glycol, and the like. In some embodiments, the composition includes a citrate/sucrose/tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid such as, for example, ethyl oleate.

The compositions can be, for example, injectable solutions, aqueous suspensions or solutions, non-aqueous suspensions or solutions, solid and liquid oral formulations, salves, gels, ointments, intradermal patches, creams, aerosols, lotions, tablets, capsules, sustained release formulations, and the like. In some embodiments, for topical applications, the pharmaceutical compositions can be formulated in a suitable ointment. In some embodiments, a topical semi-solid ointment formulation typically comprises a concentration of the active ingredient from about 1 to 20%, or from 5 to 10%, in a carrier, such as a pharmaceutical cream base. Some examples of formulations of a composition for topical use include, but are not limited to, drops, tinctures, lotions, creams, solutions, and ointments containing the active ingredient and various supports and vehicles.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect (see Langer, Science, 1990, 249, 1527 and Hanes, Advanced Drug Delivery Reviews, 1997, 28, 97). A sterile injectable preparation such as, for example, a sterile injectable aqueous or oleaginous suspension can also be prepared. This suspension may be formulated according to techniques known in the art using suitable dispersing, wetting, and suspending agents. In some embodiments, the pharmaceutical composition can be delivered in a microencapsulation device so as to reduce or prevent a host immune response against the protein.

A suitable dose is an amount of a compound that, when administered as described above, is capable of promoting an anti-TB immune response, and is preferably at least 10-50% above the basal (i.e., untreated) level. Such response can be monitored, for example, by measuring the anti-T cell responses in a patient. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide sought in a dose ranges from about 25 mcg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g. more frequent remissions, complete or partial, or longer disease-free survival) in treated patients as compared to non-treated patients. Increases in preexisting immune responses to a TB protein may correlate with an improved clinical outcome. Such immune responses may generally be evaluated using standard proliferation, cytotoxicity or cytokine assays, which may be performed using samples obtained from a patient before and after treatment.

In some embodiments, the compositions comprise about 1 nanogram to about 10 mg of nucleic acid. In some embodiments, the compositions comprise: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg.

In some embodiments, the compositions comprise about 5 nanograms to about 10 mg of nucleic acid molecule. In some embodiments, the compositions comprise about 25 nanograms to about 5 mg of nucleic acid molecule. In some embodiments, the compositions contain about 50 nanograms to about 1 mg of nucleic acid molecule. In some embodiments, the compositions contain about 0.1 to about 500 micrograms of nucleic acid molecule. In some embodiments, the compositions contain about 1 to about 350 micrograms of nucleic acid molecule. In some embodiments, the compositions contain about 5 to about 250 micrograms of nucleic acid molecule. In some embodiments, the compositions contain about to about 200 micrograms of nucleic acid molecule. In some embodiments, the compositions contain about 15 to about 150 micrograms of nucleic acid molecule. In some embodiments, the compositions contain about 20 to about 100 micrograms of nucleic acid molecule. In some embodiments, the compositions contain about 25 to about 75 micrograms of nucleic acid molecule. In some embodiments, the compositions contain about 30 to about 50 micrograms of nucleic acid molecule. In some embodiments, the compositions contain about 35 to about 40 micrograms of nucleic acid molecule. In some embodiments, the compositions contain about 100 to about 200 micrograms of nucleic acid molecule. In some embodiments, the compositions comprise about 10 to about 100 micrograms of nucleic acid molecule. In some embodiments, the compositions comprise about 20 to about 80 micrograms of nucleic acid molecule. In some embodiments, the compositions comprise about 25 to about 60 micrograms of nucleic acid molecule. In some embodiments, the compositions comprise about 30 nanograms to about 50 micrograms of nucleic acid molecule. In some embodiments, the compositions comprise about 35 nanograms to about 45 micrograms of nucleic acid molecule. In some embodiments, the compositions contain about 0.1 to about 500 micrograms of nucleic acid molecule. In some embodiments, the compositions contain about 1 to about 350 micrograms of nucleic acid molecule. In some embodiments, the compositions contain about 25 to about 250 micrograms of nucleic acid molecule. In some embodiments, the compositions contain about 100 to about 200 micrograms of nucleic acid molecule.

The compositions can be formulated according to the mode of administration to be used. In cases where compositions are injectable pharmaceutical compositions, they are sterile, pyrogen free and particulate free. An isotonic formulation can be used. Generally, additives for isotonicity can include sodium chloride, dextrose, mannitol, sorbitol and lactose. In some cases, isotonic solutions such as phosphate buffered saline are suitable. Stabilizers include gelatin and albumin. In some embodiments, a vasoconstriction agent is added to the formulation.

The compositions can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freund's incomplete adjuvant, LPS analog including monophosphoryl lipid A, muramyl peptides, quinone analogs, vesicles such as squalene and squalane, hyaluronic acid, lipids, liposomes, calcium ions, viral proteins, polyanions, polycations, or nanoparticles, or other known transfection facilitating agents. The transfection facilitating agent is a polyanion, polycation, including poly-L-glutamate (LGS), or lipid. The transfection facilitating agent is poly-L-glutamate, and more suitably, the poly-L-glutamate is present in the composition at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalane, and hyaluronic acid can also be used administered in conjunction with the genetic construct. In some embodiments, the plasmid compositions can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. In some embodiments, the transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The plasmid compositions can further comprise a genetic vaccine facilitator agent as described in U.S. Serial No. 021,579 filed Apr. 1, 1994, which is fully incorporated by reference.

The present disclosure also provides kits comprising any of the Mtb antigens, fragments thereof, fusion proteins, nucleic acid molecules, CMV vectors, or cells, described herein. The kit can include, for example, container(s), package(s) or dispenser(s) along with labels and instructions for administration or use.

Vaccine CMV vectors and pharmaceutical compositions may be presented in unit-dose or multi-dose containers, such as sealed ampoules or vials. Such containers can be hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

The present disclosure also provides methods for treatment or prevention of tuberculosis comprising administering to a subject in need thereof at least one recombinant RhCMV or HCMV vaccine vector as described herein. In some embodiments, the methods further comprise re-administering to the subject at least one recombinant RhCMV or HCMV vaccine vector described herein. In some embodiments, the recombinant RhCMV or HCMV vaccine vector of the re-administration is different than the recombinant RhCMV or HCMV vaccine vector of the initial administration.

The present disclosure also provides methods for eliciting an immune response to a Mtb antigen comprising administering to a subject in need thereof at least one recombinant RhCMV or HCMV vaccine vector as described herein.

The present disclosure also provides methods for eliciting a $CD8^+$ or $CD4^+$ T cell response to a Mtb antigen comprising administering to a subject in need thereof at least one recombinant RhCMV or HCMV vaccine vector as described herein.

In some embodiments, the recombinant RhCMV or HCMV vaccine vector is administered to the subject intravenously, intramuscularly, intraperitoneally, intranasally, or orally. In some embodiments, the subject is a human.

In some embodiments, any of the Mtb antigens, constructs, vectors, or cells described herein, or compositions comprising the same, can be administered to a mammal as an aerosol. In some embodiments, the aerosol inocula comprises saline. Conventional aerosol delivery devices include, but are not limited to, a pressurized metered dose inhaler (pMDI) and a dry power inhaler (DPI), both of which deliver a dry powder formulation, and nebulizers such as the PARI eFlow device, which delivers an aqueous dose as a fine mist. In some embodiments, the aerosol delivery device is a Pari eFlow portable electronic aerosol delivery platform attached to a delivery mask. In some embodiments, the average particle size is from about 1 μm to about 10 μm, from about 1 μm to about 5 μm, from about 3 μm to about 5 μm, from about 4 μm to about 5 μm, or from about 3.9 μm to about 4.9 μm. In some embodiments, the aerosol is in a volume from about 0.1 ml to about 5 ml, from about 0.1 ml to about 2 ml, from about 0.1 ml to about 1.5 ml, from about 0.5 ml to about 1.5 ml, from about 0.5 ml to about 1.2 ml, from about 0.7 ml to about 1.2 ml, or about 1 ml.

Effective doses of the compositions of the present disclosure, for the treatment of a condition vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

In some embodiments, the compositions can be administered to a subject by injection intravenously, subcutaneously, intraperitoneally, intramuscularly, intramedullarily, intraventricularly, intraepidurally, intraarterially, intravascularly, intraarticularly, intrasynovially, intrasternally, intrathecally, intrahepatically, intraspinally, intratumorly, intracranially, enteral, intrapulmonary, transmucosal, intrauterine, sublingual, or locally at sites of inflammation or tumor growth by using standard methods. Alternately, the compositions can be administered to a subject by routes including oral, nasal, ophthalmic, rectal, or topical. The most typical route of administration is intravascular, subcutaneous, or intramuscular, although other routes can be effective. In some embodiments, compositions are administered as a sustained release composition or device, such as a Medipad™ device. The composition can also be administered via the respiratory tract, for example, using a dry powder inhalation device, nebulizer, or a metered dose inhaler. The composition can also be administered by traditional syringes, needleless injection devices, "microprojectile bombardment gone guns," or other physical methods such as electroporation ("EP"), "hydrodynamic method", or ultrasound.

In some embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

In some embodiments, the composition can be administered to a subject by sustained release administration, by such means as depot injections of erodible implants directly applied during surgery or by implantation of an infusion pump or a biocompatible sustained release implant into the subject. Alternately, the composition can be administered to a subject by injectable depot routes of administration, such as by using 1-, 3-, or 6-month depot injectable or biodegradable materials and methods, or by applying to the skin of the subject a transdermal patch containing the composition, and leaving the patch in contact with the subject's skin, generally for 1 to 5 hours per patch.

The present disclosure also provides methods of eliciting an immune response against *Mycobacterium tuberculosis* in a mammal comprising administering to the mammal an immunologically sufficient amount of one or more CMV vectors comprising one or more of the Mtb fusion proteins described herein.

The fusion proteins and compositions described herein can be used to treat or prevent tuberculosis. In some embodiments, the method comprises administering to a human a therapeutically- or prophylactically-effective amount of any of the CMV vectors or compositions described herein such that the tuberculosis infection is diminished or prevented.

In some embodiments, the subject being treated will have been previously diagnosed as having tuberculosis. Such subjects will, thus, have been diagnosed as being in need of such treatment. Alternately, the treatment may be intended to prevent a tuberculosis infection in a subject that does not yet have tuberculosis or to a subject that is travelling to an area where tuberculosis is prevalent.

Treatment of a subject suffering from tuberculosis can be monitored using standard methods. Some methods entail determining a baseline value, for example, of an antibody level or profile in a subject, before administering a dosage of agent, and comparing this with a value for the profile or level after treatment. A significant increase such as, for example, greater than the typical margin of experimental error in repeat measurements of the same sample, expressed as one standard deviation from the mean of such measurements in value of the level or profile signals a positive treatment outcome (i.e., that administration of the agent has achieved a desired response). If the value for immune response does not change significantly, or decreases, a negative treatment outcome is indicated.

In other embodiments, a control value such as a mean and standard deviation, of level or profile is determined for a control population. Typically the individuals in the control population have not received prior treatment. Measured values of the level or profile in a subject after administering a therapeutic agent are then compared with the control value. A significant increase relative to the control value, such as greater than one standard deviation from the mean, signals a positive or sufficient treatment outcome. A lack of significant increase or a decrease signals a negative or insufficient treatment outcome. Administration of the therapeutic is generally continued while the level is increasing relative to the control value. As before, attainment of a plateau relative to control values is an indicator that the administration of treatment can be discontinued or reduced in dosage and/or frequency.

In other embodiments, a control value of the level or profile, such as a mean and standard deviation, is determined from a control population of individuals who have undergone treatment with a therapeutic agent and whose levels or profiles have plateaued in response to treatment. Measured values of levels or profiles in a subject are compared with the control value. If the measured level in a subject is not significantly different, such as by more than one standard deviation, from the control value, treatment can be discontinued. If the level in a subject is significantly below the control value, continued administration of agent is warranted. If the level in the subject persists below the control value, then a change in treatment may be indicated.

In other embodiments, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement, such as greater than a typical margin of error in repeat measurements of the same sample, is an indication that treatment can be resumed. Alternately, the value measured in a subject can be compared with a control value (mean plus standard deviation) determined in a population of subjects after undergoing a course of treatment. Alternately, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level, such as more than a standard deviation, is an indicator that treatment should be resumed in a subject.

In some methods, a baseline measurement of antibody to a given antigen in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline, such as 50%, 25% or 10%, administration of a further dosage of antigen is administered. In some embodiments, peak or subsequent measured levels less background are compared with reference levels previously determined to constitute a beneficial prophylactic or therapeutic treatment regime in other subjects. If the measured antibody level is significantly less than a reference level, such as less than the mean minus one standard deviation of the reference value in population of subjects benefiting from treatment, administration of an additional dosage of antigen is indicated.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks.

In some embodiments, the subject(s) that can be treated by the above-described methods is an animal, such as a mammal, including, but are not limited to, humans, non-human primates, rodents (including rats, mice, hamsters and guinea pigs) cow, horse, sheep, goat, pig, dog and cat. In most instances, the mammal is a human.

The present disclosure also provides CMV/TB vectors as described herein for use in the preparation of a medicament for treating or preventing a *Mycobacterium tuberculosis* infection.

The present disclosure also provides CMV/TB vectors as described herein for use in treating or preventing a *Mycobacterium tuberculosis* infection.

The present disclosure also provides uses of CMV/TB vectors as described herein in the preparation of a medicament for treating or preventing a *Mycobacterium tuberculosis* infection.

The present disclosure also provides uses of CMV/TB vectors as described herein in treating or preventing a *Mycobacterium tuberculosis* infection.

The present disclosure also provides any of the CMV/TB vectors as described herein, or any of the compositions described herein, or any of the cells described herein, or any of the methods described herein, or any of the uses described herein, substantially as described with reference to the accompanying examples and/or figures.

The following representative embodiments are presented:

Embodiment 1

A recombinant RhCMV or HCMV vector comprising a nucleic acid sequence encoding an expressible Mtb antigen selected from Ag85A-Ag85B-Rv3407, Rv1733-Rv2626c, RpfA-RpfC-RpfD, Ag85B-ESAT6, and Ag85A-ESAT6-Rv3407-Rv2626c-RpfA-RpfD.

Embodiment 2

The recombinant RhCMV or HCMV vaccine vector of embodiment 1, wherein expression of the Mtb antigen is driven by an antigen-coding sequence in operable association with a promoter selected from the group consisting of a constitutive CMV promoter, an immediate early CMV promoter, an early CMV promoter, and a late CMV promoter.

Embodiment 3

The recombinant RhCMV or HCMV vaccine vector of embodiment 2, wherein the promoter is selected from the group consisting of EF1-alpha, UL82, MIE, pp65, and gH.

Embodiment 4

The recombinant RhCMV or HCMV vaccine vector of any one of embodiments 1 to 3, comprising a deletion or modification of US2, US3, US4, US5, US6, US11, or UL97, or a homolog thereof.

Embodiment 5

The recombinant RhCMV or HCMV vaccine vector of any one of embodiments 1 to 4, comprising a deletion of Rh158-166 or a homolog thereof.

Embodiment 6

The recombinant RhCMV or HCMV vaccine vector of any one of embodiments 1 to 5, wherein the RhCMV or HCMV vaccine vector is a tropism-restricted vector.

Embodiment 7

The recombinant RhCMV or HCMV vaccine vector of embodiment 6, wherein the tropism-restrictive vector lacks genes required for optimal growth in certain cell types or contains targets for tissue-specific micro-RNAs in genes essential for viral replication or wherein the tropism-restrictive vector has an epithelial, central nervous system (CNS), or macrophage deficient tropism, or a combination thereof.

Embodiment 8

The recombinant RhCMV or HCMV vaccine vector of any one of embodiments 1 to 7, wherein the RhCMV or HCMV vaccine vector has a deletion in a gene region non-essential for growth in vivo.

Embodiment 9

The recombinant RhCMV or HCMV vaccine vector of embodiment 8, wherein the gene region is selected from the group consisting of the RL11 family, the pp65 family, the US12 family, and the US28 family.

Embodiment 10

The recombinant RhCMV vaccine vector of embodiment 9, wherein the RhCMV gene region is selected from the group consisting of Rh13-Rh29, Rh111-Rh112, Rh191-Rh202, and Rh214-Rh220, or wherein the RhCMV gene region is selected from the group consisting of Rh13.1, Rh19, Rh20, Rh23, Rh24, Rh112, Rh190, Rh192, Rh196, Rh198, Rh199, Rh200, Rh201, Rh202, and Rh220.

Embodiment 11

The recombinant HCMV vaccine vector of embodiment 9, wherein the HCMV gene region is selected from the group consisting of RL11, UL6, UL7, UL9, UL11, UL83 (pp65), US12, US13, US14, US17, US18, US19, US20, US21, and UL28.

Embodiment 12

The recombinant RhCMV or HCMV vaccine vector of any one of embodiments 1 to 11, wherein the vector comprises a deletion in a RhCMV or HCMV gene that is essential for replication within a host, dissemination within a host, or spreading from host to host.

Embodiment 13

The recombinant RhCMV or HCMV vaccine vector of embodiment 12, wherein the essential gene is UL94, UL32, UL99, UL115, or UL44, or a homolog thereof.

Embodiment 14

The recombinant RhCMV or HCMV vaccine vector of any one of embodiments 1 to 13, wherein the vector comprises a deletion in gene UL82/pp71 or a homolog thereof.

Embodiment 15

The recombinant RhCMV or HCMV vaccine vector of any one of embodiments 1 to 14, wherein the vector further comprises a second nucleic acid sequence encoding US2, US3, or US6, or a homolog thereof, wherein the vector does not encode a functional US11.

Embodiment 16

The recombinant RhCMV or HCMV vaccine vector of embodiment 15, wherein the second nucleic acid sequence encodes US2, US3, and US6.

Embodiment 17

The recombinant RhCMV or HCMV vaccine vector of embodiment 15 or embodiment 16, wherein the nucleic acid encoding a US11 open reading frame is deleted.

Embodiment 18

The recombinant RhCMV or HCMV vaccine vector of any one of embodiments 15 to 17, further comprising a third nucleic acid sequence encoding US11, and wherein the nucleic acid sequence encoding US11 comprises a point mutation, a frameshift mutation, and/or a deletion of one or more nucleotides of the nucleic acid sequence encoding US11.

Embodiment 19

The recombinant RhCMV or HCMV vaccine vector of embodiment 18, wherein the vector lacks the tegument protein pp65.

Embodiment 20

The recombinant RhCMV or HCMV vaccine vector of any one of embodiments 1 to 19, wherein the vector does not express an active UL130 protein.

Embodiment 21

The recombinant RhCMV or HCMV vaccine vector of any one of embodiments 1 to 20, wherein the RhCMV vaccine vector is Rh68-1 or Rh68-1.2.

Embodiment 22

The recombinant RhCMV or HCMV vaccine vector of embodiment 1 further comprising a microRNA recognition element (MRE) operably linked to a CMV gene that is essential or augmenting for CMV growth, and wherein the MRE silences expression in the presence of a microRNA that is expressed by a cell of myeloid lineage.

Embodiment 23

A pharmaceutical composition comprising the recombinant RhCMV or HCMV vaccine vector of any one of embodiments 1 to 22, and a pharmaceutically acceptable carrier.

Embodiment 24

A method for treatment or prevention of tuberculosis comprising administering to a subject in need thereof at least one recombinant RhCMV or HCMV vaccine vector of any one of embodiments 1 to 22.

Embodiment 25

The method of embodiment 24, further comprising re-administering to the subject at least one recombinant RhCMV or HCMV vaccine vector of any one of embodiments 1 to 22.

Embodiment 26

The method of embodiment 25, wherein the recombinant RhCMV or HCMV vaccine vector of the re-administration is different than the recombinant RhCMV or HCMV vaccine vector of the initial administration.

Embodiment 27

A method for eliciting an immune response to a Mtb antigen comprising administering to a subject in need thereof at least one recombinant RhCMV or HCMV vaccine vector of any one of embodiments 1 to 22.

Embodiment 28

A method for eliciting a CD8+ or CD4+ T cell response to a Mtb antigen comprising administering to a subject in need thereof at least one recombinant RhCMV or HCMV vaccine vector of embodiment 20.

Embodiment 29

The method of any one of embodiments 24 to 28 wherein the recombinant RhCMV or HCMV vaccine vector is administered to the subject intravenously, intramuscularly, intraperitoneally, intranasally, or orally.

Embodiment 30

The method of any one of embodiments 24 to 29 wherein the vector is an HCMV vector and the subject is a human.

Embodiment 31

A Mtb antigen selected from Ag85B-ESAT6 and Ag85A-ESAT6-Rv3407-Rv2626c-RpfA-RpfD.

Embodiment 32

The Mtb antigen of embodiment 31 which is Ag85A-ESAT6-Rv3407-Rv2626c-RpfA-RpfD.

In order that the subject matter disclosed herein may be more efficiently understood, examples are provided below. It should be understood that these examples are for illustrative purposes only and are not to be construed as limiting the claimed subject matter in any manner Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: CMV/TB Vectors

Particular aspects provide recombinant HCMV/TB vectors that can be growth-modulated in vivo (e.g., by oral administration of the antibiotic doxycycline). Heterologous antigen expression may be under the control of promoters of different kinetic classes with respect to the CMV infection cycle (e.g., EF1α—constitutive; MIE—immediate early; pp65—early; gH—late).

In particular embodiments, HCMV/TB vectors lack immune modulatory genes (e.g., Rh158-166 and Rh182-189) to enhance vector immunogenicity, safety and heterologous gene carrying capacity of the vector. For example, HCMV encodes at least four different gene products, gpUS2, gpUS3, gpUS6 and gpUS11 that interfere with antigen presentation by MHC I. All four HCMV MHC evasion molecules are encoded in the unique short region of HCMV and belong to the related US6 gene family Additional HCMV immunomodulators include, but are not limited to UL118, UL119, UL36, UL:37, UL111a, UL146, UL147, etc. Likewise, RhCMV contains analogous immune modulatory genes, that can be deleted or modified to enhance vector immunogenicity, safety and heterologous gene carrying capacity of the inventive vaccine vectors.

In additional embodiments, HCMV/TB are further optimized for anti-TB immunogenicity by insertion of multiple antigen genes, such as those disclosed herein. Alternatively, several vectors, each having a single inserted antigen may be used for co-administration.

In additional embodiments, HCMV/TB vectors contain LoxP sites strategically placed in the CMV genome to flank an essential region of the viral genome, in combination with a tetracycline (Tet)-regulated Cre recombinase.

Construction and Characterization of the RhCMV BAC.

The development of BAC technology to clone large segments of genomic DNA coupled with sophisticated λ phage-based mutagenesis systems has revolutionized the field of herpes virology enabling genetic approaches to analyze the virus. Applicants have used this system, for example, to construct an RhCMV BAC(RhCMV BAC-Cre) containing the complete RhCMV strain 68-1 genome. The RhCMV BAC-Cre was derived from an infectious, pathogenic RhCMV 68-1/EGFP recombinant virus. RhCMV BAC-Cre contains a BAC cassette inserted at a single LoxP site within the Rh181 (US1)/Rh182 (US2) intergenic region of RhCMVvLoxP. Insertion of the BAC cassette at this site results in the generation of LoxP sequences flanking the cassette. As the BAC cassette contains a Cre gene that is expressed in eukaryotic cells, transfection of this "self-excising" RhCMV BAC-Cre into fibroblasts results in efficient excision of the BAC cassette, reconstituting virus (designated RhCMVvLoxP). Characterization of the growth of the BAC-reconstituted virus (RhCMVvLoxP) in vitro and in vivo demonstrates that the various genetic manipulations did not alter the WT properties of the virus. The genomic structure of RhCMVvLoxP is identical to that of WT RhCMV except for the residual LoxP site. The presence of the LoxP sequence does not alter the expression profiles of neighboring Rh181 (US1) and Rh182 (US2) or distal (IE2) genes. RhCMVvLoxP replicates with WT kinetics both in tissue culture and in RhCMV seronegative immunocompetent RMs (n=2). Analysis of tissues from one animal terminated at 6 months post-inoculation demonstrated the presence of both RhCMV DNA and IE1-expressing cells in the spleen, consistent with the persistent gene expression observed in previous studies with WT virus. Both RMs developed vigorous anti-RhCMV antibody titers comparable to those observed in naturally infected animals. Taken together, these observations demonstrate that RhCMVvLoxP is phenotypically WT and is suitable to construct site-specific alterations for the development of vaccine vectors.

Example 2: Non-Human Primate Study #1

This challenge included four treatment groups: 1) naive non-human primates (NHPs) (e.g., Rhesus Macaques) (i.e., unvaccinated controls) (n=8); 2) NHPs vaccinated with BCG alone (n=7); 3) NHPs vaccinated with a cocktail of CMV/TB vectors alone (n=7); and 4) NHPs vaccinated with BCG and a cocktail of CMV/TB vectors. The naive NHPs were CMV-seropositive. The NHPs vaccinated with BCG were vaccinated with 0.1 ml intradermally with Statens Serum Institute (SSI) BCG vaccine. The NHPs vaccinated with a cocktail of CMV/TB vectors were vaccinated with four Rh68-1 vectors (encoding fusion proteins comprised of Ag85A-Ag85B-Rv3407, Rv1733-Rv2626, RpfA-RpfC-RpfD, and Ag85B-ESAT6). The NHPs vaccinated with BCG and a cocktail of CMV/TB vectors were primed with the SSI BCG and boosted with the same cocktail of the four Rh68-1 vectors as above. The NHPs who received the CMV/TB vectors received $5 \times 10^6$ PFU (plaque forming unit) of CMV/TB vector cocktails subcutaneously at weeks 6 and 21. The two BCG groups were given BCG at Week 0. At Weeks 6 and 21, the two CMV/TB vectors groups were immunized with the cocktail of RhCMV/TB vectors. NHP were challenged with *Mycobacterium tuberculosis* at Week 49. Endpoints included longitudinal CT scanning, gross pathology and bacterial burden.

Three of the four vectors used in this study encode classical, latency and resuscitation antigen cassettes (encoding fusion proteins comprised of Ag85A-Ag85B-Rv3407, Rv1733-Rv2626, and RpfA-RpfC-RpfD, respectively). NHP received 5E6 pfu/RhCMV vector, delivered subcutaneously. Also included was a Rh68-1 vector encoding a fusion protein comprised of Ag85AB and ESAT6.

Immunogenicity of these vectors was evaluated using intracellular cytokine staining FIG. 1 shows CD4+ and CD8+ T cell responses. PBMCs were assayed for each of the 9 antigens.

Figure 6:
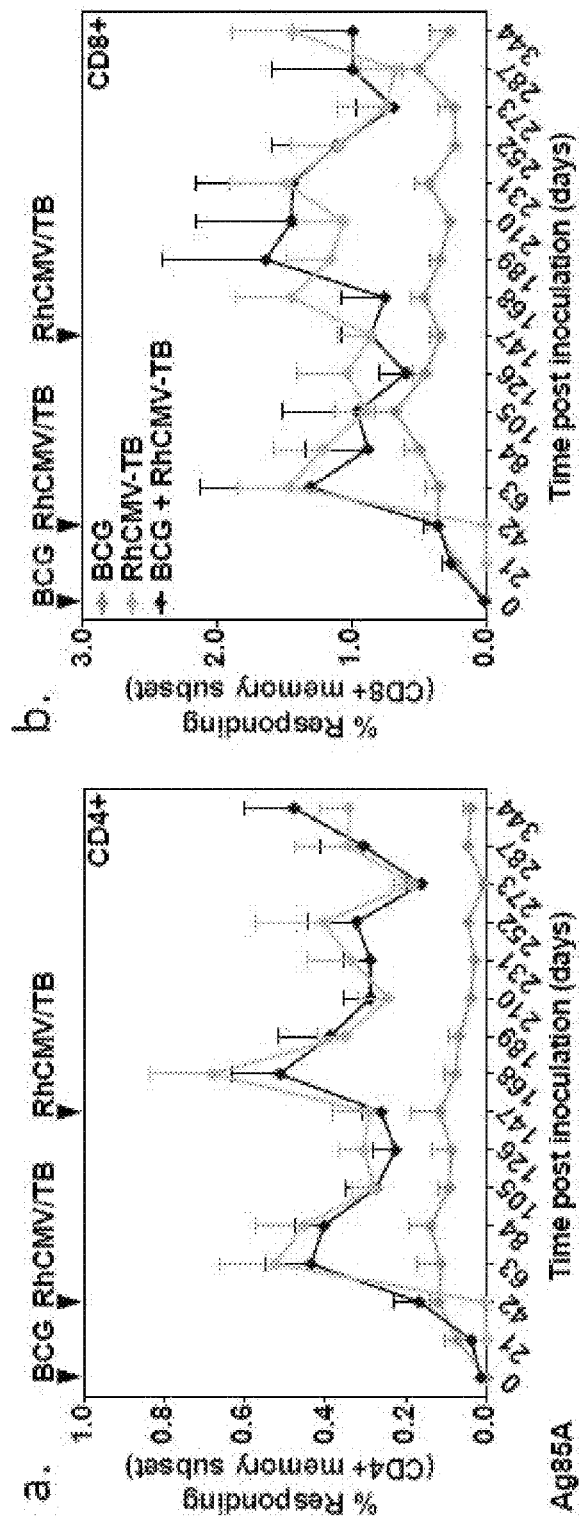
FIG. 6 (panels a and b) shows Ag85A-specific responses analyzed by intracellular cytokine staining throughout the vaccination period; shown above are the percentages of memory cells expressing either IFNγ or TNF; included are responses from peripheral blood mononuclear cells; CD4+ T cells are shown in panel a and CD8+ T cells are shown in panel b.
Figure 7:
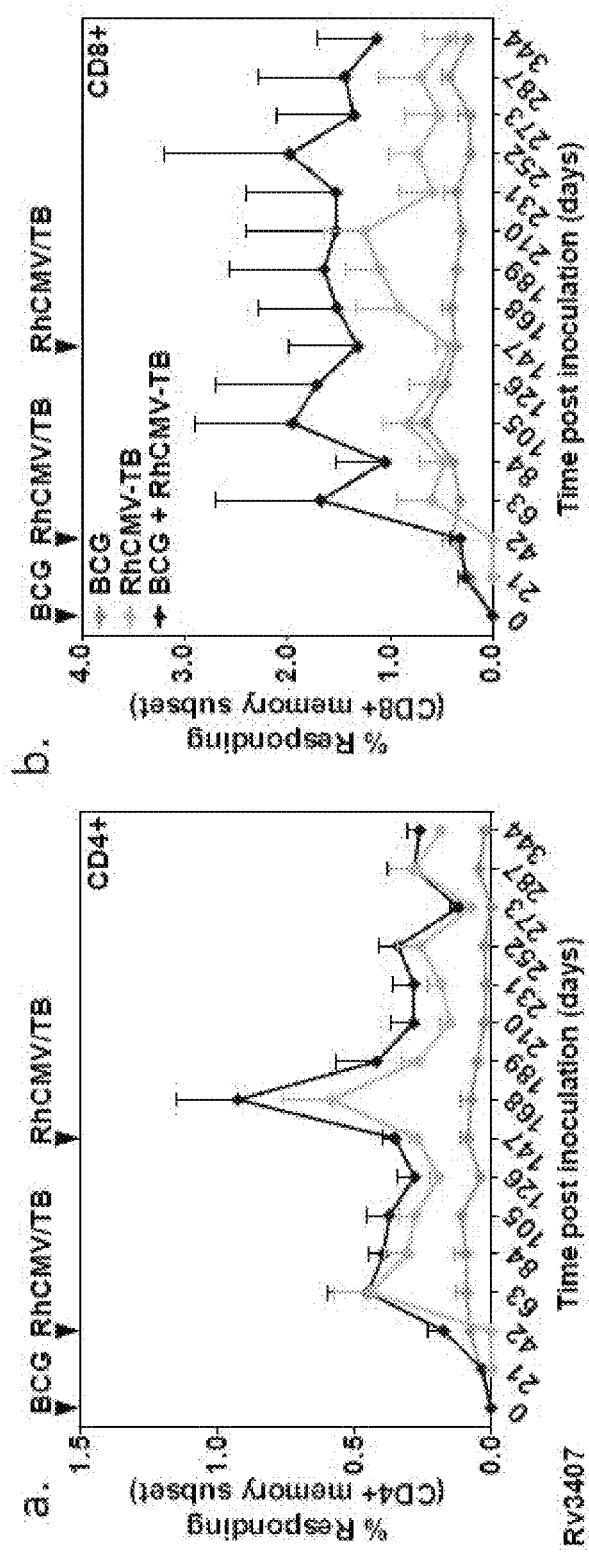
FIG. 7 (panels a and b) shows Rv3407-specific responses analyzed by intracellular cytokine staining throughout the vaccination period; shown above are the percentages of memory cells expressing either IFNγ or TNF; included are responses from peripheral blood mononuclear cells; CD4+ T cells are shown in panel a and CD8+ T cells are shown in panel b.
Figure 8:
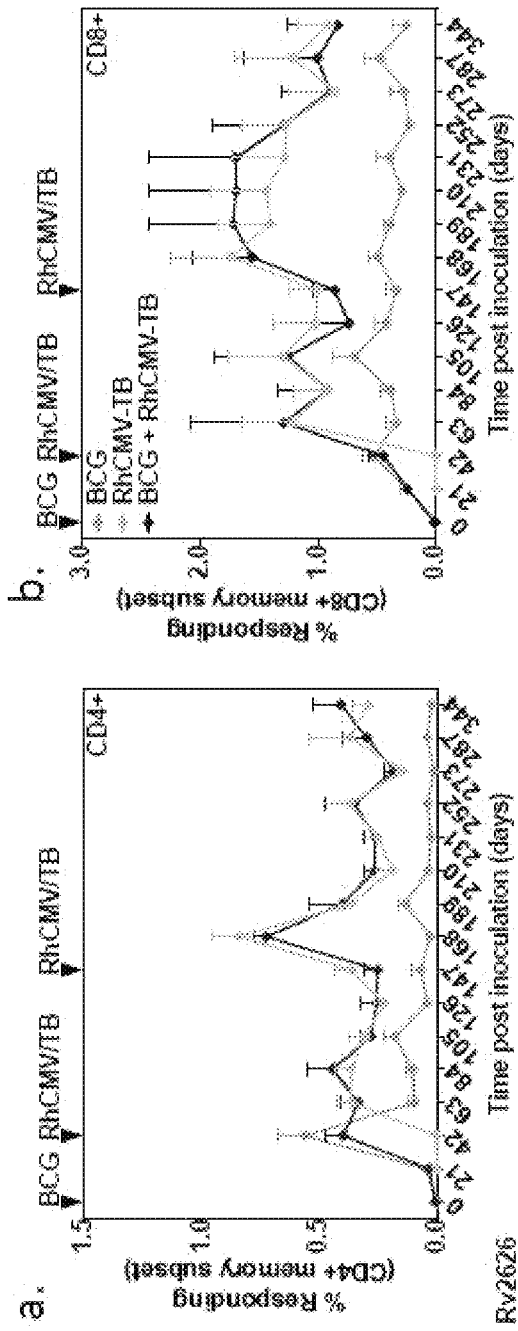
FIG. 8 (panels a and b) shows Rv2626-specific responses analyzed by intracellular cytokine staining throughout the vaccination period; shown above are the percentages of memory cells expressing either IFNγ or TNF; included are responses from peripheral blood mononuclear cells; CD4+ T cells are shown in panel a and CD8+ T cells are shown in panel b.
Figure 9:
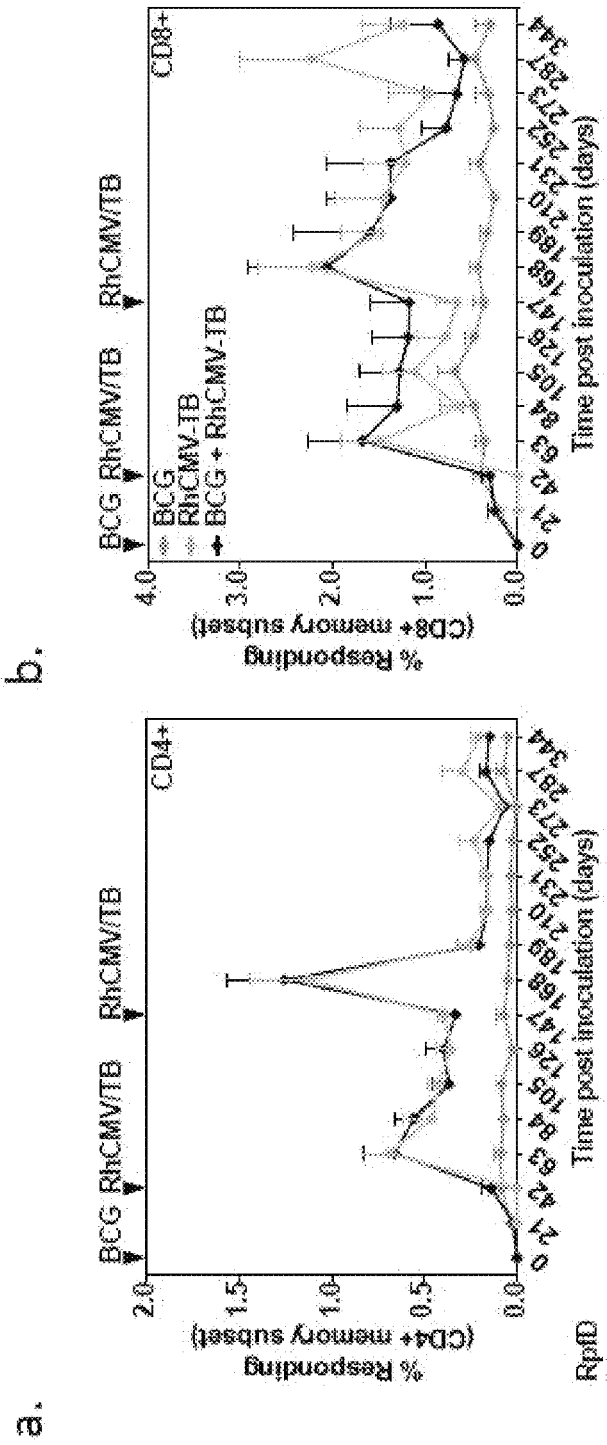
FIG. 9 (panels a and b) shows Rpm-specific responses analyzed by intracellular cytokine staining throughout the vaccination period; shown above are the percentages of memory cells expressing either IFNγ or TNF; included are responses from peripheral blood mononuclear cells; CD4+ T cells are shown in panel a and CD8+ T cells are shown in panel b.
Figure 10:
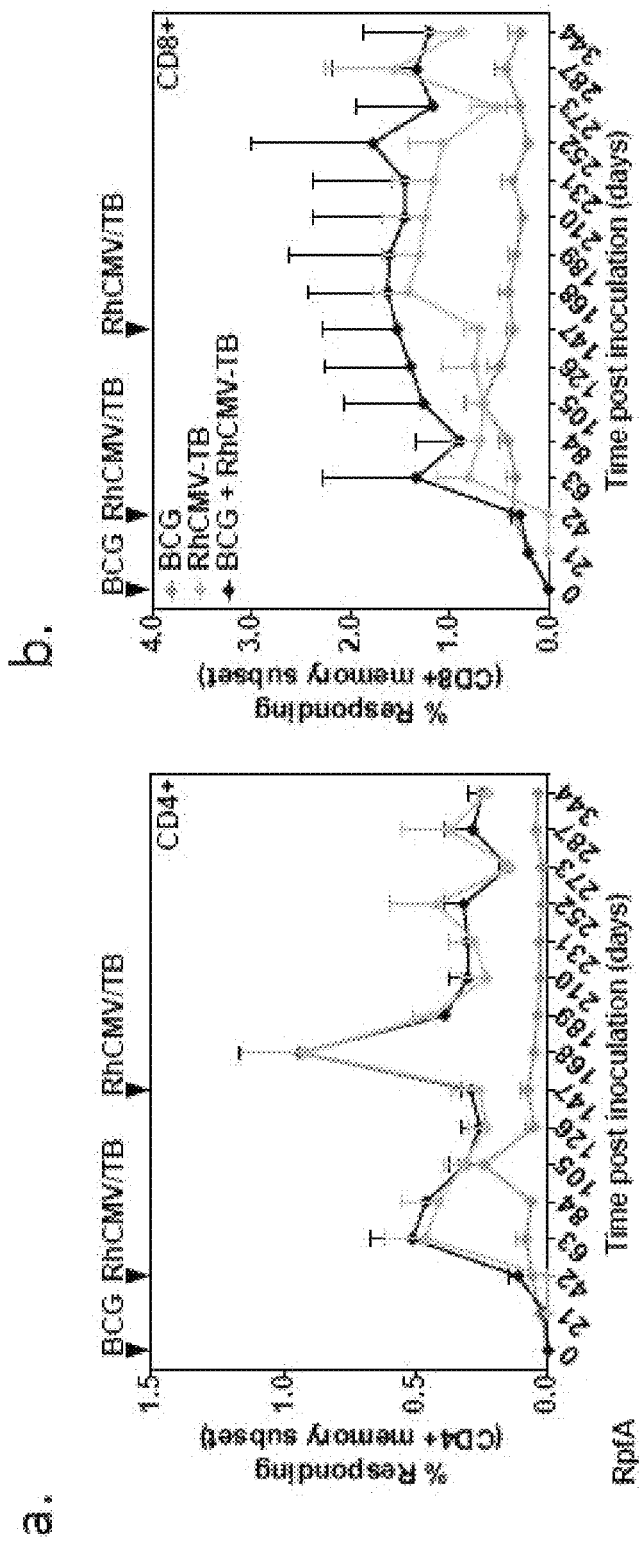
FIG. 10 (panels a and b) shows RpfA-specific responses analyzed by intracellular cytokine staining throughout the vaccination period; shown above are the percentages of memory cells expressing either IFNγ or TNF; included are responses from peripheral blood mononuclear cells; CD4+ T cells are shown in panel a and CD8+ T cells are shown in panel b.

FIGS. 2A, 2B, 2C, and 2D show ESAT-6-specific responses following vaccination. FIGS. 3A, 3B, 3C, and 3D show Rv1733-specific responses following vaccination. FIGS. 4A, 4B, 4C, and 4D show RpfC-specific responses following vaccination. FIGS. 5A, 5B, 5C, and 5D show Ag85B-specific responses following vaccination. FIGS. 6A and 6B show Ag85A-specific responses following vaccination. FIGS. 7A and 7B show Rv3407-specific responses following vaccination. FIGS. 8A and 8B show Rv2626-specific responses following vaccination. FIGS. 9A and 9B show Rpm-specific responses following vaccination. FIGS. 10A and 10B show RpfA-specific responses following vaccination.

Figure 11:
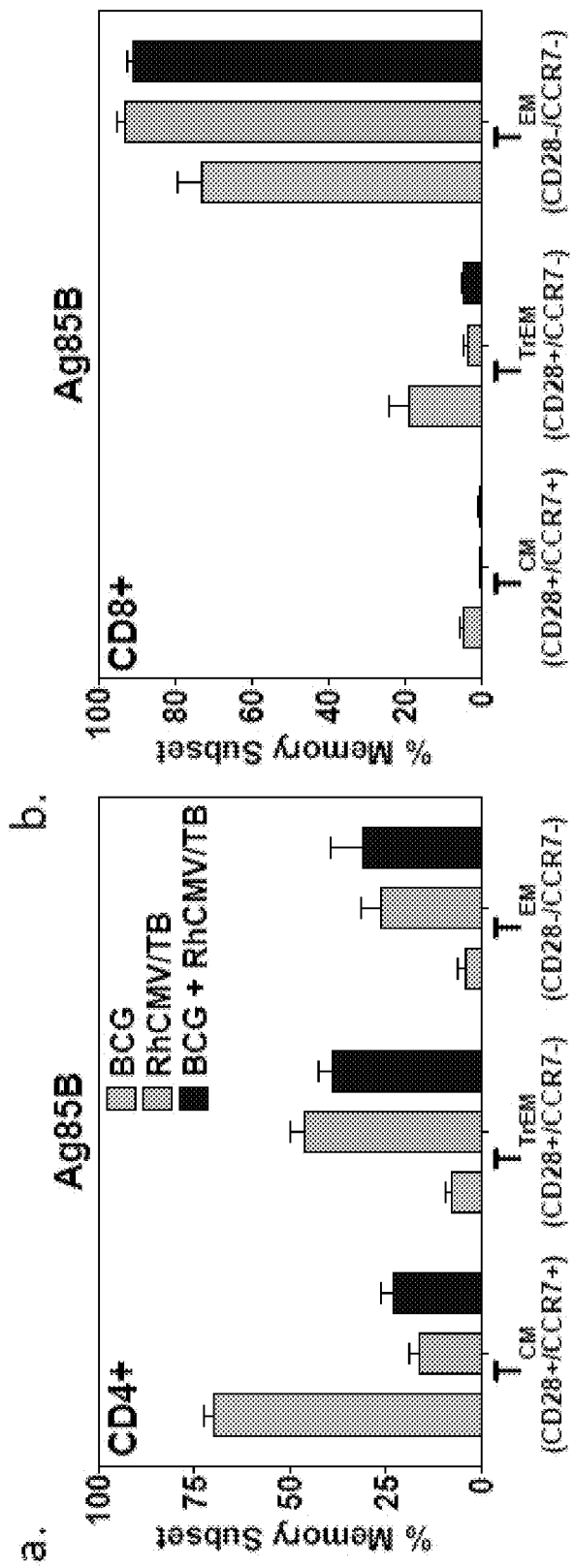
FIG. 11 (panels a and b) shows Ag85B-specific cells phenotyped by flow cytometry and classified as naive, Tcm (central memory), TrEM (transitional effector memory), or Tem (effector memory) T cells; CD4+ T cells are shown in panel a and CD8+ T cells are shown in panel b; analysis was performed in the plateau phase, at days 316/318 after BCG vaccination.

FIG. 11 shows the phenotypic differentiation of BCG- and RhCMV-induced T cells in blood.

Figure 12:
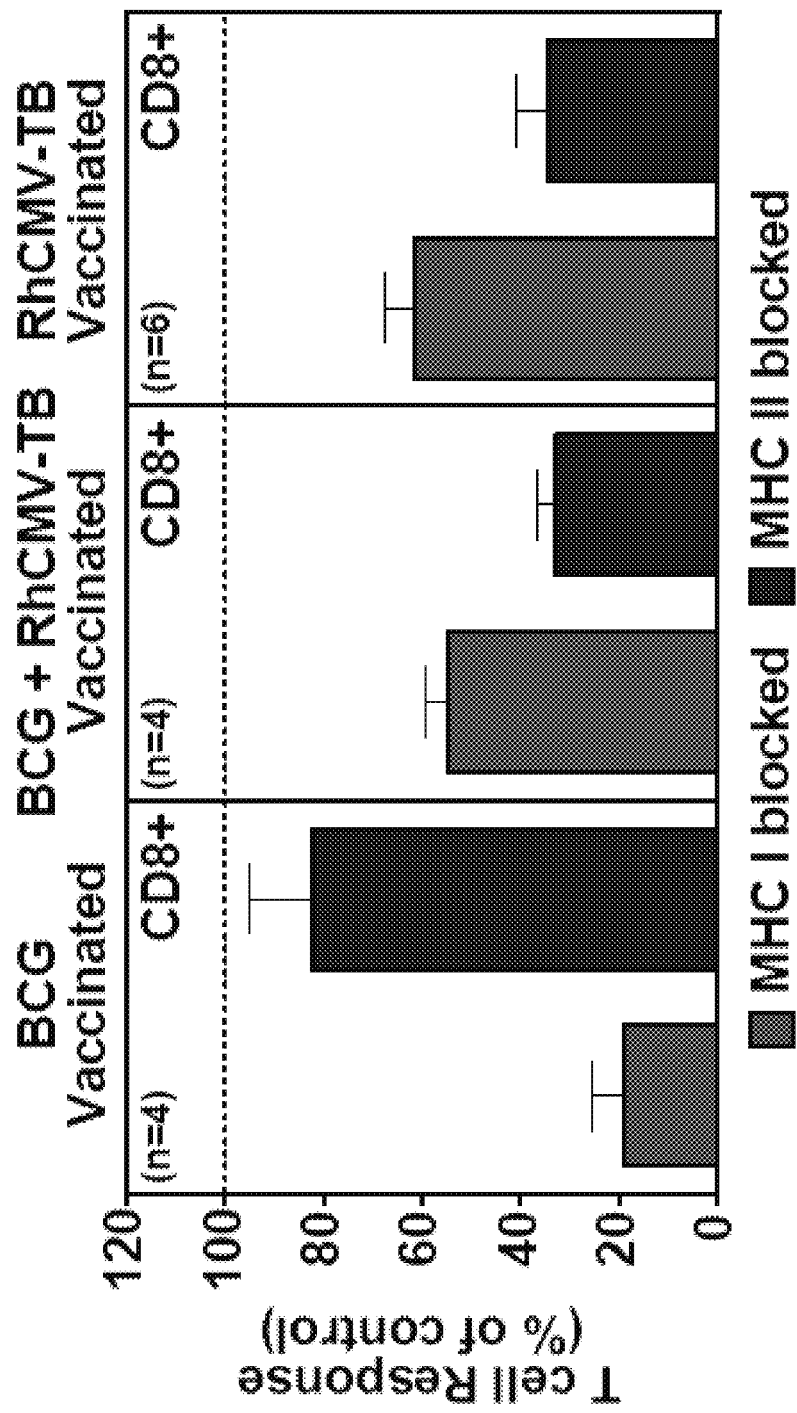
FIG. 12 shows T cells stimulated with antigen in the presence of antibody to block MHC I (red) or MHC II (blue); CD8+ T cell responses induced by BCG are primarily inhibited by blocking MHC I; in contrast, responses induced by RhCMV 68-1 are primarily inhibited by blocking MHC II.

FIG. 12 shows that these Rh68-1 vectors, as expected, induce CD8 T cells that are primarily restricted by MHC II.

The RhCMV vectors were highly immunogenic, showing robust responses in both peripheral blood mononuclear cells (PBMCs) as well as bronchoalveolar lavage (BAL). Vaccination with Rh68-1 also significantly reduced disease progression as compared to naive controls.

Efficacy was evaluated by several means, including CT scan analysis (volume of lung involvement), necropsy score (size, number and distribution of gross lesions; lung, lung-draining lymph nodes, and total (which includes distant dissemination)), and necropsy *Mycobacterium tuberculosis* cultures (40 lung samples by sterology (30 right; 10 left); 9 lymph nodes (6 lung draining and 3 non-mediastinal); and 9 extra-pulmonary tissues (5 liver, 2 kidney, spleen, and pancreas)).

For pulmonary necropsy scoring, individual lobes were scored on 5 mm sections. The following scores were given for granuloma prevalence: no visible lesions=1; 1-3 lesions=2; 4-10 lesions=3; 11-15 lesions=4; 16-20 lesions=5; >20 lesions=6; and Miliary <50% of lobe=7. The following scores were given for largest granuloma size: none visible=1; <1-2 mm=2; 3-4 mm=3; 5-10 mm=4; 11-20 mm=5; >20 mm=6; confluent or miliary lesions involving <50% of lobe=7; and confluent or miliary lesions involving >50% of lobe=8. The following scores were given for additional scoring criteria (1=absent; 2=present): parietal pleural adhesions associated with granulomatous disease, parietal pleural thickening associated with granulomatous disease; granulomatous disease with cavitation, and granulomatous disease involving parietal pleura, diaphragm or body wall.

For thoracic lymph node necropsy scoring, the following scores were given for size: nodes visible but not enlarged (≤5 mm)=0; nodes visibly enlarged (≤5-10 mm) (unilateral) =1; nodes visibly enlarged (≤5-10 mm) (bilateral)=2; and nodes visibly enlarged (>1 cm) (unilateral/bilateral)=3. The following scores were given for granuloma prevalence: no granulomas visible on capsular or cut surface=0; focal or multifocal, circumscribed, non-coalescing granulomas <2 mm=1; coalescing solid or caseous granulomas occupying <50% of node=2; coalescing solid or caseous granulomas occupying >50% of node=3; and complete granulomatous nodal effacement=4. The following scores were given for additional scoring criteria (absent=1; present=2): other thoracic lymph nodes.

For liver and spleen necropsy scoring, the following scores were given for prevalence: no visible granulomas=0; 1-3 visible granulomas=1; 4-10 visible granulomas=2; >10 visible granulomas=3; and miliary pattern=4. The following scores were given for granuloma size: none present=0; <1-2 mm=1; 3-4 mm=2; and >4 mm=3.

For miscellaneous organs and tissue, the following scores were given for prevalence: no visible granulomas=0; 1-3 visible granulomas=1; 4-10 visible granulomas=2; >10 visible granulomas=3; and miliary pattern=4. The following scores were given for granuloma size: none present=0; <1-2 mm=1; 3-4 mm=2; and >4 mm=3.

Figure 13:
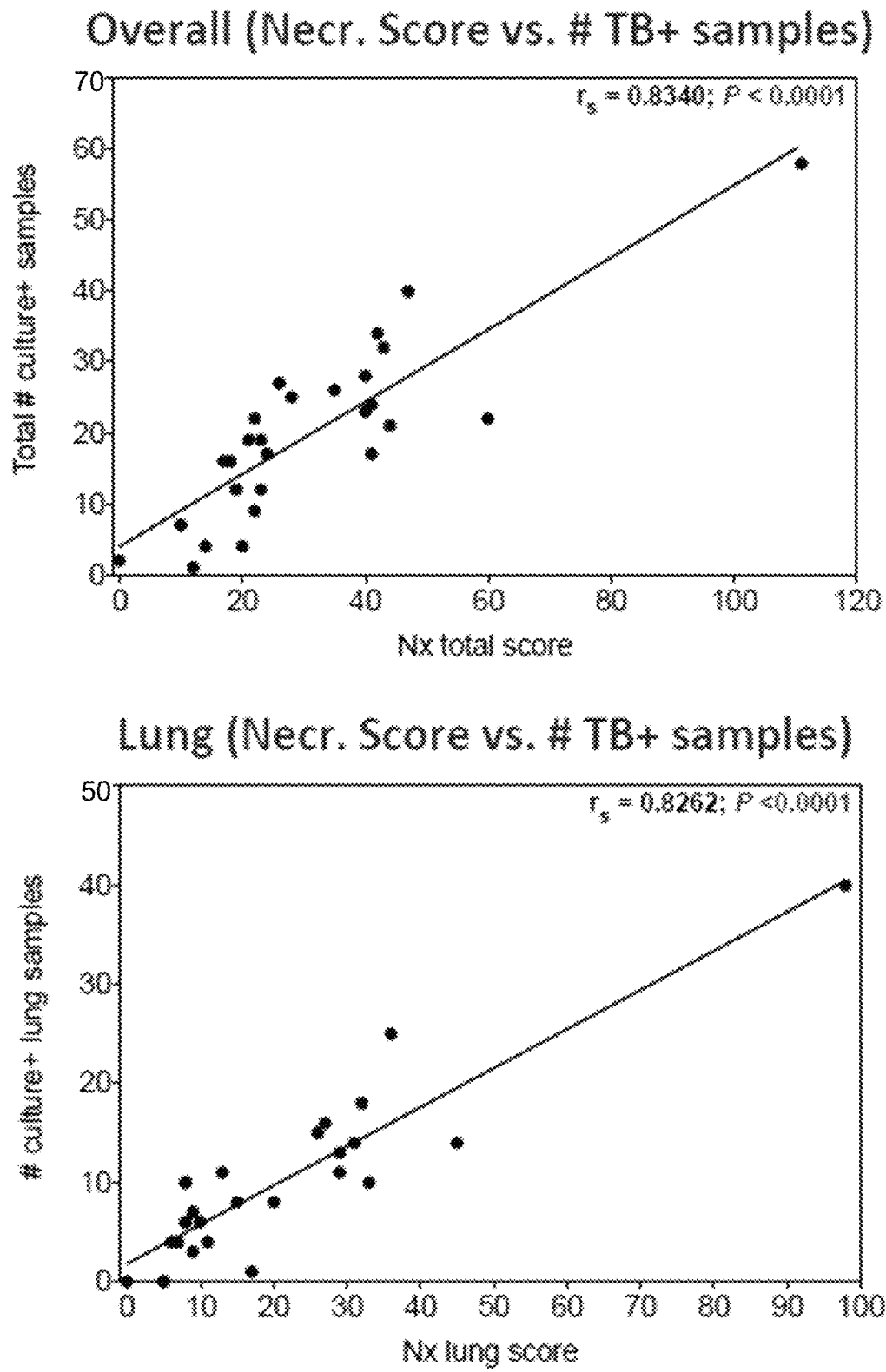
FIG. 13 shows correlation between various pairings of efficacy criteria; also included in each analysis are slope (rs) and p value.
Figure 13:
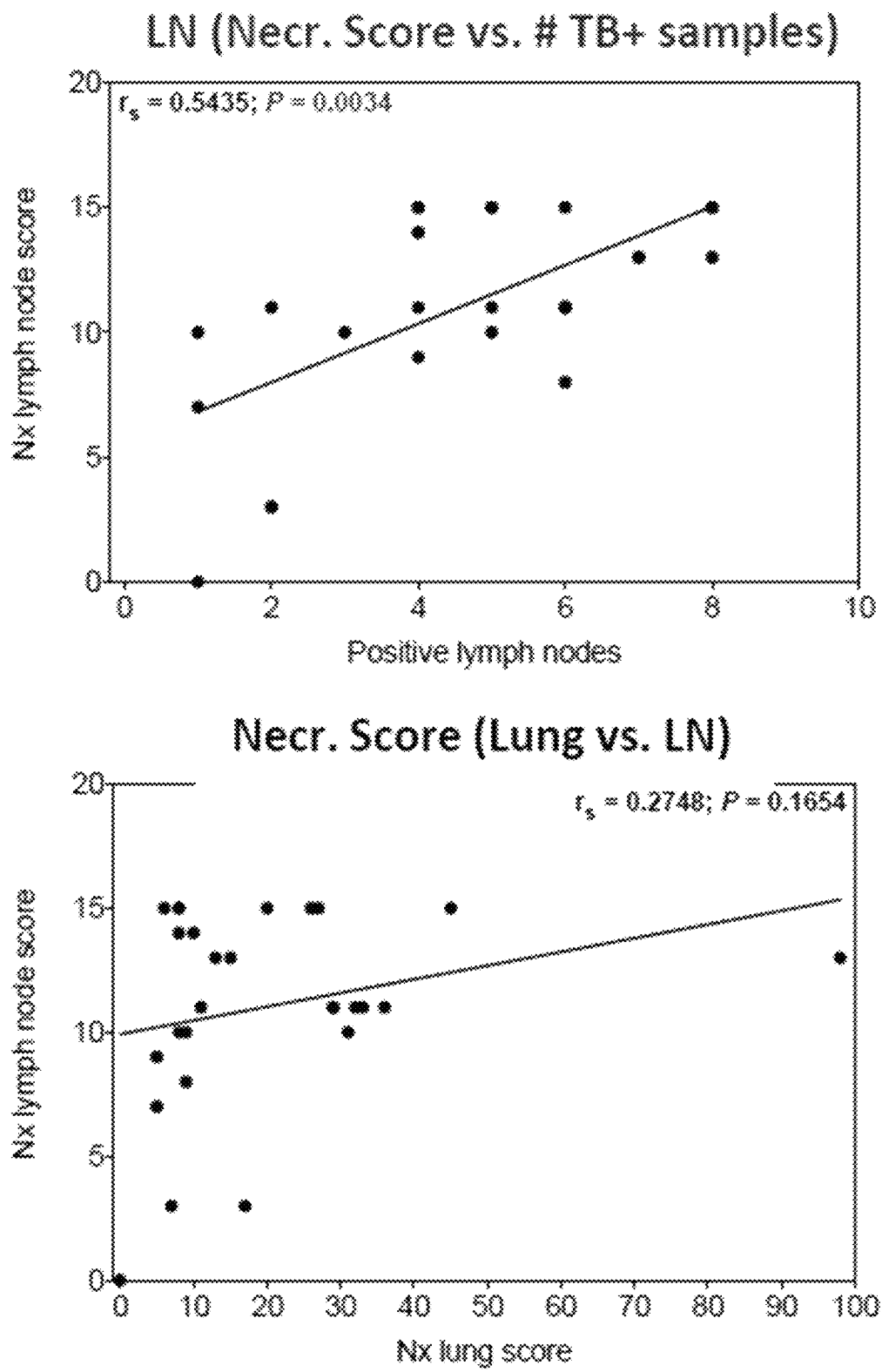
Figure 13:
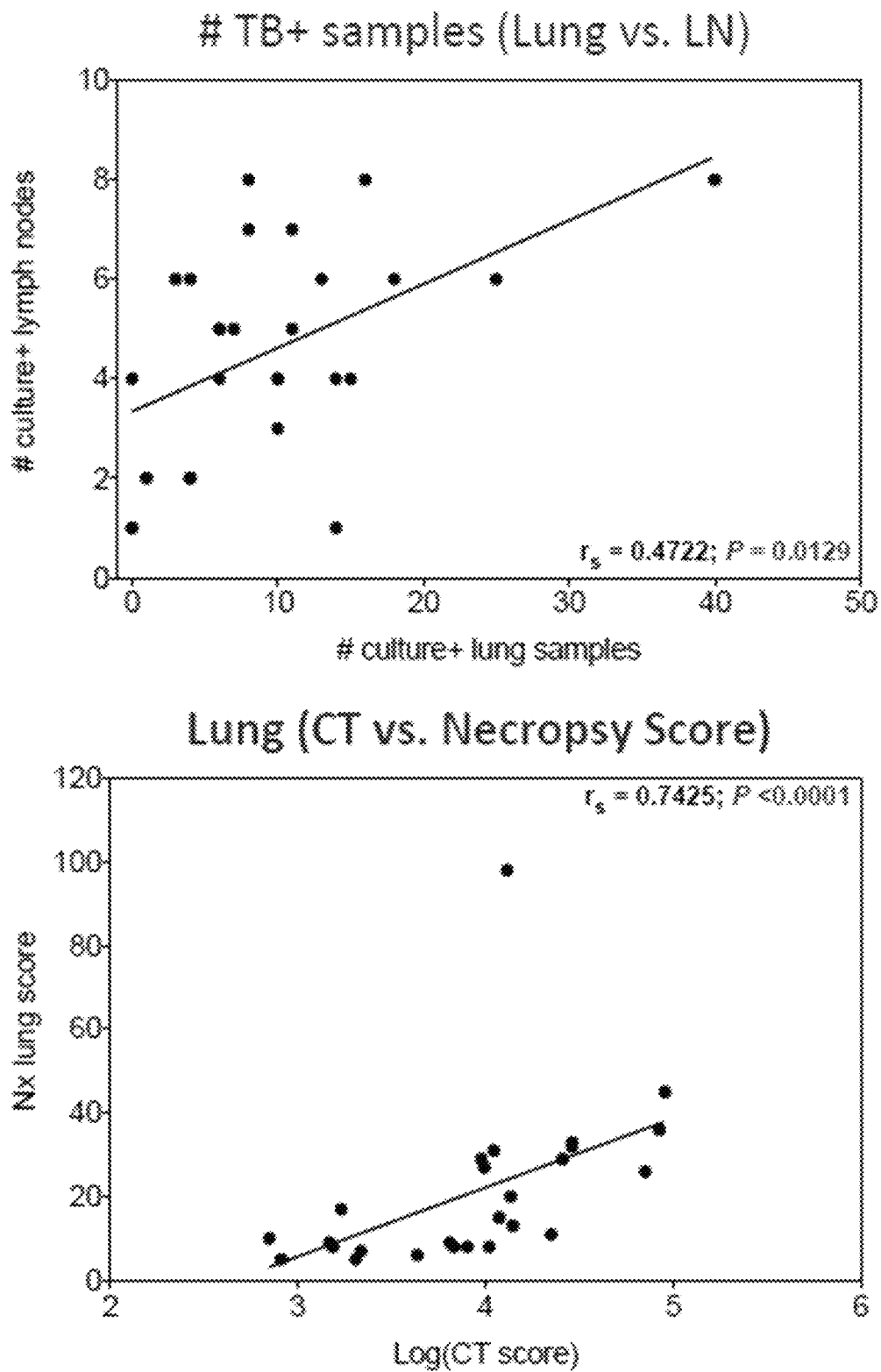
Figure 13:
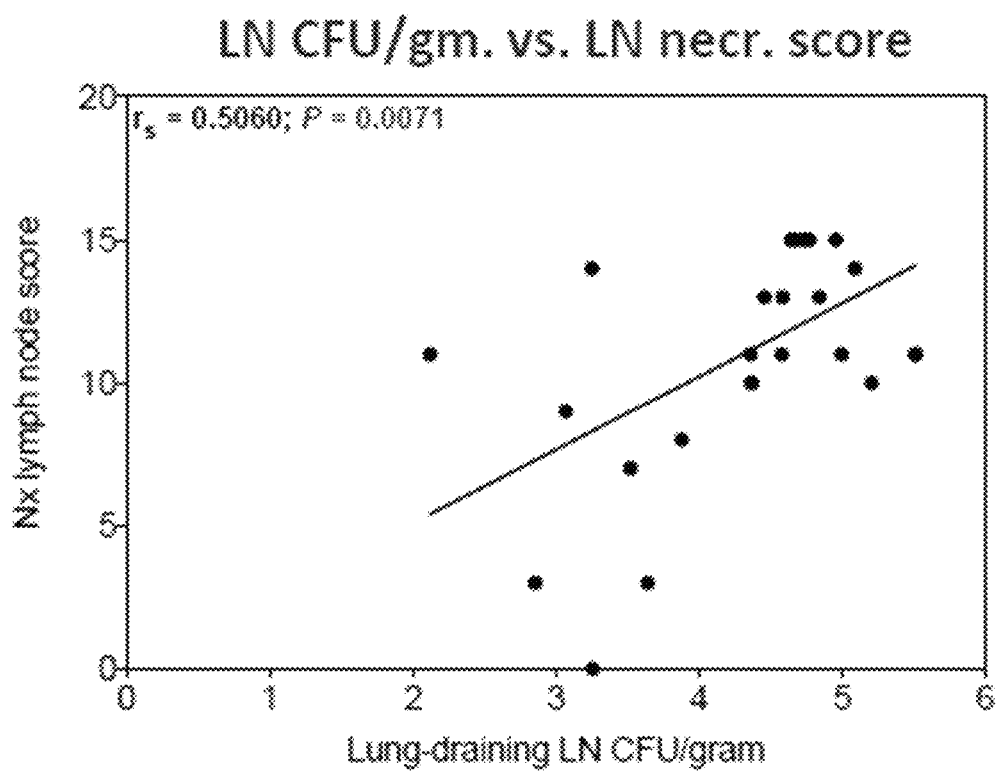
Figure 15:
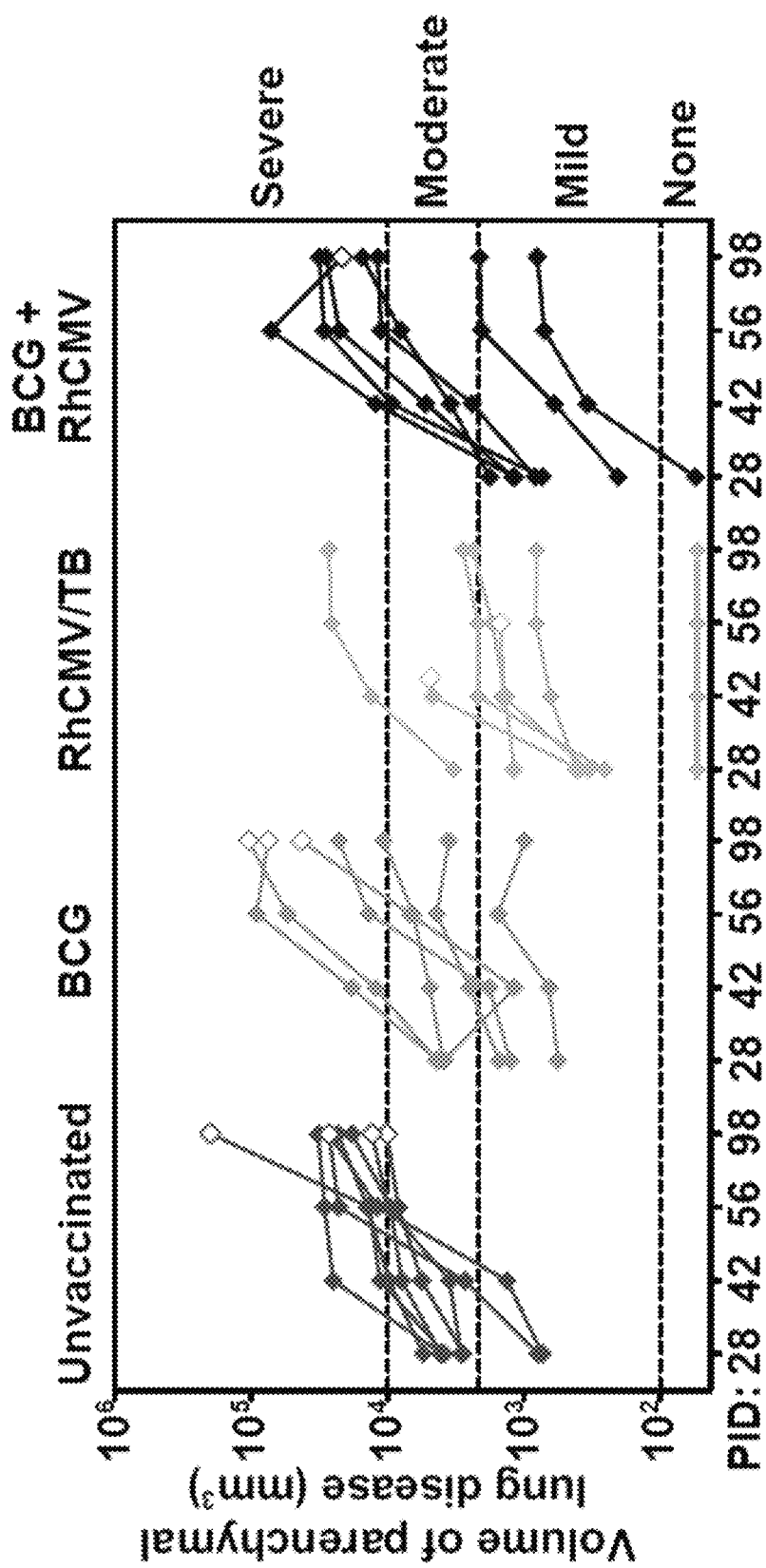
FIG. 15 shows the volume of parenchymal disease present at the time points indicated (or, for data points shown with open symbols, at necropsy).
Figure 16:
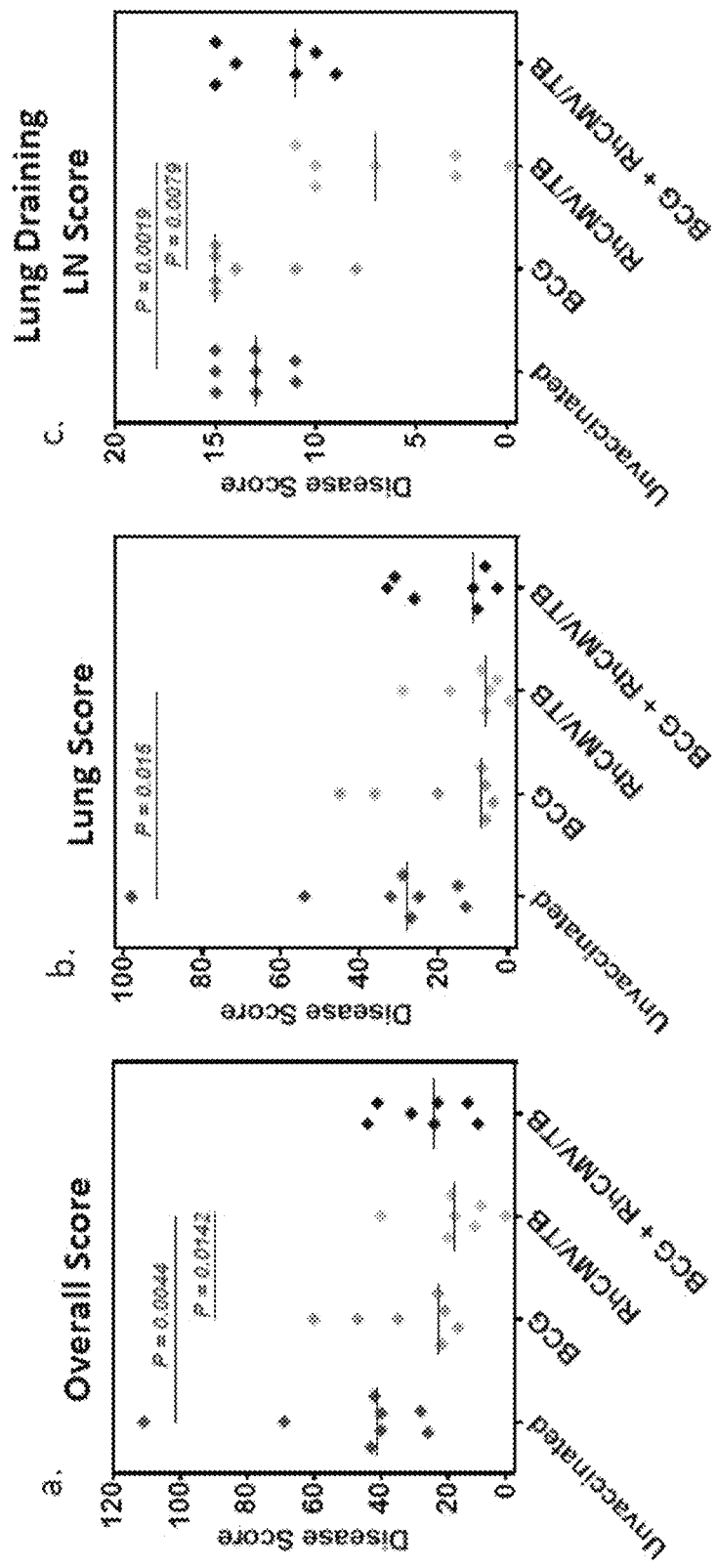
FIG. 16 (panels a, b, and c) shows the necropsy score overall (panel a), in the lung alone (panel b) and in lung draining lymph nodes (panel c).
Figure 17:
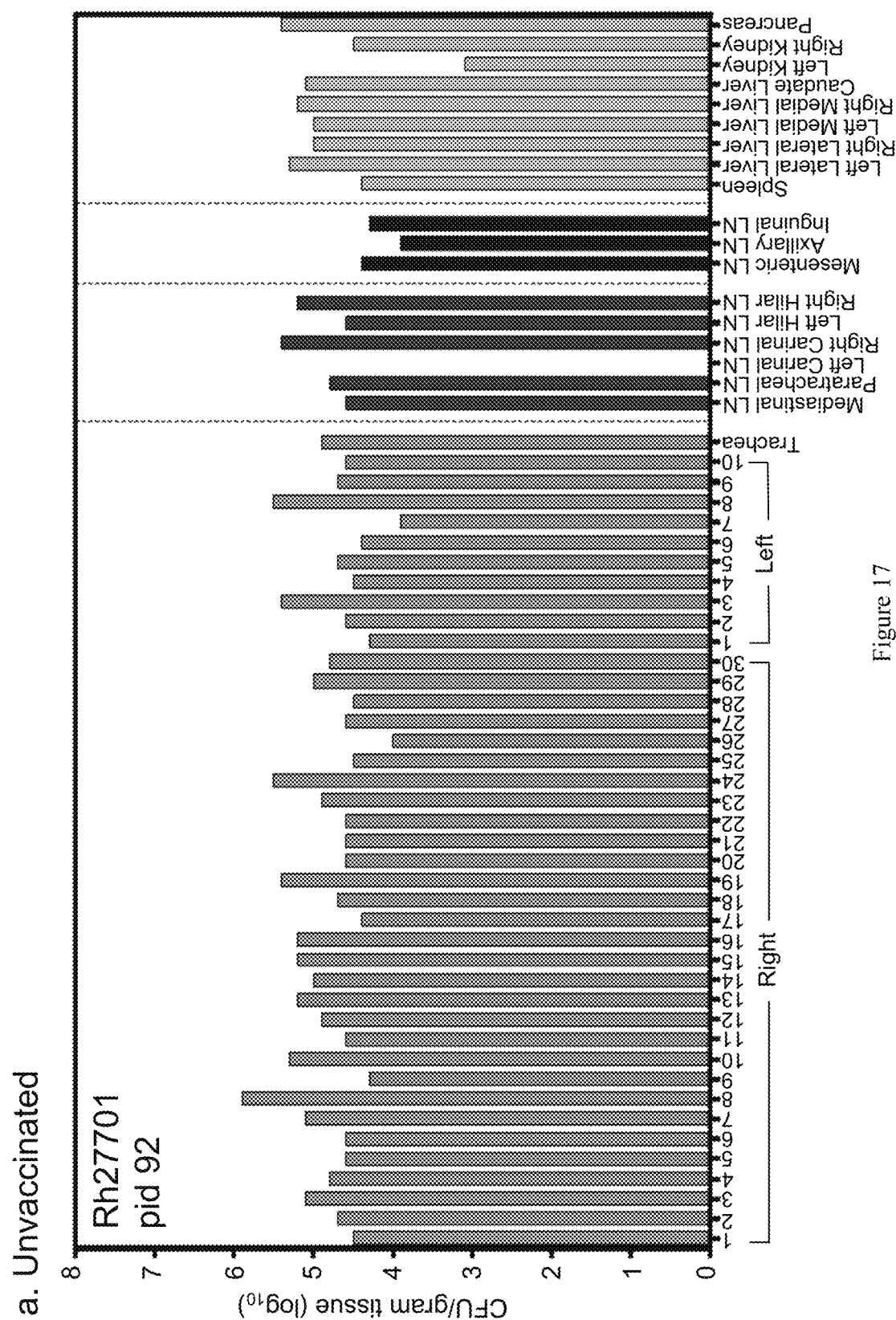
FIG. 17 (panels a, b, c, and d) shows the bacterial burden (CFU/g tissue) present in random samples from the lung/trachea (light blue), draining lymph nodes (red), peripheral lymph nodes (dark blue), and extrapulmonary tissues (green); shown are representative NHP from each group, including unvaccinated (panel a), BCG (panel b), CMV (panel c), and BCG+CMV (panel d).
Figure 17:
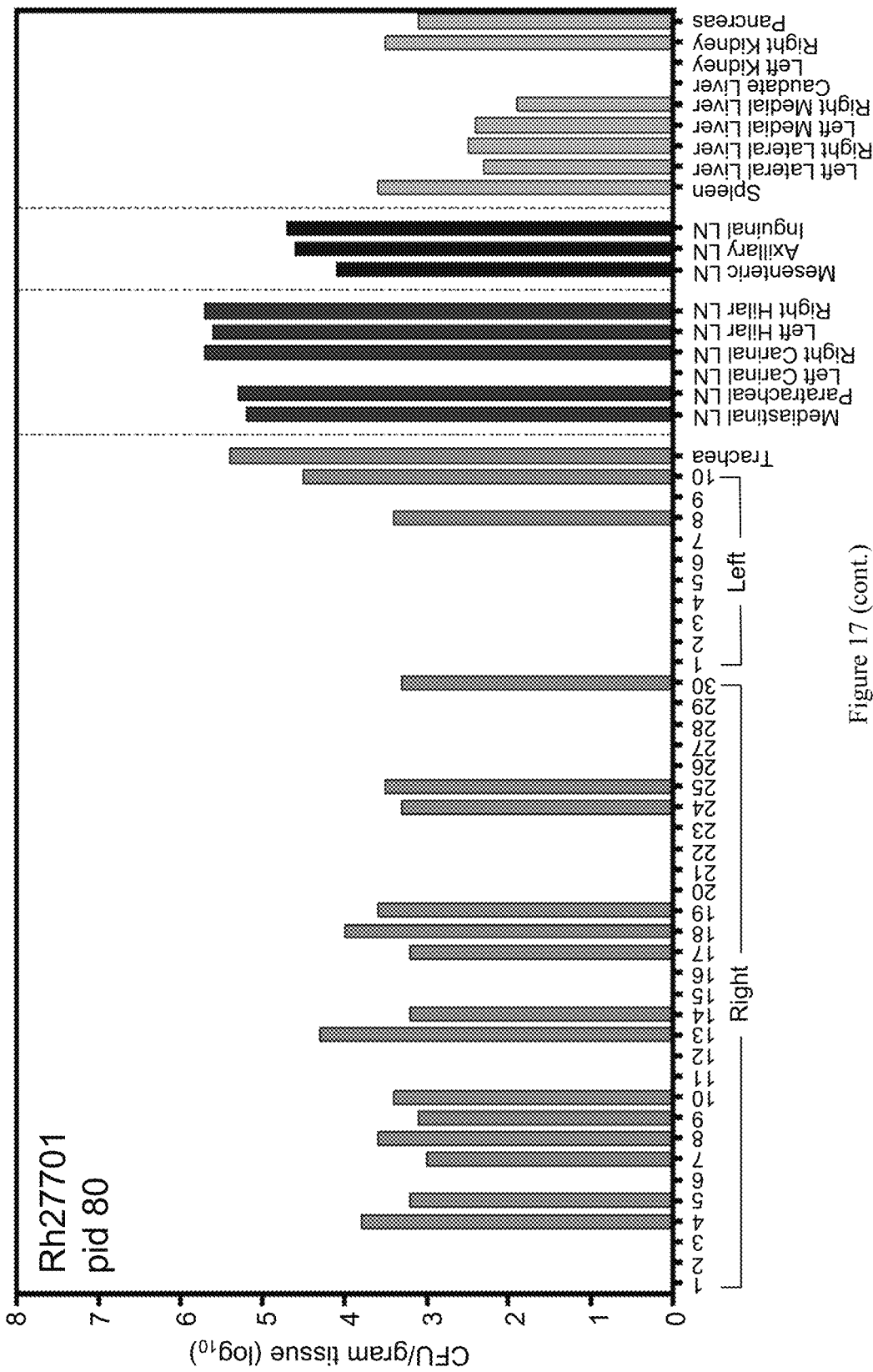
Figure 17:
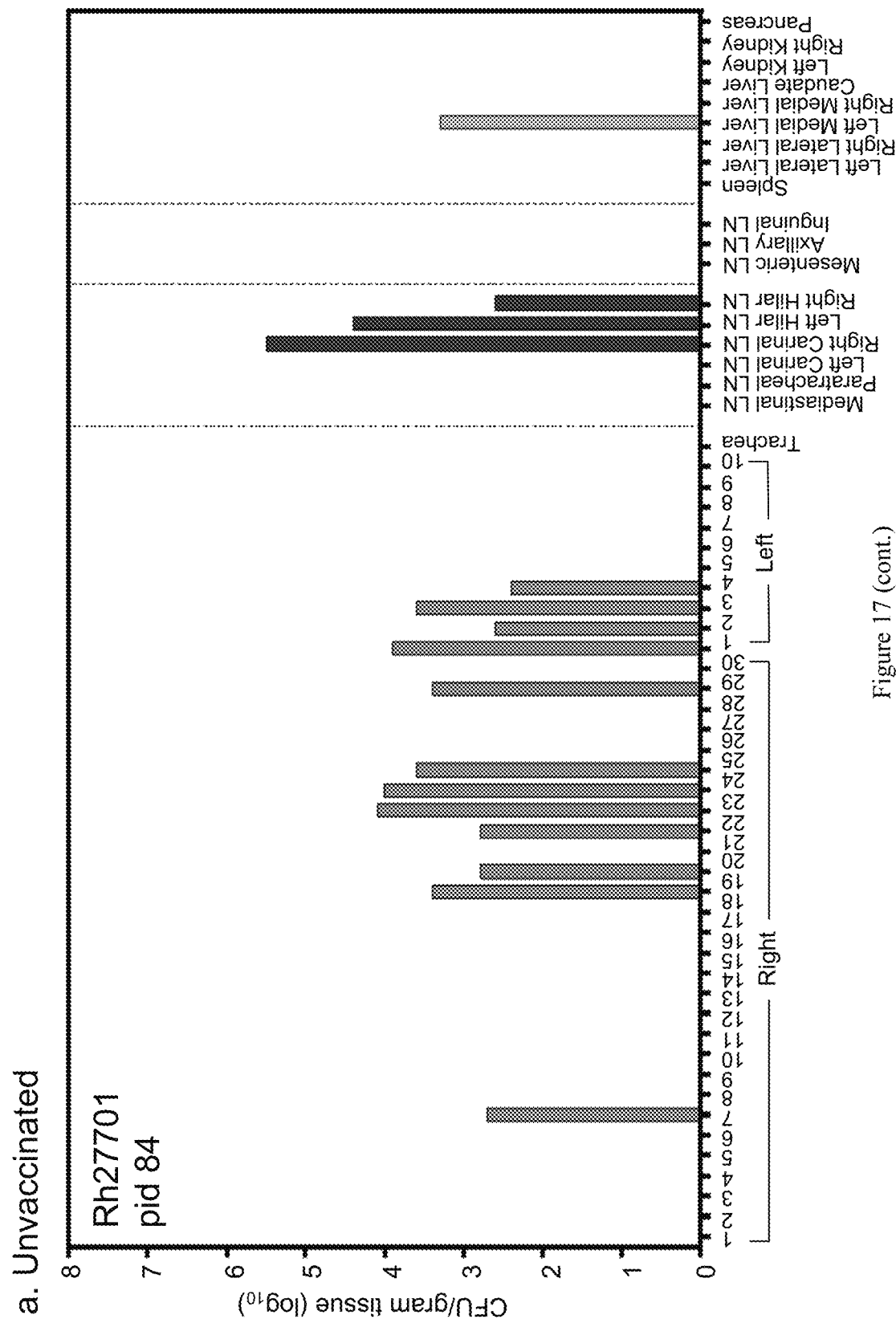
Figure 17:
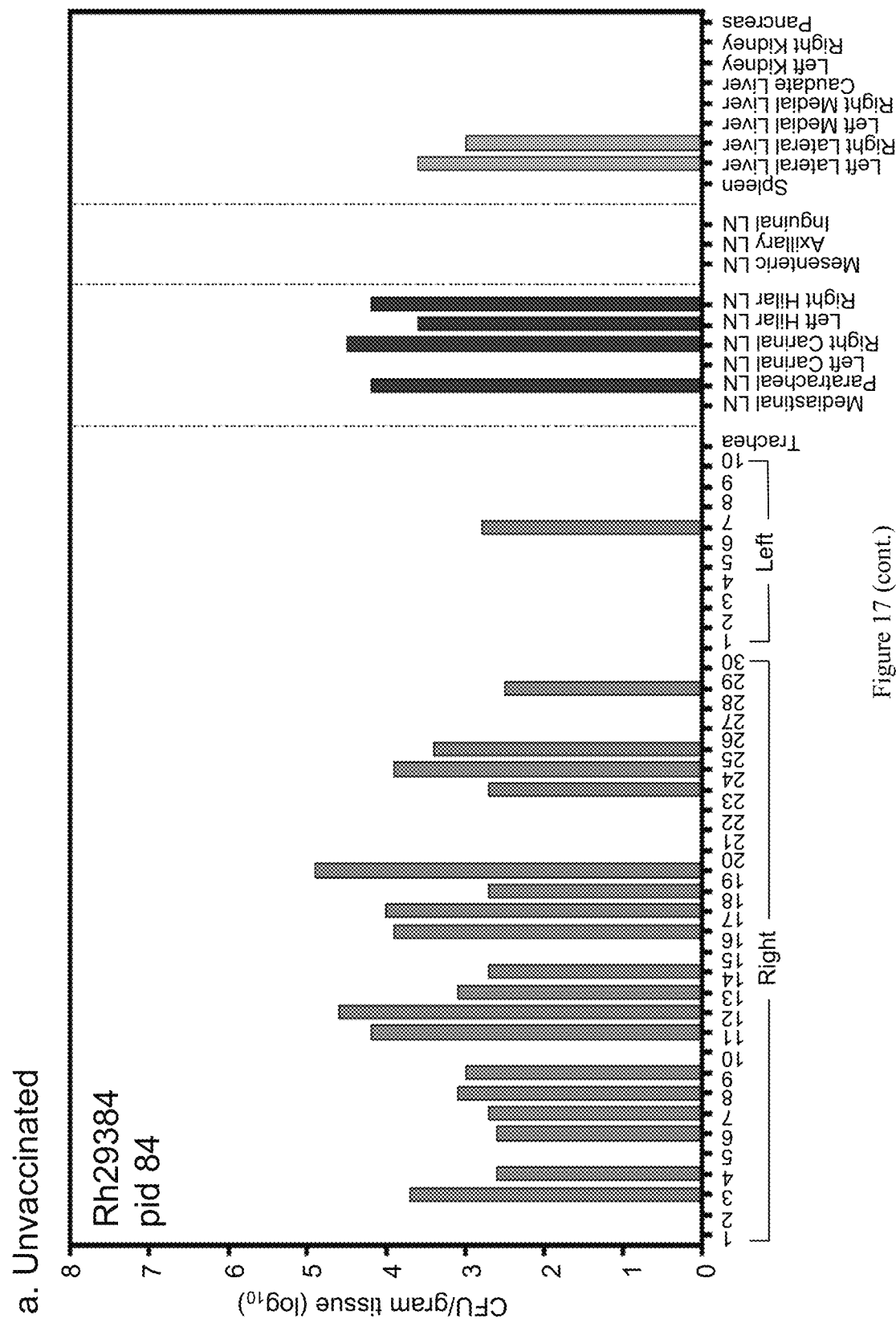
Figure 17:
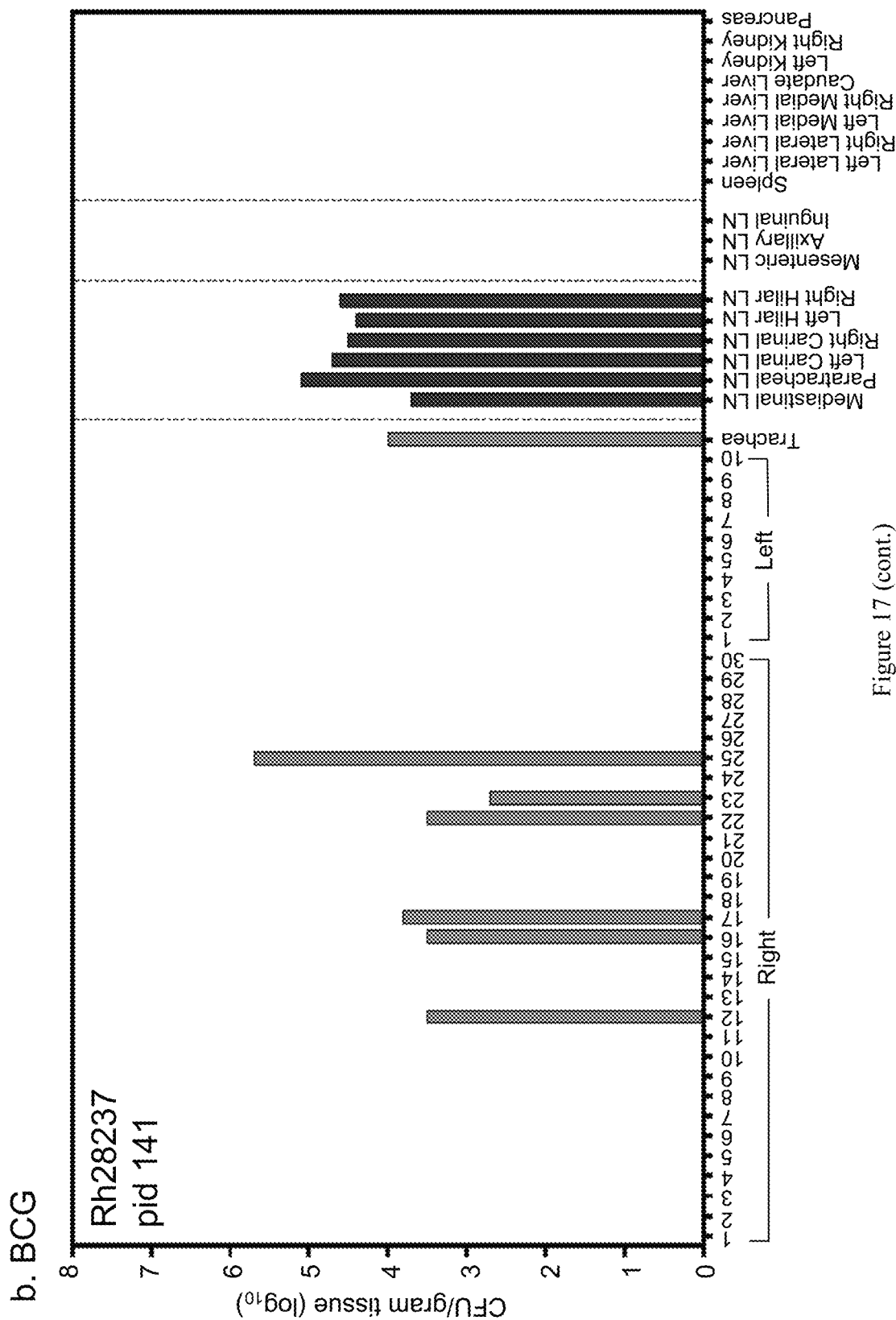
Figure 17:
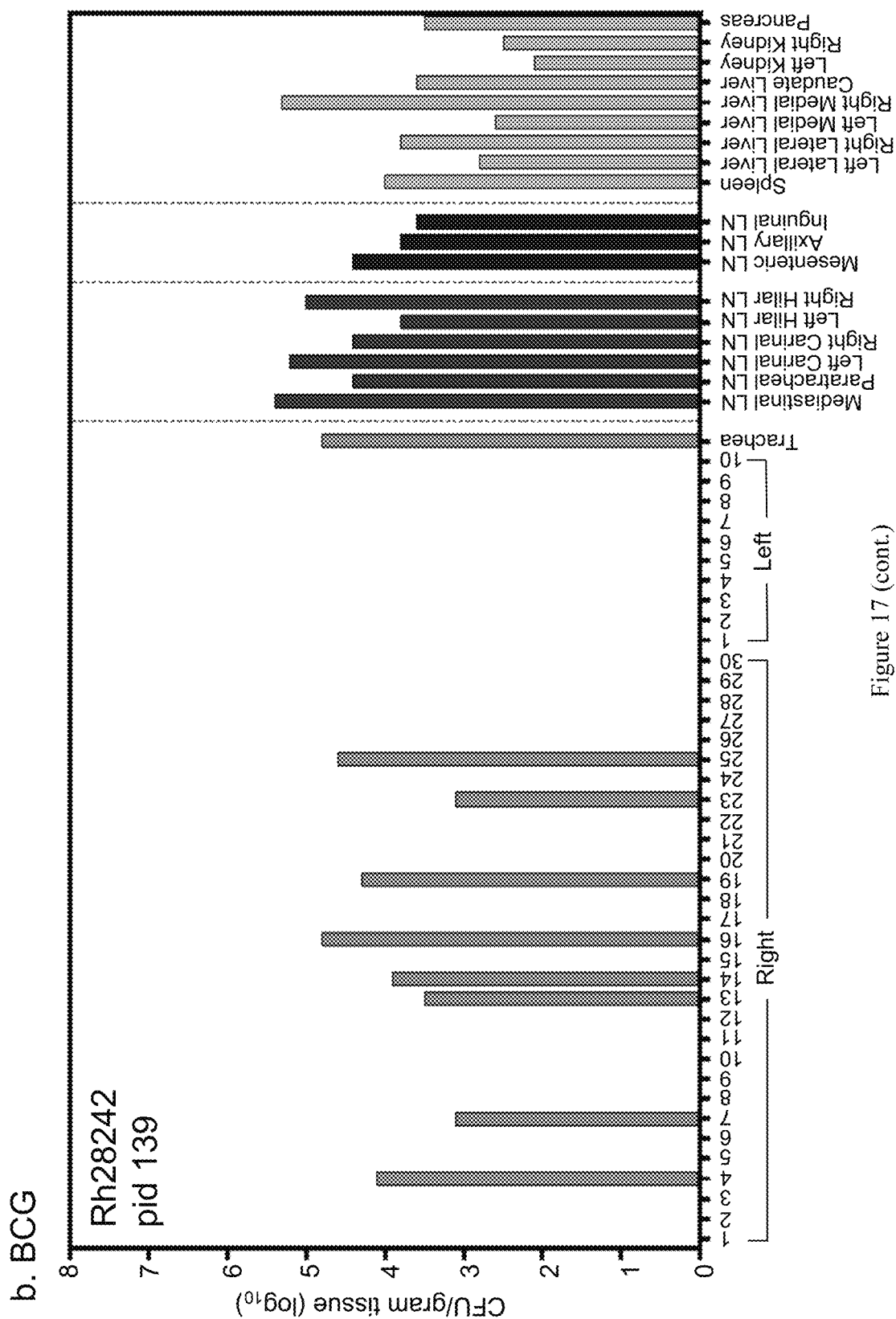
Figure 17:
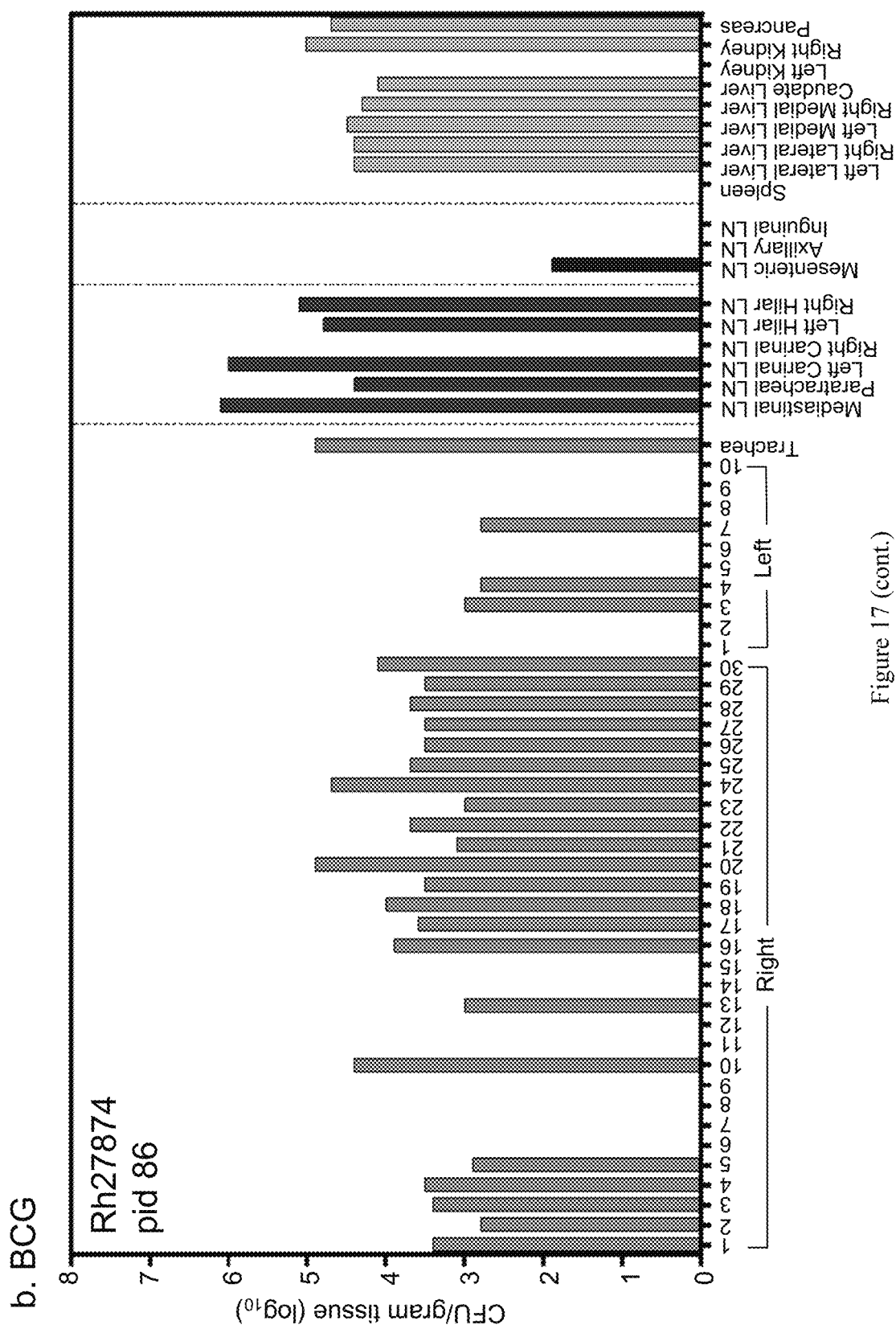
Figure 17:
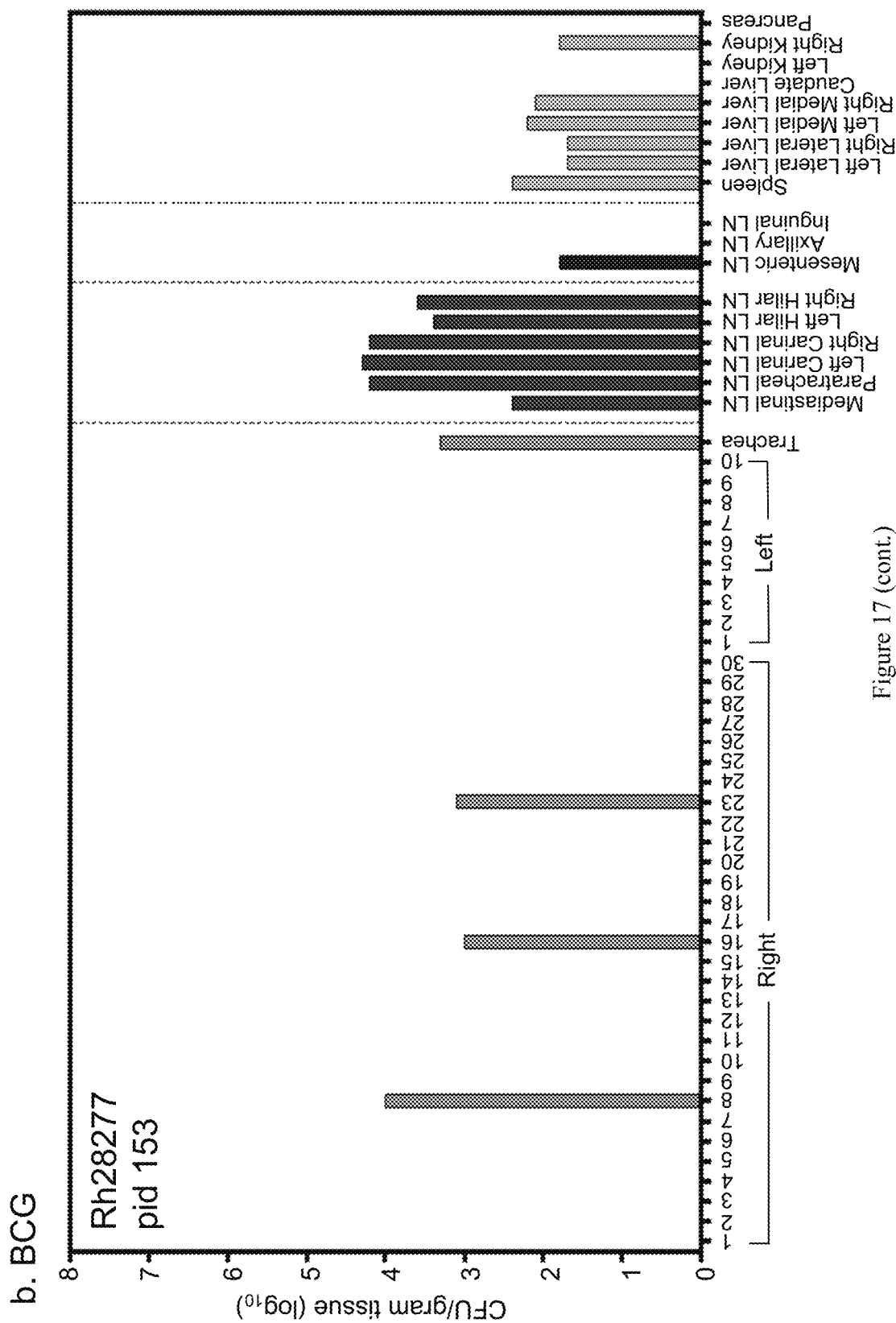
Figure 17:
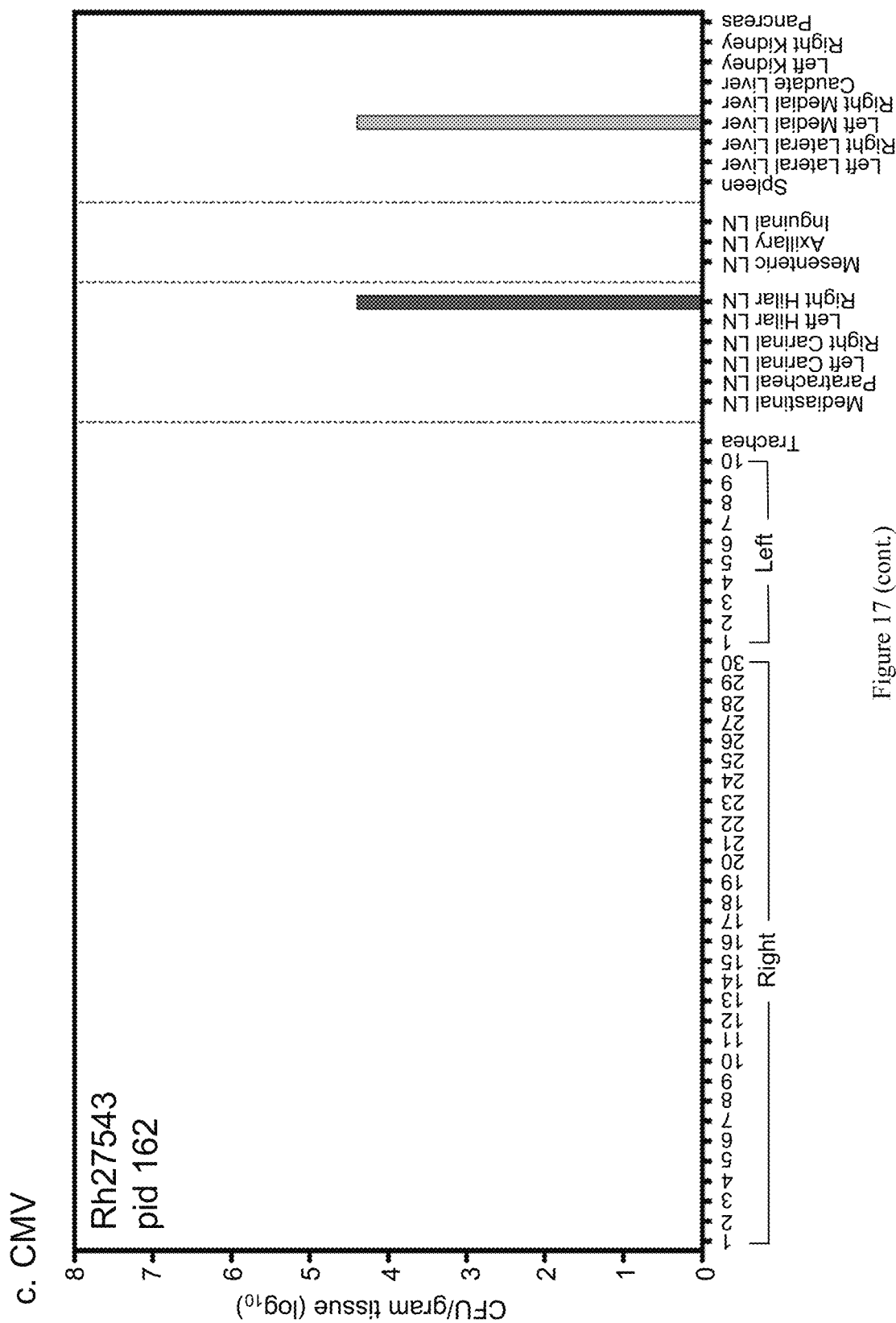
Figure 17:
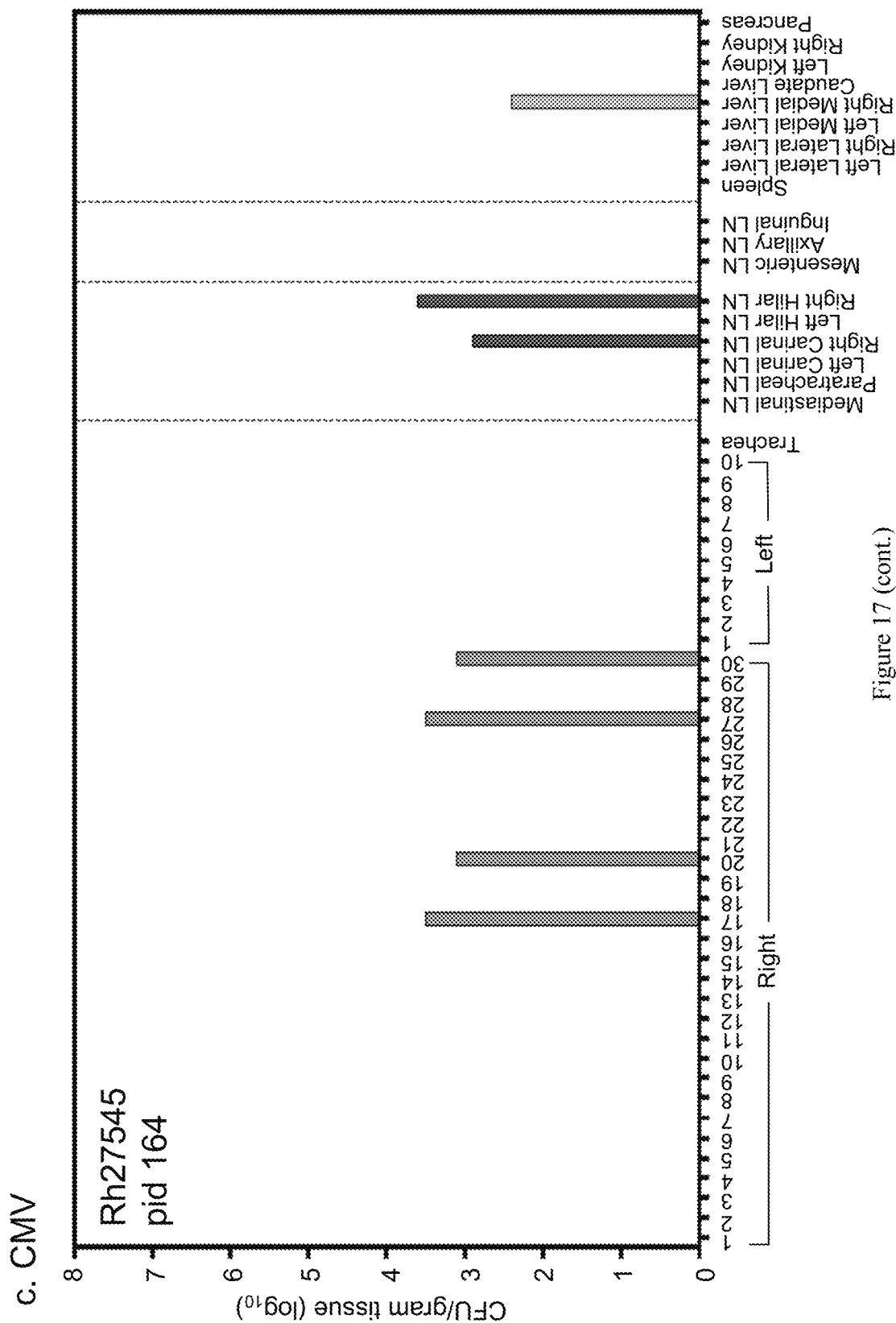
Figure 17:
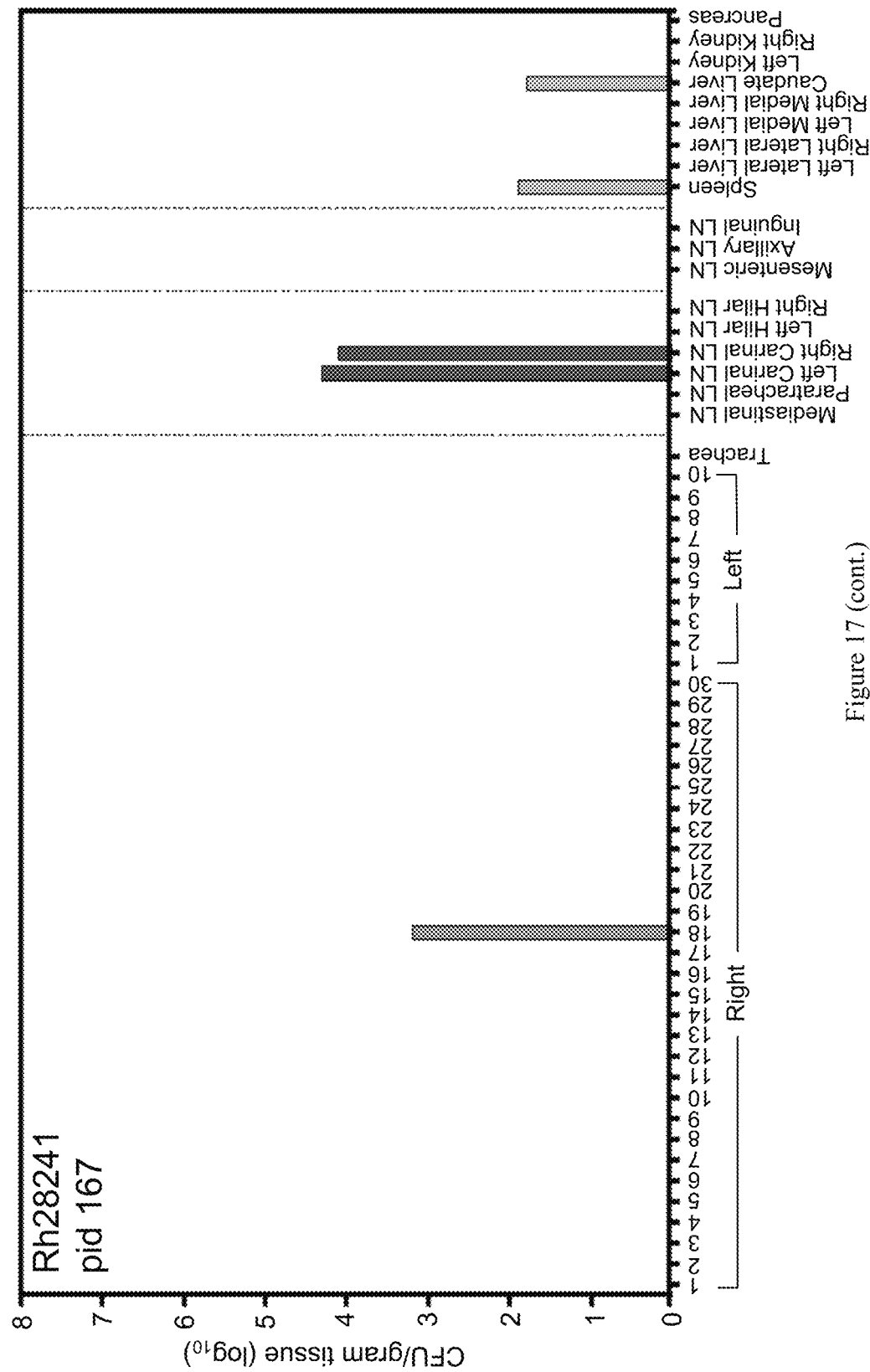
Figure 17:
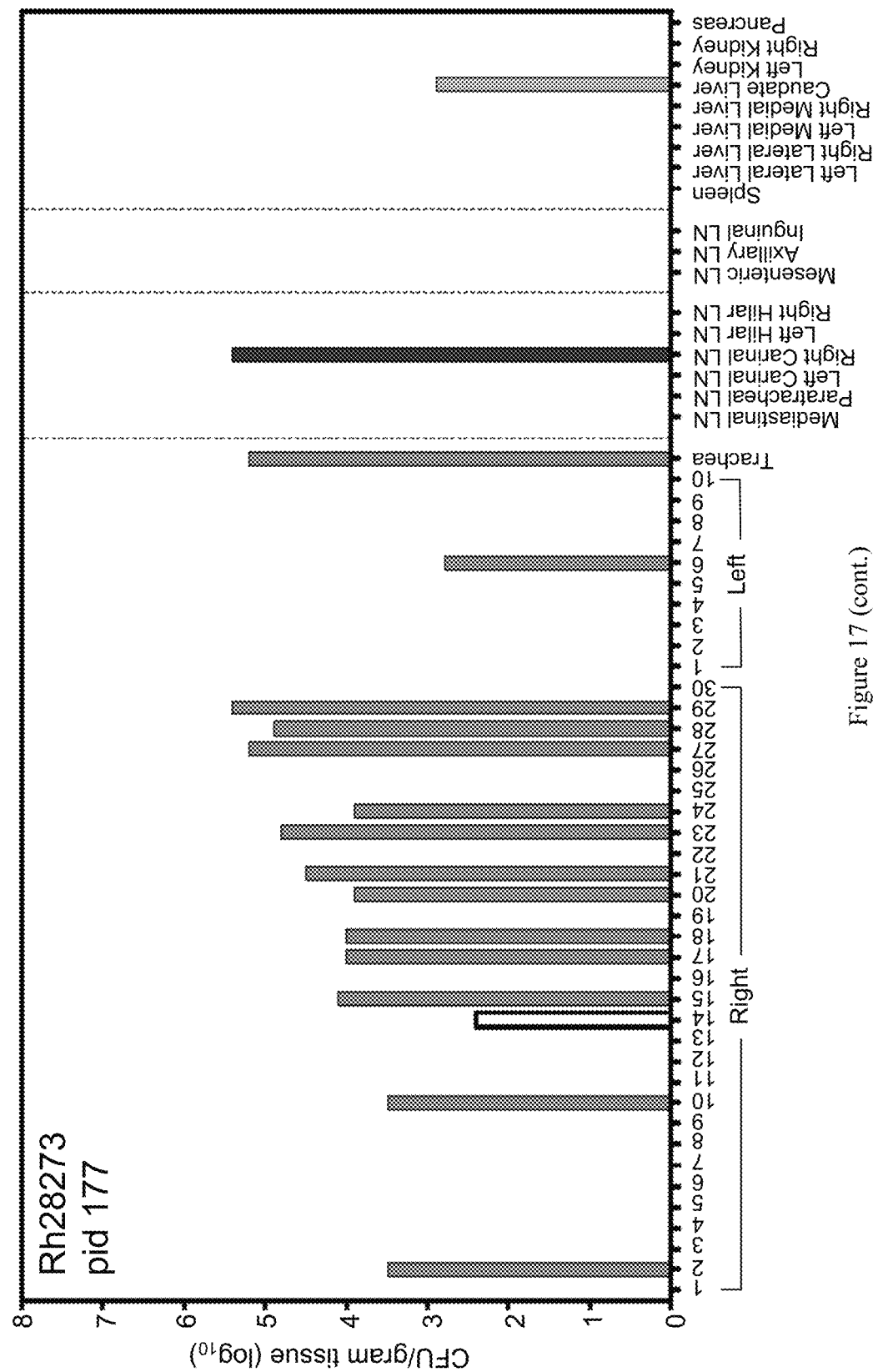
Figure 17:
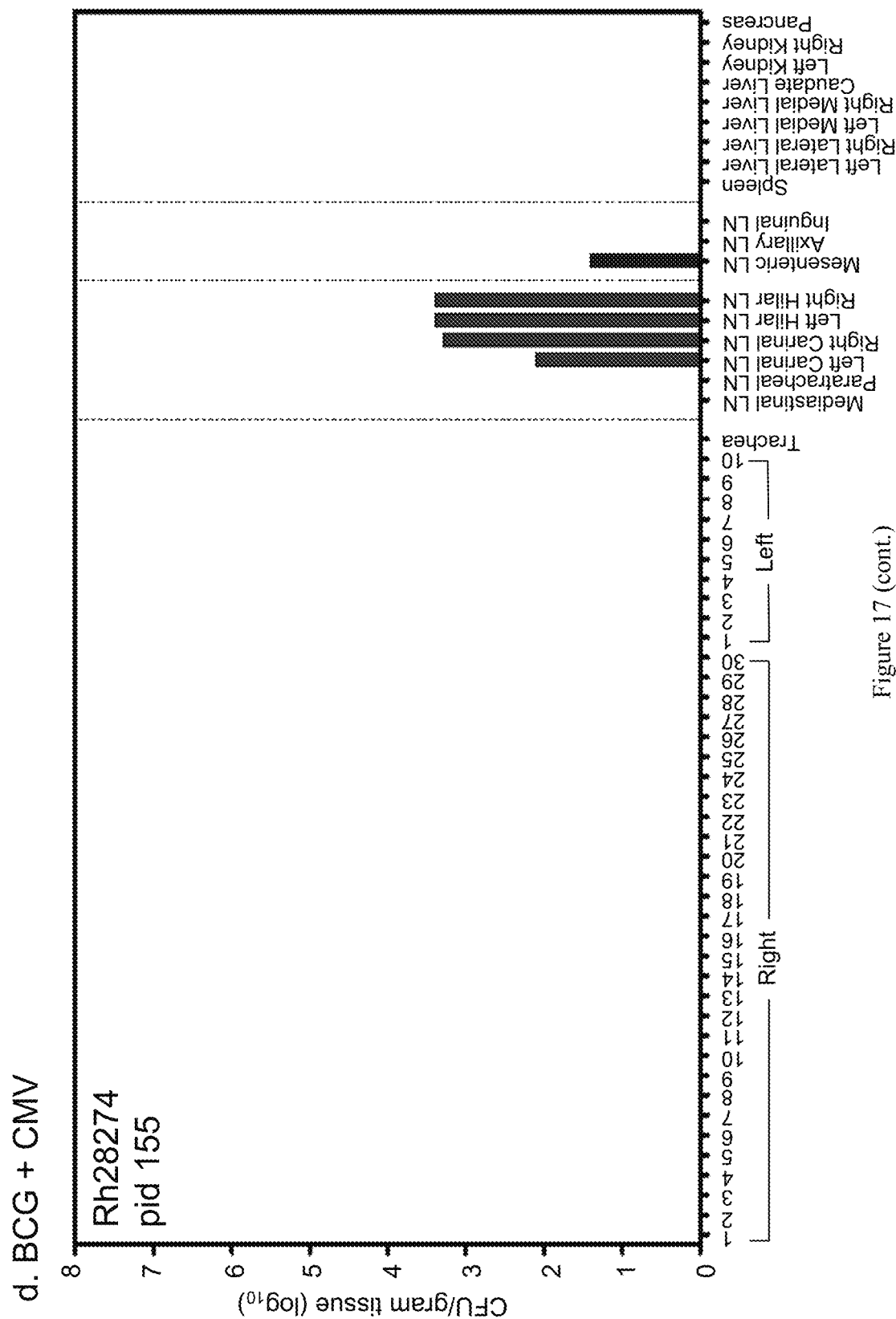
Figure 17:
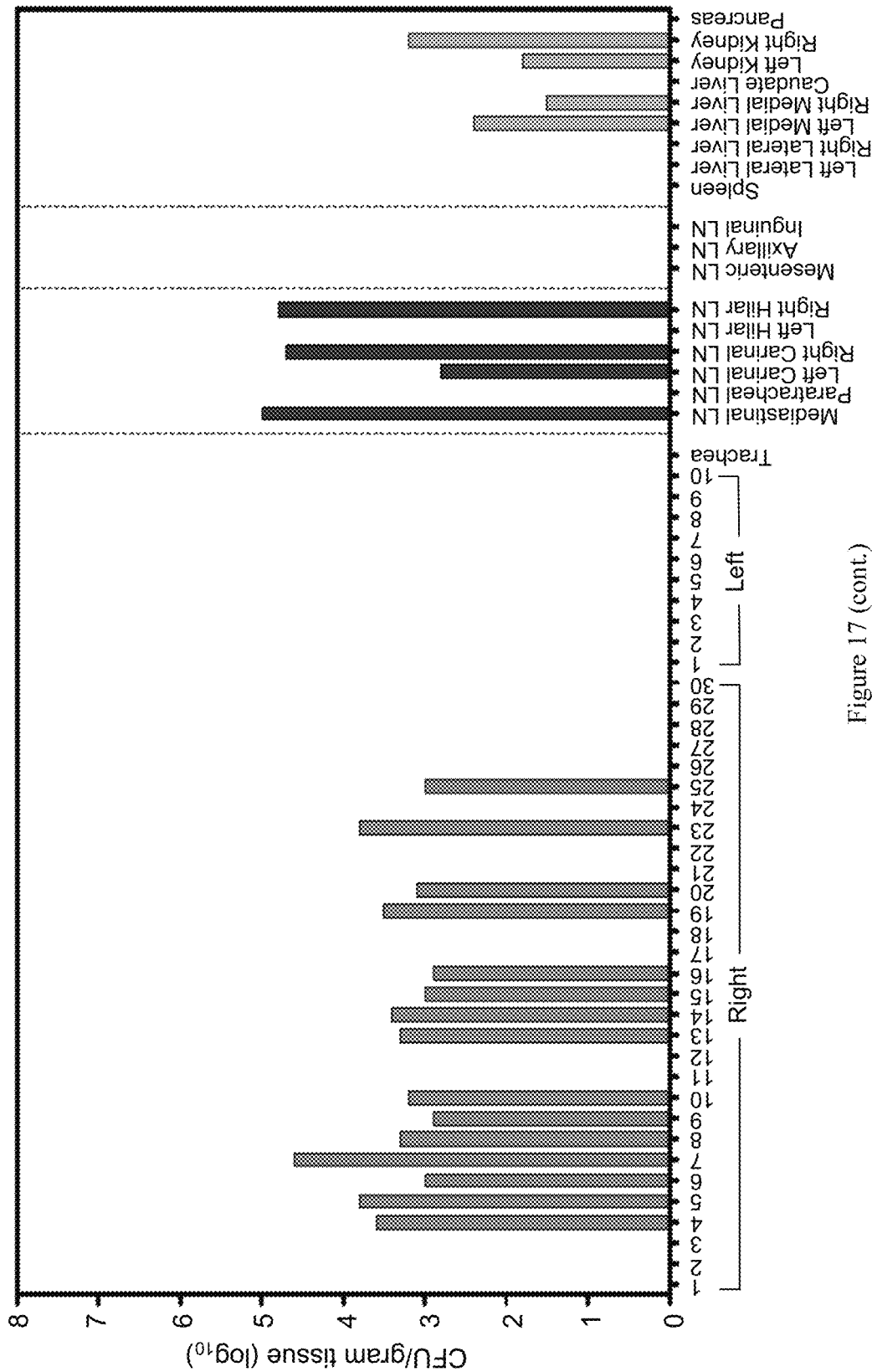
Figure 17:
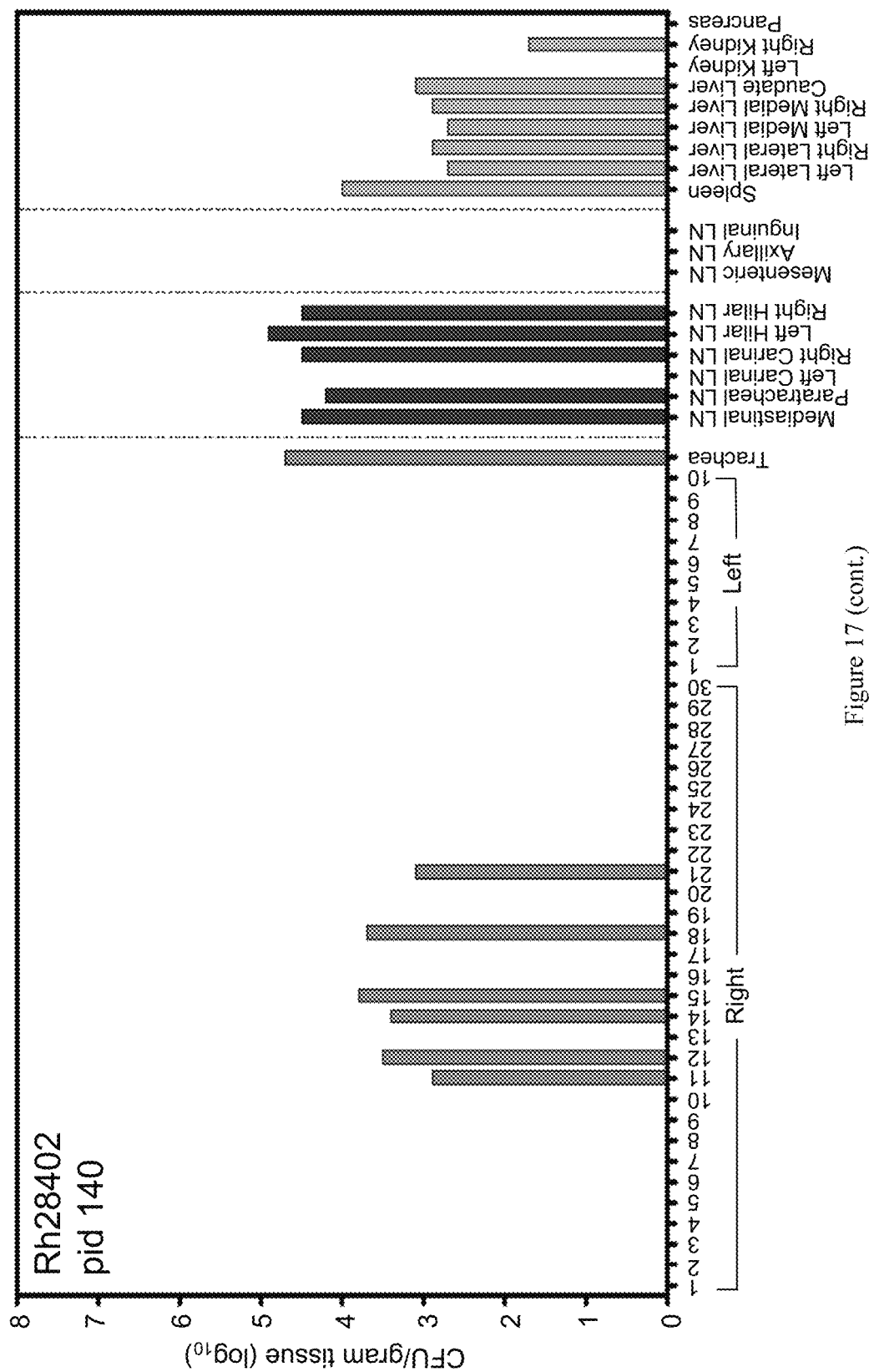
Figure 18:
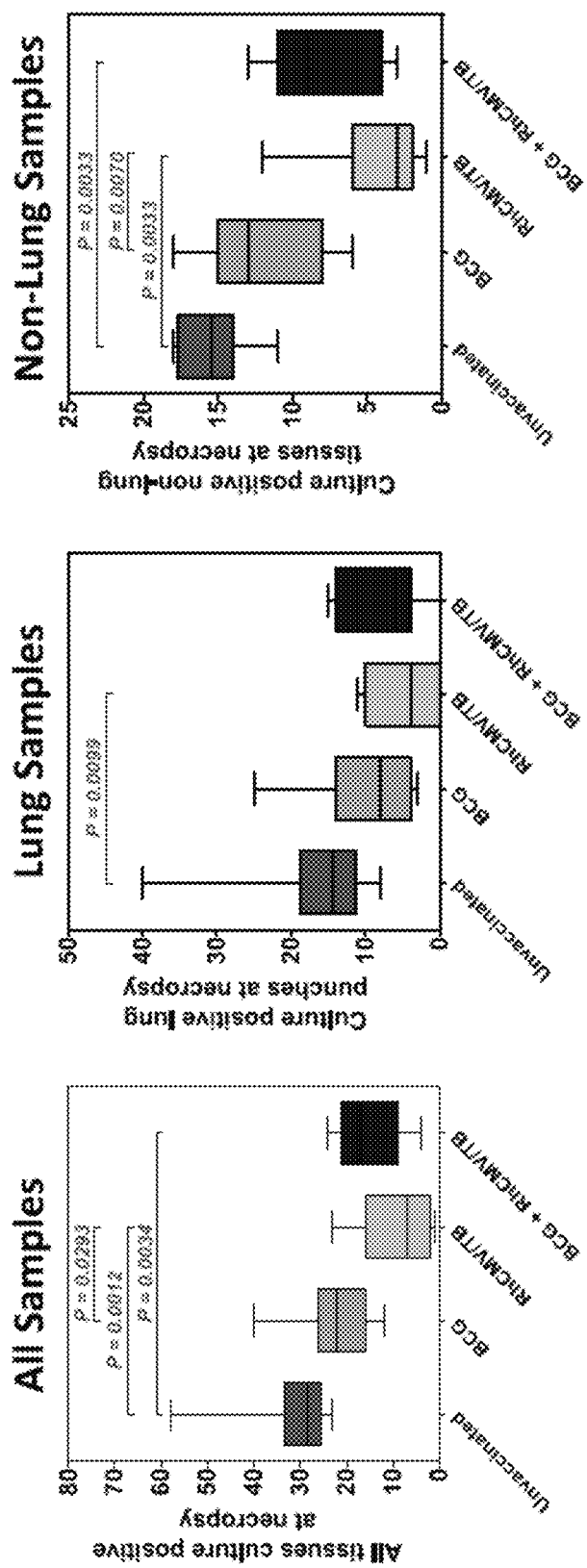
FIG. 18 shows the number of Mtb culture-positive samples present in random biopsies from NHP; overall culture scores are broken out into lung and non-lung compartments.
Figure 19:
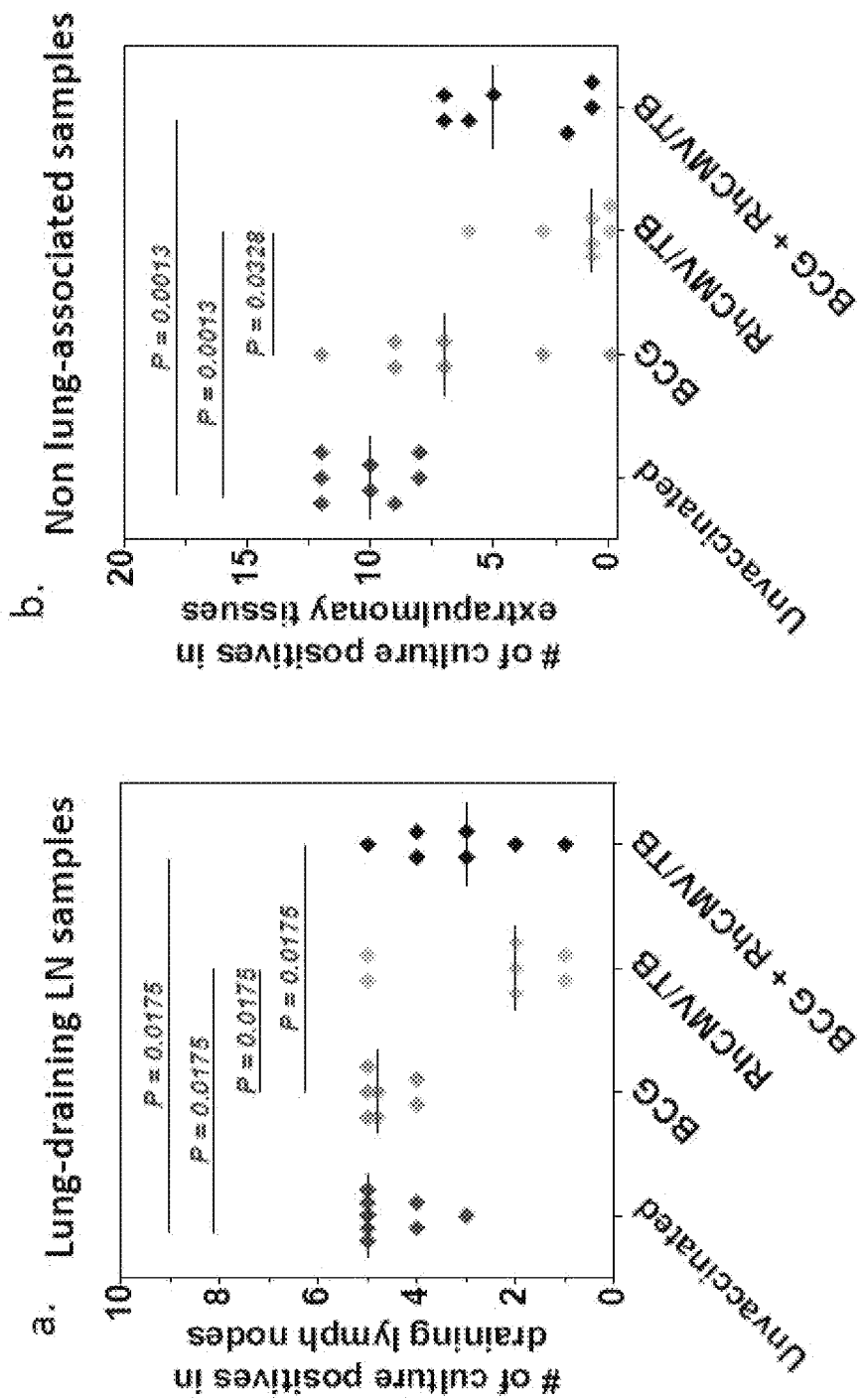
FIG. 19 (panels a and b) shows non-lung samples further broken out into lung draining lymph node samples (panel a) and non-lung associated samples (panel b); non-lung associated samples include liver, kidney, and spleen.
Figure 20:
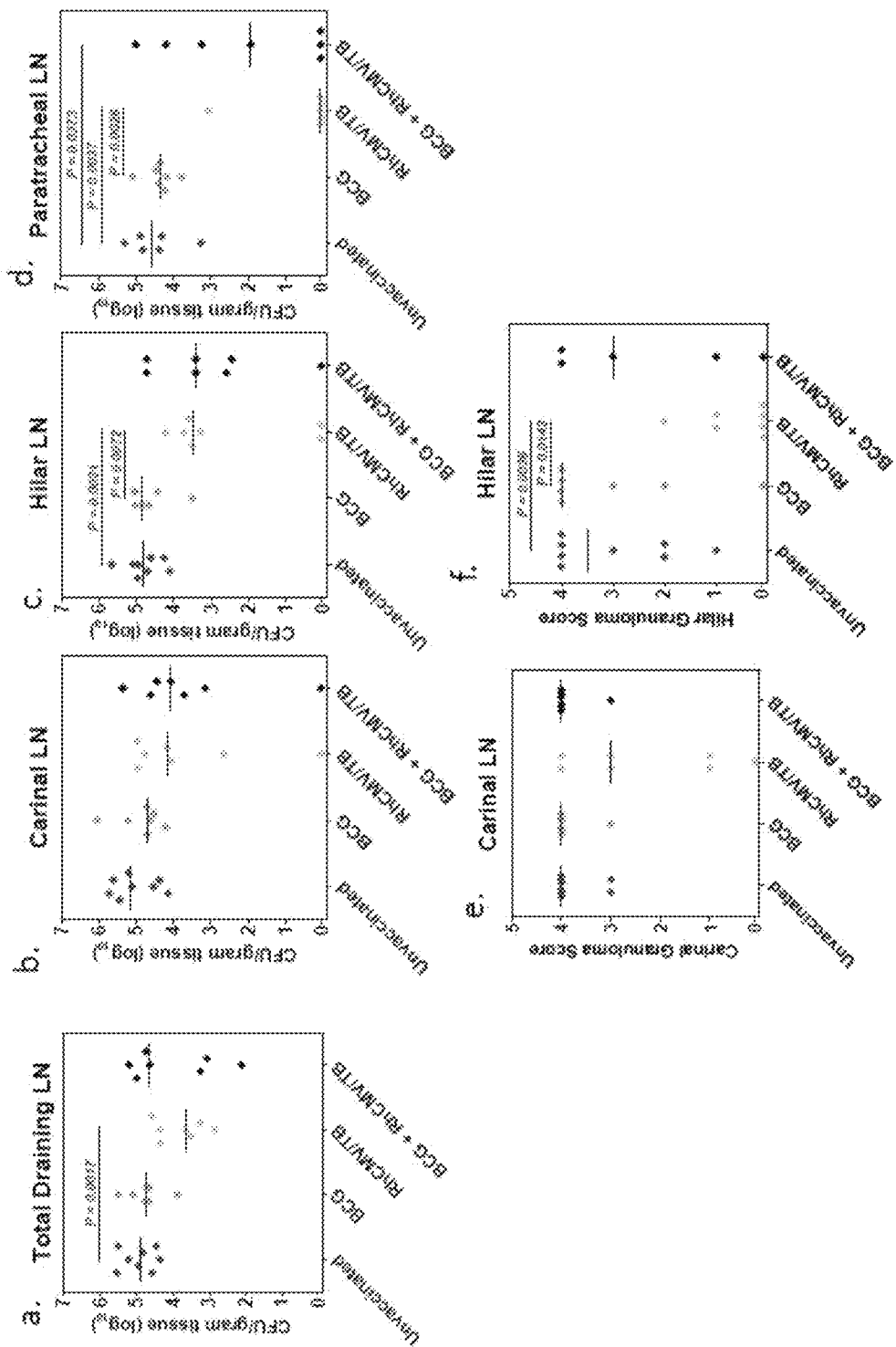
FIG. 20 (panels a, b, c, d, e, and f) shows the bacterial burden in all lung-draining lymph nodes (panel a), as well as specific lung draining lymph nodes (panels b, c, and d); also included is the granuloma score for the carinal (panel e) and hilar (panel f) lymph nodes.

FIG. 13 shows the correlation of various efficacy criteria (i.e., necropsy <16 weeks for cause, and >16 weeks randomized) for a bi-weekly and pre-necropsy CT Scan (lung disease only). The necropsy score accounted for the size, number and distribution of gross lesions in the lung, lung draining lymph nodes, and distal sites. In particular, 40 lung samples (30 right; 10 left), 9 lymph nodes (6 lung draining and 3 non-mediastinal), and 9 extra-pulmonary tissue (5 liver, 2 kidney, spleen, and pancreas) were analyzed by sterology. FIG. 14 shows CT Scans at 14 weeks post-infection. FIG. 15 shows the quantification of pulmonary disease by CT scan. FIG. 16 shows the gross pathology scores. These scores reflect the number of granulomas present, the size of the granulomas, and any complex pathologies (pleural thickening, pneumonia, etc). Included are overall scores (which include lung, lung draining lymph nodes, liver and spleen), as well as separated scores for the lung and lung draining lymph nodes. FIGS. 17 and 18 show the extent of disease and dissemination. RhCMV/TB vector vaccination alone achieved 73% efficacy against overall disease spread, which was statistically superior to both unvaccinated and BCG vaccination alone. Monkeys primed with BCG 6 weeks before RhCMV/TB vaccination were still significantly protected against overall disease spread, but protection was less than that observed in the RhCMV/TB vaccination alone. FIG. 19 shows the extent of disease and dissemination in non-lung samples. FIG. 20 shows the extent of disease and dissemination in lymph nodes.

Figure 21:
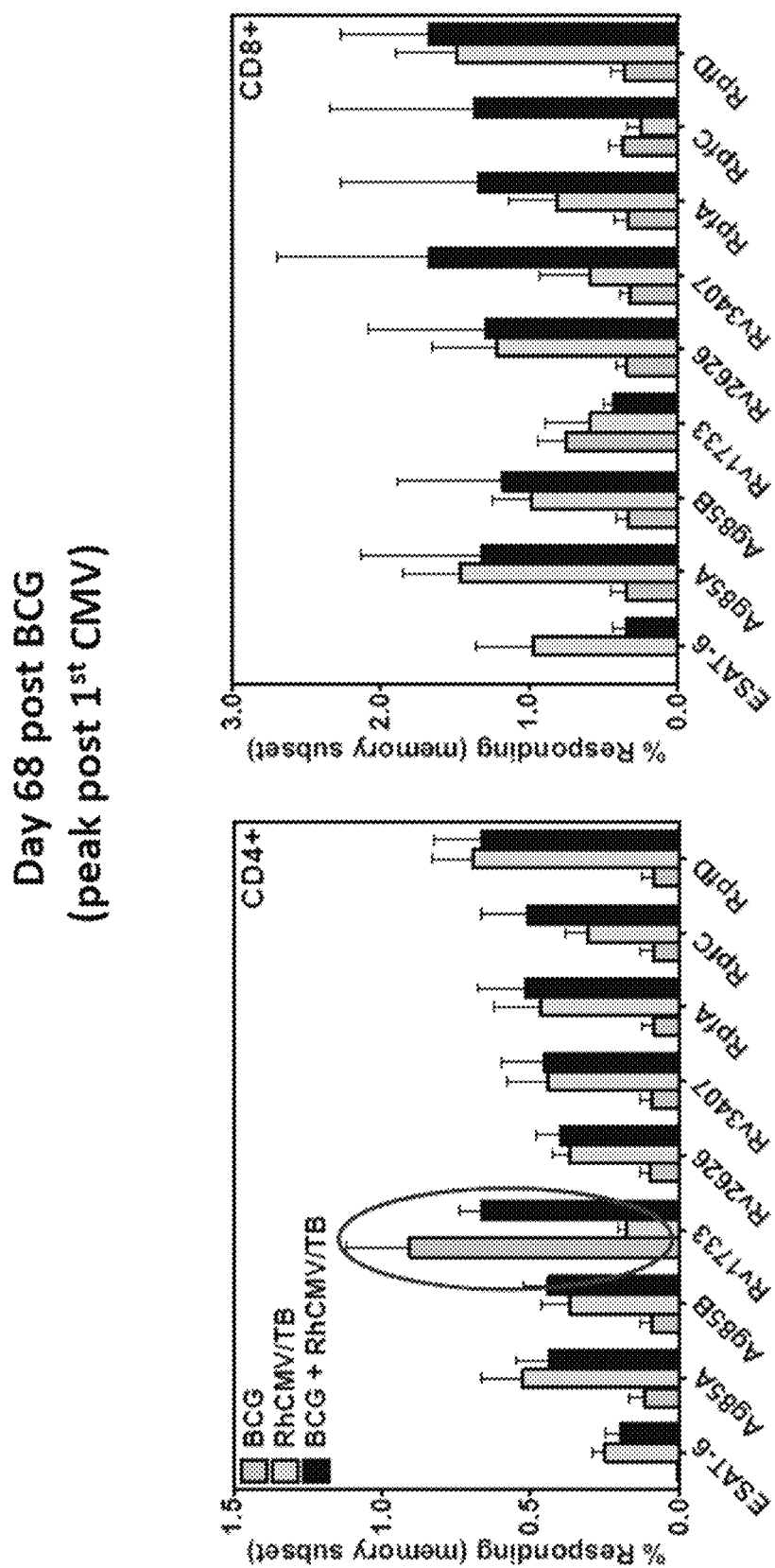
FIG. 21 shows the T cell response against each antigen is shown at various time points throughout the vaccination phase.
Figure 21:
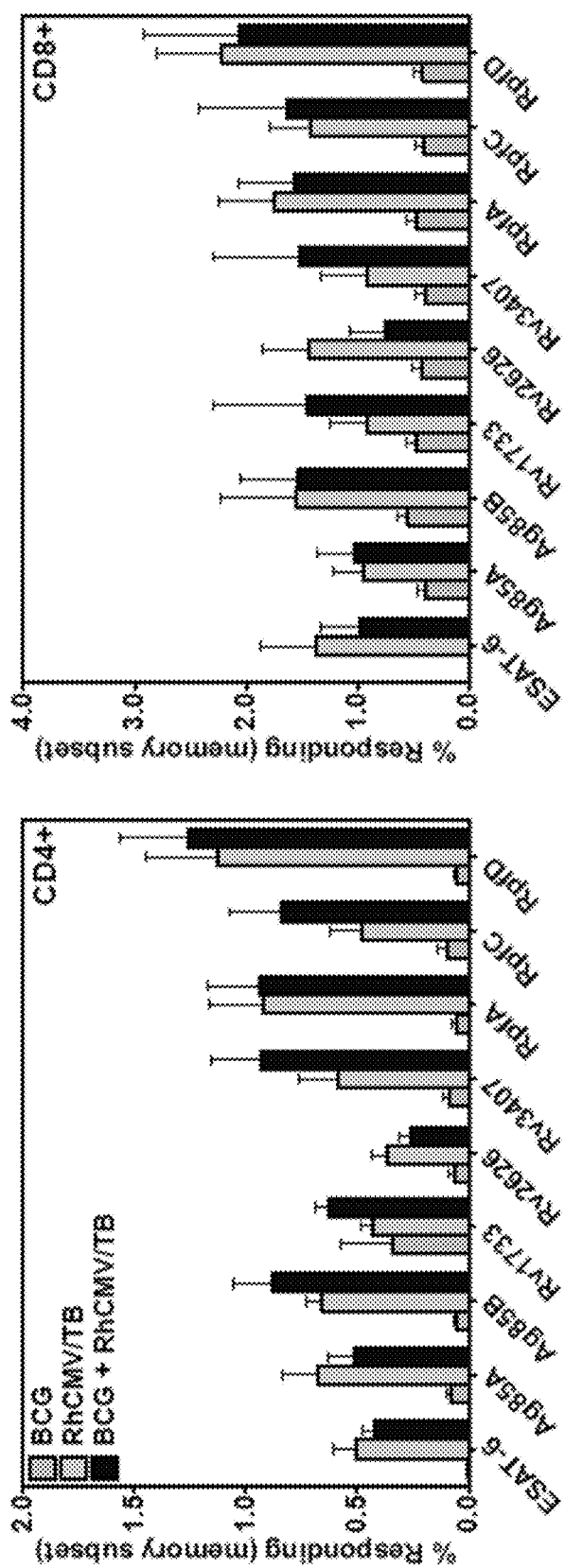
Figure 21:
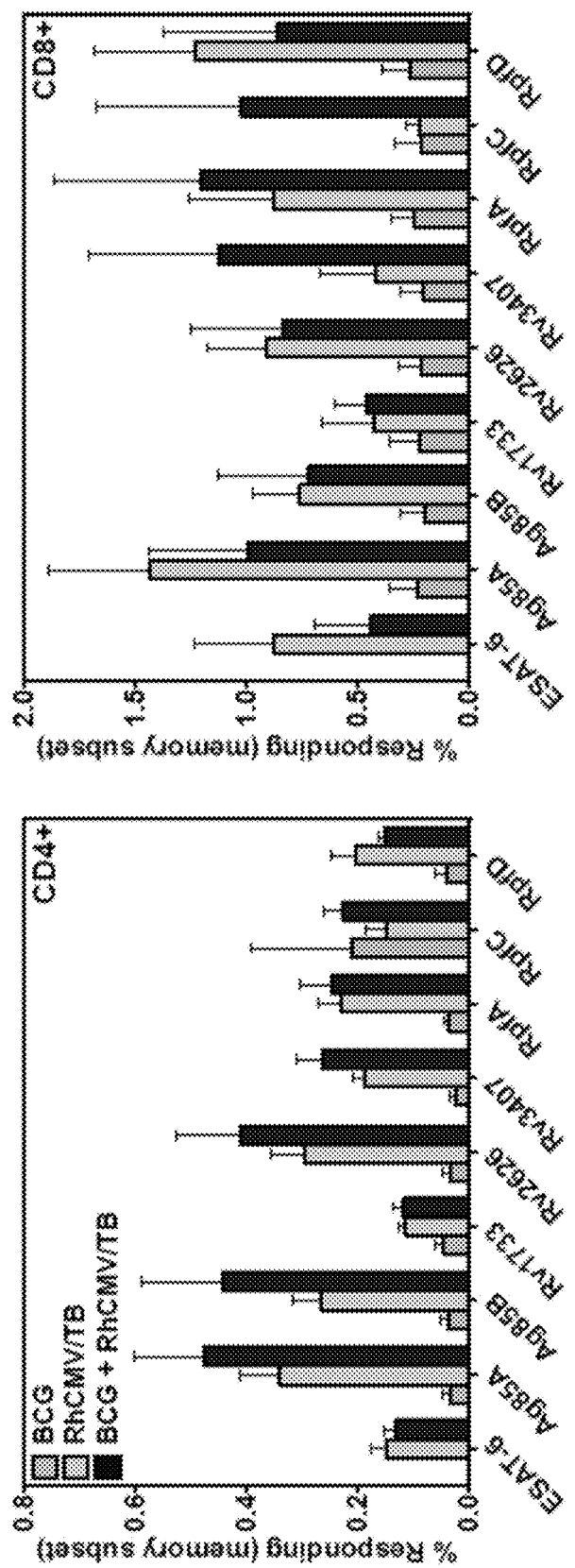
Figure 22:
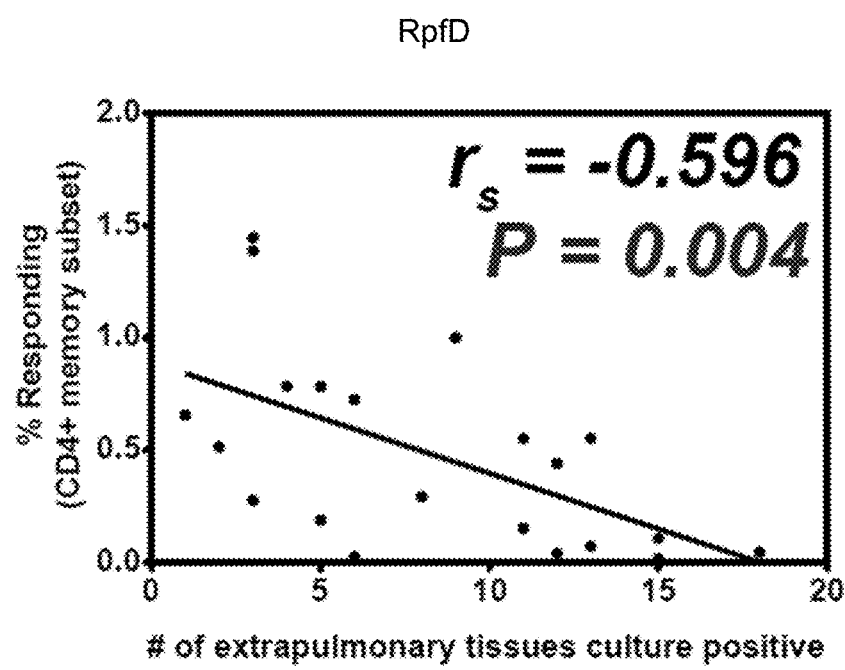
FIG. 22 shows a correlation between the CD4 T cell response against each antigen, shown at various time points throughout the vaccination phase, and the extent of extrapulmonary spread.
Figure 22:
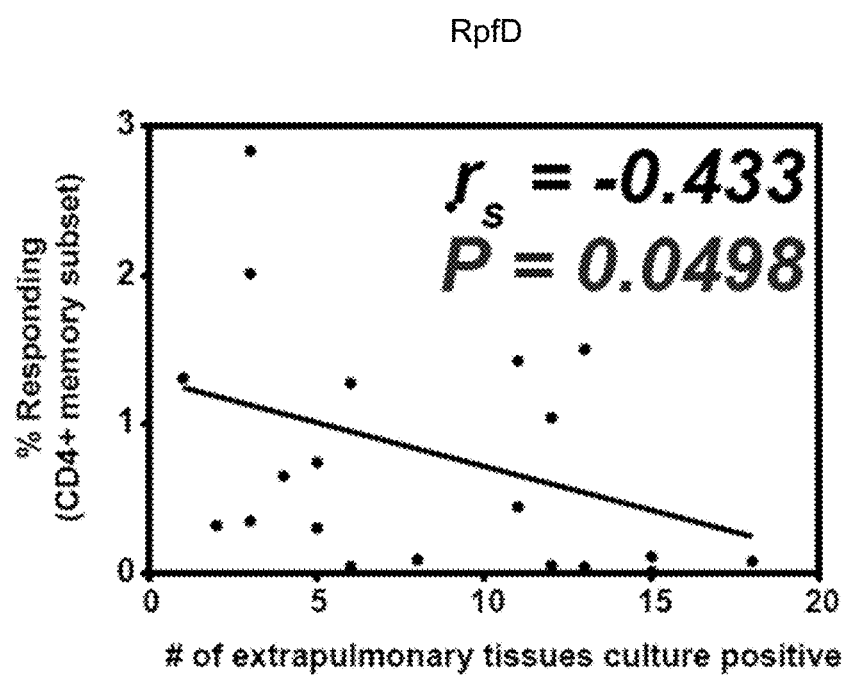
Figure 22:
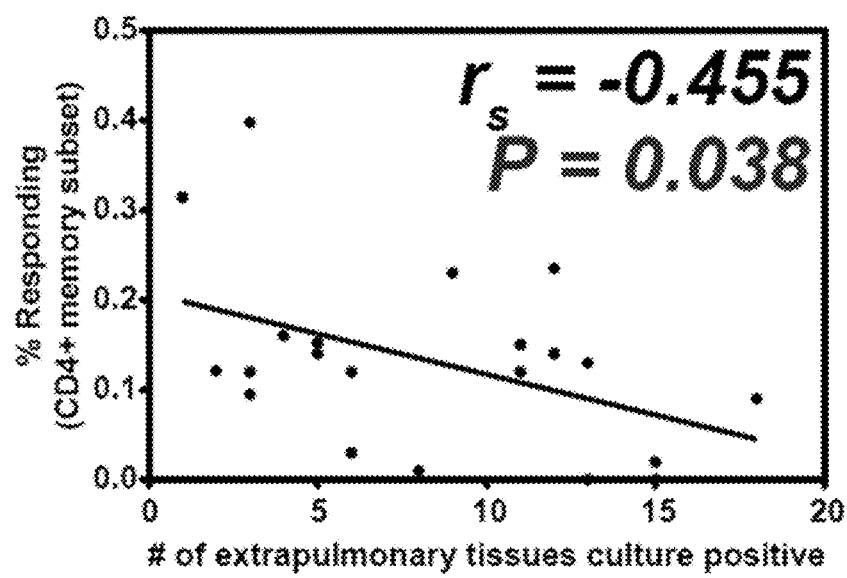
Figure 23:
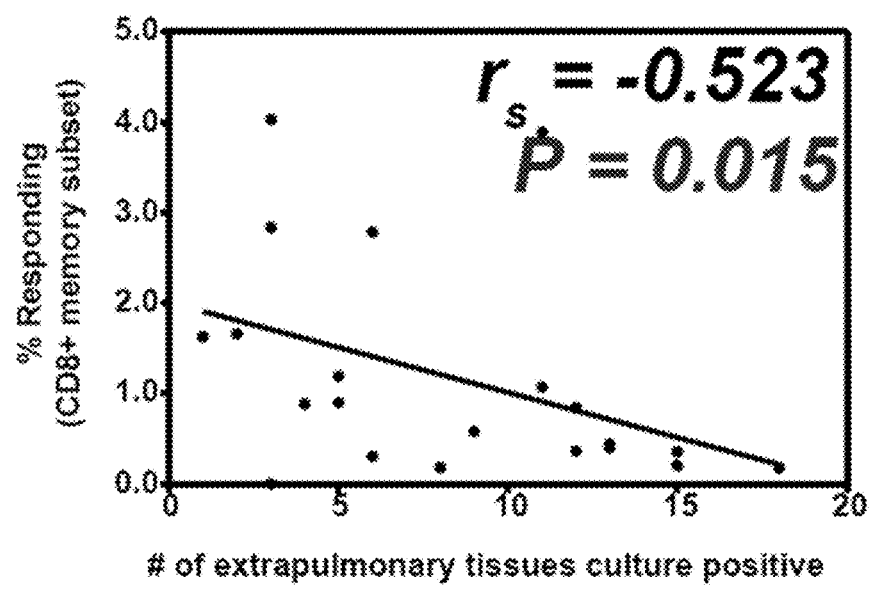
FIG. 23 shows a correlation between the CD8 T cell response against each antigen, shown at various time points throughout the vaccination phase, and the extent of extrapulmonary spread.
Figure 23:
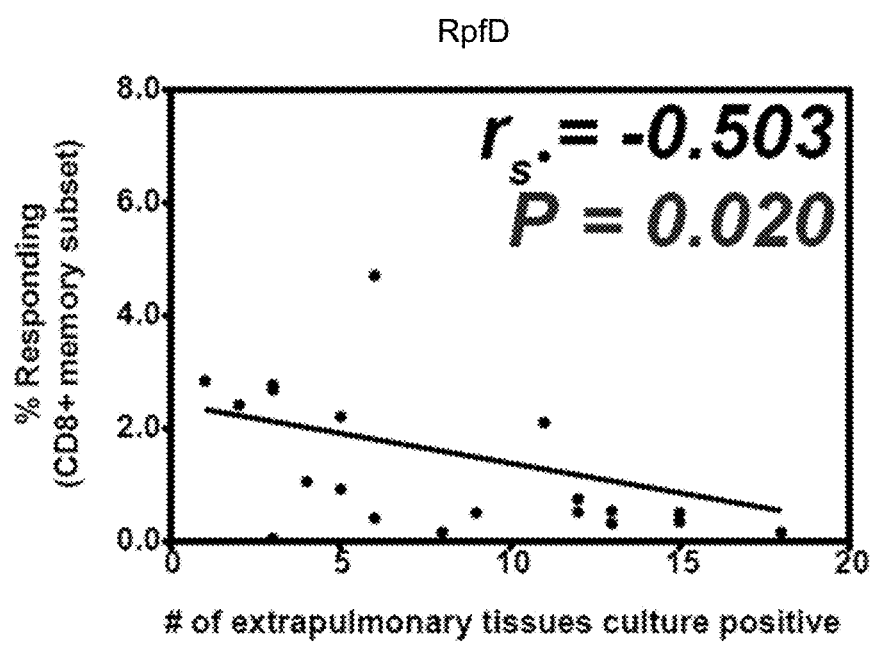
Figure 23:
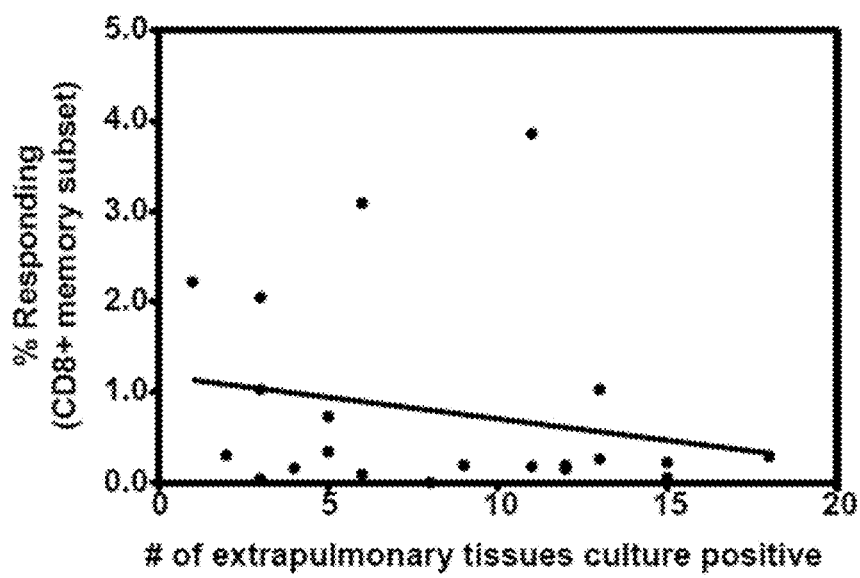

FIG. 21 shows comparative T cell response analysis. FIG. 22 shows correlation of CD4 T cell responses with extra-pulmonary spread. FIG. 23 shows correlation of CD8 T cell responses with extrapulmonary spread. In summary, the strongest correlate is between peak ESAT6-specific CD4+ T cell responses in blood after first CMV vector vaccination (correlation weakens but is still significant after exclusion of BCG group). Blood response correlates are strongest for extent of extrapulmonary disease (vs. extent of lung disease). The "best" blood CD4+ responses are: ESAT6, RpfA, RpfD, Rv2626, Rv3407. The "best" blood CD8+ responses: same as CD4+Ag 85A and 85B. Few BAL responses correlate with outcome.

Figure 24:
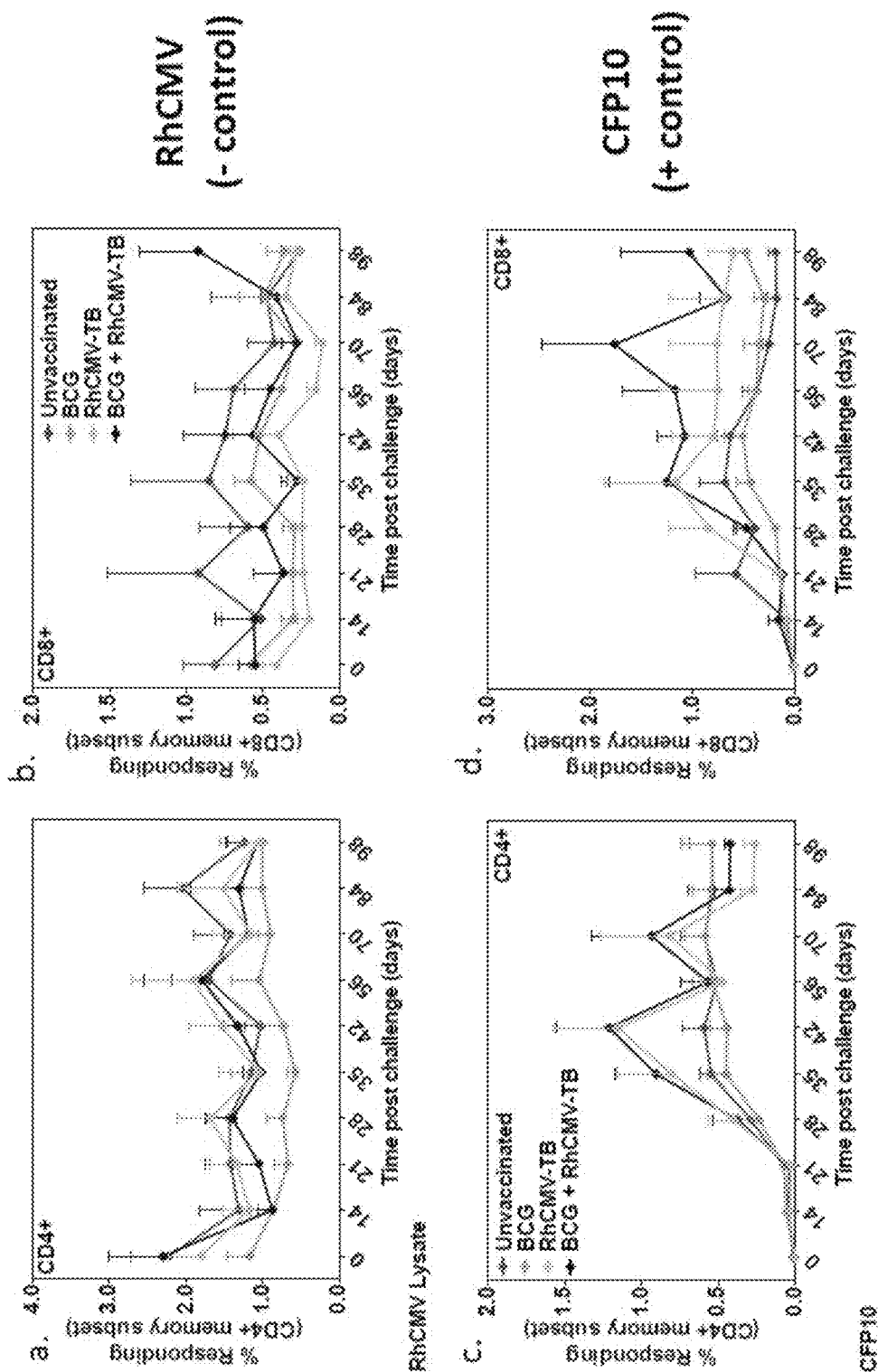
FIG. 24 (panels a, b, c, and d) shows infection by detection of de novo immune responses. PBMCs were stimulated with RhCMV lysate (panels a and b) or CFP peptides (panels c and d); responses were analyzed by intracellular cytokine staining; shown are the percentages of memory cells expressing either IFNγ or TNF; included are responses from peripheral blood mononuclear cells; CD4+ (panels a and c) and CD8 (panels b and d) T cells responses are shown.
Figure 25:
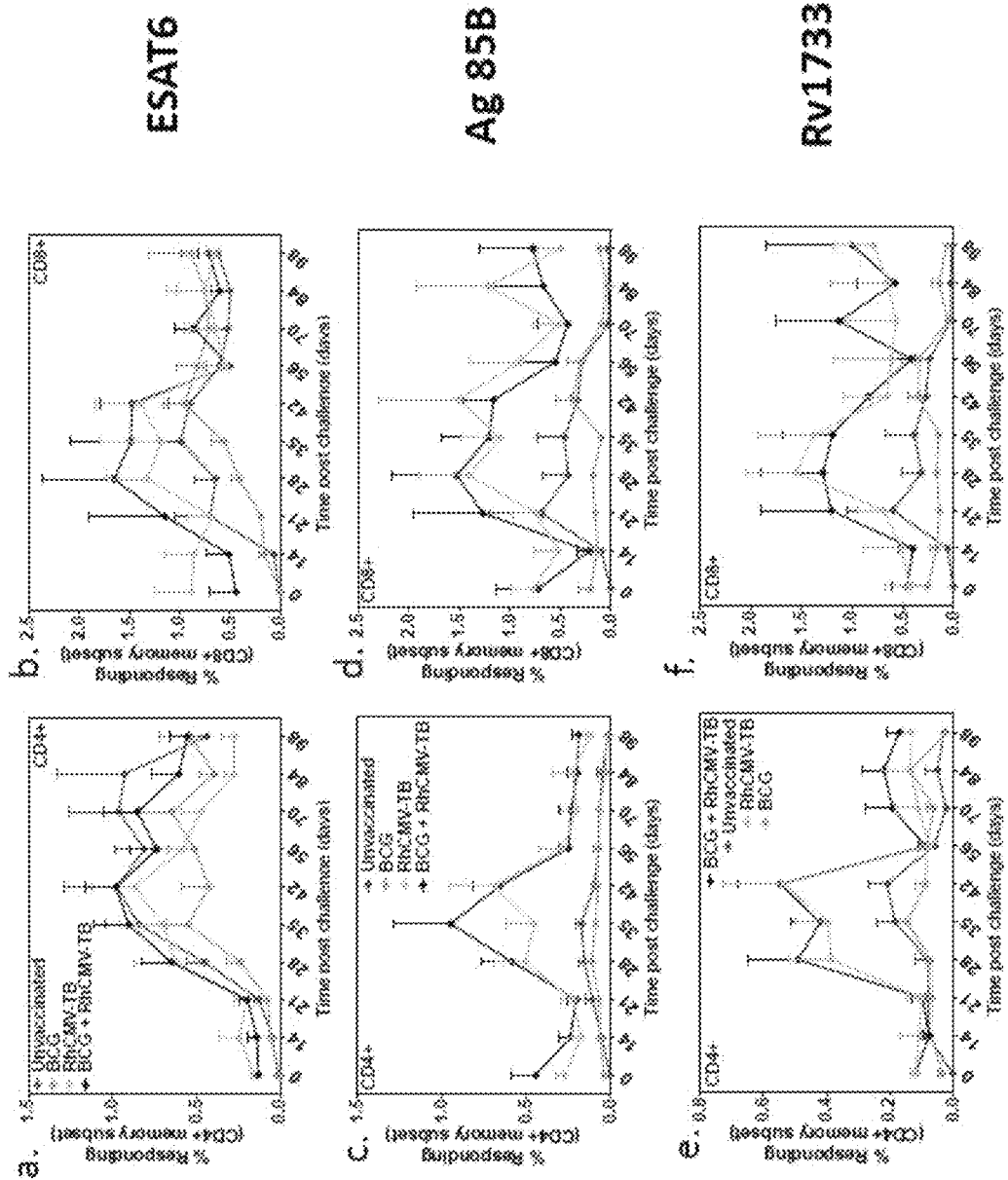
FIG. 25 (panels a, b, c, d, e, and f) shows RhCMV-induced immune responses analyzed post-challenge; PBMCs were stimulated with ESAT6 (panels a and b), Ag85B (panels c and d), and Rv1733 (panels e and f); responses were analyzed by intracellular cytokine staining; shown are the percentages of memory cells expressing either IFNγ or TNF; CD4+(panels a, c, and e) and CD8+(panels b, d, and f) T cells responses.

FIG. 24 shows confirmation of infection by immune analysis, whereby CFP10, an Mtb antigen not included in the RhCMV constructs, was used to confirm infection by detection of de novo immune responses. FIG. 25 shows post-challenge immune responses in PBMCs.

Figure 26:
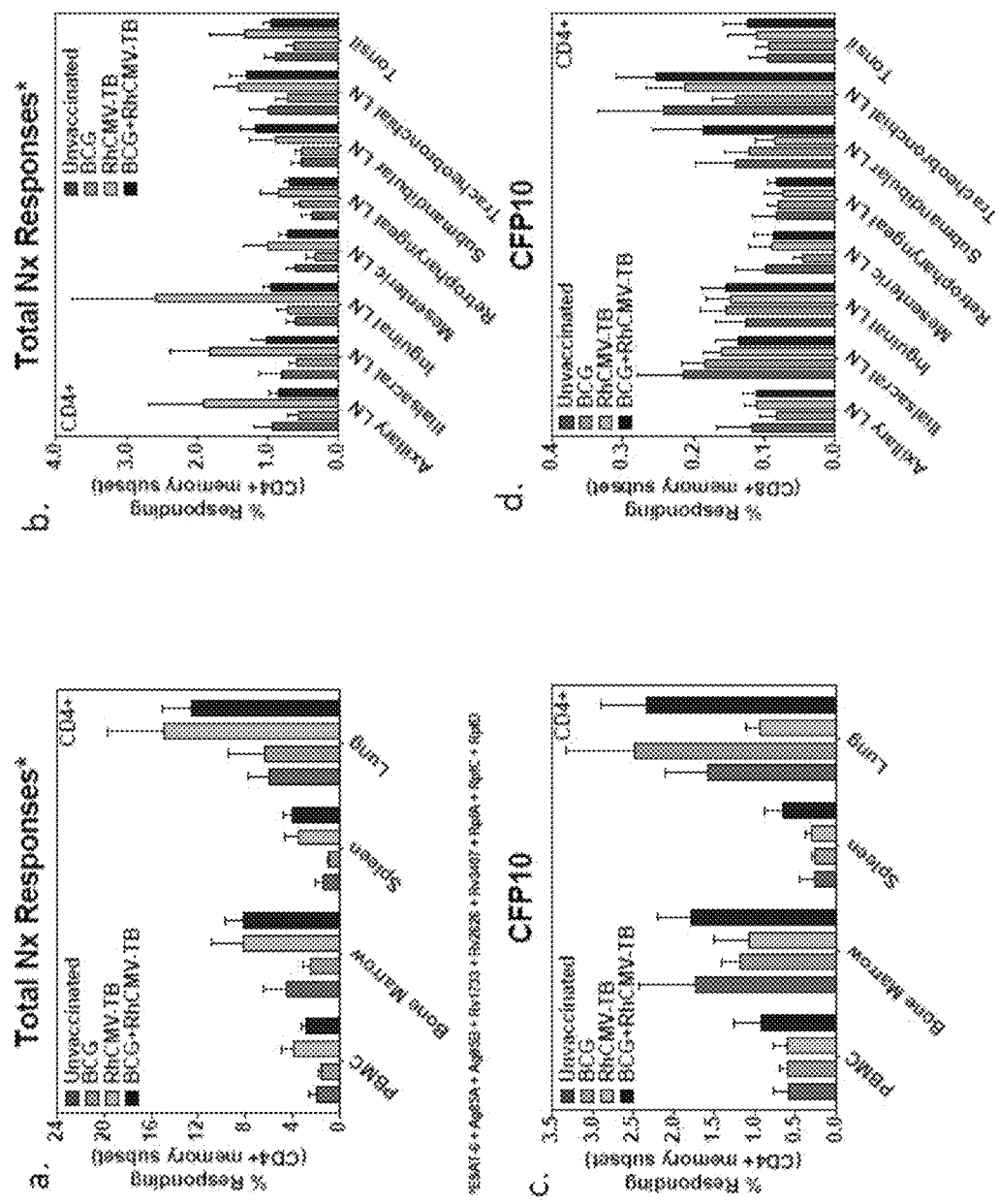
FIG. 26 (panels a, b, c, and d) show the total RhCMV-induced immune responses in various compartments analyzed post-necropsy (panels a and b) and de novo CFP10 responses induced by infection (panels c and d); shown above are the percentages of memory cells expressing either IFNγ or TNF.
Figure 27:
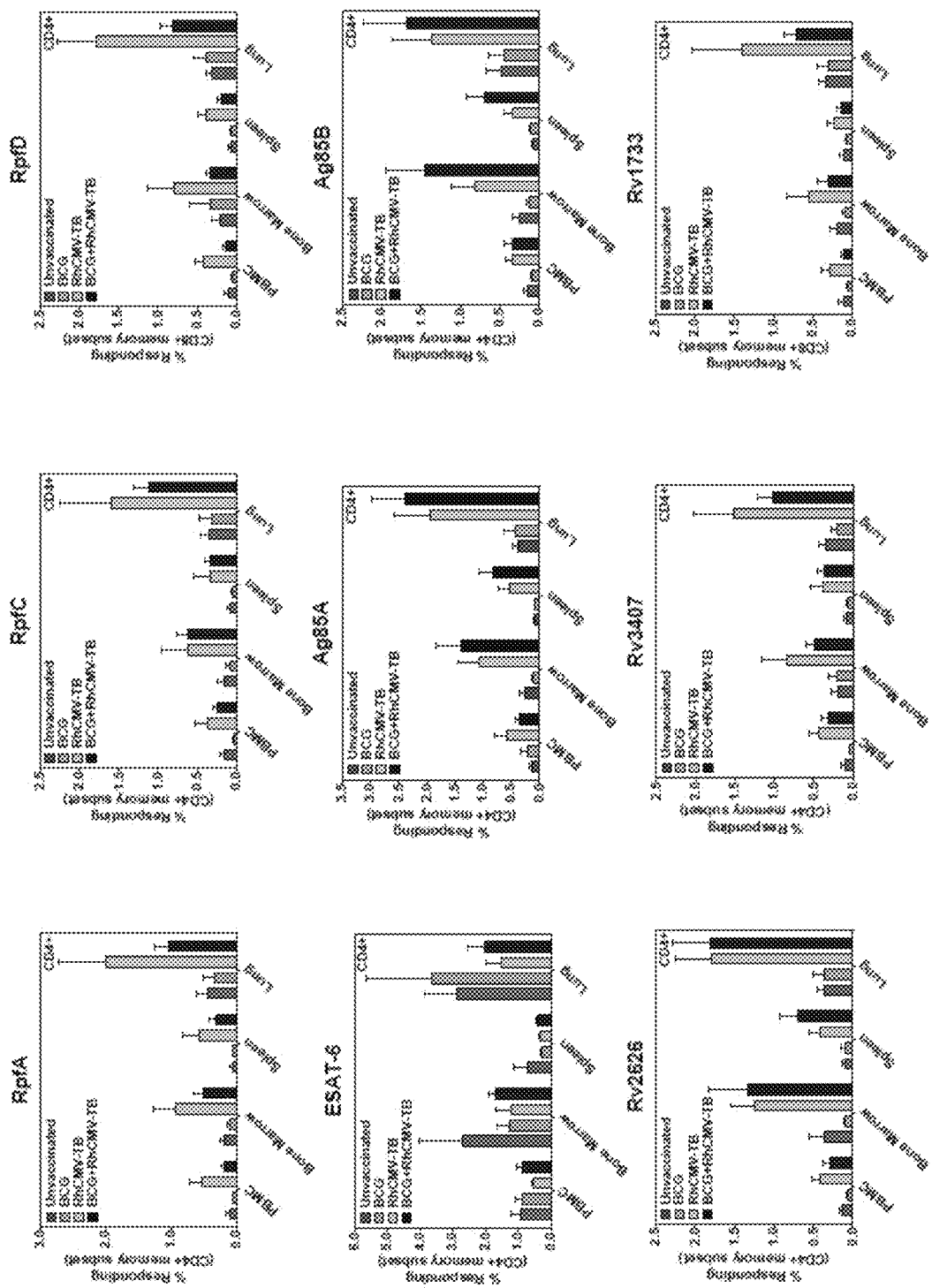
FIG. 27 shows individual antigen-specific CD4+ T cell responses in various compartments analyzed post-necropsy; shown above are the percentages of memory cells expressing either IFNγ or TNF.
Figure 28:
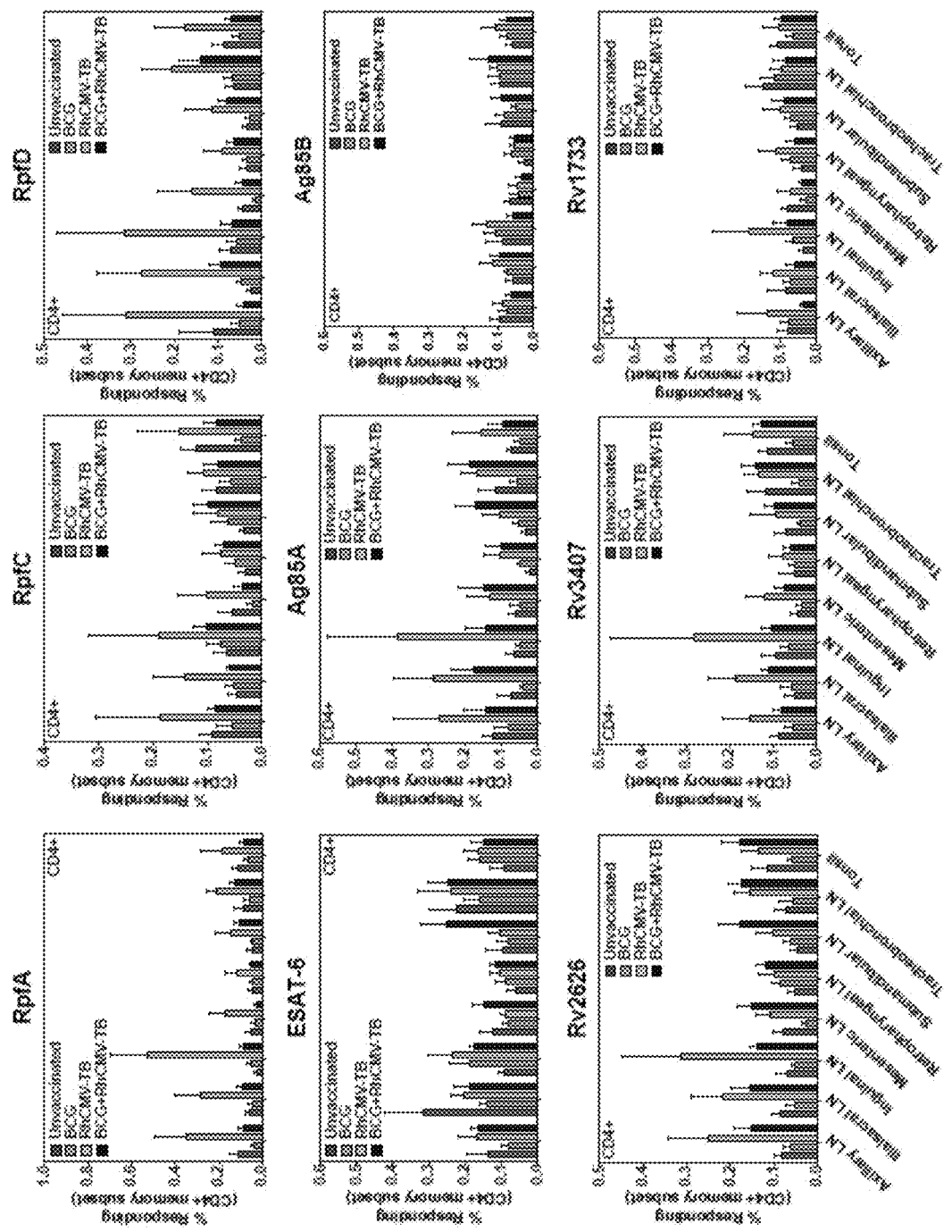
FIG. 28 shows individual antigen-specific CD4+ T cell responses in various lymph nodes analyzed post-necropsy; shown above are the percentages of memory cells expressing either IFNγ or TNF.
Figure 29:
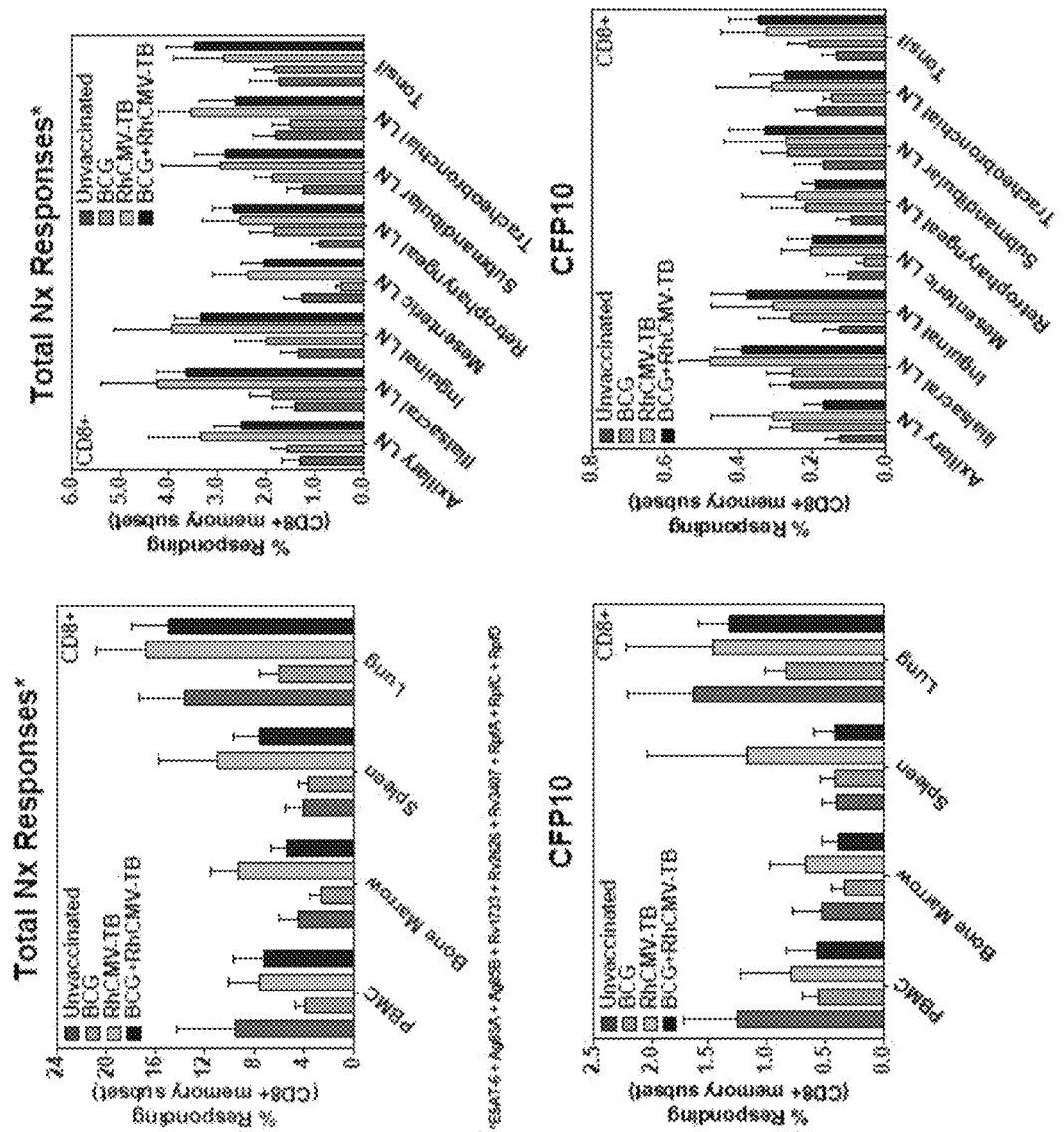
FIG. 29 shows the total RhCMV-induced immune responses in various compartments analyzed post-necropsy; panels c and d show de novo CFP10 responses induced by infection; shown above are the percentages of memory cells expressing either IFNγ or TNF.
Figure 30:
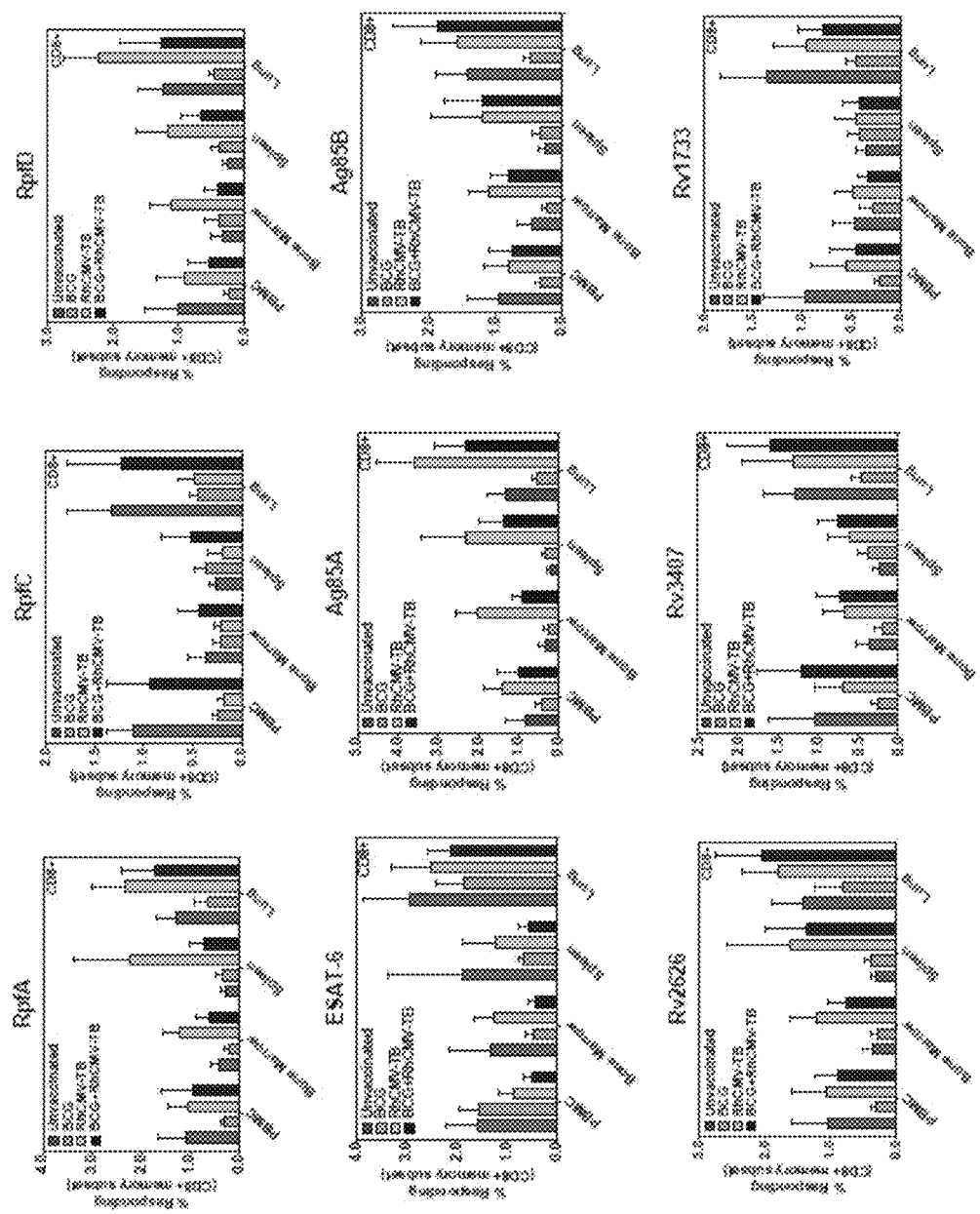
FIG. 30 shows the individual antigen-specific CD8+ T cell responses in various compartments analyzed post-necropsy; shown above are the percentages of memory cells expressing either IFNγ or TNF.
Figure 31:
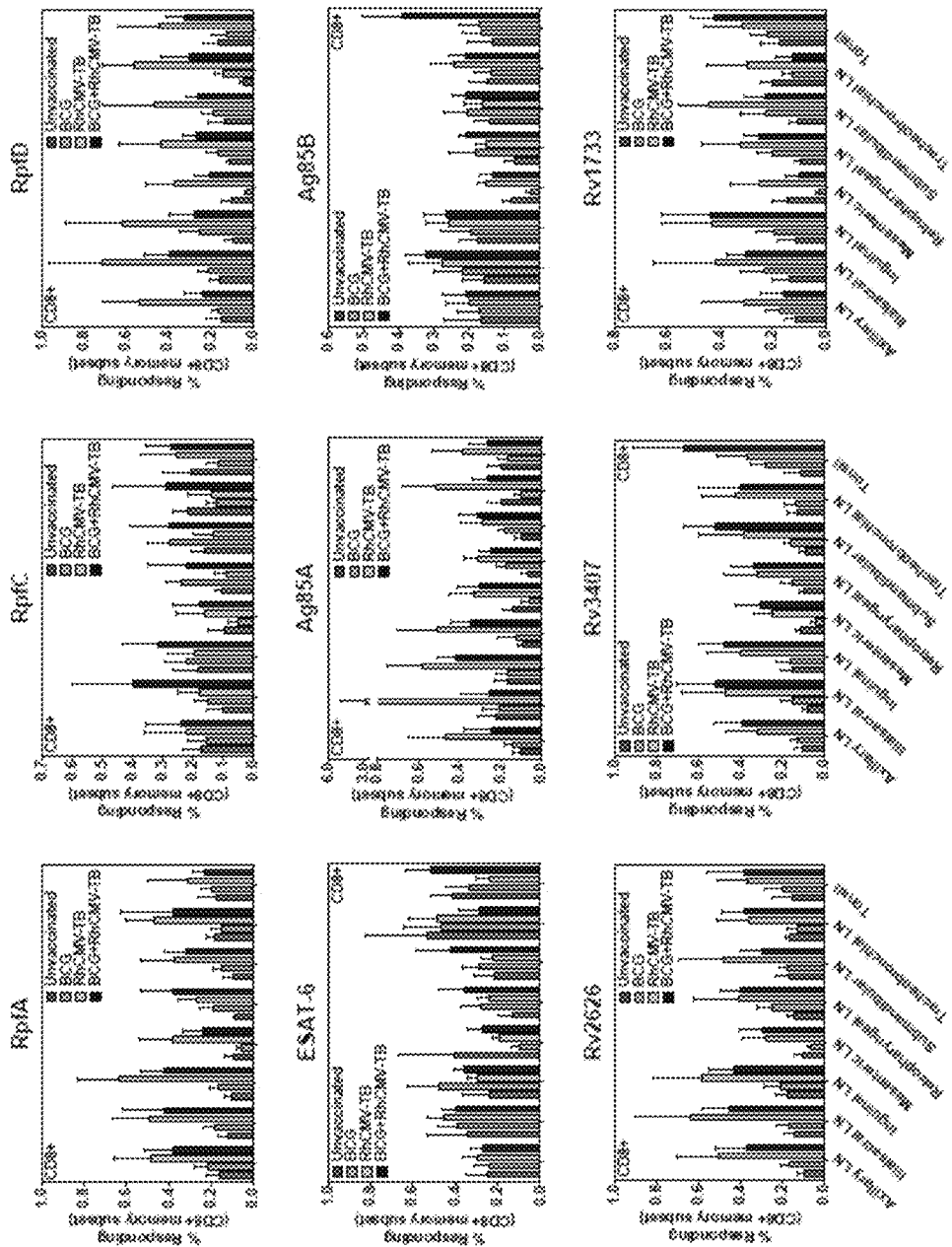
FIG. 31 shows individual antigen-specific CD8+ T cell responses in various lymph nodes analyzed post-necropsy; shown above are the percentages of memory cells expressing either IFNγ or TNF.

FIGS. 26 and 27 show CD4 T cell responses post-necropsy. FIG. 28 shows antigen-specific CD4 T cell responses in lymph nodes analyzed post-necropsy. FIGS. 29 and 30 show CD8 T cell responses post-necropsy. FIG. 31 shows antigen-specific CD8 T cell responses in lymph nodes analyzed post-necropsy. Overall, TB infection-elicited CFP10-specific CD4+ and CD8+ T cell responses are similar between all RM groups. CMV vectors maintain higher frequencies of TB insert-specific CD4+ T cells responses in PBMC, BM, spleen and lung for all inserts except ESAT6. This difference is less apparent in LN samples, except for RpfA and RpfD (although in certain LNs, RpfC, 85A, Rv2623, and Rv3407 Ag responses are also highest in the CMV vector vaccinated group). TB insert specific CD8+ T cell responses are more variable (and tend to be higher in unvaccinated RM), but responses to RpfA, RpfD, 85A, Rv2626 and Rv3407 still tend to be higher in CMV vector-vaccinated animals in most tissues.

Figure 32:
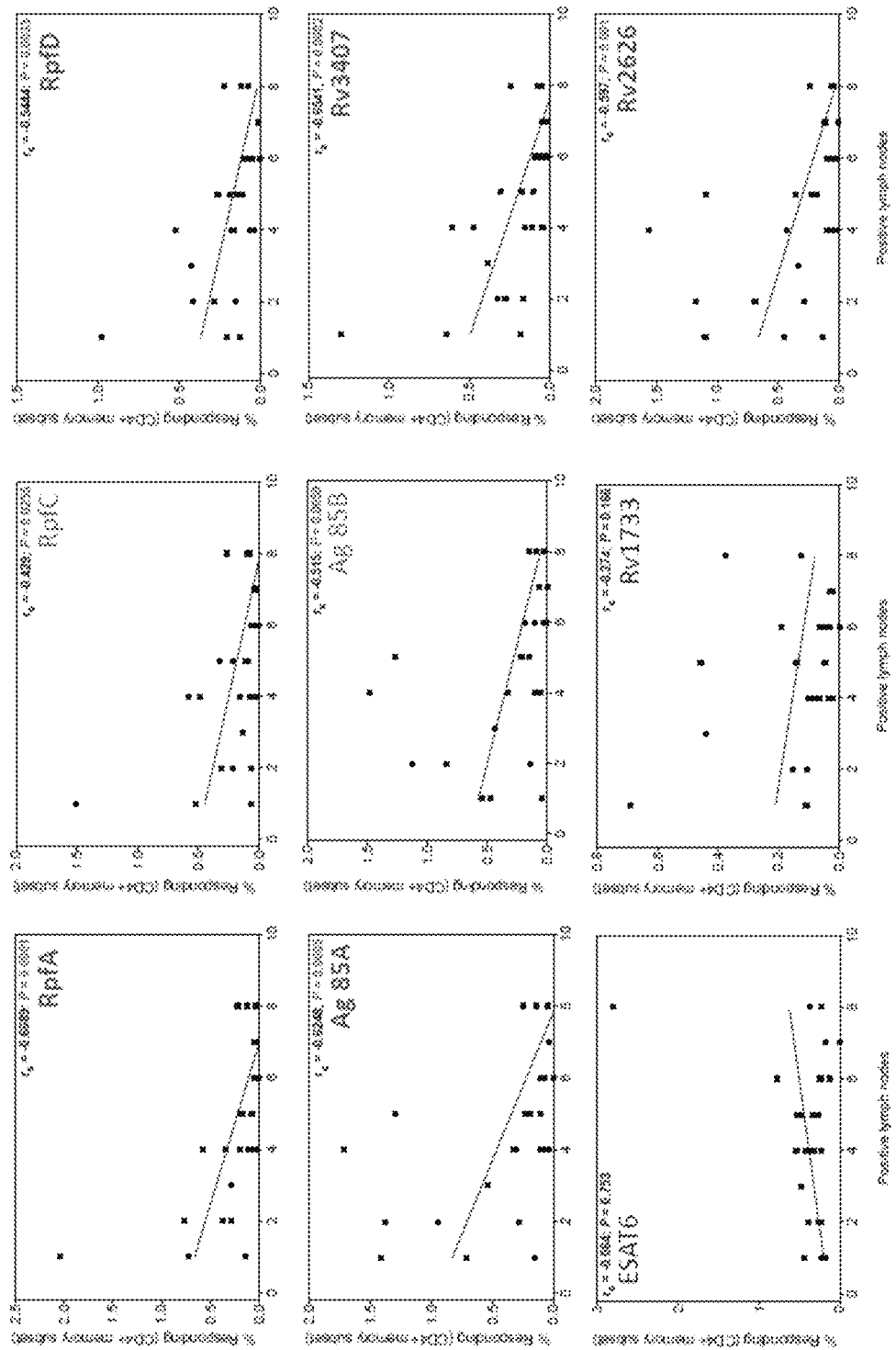
FIG. 32 shows a correlate analysis comparing the splenic CD4+ T cell response with the number of culture-positive lymph nodes.

FIG. 32 shows post-necropsy correlation between splenic CD4 T cell responses and lymph node culture. A correlation of CD4+ responses to non-lung disease was observed for Ag85A, RpfA, RpfD, Rv2626, and Rv3407 (moderate to strong), as well as for Ag85B and RpfC (although weaker). A correlation of CD8+ responses to lung disease was observed for RpfA and RpfD (moderate), as well as for ESAT6 (although weaker). A correlation of CD8+ responses to non-lung disease was observed for Ag85A, RpfA, and RpfD (strong), as well as for Rv2626, Rv3407, and Ag85B (moderate). Peak ESAT6-specific responses (particularly CD4+) during vaccination correlated with reduced extra-pulmonary disease after challenge, but not at necropsy (as TB infection eventually induced high frequency ESAT6-specific responses in all animals).

In general, CMV vectors elicit and maintain higher TB insert-specific CD4+ and CD8+ T cell responses than BCG. These responses are associated with significant protection against both pulmonary and extra-pulmonary disease progression. BCG was associated with, at best, a trend towards modest pulmonary protection, but extra-pulmonary disease was no different than that of unvaccinated controls. Indeed, the administration of BCG prior to CMV vector vaccination partially abrogated CMV vector-mediated protection, in particular for extra-pulmonary spread. T cell responses to some, but not all, TB inserts were lower in some tissues in the animals receiving both BCG and CMV vectors compared to those receiving CMV vectors alone, but it remains to be determined whether this or another mechanism (e.g., BCG elicited responses promoting bacterial spread) account for the reduced protection associated the BCG "prime." Correlates of protection were stronger for extra-pulmonary disease than pulmonary disease and point to RpfA, RpfD, Ag85A, Rv2626 and Rv3407 (and possibly ESAT6) being the most effective vaccine inserts.

In summary, RhCMV/TB vector-vaccinated RM show significantly reduced disease (both pulmonary and extra-pulmonary) by all criteria. RhCMV/TB vectors elicited and maintained higher (and qualitatively different) TB insert-specific CD4+ and CD8+ T cell responses than BCG. RhCMV/TB vector vaccination provided significant protection against both pulmonary and extra-pulmonary disease progression (73% overall). BCG was associated with a trend towards modest pulmonary protection compared to unvaccinated controls, but extra-pulmonary disease was no different than that of unvaccinated controls. The combination of BCG and RhCMV/TB vectors is less effective than RhCMV/TB vector vaccination alone with the BCG component reducing both pulmonary and extra-pulmonary protection. RhCMV/TB vector-vaccinated RM may manifest a marked enhanced early response to infection in carinal LNs. The outcome (extra-pulmonary spread) predominantly correlated with CD4+ T cell responses to Ag85A, Rpf-A/C/D, Rv3407, Rv2626, and ESAT6.

Example 3: Non-Human Primate Study #2

The second study was designed to confirm and extend previous findings of CMV-induced protection against *Mycobacterium tuberculosis* in rhesus macaques. In the original study, significant protection was induced by a cocktail of CMV vectors (strain 68-1), encoding a total of 9 antigens.

The second NHP study consisted of four vaccine groups: 1) Strain 68-1 RhCMV/TB-9Ag vector set (n=9); 2) Strain 68-1.2 RhCMV/TB-9Ag vector set (n=9); 3) Strain 68-1 RhCMV/TB-6Ag single vector (n=9); and 4) unvaccinated. Group 1) consisted of Macaques vaccinated with a cocktail of four Rh68-1 vectors (encoding fusion proteins comprised of Ag85A-Ag85B-Rv3407, Rv1733-Rv2626, RpfA-RpfC-RpfD, and Ag85B-ESAT6). Group 2) consisted of Macaques vaccinated with a cocktail of four Rh68-1.2 vectors (encoding fusion proteins comprised of Ag85A-Ag85B-Rv3407, Rv1733-Rv2626, RpfA-RpfC-RpfD, and Ag85B-ESAT6). Group 3) consisted of Macaques vaccinated with a single Rh68-1 vector (encoding a fusion protein comprised of Ag85A-ESAT6-Rv3407-Rv2626c-RpfA-RpfD).

At weeks 0 and 14, NHP in Groups 1)-3) were vaccinated with the RhCMV/TB vectors described above. NHP were challenged with *Mycobacterium tuberculosis* (Erdman E11-10 mTB at 10 CFU given intrabronchially) at week 55. There was not BAL post-challenge. The outcomes analyzed were the same as those described above in Example 2.

The 4 Rh68-1 vectors used in the first study were used again here (see above for information on construction). Three of the four Rh68-1.2 vectors used in this study encode classical, latency and resuscitation antigen cassettes (encoding fusion proteins comprised of Ag85A-Ag85B-Rv3407, Rv1733-Rv2626, and RpfA-RpfC-RpfD, respectively). The Rh68-1 vector encoding a six-antigen fusion protein (comprising antigens Ag85A, ESAT6, Rv3407, Rv2626, RpfA and RpfD) and Rh68-1.2 vector encoding Ag85B and ESAT6 were also used.

Figure 33:
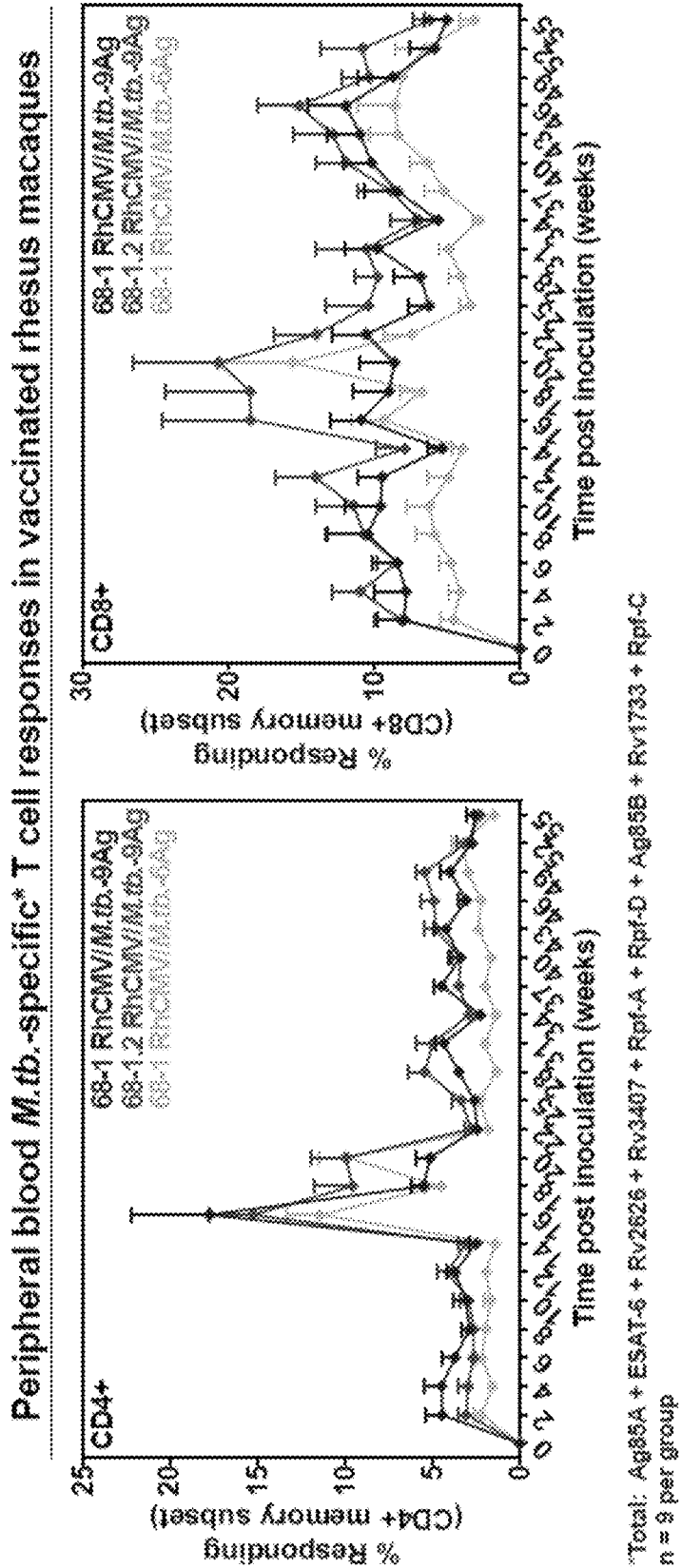
FIG. 33 shows immune responses induced by vaccination analyzed by intracellular cytokine staining throughout the vaccination period; shown are the percentages of memory cells expressing either IFNγ or TNF; included are responses from peripheral blood mononuclear cells; CD4+ T cells and CD8+ T cells are shown; the data points represent a summation of the antigens assayed, which are indicated below the panel.
Figure 34:
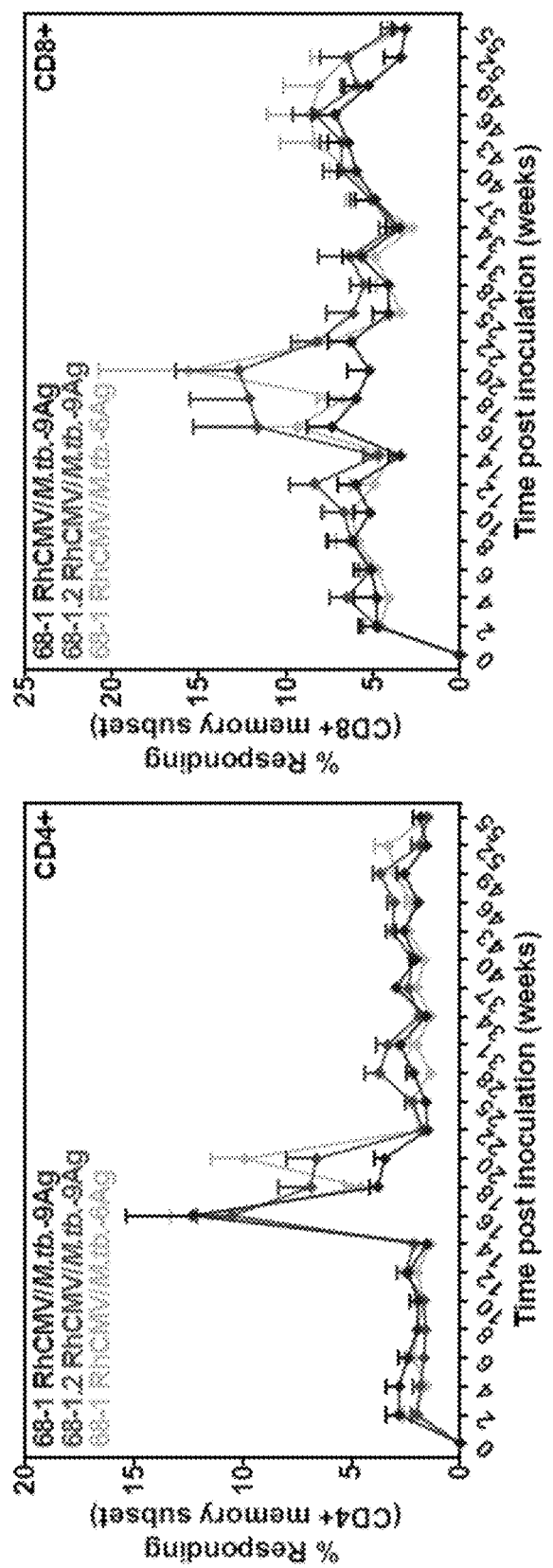
FIG. 34 shows immune responses induced by vaccination normalized between vectors by summing only those antigens present in each vector (antigens noted below the panel); responses were analyzed by intracellular cytokine staining throughout the vaccination period; shown are the percentages of memory cells expressing either IFNγ or TNF; included are responses from peripheral blood mononuclear cells; CD4+ T cells and CD8+ T cells are shown.
Figure 35:
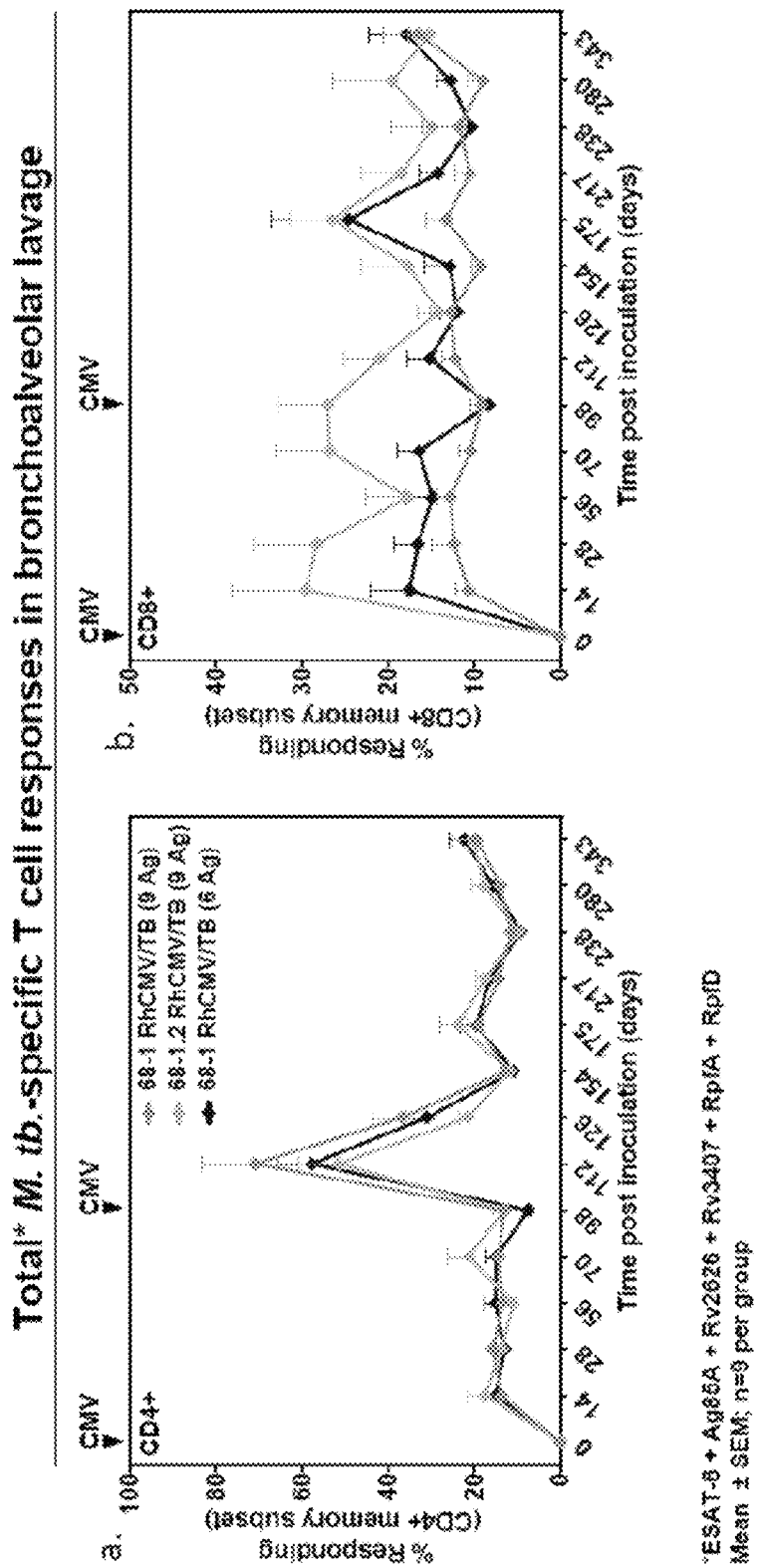
FIG. 35 (panels a and b) shows immune responses induced by vaccination analyzed by intracellular cytokine staining throughout the vaccination period; shown are the percentages of memory cells expressing either IFNγ or TNF; included are responses from BAL; CD4+ T cells are shown in panel a and CD8+ T cells are shown in panel b; the data points represent a summation of the antigens assayed, which are indicated below the panel.

Immunogenicity of these vectors was evaluated using intracellular cytokine staining FIG. 33 shows PBMC immune responses following vaccination with RhCMV vectors; all vaccines showed robust immunogenicity. FIG. 34 shows comparing immunogenicity induced by each RhCMV vector; all vaccines showed equivalent immunogenicity to common inserts. FIG. 35 shows BAL immune responses following vaccination with RhCMV vectors. In addition, for Strain 68-1 RhCMV/TB vectors (UL128/UL130-deleted), all CD8+ T cell responses were MHC-II- and MHC-E-restricted, whereas for Strain 68-1.2 RhCMV/TB vectors (UL128/UL130-intact), all CD8+ T cell responses were MHC-Ia-restricted (data not shown).

Figure 36:
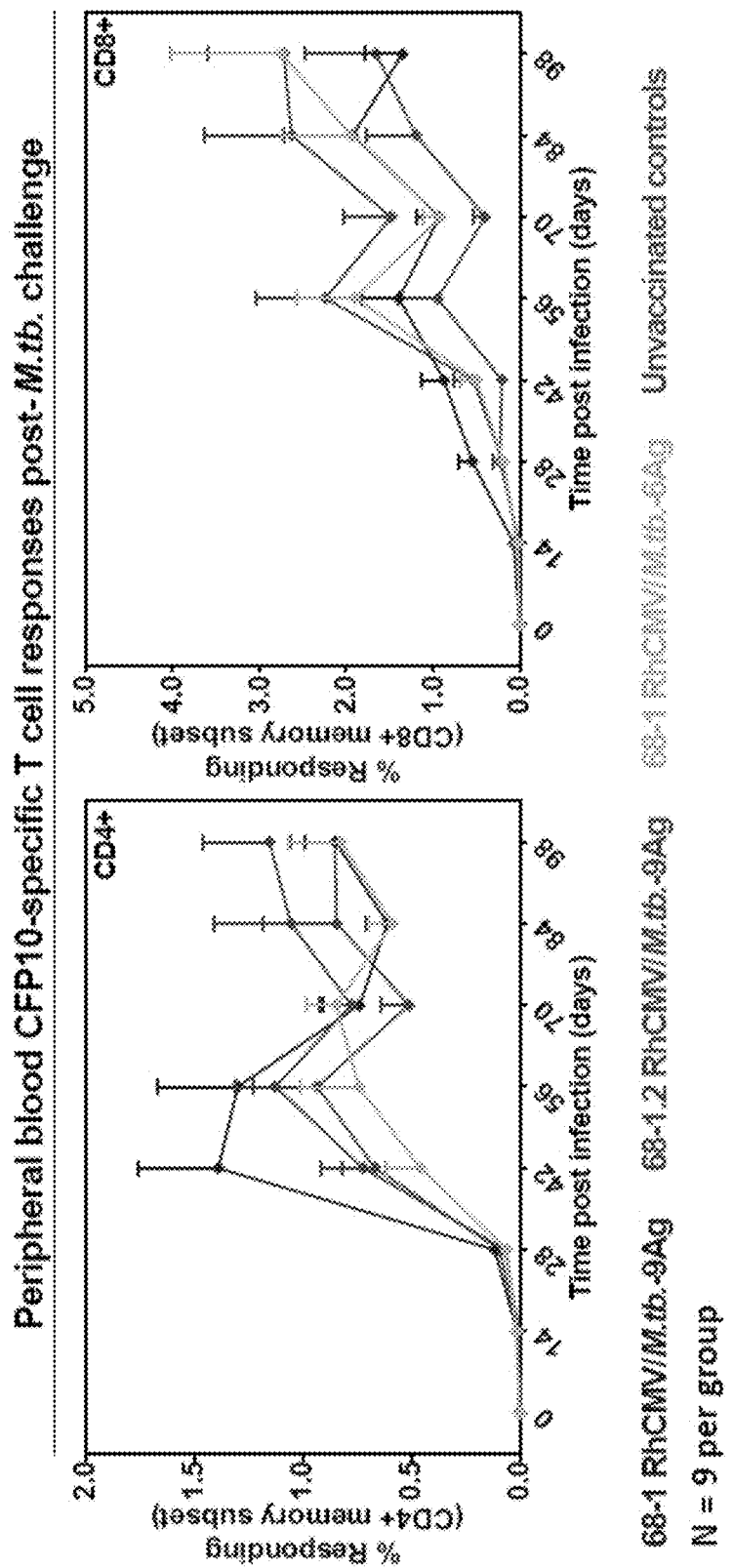
FIG. 36 shows peripheral blood CFP10-specific T cell responses post-Mtb challenge.
Figure 37:
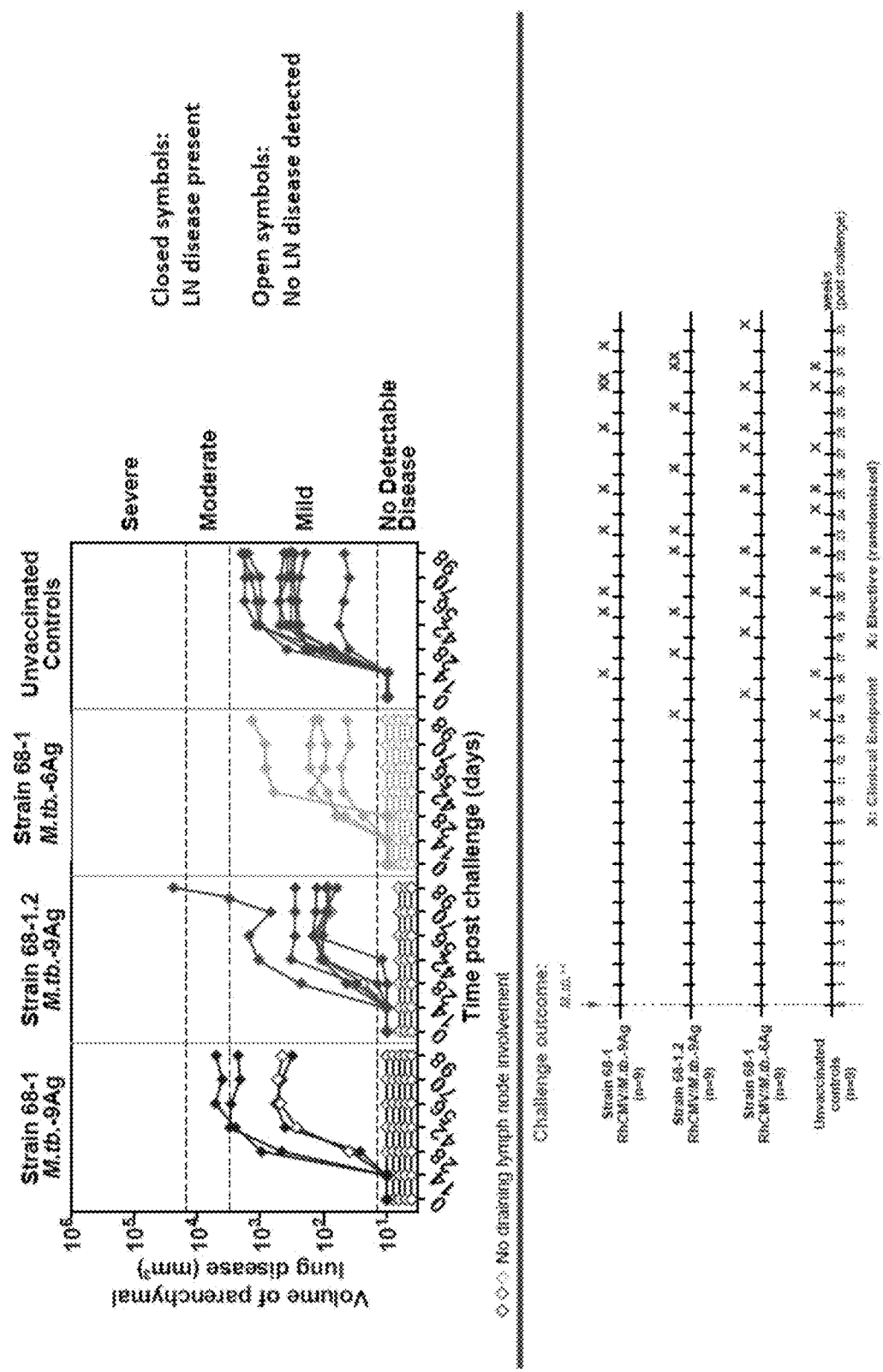
FIG. 37 shows clinical outcome data from longitudinal CT scans, which is used to quantify the volume of lung disease present post-challenge.
Figure 38:
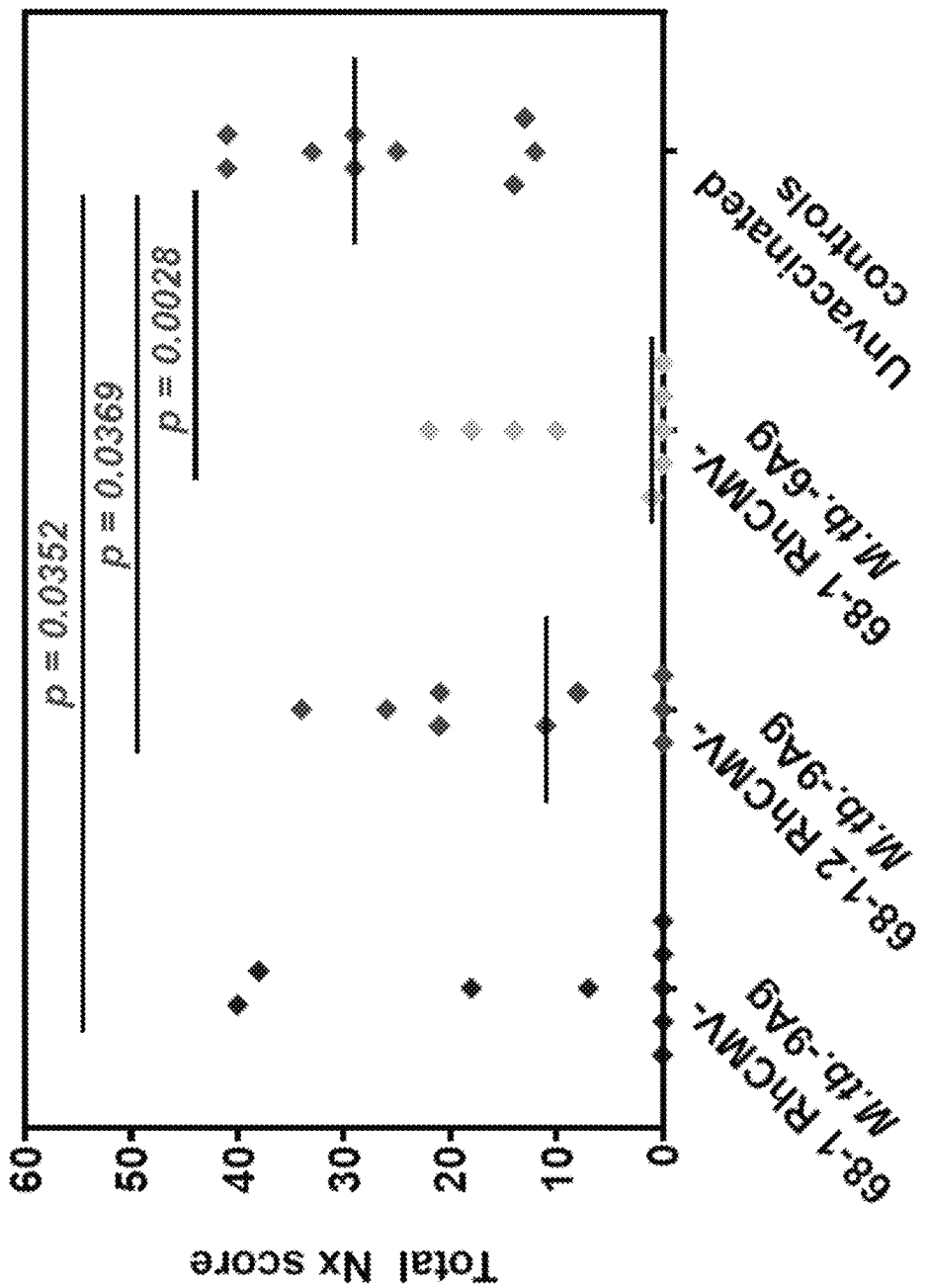
FIG. 38 shows a necropsy score.
Figure 39:
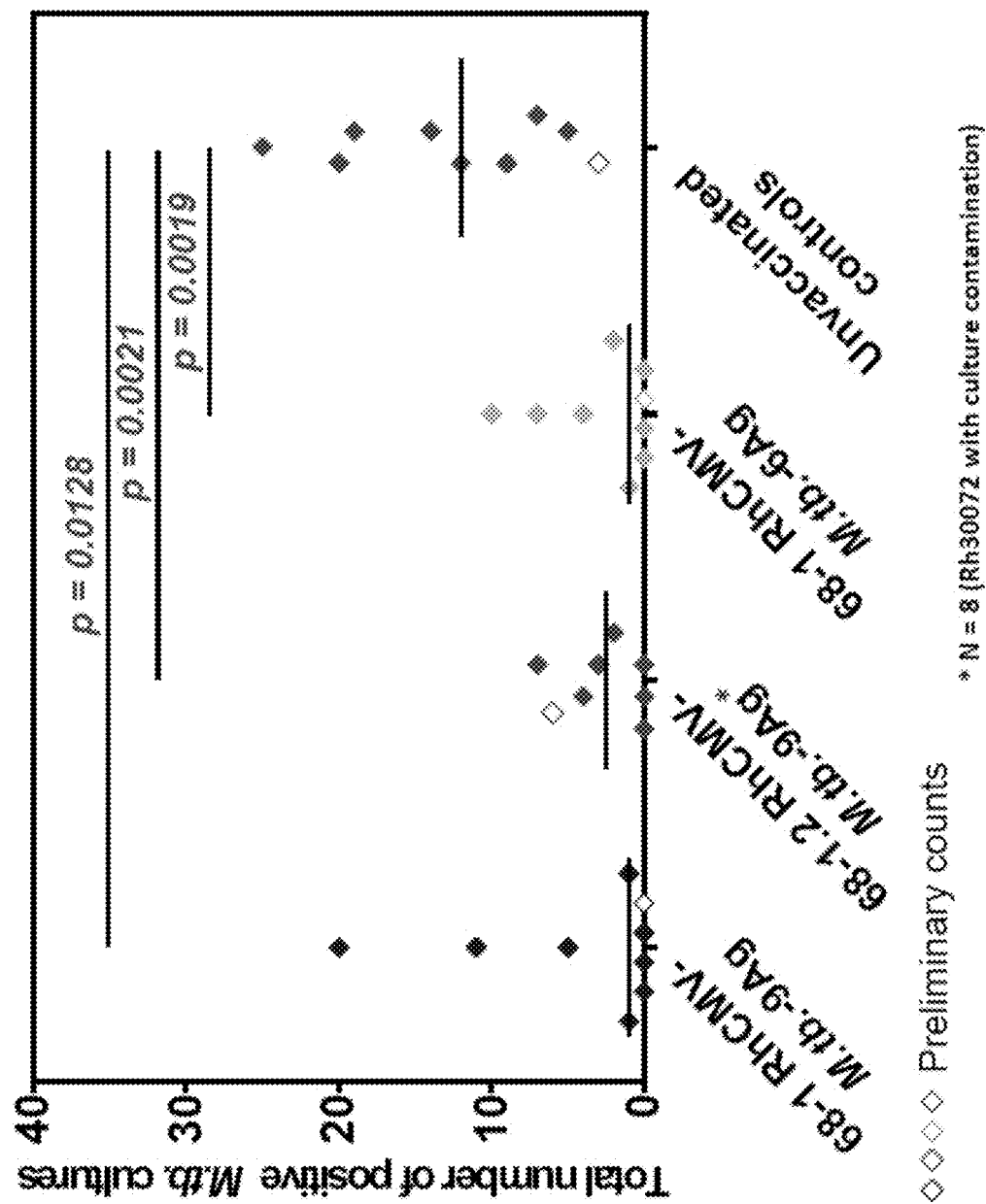
FIG. 39 shows a culture score.
Figure 40:
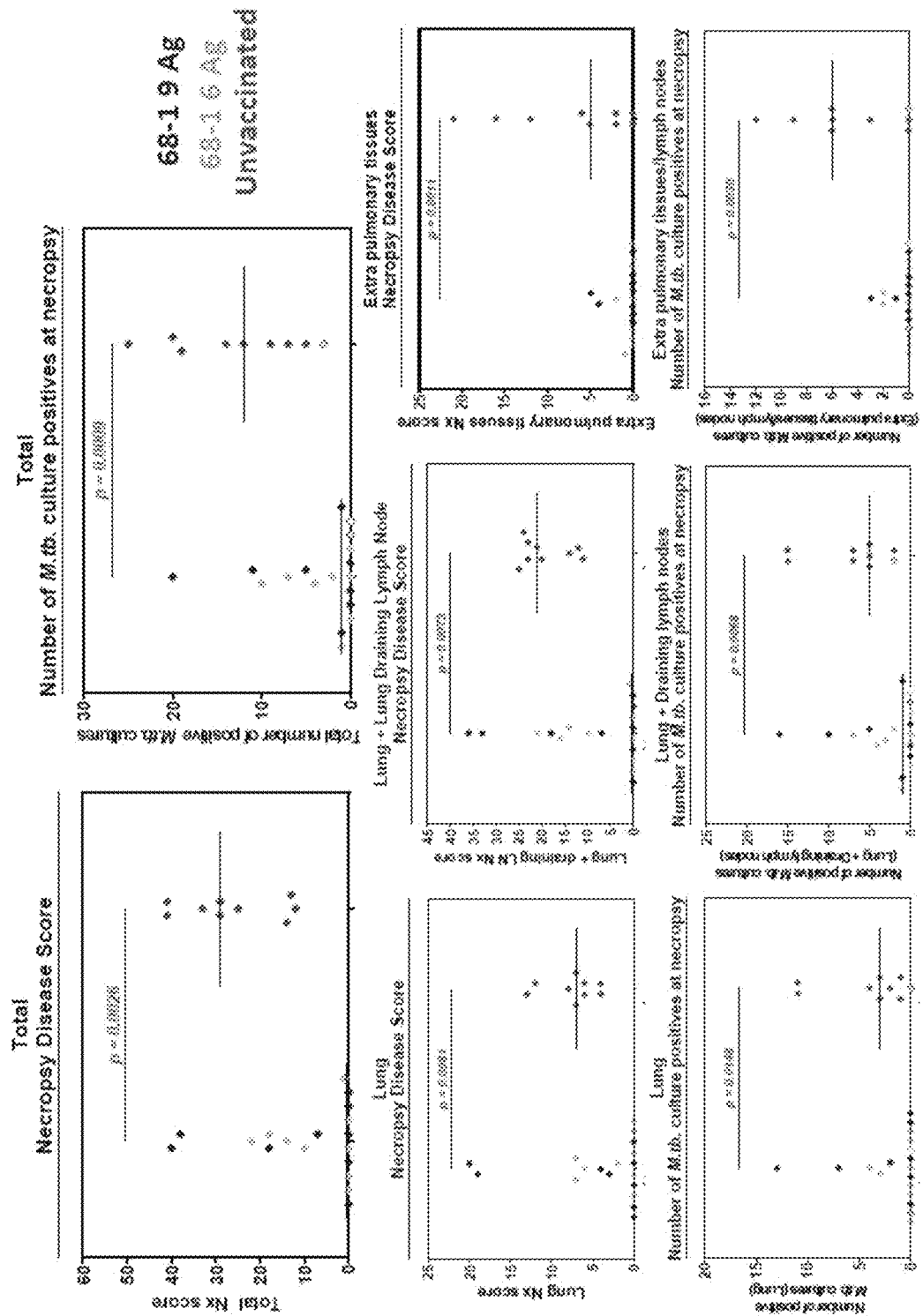
FIG. 40 shows overall efficacy of Strain 68-1 RhCMV/TB vectors.
Figure 41:
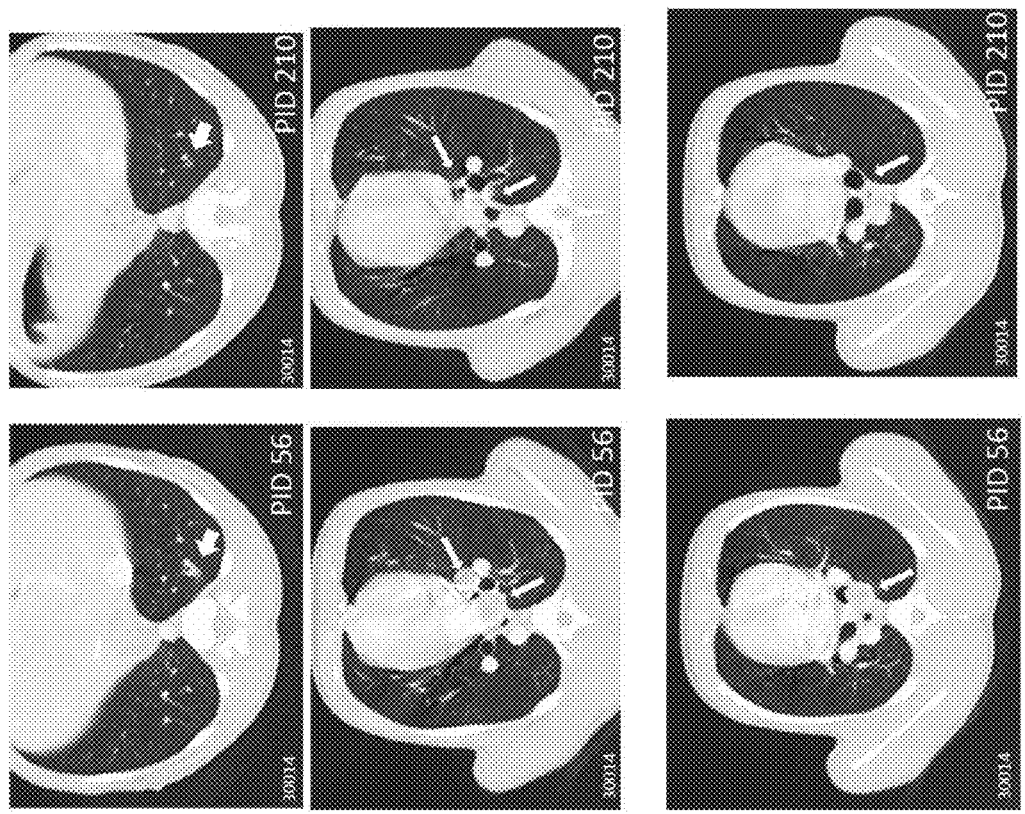
FIG. 41 shows late disease resolution in a Strain 68-1 RhCMV/TB-6Ag single vector vaccination.
Figure 42:
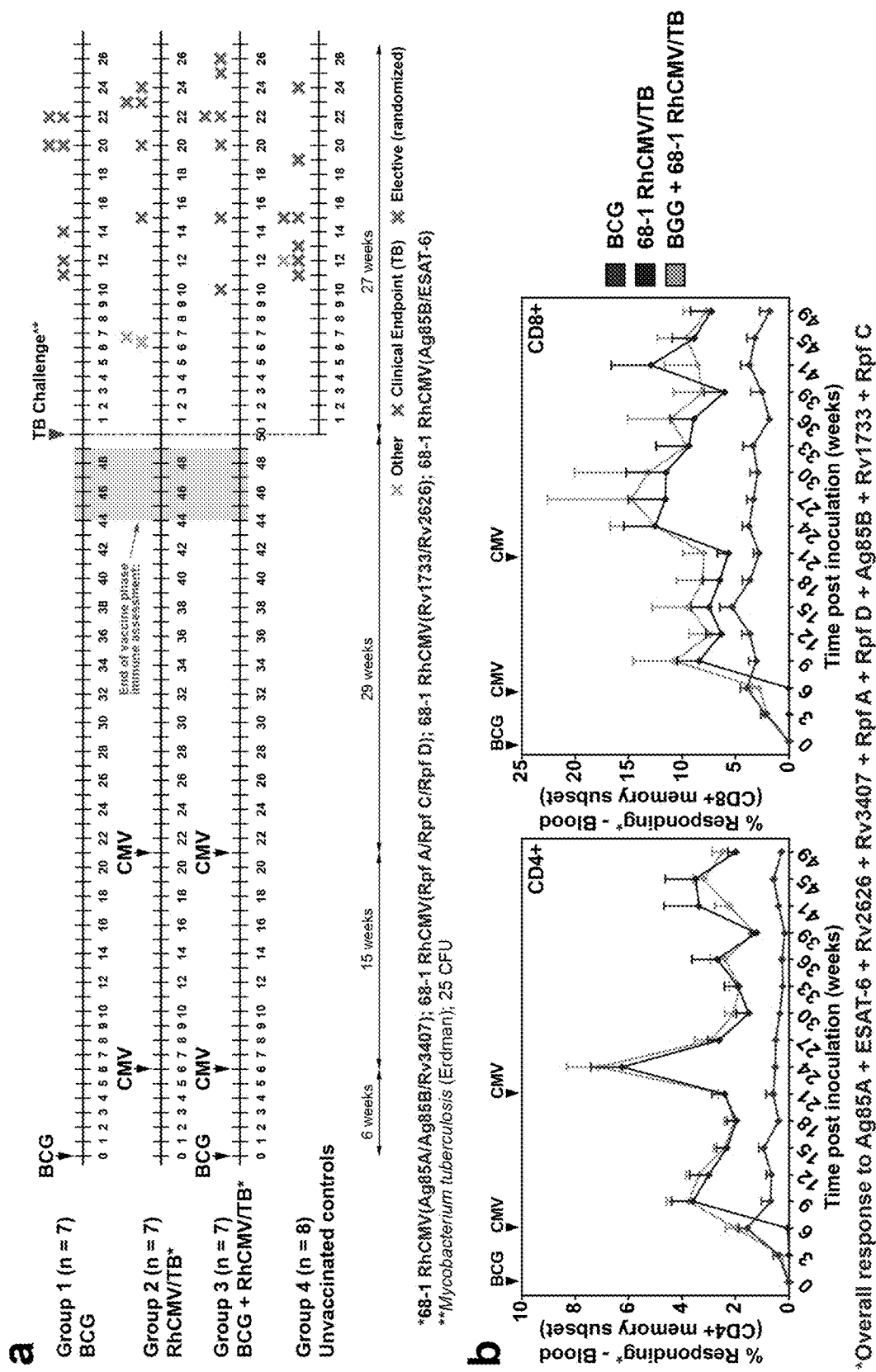
FIG. 42 (panels a, b, c, d, e, and f) shows the immunogenicity of RhCMV/TB and BCG vaccines for Study 3.
Figure 42:
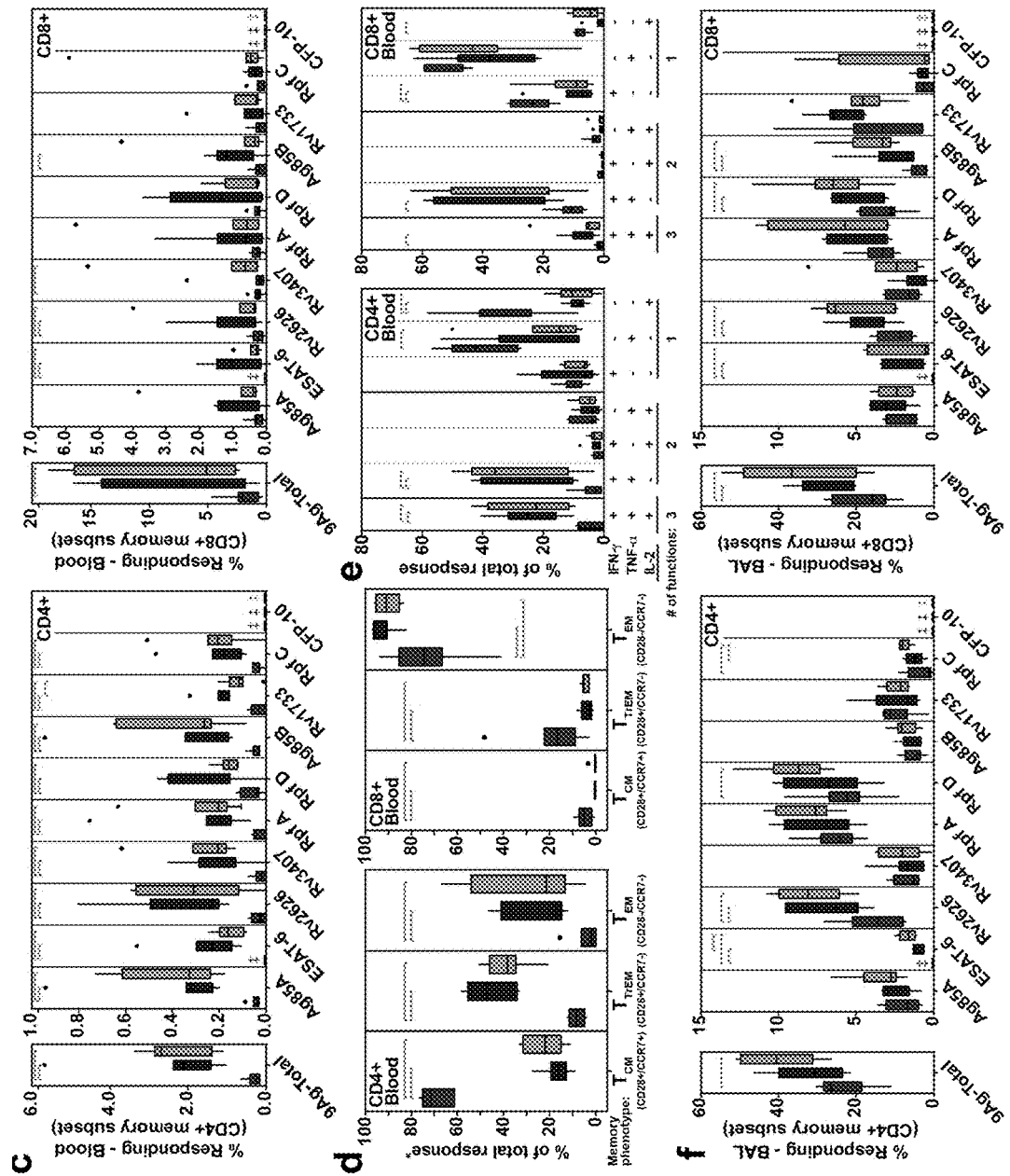

FIG. 36 shows Peripheral blood CFP10-specific T cell responses post-Mtb challenge. All monkeys showed de novo responses to Mtb post challenge. FIG. 37 shows clinical outcome data from longitudinal CT scans, which is used to quantify the volume of lung disease present post-challenge. There is clear evidence of protection in each of the vaccinated groups. FIGS. 38 and 39 show a necropsy score and culture, respectively. FIG. shows overall efficacy of Strain 68-1 RhCMV/TB vectors. FIG. 41 shows late disease resolution in a Strain 68-1 RhCMV/TB-6Ag single vector vaccination. FIG. 42 shows, at necropsy, the monkey manifested a pathologic extent of a disease score of 10 with only a single Mtb culture. The data suggests that Strain 68-1 RhCMV vector-elicited T cell responses may not only be able to prevent development of TB lesions, but may also be capable of mediating their regression.

In summary, low dose (10 bacteria) Erdman E11-10 strain mTB challenge resulted in considerably less aggressive disease than previous studies using a >25 bacteria challenge dose, but all unvaccinated controls still showed both pulmonary and draining LN disease. Strain 68-1 RhCMV/TB vector vaccination, either the 9 Ag vector set, or the single 6 Ag insert vector, provided striking protection against both pulmonary and extra-pulmonary disease after low dose mTB challenge: 1) 10 of 18 NHPs (56%) with no pathologic evidence of infection (7 of which were also completely culture negative) vs. 0% of unvaccinated controls; and 2) 12 of 18 NHPs (67%) with less disease (as measured by both Path Score and Culture) than the unvaccinated control with the least extent of disease progression; and 3) efficacy of the Strain 68-1 RhCMV/TB-6Ag single vector ≥Strain 68-1 RhCMV/TB-9Ag vector set. Strain 68-1.2 RhCMV/TB-9Ag vaccination resulted in significant overall protection.

In addition, Strain 68-1 RhCMV/TB vector vaccination protects highly TB susceptible rhesus macaques from progressive pulmonary and extra-pulmonary TB disease after both high and low dose intrabronchial Erdman strain mTB challenge. In the high dose challenge model, BCG was not significantly protective and the combination of BCG and Strain 68-1 RhCMV/TB vector vaccination was less protective than Strain 68-1 RhCMV/TB vector vaccination alone. Current data suggest vector-elicited CD4+ T cell responses are the primary protective correlate. To date, the single 6 Ag (polyprotein) expressing RhCMV vector provides the best overall protection, but it remains possible that different or additional TB Ag inserts would increase efficacy.

Example 4: General Methodology for Studies #3 and #4

Rhesus Macaques:

Sixty-five purpose-bred, pedigreed, male RM (*Macaca mulatta*) of Indian genetic background were used in studies 3 and 4. At assignment, these RM were specific-pathogen free (SPF) as defined by being free of Macacine herpesvirus 1, D-type simian retrovirus, simian T-lymphotrophic virus type 1, simian immunodeficiency virus, and Mtb. All RM used in this study were housed at the Oregon National Primate Center (ONPRC) in Animal Biosafety level (ABSL)-2 (vaccine phase) and ABSL-3 rooms (challenge phase) with autonomously controlled temperature, humidity, and lighting. RM were single cage housed due to the infectious nature of the study and had visual, auditory and olfactory contact with other animals. Because the RM were single cage housed, an enhanced enrichment plan was designed and overseen by nonhuman primate behavior specialists. RM were fed commercially prepared primate chow twice daily and received supplemental fresh fruit or vegetables daily. Fresh, potable water was provided via automatic water systems. All RM were observed twice daily to assess appetite, attitude, activity level, hydration status and evidence of disease (tachypnea, dyspnea, coughing). Physical exams including body weight and complete blood counts were performed at all protocol time points. RM care and all experimental protocols and procedures were approved by the ONPRC. The ONPRC is a Category I facility. The Laboratory Animal Care and Use Program at the ONPRC is fully accredited by the American Association for Accreditation of Laboratory Animal Care (AAALAC), and has an approved Assurance (#A3304-01) for the care and use of animals on file with the NIH Office for Protection from Research Risks. The IACUC adheres to national guidelines established in the Animal Welfare Act (7 U.S.C. Sections 2131-2159) and the Guide for the Care and Use of Laboratory Animals (8th Edition) as mandated by the U.S. Public Health Service Policy.

Animal Procedures:

RM were sedated with ketamine HCl or Telazol® for intradermal and subcutaneous vaccine administration, venipuncture, bronchoalveolar lavage, lymph node biopsy, intrabronchial Mtb inoculation and computed tomography (CT) procedures. Mtb Erdman K01 was diluted in saline, lightly sonicated and bacteria were delivered to a segmental bronchus in the right caudal lung lobe using a bronchoscope. The RM in Studies 3 and 4 received 25 and 10 colony forming units (CFU), respectively, in a volume of 2 ml. Pre- and post-challenge axial CT scans (2.5 mm slices) were obtained using a multi-section CT scanner using helical technique, collimation 3 mm and pitch 1.5 (CereTom, Neurologica Corp., Danvers, Mass.) and reconstructed as 1.25 mm slices to improve detection sensitivity. Nonionic iodinated contrast (Isovue 370, 1-2 nal/kg, Bracco Diagnostics, Princeton N.J.) was administered IV at a rate of 1-2 ml/s. CT scans were obtained with 120 kVp and 200 mA. All animals were imaged pre-challenge, at two-week intervals for the duration of the studies and immediately prior to necropsy. Scans were interpreted by a veterinarian who was blinded to the identity of the subject. Lesion area in sequential scans was determined from transverse slices through entire lung fields using the IMPAX 6.5.5.3020 software area tool (AGFA HealthCare N.V., Mortsel, Belgium) and lesion volume determined by multiplying area by 1.25. One RM developed extensive bilateral miliary disease with estimated lesion volume >200,000 mm$^3$ and no further attempts to estimate lesion volume were made in this animal.

Necropsy:

The humane criteria for removing RM with end-stage TB from the studies are as follows: 1) marked lethargy, 2) severe dyspnea at rest and/or failure to maintain adequate oxygenation (85%) based on pulse oximetry or blood gas analysis, 3) hemoptysis, 4) weight loss (>15% in 2 weeks; >25% over any time course in an adult animal), 5) hypothermia <96° F. with supplemental heating, 6) persistent anemia (<20% for 2 weeks), 7) dehydration unresponsive to oral rehydration therapy for 3 days, 8) non-responsiveness to therapy for spontaneous diseases conditions, 9) poor appetite, requiring more than 3 orogastric tube feedings in 7 days, 10) obtundation, 11) neurologic deficits, and 12) persistent self-injurious behavior unresponsive to a change in location or enrichment. RM that manifested one or more of these end-stage criteria were immediately necropsied. RM that remained clinically well after post-infection week 16 were randomized and scheduled for euthanasia and necropsy at the rate of two per week. There were 3 exceptions to this general rule of necropsy initiated by end-stage disease criteria or randomization (designated as "other"). One non-end-stage RM (D1) in Study 3 was euthanized on the same day as an end-stage RM because the IACUC does not permit housing a single RM alone in a room. Two additional RM (N1, N3) in Study 3 were euthanized because of failure to maintain adequate oxygenation following a bronchoalveolar lavage procedure that was not attributable to end-stage Mtb disease. To avoid this issue in Study 4, BALs were not performed after challenge in this study.

At the humane or scheduled endpoint RM were euthanized with sodium pentobarbital overdose (>50 mg/kg) and exsanguinated via the distal aorta. The necropsy procedure included complete gross pathologic evaluation of abdominal organs and tissues and the brain prior to entering the thoracic cavity to avoid contamination. Macroscopic granulomas in liver, spleen, kidney and the brain were counted, measured and photographed in serial 5 mm tissue slices whereas granulomas occurring in extra thoracic lymph nodes, the gastrointestinal tract and soft tissues were collected, measured and photographed with minimum sectioning and given a numeric point value score using a semi-quantitative grading system (see, FIG. 48). Granulomas (≤10) occurring in these tissues were bisected and one half collected in pre-weighed sterile media tubes for mycobacterial culture (see below) and the remaining half immersed in 10% neutral-buffered formalin for histologic analysis. Representative granulomas were selected for mycobacterial culture and histology from tissues with >10 granulomas. Single small granulomas (≤1 mm) were utilized entirely for bacteriology. Representative samples of all abdominal organs and tissues and the brain were collected and then fixed in 10% neutral-buffered formalin for histologic analysis. Additional samples from these tissues were collected for mononuclear isolation and for mycobacterial culture. The pleura and thoracic wall were examined on entering the thoracic cavity and macroscopic granulomas and adhesions were collected, counted, measured, photographed, scored as described (see, FIG. 48) and sampled for quantitative bacteriology and histology. The thoracic viscera were removed en bloc, and then transferred to a sterile cutting board for examination and dissection. Extreme care was taken to avoid mycobacterial contamination of thoracic tissues by spillage of granuloma contents during dissection, and this was accomplished in all but 1 RM in which gross spillage of granuloma contents was observed upon opening the thoracic cavity. The heart was removed and examined and pulmonary and mediastinal lymph nodes and individual lung lobes were dissected free, weighed and photographed. Lymph nodes were divided into samples for mycobacterial culture, histopathology, and mononuclear cell isolation (with mycobacterial culture prioritized if tissue was limiting). Macroscopic granulomas in individual lung lobes were counted, measured, photographed and scored in serial 5 mm tissue slices. Samples for mycobacterial culture and histology from the right and left lung slices were harvested using a nonbiased stereologic sampling method. Individual 6 mm lung tissue cores (30 from the right lung and from the left lung) were bisected and one-half collected in pre-weighed sterile media tubes for bacteriology and the remaining half immersed in 10% neutral-buffered formalin for histologic analysis. Additionally, representative samples of all lung lobes and the heart were collected and immersed in 10% neutral-buffered formalin. Tissues for histologic analysis were routinely processed and embedded in paraffin. Sections (6 mm) were stained with hematoxylin and eosin. Selected tissues were stained by the Ziehl-Neelsen method for acid-fast bacteria.

Vaccines:

The 68-1 and 68-1.2 RhCMV/TB vectors were constructed by bacterial artificial chromosome (BAC) recombineering and were reconstituted and amplified into vector preparations as previously described (Hansen et al., Nature, 2011, 473, 523-527; Hansen et al., Nature, 2013, 502, 100-104; Hansen et al., Science, 2013, 340, 1237874; and Hansen et al., Nat. Med., 2009, 15, 293-299). The Mtb Ags to be included in these vectors were selected by a bioinformatics selection criteria starting with the scoring of 4000 Mtb open reading frames by 11 criteria (Zvi et al., BMC Med. Genomics, 2008, 1, 18). Those criteria included immunogenicity, vaccine efficacy, expression in granulomas, secretion, and role in hypoxic survival. The top candidates were then further screened by a deeper bioinformatics analysis of predicted T cell epitopes and curated to include antigens that are active during different stages of TB infection. In addition, all antigens had been shown to be at least partially protective in a mouse challenge model. The final choice of 9 Mtb proteins for the vaccine inserts included 3 representative proteins from so-called acute phase (85A, 85B, ESAT6), latency (Rv1733c, Rv3407, Rv2626c) and resuscitation (Rpf A, Rpf C and RpfD) class of Mtb Ags. These 9 Ags were expressed in 4 different RhCMV/TB vectors (to be used in combination) for both the 68-1 and 68-1.2 backbones, as follows: 1) Ag85A/Ag85B/Rv3407 (GenBank #KY611401), 2) Rv1733/Rv26226 (GenBank #KY611402), 3) RpfA/RpfC/RpfD (GenBank #KY611403), and 4) Ag85B/ESAT-6 (GenBank #KY611404). The GenBank Accession #s correspond the to the sequences as they are found in the final vectors. Polyprotein #s 1-3 were inserted into the nonessential Rh211 open reading frame under the control of murine CMV IE promotor. Polyprotein #4 was inserted in the same region of the RhCMV genome but under the control of the EF1α promotor (see, FIG. 46, panel a). For the single 6 Ag-expressing, 68-1 RhCMV/TB vector, a single polyprotein insert consisting of 2 Ags from each of 3 classes described above (acute: ESAT-6, Ag85A; latency: Rv3407, Rv2626; resuscitation: RpfA, RpfD; GenBank #KY611405) was used to replace the nonessential Rh107 gene, placing its expression under the control of the endogenous Rh107 promoter (see, FIG. 46, panels a and b). All BACs were analyzed by restriction digestion to confirm genomic integrity and were further examined by next generation sequencing (NGS) on an Illumina MiSeq sequencer to ensure the absence of any unintended mutations in the transgene. To reconstitute the vaccine vectors, the BACs were electroporated into telomerized or primary rhesus fibroblasts and kept in culture until full cytopathic effect was achieved. At this point, transgene expression was confirmed by immunoblot of infected cell lysates and vaccine stocks were generated by the OHSU Molecular Virology Support Core (MVSC). Overall genomic integrity and transgene expression of the final vaccine stocks were confirmed by immunoblots, NGS, and pilot immunogenicity studies in RM. In addition, expression of the ORFs neighboring the TB Ag insertion site was confirmed by RT-PCR. RhCMV/TB vector stocks were titered using primary rhesus fibroblasts in a TCID50 assay. Study 3 and 4 RM were vaccinated by subcutaneous administration of $5 \times 10^6$ pfu of each of the designated RhCMV/TB vectors. For the RM receiving the 4 vector set, each vector was administered in a separate limb (right arm, left arm, right leg, left leg). RM were given the test vaccines twice, with the second dose (homologous boost) administered 15 weeks (Study 1) or 14 weeks (Study 2) after the first dose. The BCG vaccine (Danish strain 1331; Batch #111005A) was obtained from the Statens Serum Institute (Copenhagen, Denmark) and was reconstituted per the manufacturer's instructions (Diluent Batch #386587B). RM were BCG-vaccinated by the intradermal administration of 100 μl of vaccine containing $5.5 \times 10^5$ CFUs into the mid-back.

Immunologic Assays:

Mtb-specific CD4+ and CD8+ T cell responses were measured in blood, BAL and tissues by flow cytometric ICS, as previously described (Hansen et al., Science, 2013, 340, 1237874; Hansen et al., Science, 2016, 351, 714-720; and Hansen et al., Nat. Med., 2009, 15, 293-299). Briefly, mononuclear cell preparations from blood, BAL or tissue were incubated at 37° C. in a humidified 5% $CO_2$ atmosphere with overlapping, consecutive 15-mer peptide mixes (11 amino acid overlap) comprising these proteins, or individual 15-mer peptides from these proteins, and the co-stimulatory molecules CD28 and CD49d (BD Biosciences) for 1 hour, followed by addition of brefeldin A (Sigma-Aldrich) for an additional 8 hours. Co-stimulation without antigenic peptides served as a background control. As previously described (Hansen et al., Science, 2016, 351, 714-720), the MHC restriction (MHC-Ia, MHC-E, MHC-II) of a peptide-specific response was determined by pre-incubating isolated mononuclear cells for 1 hour at room temperature (prior to adding peptides and incubating per the standard ICS assay) with the following blockers: 1) the pan anti-MHC-I mAb W6/32 (10 mg/ml), 2) the MHC-II-blocking CLIP peptide (MHC-II-associated invariant chain, amino acids 89-100; 20 µM), and 3) the MHC-E-blocking VL9 peptide (VMAPRTLLL; SEQ ID NO:31; 20 µM). Blocking reagents were not washed, but remain throughout the assay. Following incubation, stimulated cells were fixed, permeabilized and stained as previously described (Hansen et al., Science, 2013, 340, 1237874; Hansen et al., Science, 2016, 351, 714-720; and Hansen et al., Nat. Med., 2009, 15, 293-299) using combinations of the following fluorochrome-conjugated mAbs: SP34-2 (CD3; Pacific Blue, Alexa700), L200 (CD4; AmCyan, BV510), SK-1 (CD8α; PerCP-Cy5.5), MAB11 (TNF-α; FITC, PE), B27 (IFN-γ; APC), FN50 (CD69; PE, PE-TexasRed), B56 (Ki-67; FITC), and in polycytokine analyses, JES6-5H4 (IL-2; PE, PE Cy-7). To determine the cell surface phenotype of Mtb-specific CD8+ T cells, mononuclear cells were stimulated as described above, except that the CD28 co-stimulatory mAb was used as a fluorochrome conjugate to allow CD28 expression levels to be later assessed by flow cytometry, and in these experiments, cells were surface-stained after incubation for lineage markers CD3, CD4, CD8, CD95 and CCR7 (see below for mAb clones) prior to fixation/permeabilization and then intracellular staining for response markers (CD69, IFN-γ, TNF-α). Data was collected on an LSR-II (BD Biosciences). Analysis was performed using FlowJo software (Tree Star). In all analyses, gating on the lymphocyte population was followed by the separation of the CD3+ T cell subset and progressive gating on CD4+ and CD8+ T cell subsets. Antigen-responding cells in both CD4+ and CD8+ T cell populations were determined by their intracellular expression of CD69 and one or more cytokines (either or both of the IFN-γ and TNF; ±IL-2 in polycytokine analyses). After subtracting background, the raw response frequencies were memory corrected, as previously described (Hansen et al., Nature, 2011, 473, 523-527 and Hansen et al., Nat. Med., 2009, 15, 293-299) using combinations of the following fluorochrome-conjugated mAbs to define the memory vs. naive subsets SP34-2 (CD3; Alexa700, PerCP-Cy5.5), L200 (CD4; AmCyan), SK-1 (CD8α; APC, PerCP-cy-5.5), MAB11 (TNF-α; FITC), B27 (IFN-γ; APC), FN50 (CD69; PE), CD28.2 (CD28; PE-TexasRed), DX2 (CD95; PE), 15053 (CCR7; Pacific Blue), and B56 (Ki-67; FITC). For memory phenotype and polycytokine analysis of Mtb Ag-specific T cells, all cells expressing CD69 plus one or more cytokines were first Boolean gated, and then this overall Ag-responding population was subdivided into the subsets of interest on the basis of surface phenotype or cytokine production pattern.

Mycobacterial Culture:

Tissues routinely collected at necropsy for Mtb burden analysis in both Study 3 and 4 included: 30 stereologic punches from right lung lobes, 10 punches from left lung lobes, trachea, left hilar LN, right hilar LN, left carinal LN, right carinal LN, paratracheal LN, mediastinal LN, axillary LN, inguinal LN, mesenteric LN, spleen, pancreas, left medial lobe of liver, right medial lobe of liver, left lateral lobe of liver, right lateral lobe of liver, liver caudate, left kidney, and right kidney. In Study 4, retropharyngeal LN, tonsil, submandibular LN, and iliosacral LN were also collected and cultured. In one RM in Study 4, mycobacterial culture analysis was not reported due to gross contamination of thoracic tissues with granuloma contents. Tissues were collected in HBSS and were then homogenized in an IKA grinder tube with a IKA Ultra-Turrax Tube Drive homogenizer. The tissue homogenate was then filtered over a 70 µm wire screen to remove debris and 200 µl of this material was plated neat and in serial dilutions (1/10, 1/100) on 7H11 agar plates (Remel). All plates were incubated at 37° C. and *M. tuberculosis* growth was enumerated 28 and 42 days later. Bacterial burden was calculated in CFU per gram of tissue. A tissue was considered Mtb+ if any colonies with the correct morphologic features were identified. Selected cultures were analyzed by the Ziehl-Neelsen method for acid-fast bacteria to confirm colony morphologic features.

Data Preparation for Statistical Analysis:

Three outcome measures were evaluated for evidence of a difference across treatment arms within each study: CT scan area-under the curve from challenge to day 112 post-challenge, pathologic score at necropsy, and Mtb culture at necropsy. The equivalence of the three Study 4 vaccine groups by these outcome measures (see, FIG. 49) justified a pooled analysis. An outcome measure that combines necropsy score and culture results into a single value that can be evaluated across both efficacy studies was evaluated. Associations between these outcomes and Mtb-specific T cell responses measured by ICS were assessed.

Area under the log CT scan-determined pulmonary disease volume curve: The AUC of the log-transformed CT scan-determined pulmonary disease volume measurements from time 0 (set to 0) to day 112 was computed. Missing values for monkeys taken to necropsy before the full series of scheduled CT scan time points were imputed. The AUC of this augmented data was computed. The imputation procedure that was employed used linear regression to estimate missing values from previous time points. As a sensitivity analysis, the missing values were imputed using a more conservative rule (replacing missing values with the largest non-missing value at the same time point among monkeys receiving the same treatment, excluding for further conservatism one high-valued outlier unvaccinated RM); the resulting AUCs were highly insensitive to this procedure (Pearson correlation over 0.99 for both studies).

Necropsy score data: The non-negative count valued necropsy scores are amenable to Poisson modeling. Model evaluations supported inclusion of the additional parameter for overdispersion in the negative binomial model. In TB Study 4, the estimated extra parameter was zero, so this model was equivalent to a simple Poisson model. For this Poisson model, a sandwich-based estimates of variance-covariance matrices was employed as an alternative method to account for overdispersion, using the vcovHC function in the sandwich package (Zeileis, J. Stat. Software, 2004, 11, 1-17 and Zeileis, J. Stat. Software, 2006, 16, 1-16) in R.

Necropsy culture data: Necropsy culture inputs were quantitative measures of culture growth with multiple replicates per tissue. These data were treated as binary indicators of a culture being positive versus negative (zero), and the total number of positive cultures was evaluated. Model evaluations of necropsy culture outcome data favored the more expressive negative binomial models over Poisson models, and did not support using the ZIP model. One animal in TB Study 4 (Rh30072) was missing necropsy culture data but did have necropsy score data; the analyses of the culture data therefore excluded this RM, but as described below, the missing value for use in computing the combined scaled outcome measure was imputed.

Figure 50:
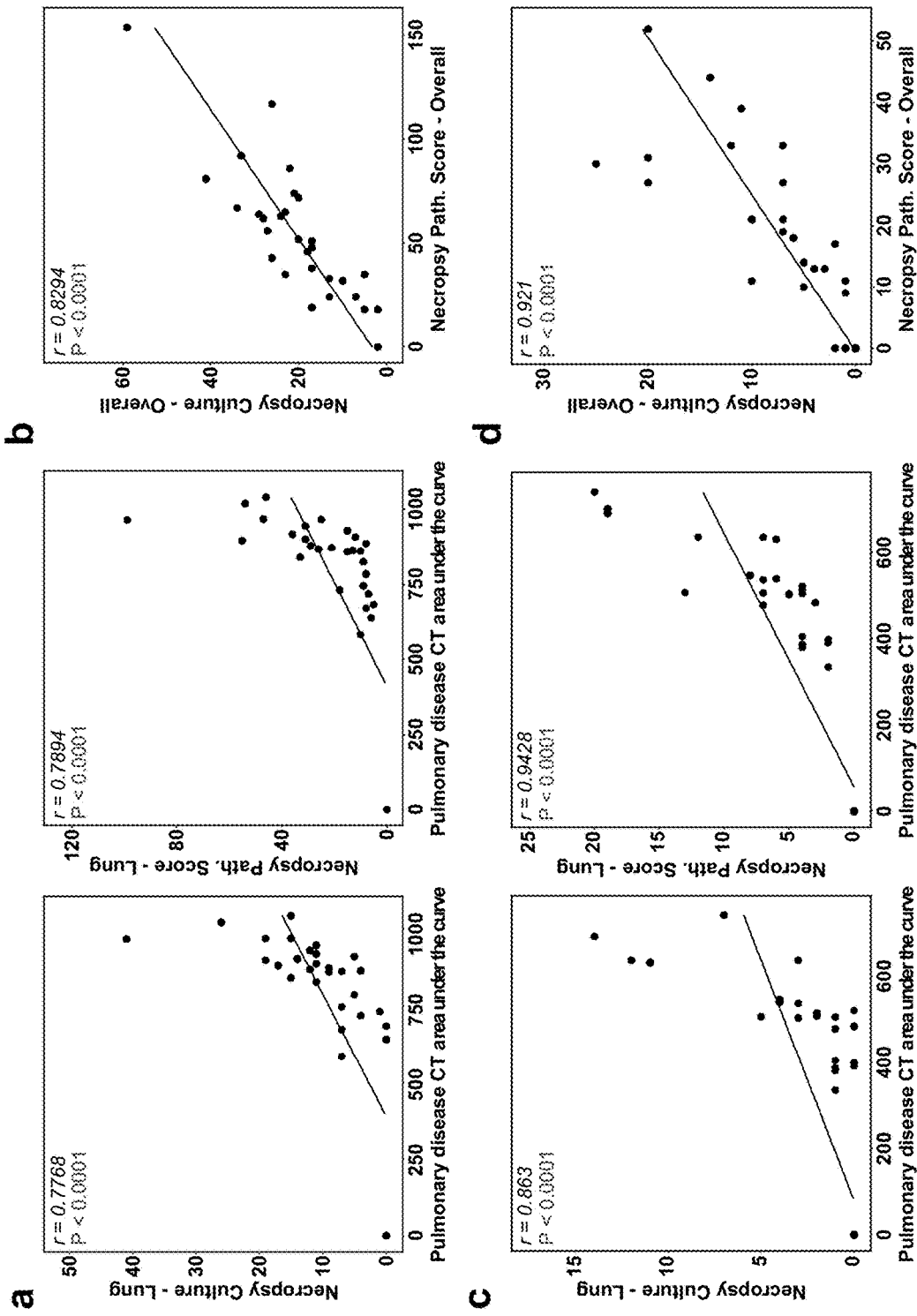
FIG. 50 (panels a, b, c, and d) shows a comparison of different measures of TB infection outcome.

Combined scaled outcome measure: As shown in FIG. 50, a strong correlation between the necropsy score and necropsy culture outcome measures within each study was observed, although the scales were different: necropsy cultures are about one third as large as necropsy scores, across both studies. The intermediate, study-specific combined scaled outcome measure was created to gain measurement precision by averaging these two very similar outcome measures. To ensure that each receives equal weight in the combined measure, and to maintain discreteness in support of Poisson analysis of the statistic, the inputs were scaled by multiplying the necropsy culture values by 3 and then adding these to the necropsy scores. For Study 4, one RM (I3) had a missing necropsy culture value. For this animal, the combined scaled outcome measure was computed using an imputed necropsy culture value, which was obtained by multiplying the observed necropsy score value by the estimated coefficient from a simple linear regression model relating the two values. This monkey's necropsy score value was 29, its imputed necropsy culture value was 8, and its combined scaled outcome measure value was 53. A negative binomial regression model of these study-specific combined measures versus treatment and study was employed, and used the estimated coefficient on study (0.3796) to further scale the TB Study 3 combined scaled outcome values. Therefore, the combined scaled outcome variable for TB Study 3 RM is the study-specific value multiplied by 0.3796 and then rounded to maintain the discreteness of the final variable for Poisson analysis.

Figure 44:
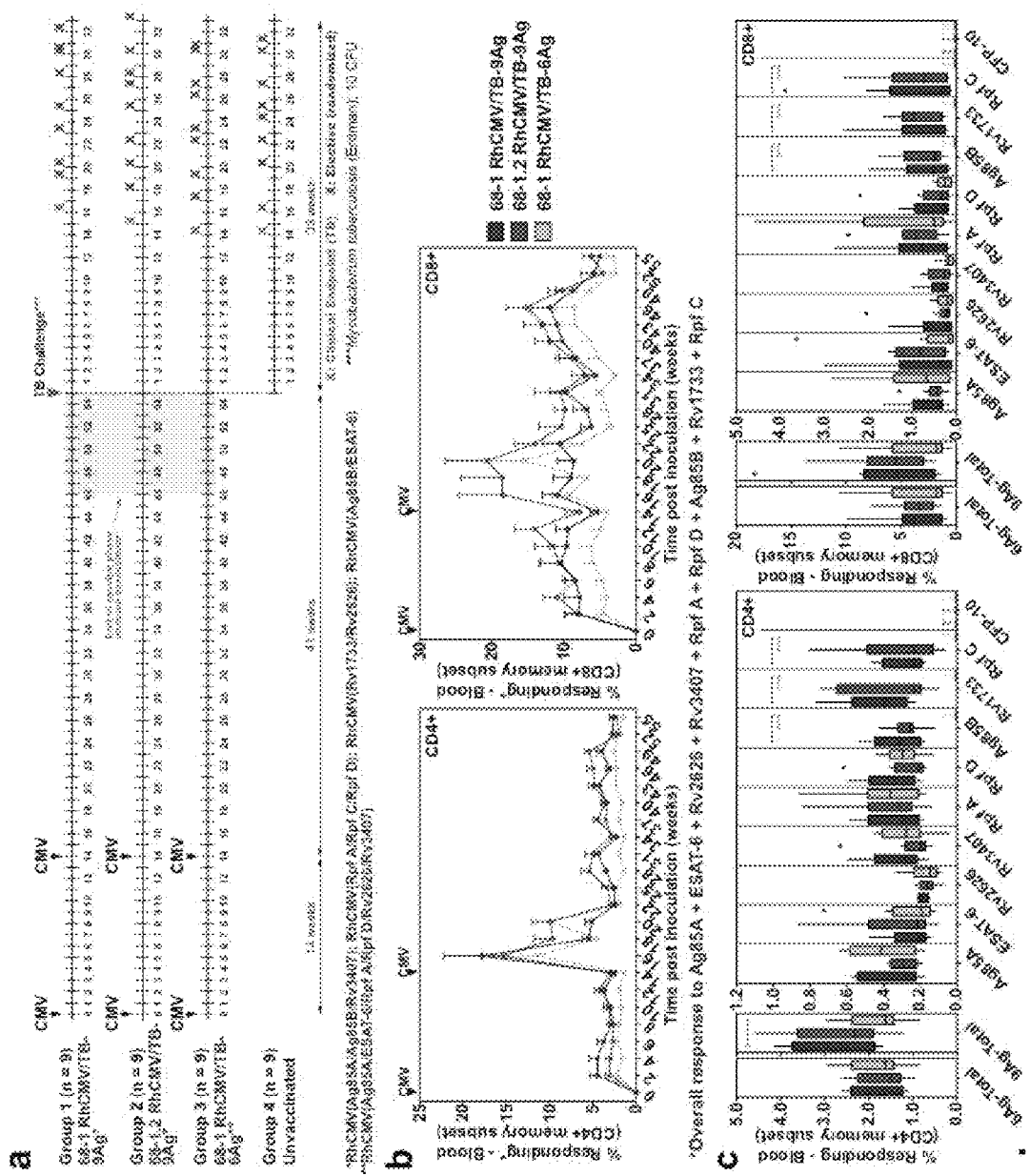
FIG. 44 (panels a, b, c, d, e, f, and g) shows the immunogenicity of RhCMV/TB vaccines for Study 4.
Figure 44:
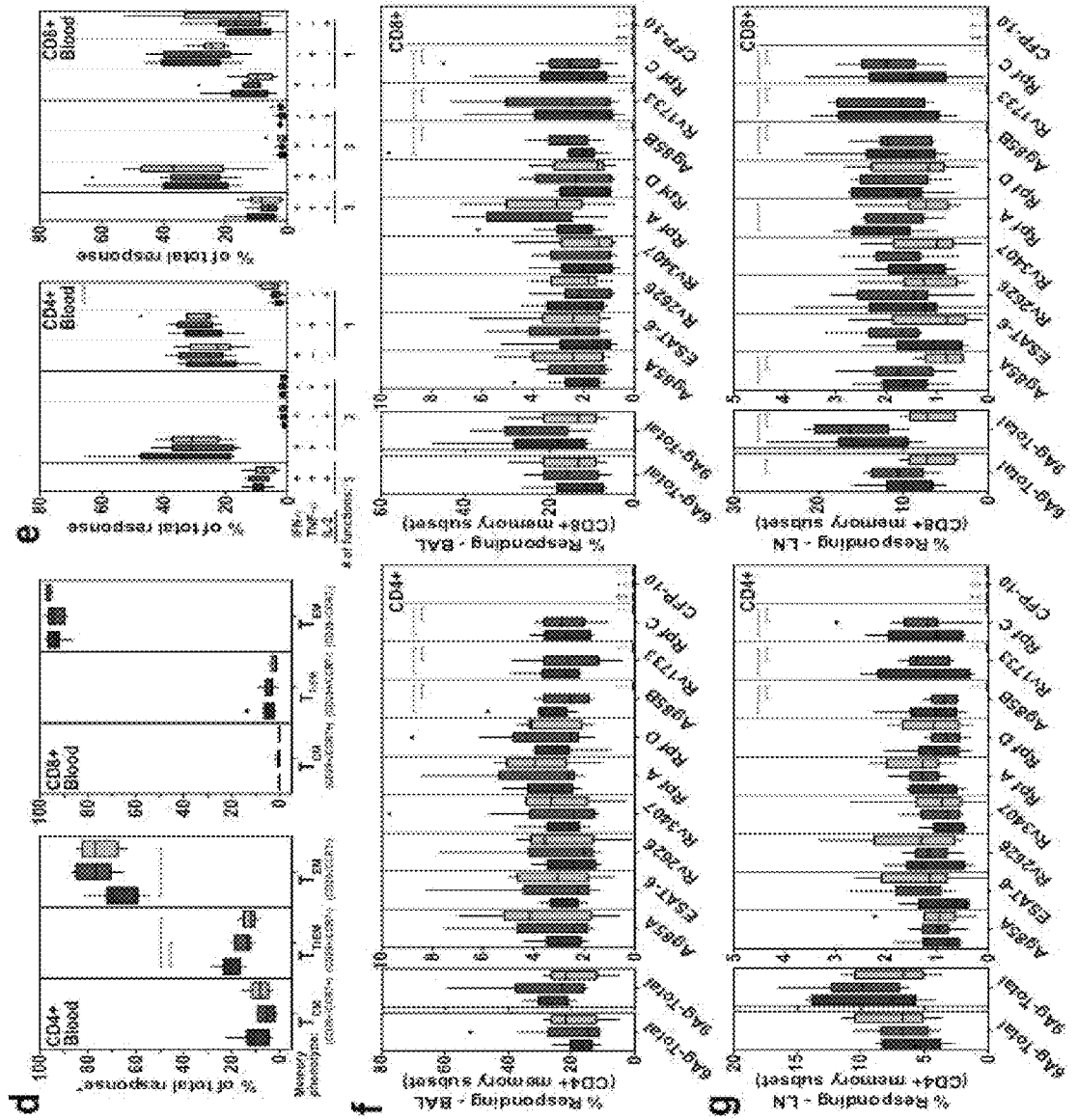

End of vaccine phase T cell response data: Longitudinal flow cytometric ICS measures of CD4+ and CD8+ immune responses targeting the 9 individual genes in the RhCMV vaccines, and CFP10 was evaluated. The primary summary of these data was a measure of the immune response at the end of vaccine phase. These pre-challenge baseline immunogenicity values are geometric means of three independent measurements over the time periods shown in FIG. 42 (panel a) and FIG. 44 (panel a). Totals over 6 or 9 antigens were computed prior to log-transformation and normalization. Normalization shifts and scales these values to have mean zero, standard deviation 1 so that units have the interpretation of z-scores measuring the number of standard deviations an immune measurement (on the log scale) is from the overall (study-specific) mean of that measurement.

Statistical Analysis:

All statistical analyses were conducted in R40.

Figure 51:
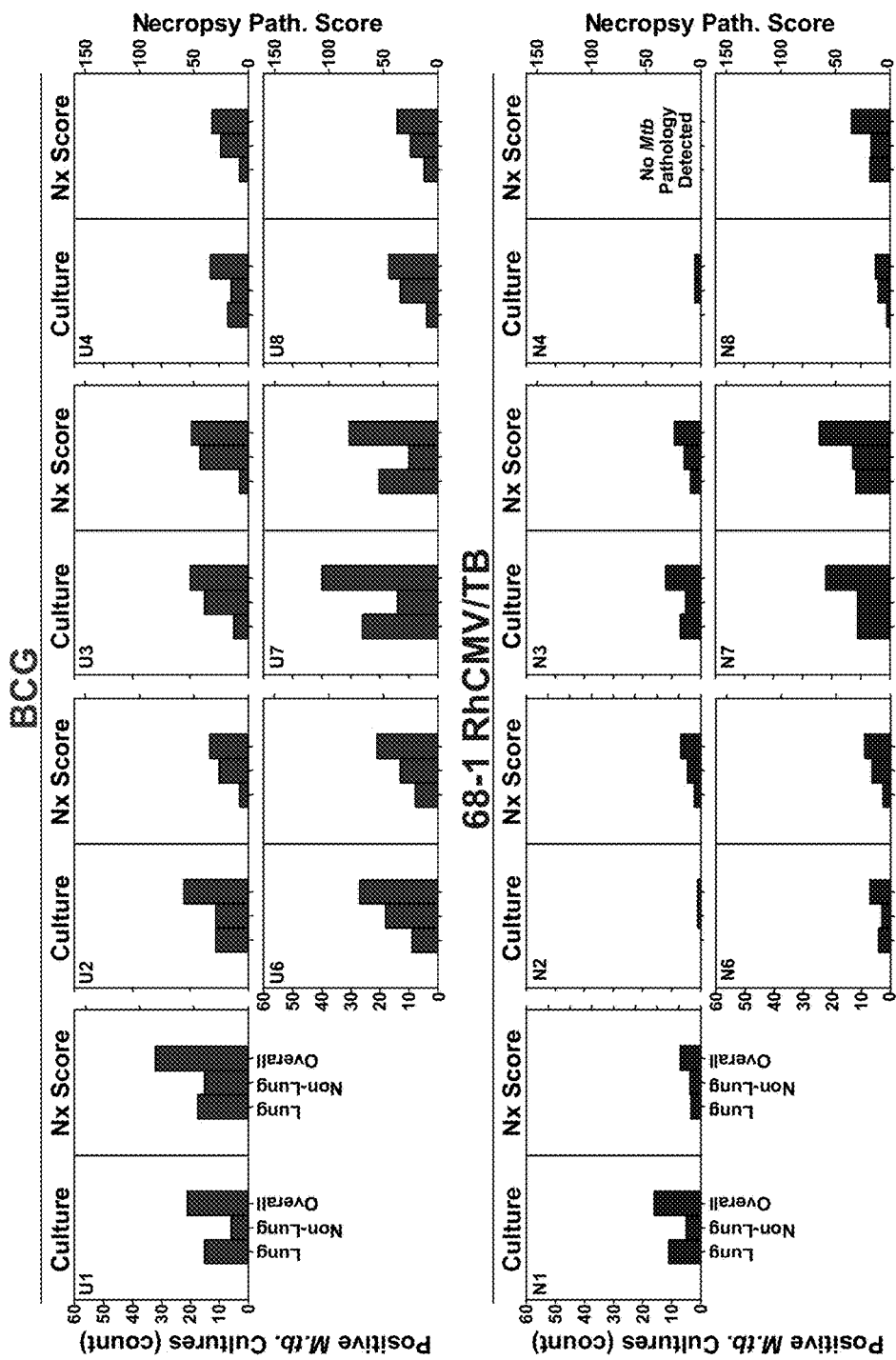
FIG. 51 shows a summary of TB disease outcome at necropsy of Study 3.
Figure 51:
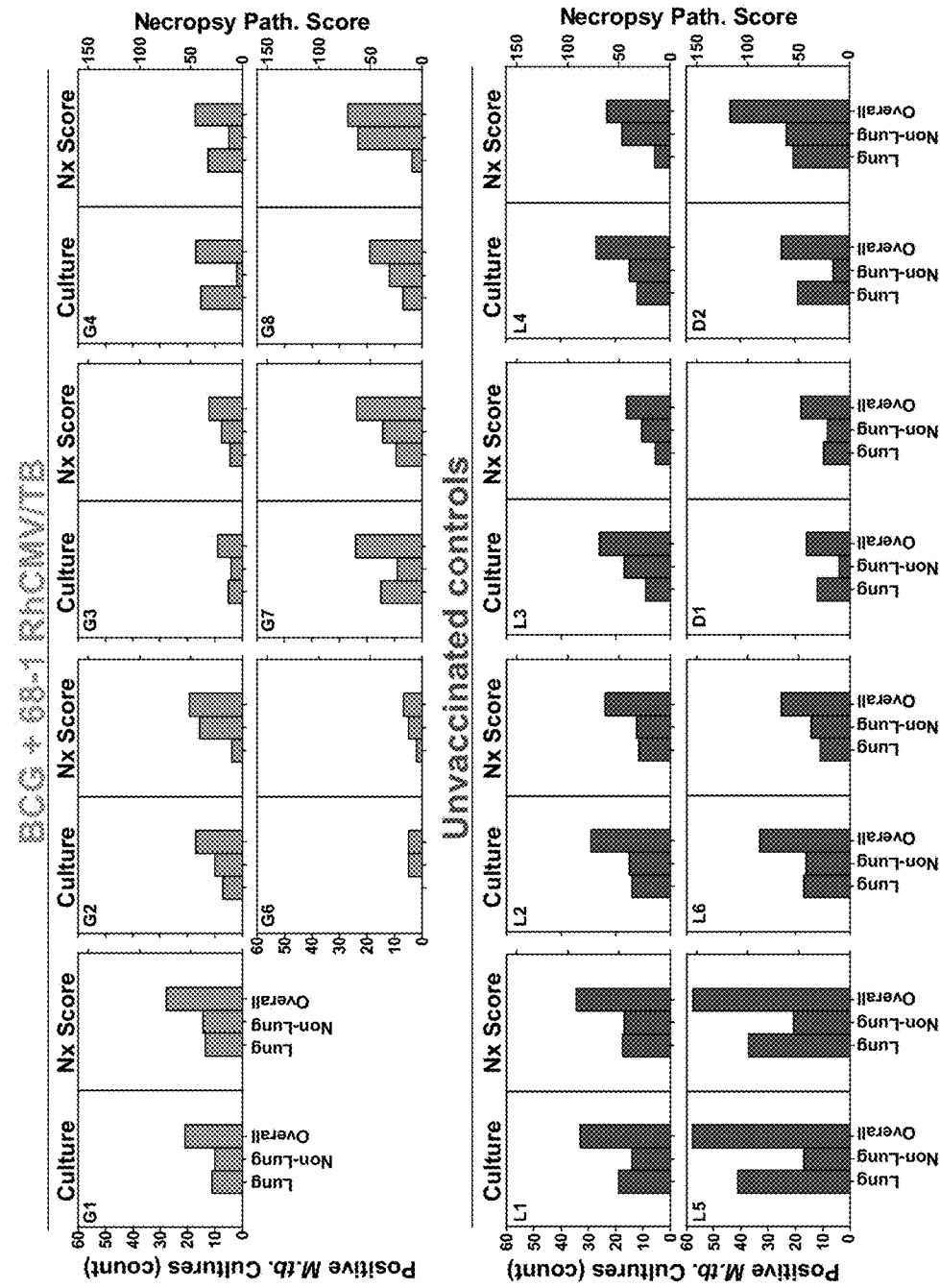

Efficacy: Non-parametric tests were employed for primary comparisons and parametric models were used for estimating confidence intervals of treatment effects. For comparisons of outcome measures across pairs of groups, we used two-sided Wilcoxon tests. Boxplots show unadjusted p-values of only the pairwise comparisons that are significant at the 0.05 level. Holm adjustment was employed for the specified primary non-parametric comparisons: between unvaccinated and vaccinated TB Study 3 groups, and separately between BCG-only and other vaccinated groups. For TB Study, 4 similarly applied Holm-adjustment within groups of comparisons between unvaccinated and vaccinated TB Study 4 groups individually, and between the original 68-1 9Ag vector and the two modifications (68-1 6Ag, and 68-1.2 9Ag). Boxplots show unadjusted p-values; Holm-adjusted p-values are shown in FIG. 51. Vaccine efficacy is reported as 100%-W, where W is 100 times the estimated rate (or confidence limit) of the Poisson or negative binomial model representing a count-valued outcome measure (necropsy score, necropsy culture, or the combined scaled outcome measure) among a vaccine group, as a fraction of the rate for Unvaccinated RM. For analysis of correlations across outcome variables, Spearman's rank-transformed correlation statistic (r) and test were used. For Spearman's test, p-values were computed via the asymptotic t approximation using the cor.test method in R.

Immunogenicity and correlates analysis: For comparisons of immunogenicity across vaccine-receiving treatment groups at pre-challenge baseline, Kruskal-Wallis (KW) tests were employed. The boxplots indicate significance of pairwise Wilcoxon tests if both KW and Wilcoxon tests had unadjusted p-values ≤0.05. Due to the missing of blood immunology data from week 41 of RM U6 (Study 3; BCG-only group), for FIG. 42 (panel d), n=6 for the BCG group; and for FIG. 42 (panel c), the data point for the data point for this RM used only 2, rather than 3, time points for averaging. For analysis of immune response correlations with the combined scaled outcome measure (defined above) among RM receiving RhCMV and no BCG, Spearman's statistic and test was computed, and the scatterplots also show the curve of the best-fitting negative binomial model. The low correlations (see, FIG. 55) were confirmed through sensitivity analyses that also found in each study separately and in each outcome measure, so the lack of significance is not an artifact of these analysis choices. Extensive non-parametric analyses as well as parametric analyses employing negative binomial models to estimate single-parameter and multi-parameter associations between this combined scaled measure and pre-challenge immune responses to RhCMV immunogens revealed no statistically supported immune correlates of that outcome, or of other related outcomes.

Example 5: Studies #3 and #4

To initially test the hypothesis that TEM responses elicited by RhCMV/TB vectors would manifest a higher efficacy than BCG, 3 groups of RM (n=7 each; all naturally RhCMV-infected at study assignment) were vaccinated with: 1) RhCMV/TB vectors alone (a set of 4 RhCMV vectors based on the 68-1 strain that together express 9 different Mtb proteins: ESAT-6, Ag85A, Ag85B, Rv3407, Rv1733, Rv2626, RpfA, Rpf C, Rpf D; see, FIG. 46, panel a), 2) BCG alone, and 3) BCG followed by RhCMV/TB, according to the protocol outlined in FIG. 42, panel a. As expected, RhCMV/TB vectors elicited and maintained high frequency CD4+ and CD8+ T cell responses in blood to all 9 Mtb inserts, as measured by overlapping 15-mer peptide mix-induced expression of intracellular TNF and/or IFN-γ by flow cytometric intracellular cytokine (ICS) analysis, and in plateau phase, these responses were predominantly effector differentiated, manifesting either a fully differentiated TEM phenotype (CD8+) or a mixed transitional and fully differentiated TEM phenotype (CD4+) (see, FIG. 42, panels b-d). About half of the RhCMV/TB-elicited, Mtb Ag-specific CD4+ and CD8+ T cells responding in the ICS assays produced both TNF and IFN-γ (with or without IL-2) with the remainder predominantly producing TNF alone (see, FIG. 42, panel e). BCG elicited circulating CD4+ and CD8+ T cell responses to 8 of the 9 insert Ags (all except ESAT-6, which is not expressed by BCG22). These responses predominantly manifested a central memory phenotype for the CD4+ T cells and a fully differentiated TEM phenotype for the CD8+ T cells. However, in peripheral blood, the overall magnitude of the BCG-elicited T cell responses to these Ags was considerably less (5-10-fold) than in RhCMV/TB-vaccinated RM, and the majority of these T cells produced either TNF or IL-2 alone (CD4+) or TNF or IFN-γ alone (CD8+), but not both TNF and IFN-γ (see, FIG. 42, panels b-e). Indeed, the BCG-induced CD4+ and CD8+ T cell response to these Ags was not large enough to measurably change the plateau-phase magnitude, phenotype and function of the TB Ag-specific responses in the RM that received both BCG and RhCMV/TB relative to the RM that received RhCMV/TB vaccination alone (see, FIG. 42, panels b-e). Differences in response magnitude between BCG- and RhCMV/TB-vaccinated RM were less apparent in bronchoalveolar lavage (BAL) fluid, with the responses in the latter group only marginally higher than in the former group (see, FIG. 42, panel f).

Referring to FIG. 42, the immunogenicity of RhCMV/TB and BCG vaccines in Study 3 is shown. Panel a is a schematic of the vaccination and challenge protocol and RM groups of Study 3. Panel b shows a longitudinal analysis of the overall CD4+ and CD8+ T cell response to the 9 Mtb insert proteins after vaccination with the designated vaccines. The background-subtracted frequencies of cells responding with TNF and/or IFN-γ production by flow cytometric ICS assay to peptide mixes comprising each of the Mtb proteins within the memory CD4+ or CD8+ T cell subset were summed with the figure showing the mean (±SEM) of these overall (summed) responses at each time point. Panel c shows boxplots comparing the individual Mtb protein (each of the 9 Mtb inserts plus the non-insert CFP-10)-specific and overall (summed) Mtb-specific CD4+ and CD8+ T cell response frequencies (defined by TNF and/or IFN-γ production) in peripheral blood between the vaccine groups at the end of the vaccine phase (each data point is the mean of response frequencies in 3 separate samples from weeks 44-49; ‡ indicates no response detected). Penal d shows boxplots comparing the memory differentiation of the vaccine-elicited CD4+ and CD8+ memory T cells in peripheral blood responding to Ag85A with TNF and/or IFN-γ production at the end of vaccine phase (week 47). Memory differentiation state was based on CD28 vs. CCR7 expression, delineating central memory (TCM), transitional effector memory (TTREM), and effector memory (TEM), as designated. Penal e shows boxplots comparing the frequency of vaccine-elicited CD4+ and CD8+ memory T cells in peripheral blood responding to Ag85A with TNF, IFN-γ and IL-2 production, alone and in all combinations at the end of vaccine phase (week 49). Panel f shows boxplots comparing the individual Mtb protein-specific and overall (summed) Mtb-specific CD4+ and CD8+ T cell response frequencies (defined by TNF and/or IFN-γ production) in bronchoalveolar lavage (BAL) fluid between the vaccine groups at the end of the vaccine phase (weeks 46-47; ‡ indicates no response detected). In panels c-f, the Kruskal-Wallis (KW) test was used to determine the significance of differences between vaccine groups with the Wilcoxon rank sum test used to perform pair-wise analysis if KW p values were ≤0.05; brackets indicate pair-wise comparisons with Wilcoxon p values ≤0.05.

Figure 46:
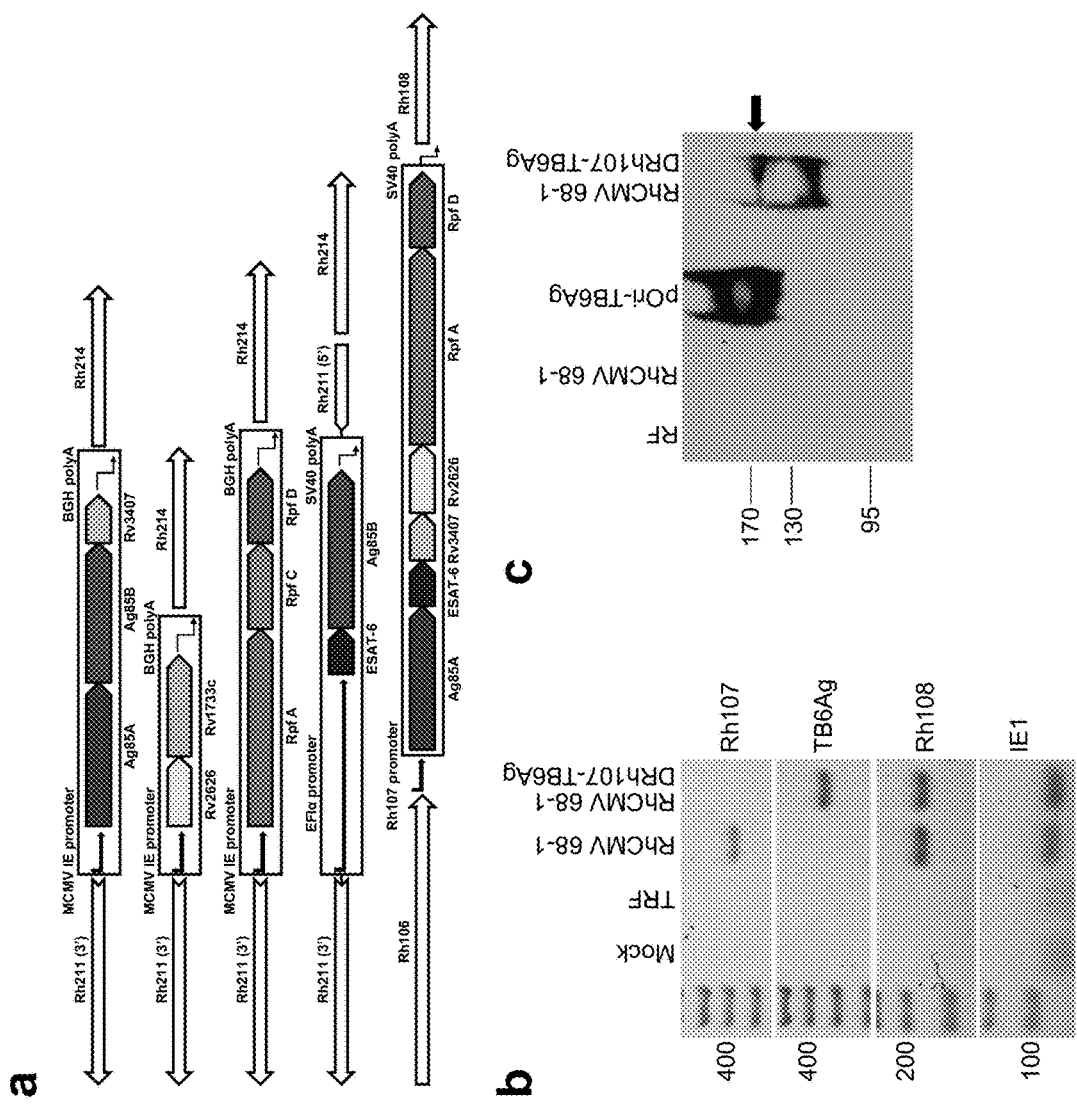
FIG. 46 (panels a, b, and c) shows RhCMV/TB vectors used in Study 3 and 4.

Referring to FIG. 46, a description of RhCMV/TB vectors is shown. Panel a is a diagram showing the insertion sites for TB Ag cassettes in either the RhCMV 68-1 and 68-1.2 BAC backbones. The top 4 constructs use exogenous promoters (either MCMV IE or EF1a) to drive insert expression, whereas the bottom construct (68-1 RhCMV/TB-6Ag) replaces the Rh107 open reading frame with the 6 Ag insert, and relies upon the endogenous Rh107 promoter to regulate insert expression. Panel b shows a RT-PCR analysis of the 68-1 RhCMV/TB-6Ag vector confirming deletion of Rh107, concomitant expression of the 6 Ag TB insert and unchanged expression of both IE1 and the adjacent Rh108 open reading frame. In this experiment, telomerized rhesus fibroblasts (TRF) were infected with the vector at a multiplicity of infection (MOI) of 3 and RNA was harvested and cDNA generated at 48 hours post-infection. RT-PCR was performed using primers specific for internal regions of the indicated genes to demonstrate deletion of Rh107 and expression of the 6Ag insert as well as surrounding open reading frames. Panel c shows a Western Blot analysis of the HA-tagged 6 Ag insert expression (arrow) by the 68-1 RhCMV/TB-6Ag vector. TRFs were infected with RhCMV 68-1 or the 68-1 RhCMV/TB-6Ag vector (RhCMV 68-1 ΔRh107-TB6Ag) at an MOI=3, harvested at full cytopathic effect, and subjected to western blotting directed at the HA tag. HeLa cells transfected with a plasmid expressing the 6 Ag insert (pOri-TB6Ag) are shown as a control.

Fifty weeks after initial vaccination, the 3 groups of vaccinated RM and a control group of unvaccinated RM (n=8; also naturally CMV+) were challenged by intrabronchial instillation of 25 colony-forming units (CFUs) of Erdman strain Mtb bacteria into the right lower lobe. The effectiveness of challenge was confirmed by de novo development of CD4+ and CD8+ T cell responses to the CFP-10 Ag in all RM (see, FIG. 43, panel a, and FIG. 47, panel a; the Mtb-expressed CFP-10 Ag was not included in the RhCMV/TB vectors, and, like ESAT-6, is not expressed by BCG22). The development of pulmonary disease after challenge was monitored every two weeks by CT scan assessment of lesional volume, but primary outcome was determined by pathologic examination (pathologic score; see, FIG. 48) and by extensive mycobacterial culture of lung (sampled using stereology), as well as lung-draining and other chest lymph nodes (LNs), peripheral LNs and selected organs (spleen, liver, kidney, pancreas) at necropsy (see Methods), with necropsy performed either at clinical endpoint, or after 20 weeks post-infection (pi), by randomization (see, FIG. 42, panel a). Pulmonary disease developed rapidly in unvaccinated control RM with progression to severe (>10,000 mm$^3$) lung parenchymal disease by CT scan in 7/8 RM by day 56 pi and all RM by day 98 pi (see, FIG. 43, panel b). In both RM groups that received BCG, the development of pulmonary disease was more variable, but 5 of 7 RM in each group developed severe disease by day 98 pi. In contrast, 5 of 7 of the RM vaccinated with RhCMV/TB vectors alone developed only mild pulmonary disease (<3, 000 mm$^3$, n=4) or no disease (n=1), and the overall area-under-the-curve (AUC) of pulmonary lesion volume of this group during the first 16 weeks pi was significantly reduced from the unvaccinated control group (see, FIG. 43, panel c, and FIG. 49, panel a).

Figure 43:
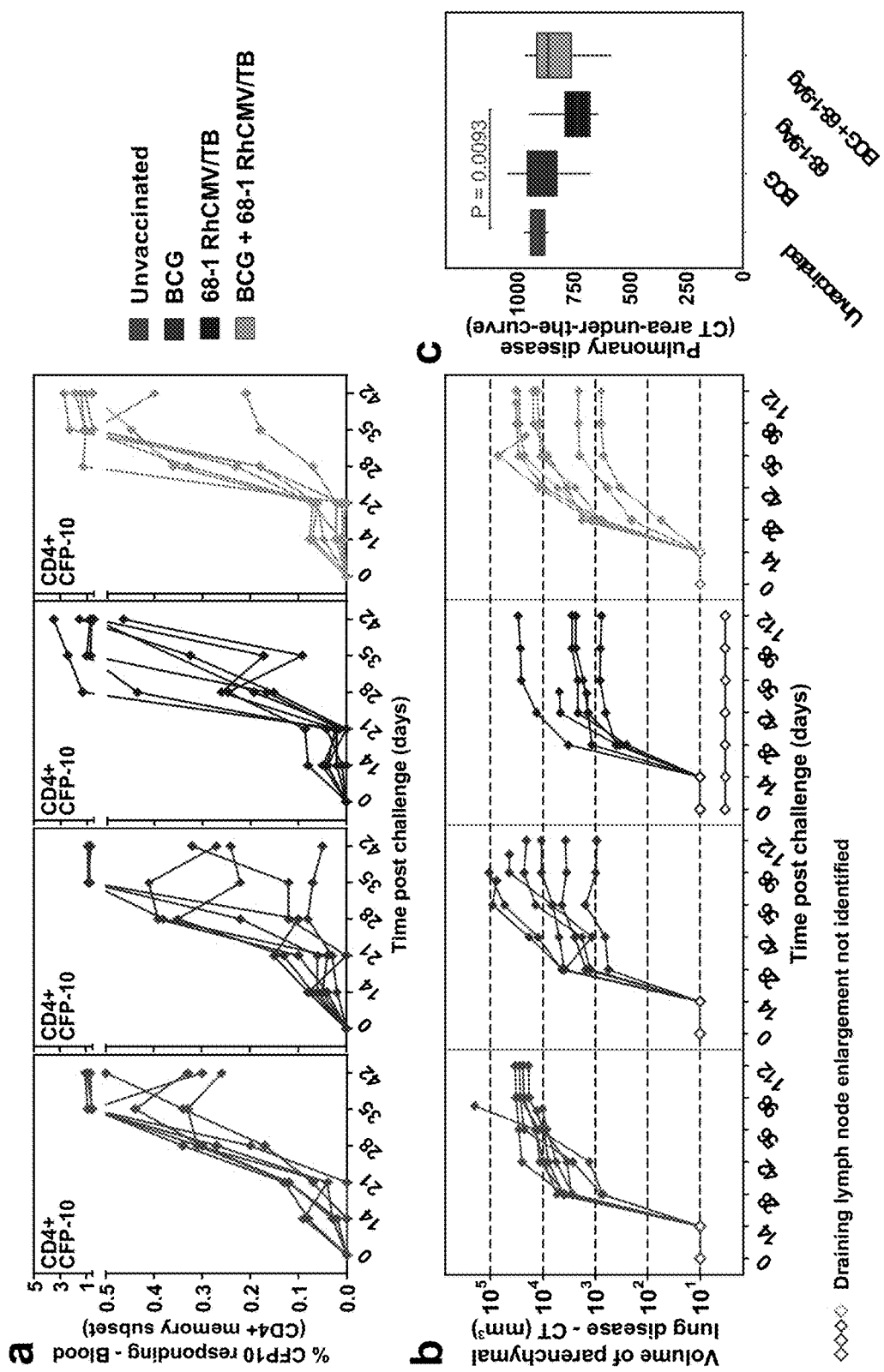
FIG. 43 (panels a, b, c, d, e, and f) shows the outcome of Mtb challenge for Study 3.
Figure 43:
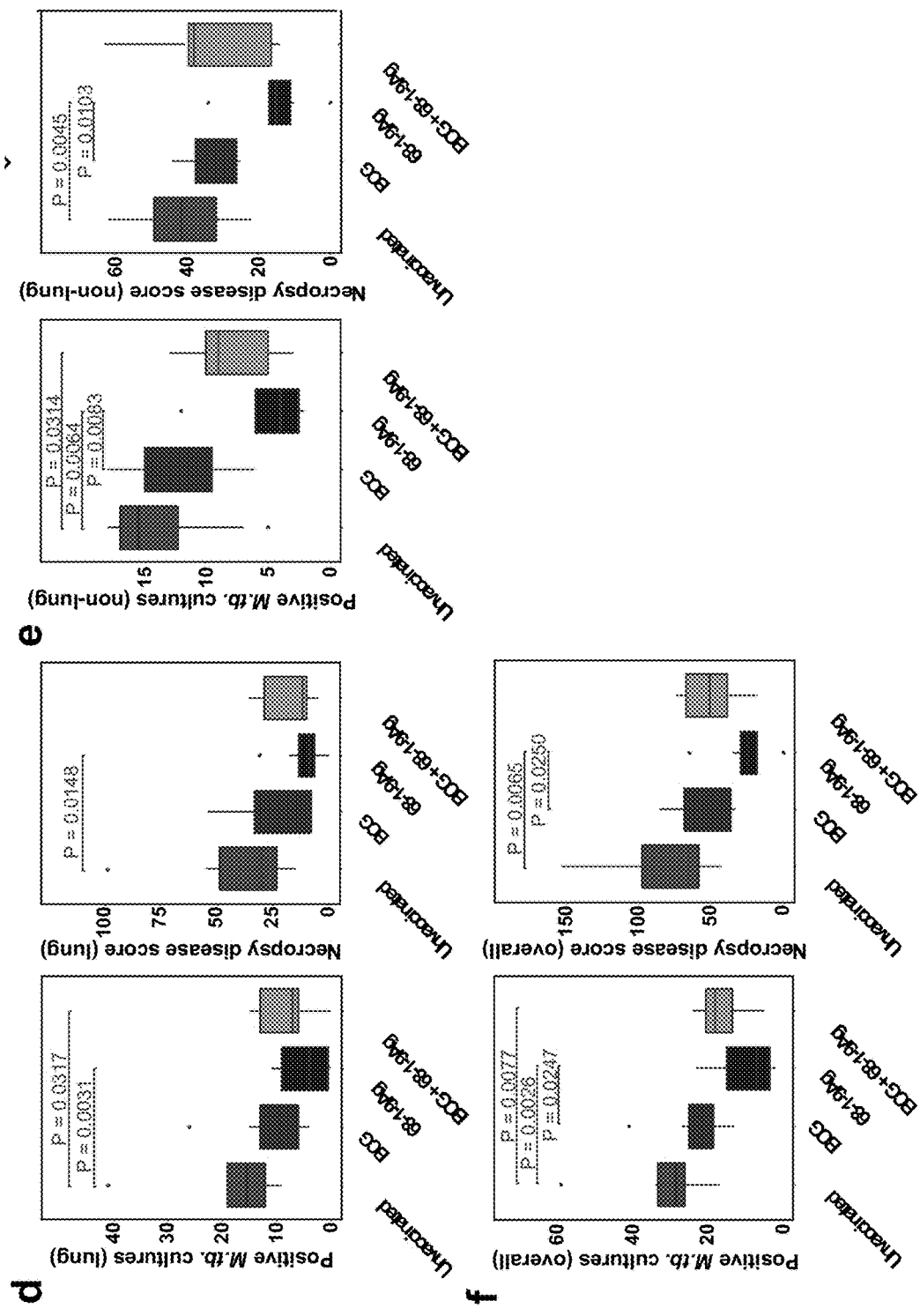

Referring to FIG. 43, the outcome of Mtb challenge (Study 3) is shown. Panel a shows the development of peripheral blood CD4+ T cell responses to the peptide mixes comprising the non-vaccine insert Mtb protein CFP-10 in all Study 3 RM after Mtb challenge by flow cytometric ICS analysis (response defined by TNF and/or IFN-γ production after background subtraction in memory subset; CFP-10-specific CD8+ T cell responses shown in FIG. 47, panel a).

Panel b shows CT quantification of disease volume in the pulmonary parenchyma after Mtb challenge (presence or absence of draining LN enlargement indicated by closed vs. open symbols). Panel c shows boxplots comparing the AUC of CT-determined pulmonary lesional volume (day 0-112) of the 4 RM groups. Panels d-e show boxplots comparing the extent of TB at necropsy measured by Mtb recovery with mycobacterial culture and by pathologic disease score in lung parenchyma (panel d), all non-lung parenchymal tissues (panel e) and all tissues (panel f). In panels c-f, unadjusted Wilcoxon p values ≤0.05 are shown (see, FIG. 49, panel a).

Figure 47:
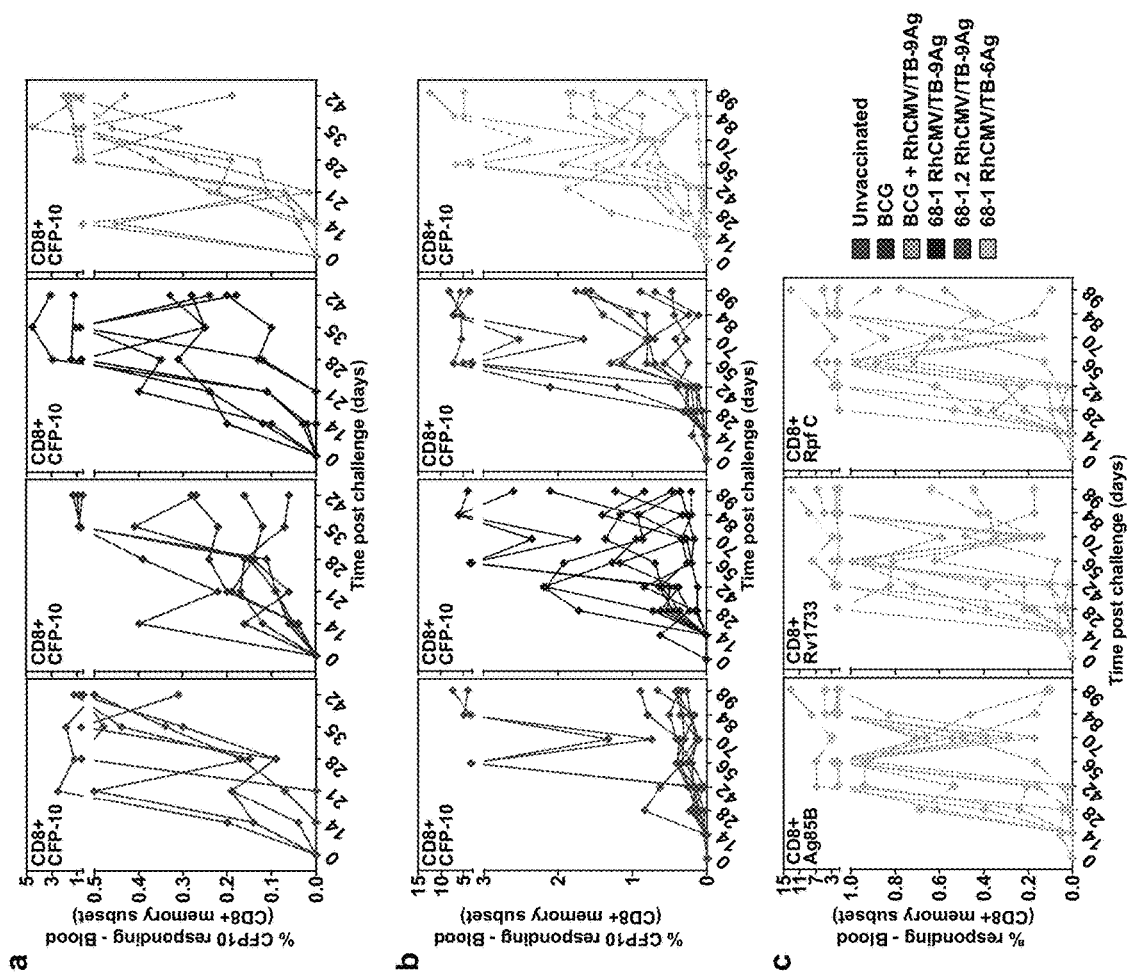
FIG. 47 (panels a, b, and c) shows the development of de novo Mtb-specific CD8+ T cell responses after Mtb challenge.

Referring to FIG. 47, the development of de novo Mtb-specific CD8+ T cell responses after Mtb challenge is shown. Panels a and b show the development of peripheral blood CD8+ T cell responses to the peptide mixes comprising the non-vaccine insert Mtb protein CFP-10 in Study 3 (panel a) and Study 4 (panel b) RM after Mtb challenge by flow cytometric ICS analysis (response defined by TNF and/or IFN-γ production after background subtraction in memory subset). Corresponding CFP-10-specific CD4+ T cell responses are shown in FIG. 43, panel a and FIG. 45, panel a. All Mtb-challenged RM, including vaccinated RM that did not manifest post-challenge disease, showed multiple post-challenge samples with above-threshold CFP-10-specific CD4+ and CD8+ T cell responses, indicating a de novo response to challenge. Panel c shows the development of peripheral blood CD8+ T cell responses to the peptide mixes comprising the Ag85B, Rv1733 and Rpf proteins in Study 4, group 3 RM, who received the RhCMV/TB-6Ag vaccine lacking these insert Ags (corresponding CD4+ T cell responses shown in FIG. 45, panel b). Again, de novo post-challenge induction of responses to these 3 Mtb proteins was observed in all group 3 RM.

Referring to FIG. 48, the pathologic scoring of TB disease at necropsy is shown. The tables show the criteria and scoring system used to quantify the pathologic extent of TB disease at necropsy in Study 3 and 4 RM. Note that every RM receives a separate score for 7 lung lobes, chest wall, each separate lymph node group (both chest and non-chest), liver, spleen, and each other involved organ, with the sum of these scores being the overall Pathologic Score. The sum of the scores for the 7 lung lobes is the Lung Pathologic Score, with the sum of all other scores (including chest wall and lymph nodes) being the Non-Lung Pathologic Score. The sum of all scores (Lung and Non-Lung) is the Overall Pathologic Score.

Referring to FIG. 49, a summary of outcome statistics is shown. Panels a and b show Study 3 analysis. Panels c and d show Study 4 analysis. Panel e shows the combined analysis.

The CT-determined lesional AUC through week 16 pi closely correlated with pulmonary parenchymal disease at necropsy as measured by both pathologic scoring and mycobacteria culture (see, FIG. 50, panel a), and as such, the extent of lung disease at necropsy was significantly reduced in the RhCMV/TB vector group compared to unvaccinated controls by both these measures (see, FIG. 43, panel d, and FIG. 49, panel a). No significant pulmonary disease reduction was observed in the BCG-only vaccinated cohort by either necropsy measure, and the BCG+RhCMV/TB vaccine regimen resulted in only a modest reduction in mycobacterial burden. TB is typically not restricted to pulmonary parenchyma in RM given this dose of Erdman strain Mtb and necropsy analysis revealed extensive extra-pulmonary disease in the unvaccinated RM, including both lung-associated lymph node involvement and extra-thoracic spread (see, FIG. 51). The extent of disease as measured by pathologic score was closely correlated with the extent of disease measured by mycobacterial culture (see, FIG. 50, panel b), and by both criteria, extra-pulmonary disease was dramatically reduced in the RhCMV/TB-vaccinated cohort, resulting in a significant reduction in the overall extent of disease in this cohort relative to unvaccinated RM (see, FIG. 43, panels e and f; FIG. 49, panel a; and FIG. 51). By Poisson modeling, the overall extent of disease was reduced in the RhCMV/TB-vaccinated group by 68.7% by mycobacterial culture (P<0.0001) and 67.3% by pathologic score (P<0.0001) relative to unvaccinated controls (see, FIG. 49, panel b). In contrast, the extent of extra-pulmonary and overall disease in BCG-only-vaccinated RM was not significantly different from unvaccinated RM by either criteria, and in keeping with this, the extent of extra-pulmonary and overall disease in the RM given the RhCMV/TB vaccine alone was also significantly reduced from the BCG-only-vaccinated RM. Using the same Poisson modeling, RhCMV/TB vaccination reduced overall disease relative to BCG vaccination by 57.7% (P=0.0007) and 51.4% (P=0.01) for mycobacterial culture and pathologic score, respectively (see, FIG. 49, panel b). Pre-vaccination of RM with BCG 6 weeks prior to initial RhCMV/TB vaccination appeared to substantially reduce the extra-pulmonary, as well as pulmonary, efficacy of RhCMV/TB vaccination alone, as the BCG+RhCMV/TB-vaccinated group showed only a very modest reduction in mycobacterial recovery in all sites relative to unvaccinated controls (see, FIG. 43, panels d-f; FIG. 49, panel a; and FIG. 51).

Referring to FIG. 50, a comparison of different measures of TB infection outcome is shown. Panels a and b show the correlation of pulmonary parenchymal disease as measured by CT scan-determined disease volume (AUC through day 112) post-infection vs. Mtb culture of lung samples (panel a) and lung pathologic score (panel b) at necropsy of Study 3 RM. Panel c shows the correlation of overall Mtb culture vs. overall pathologic score at necropsy of Study 3 RM. Panels c and d show the same analysis for Study 4 RM. Spearman correlation coefficients (r) and associated p values are shown in each plot.

Referring to FIG. 51, a summary of TB disease outcome at necropsy of Study 3 is shown. The lung, non-lung, and overall extent of Mtb disease by mycobacterial culture (#positive cultures; left y axis) and pathologic scoring (right y-axis; see FIG. 48) is shown for each individual Study 3 RM.

Figure 52:
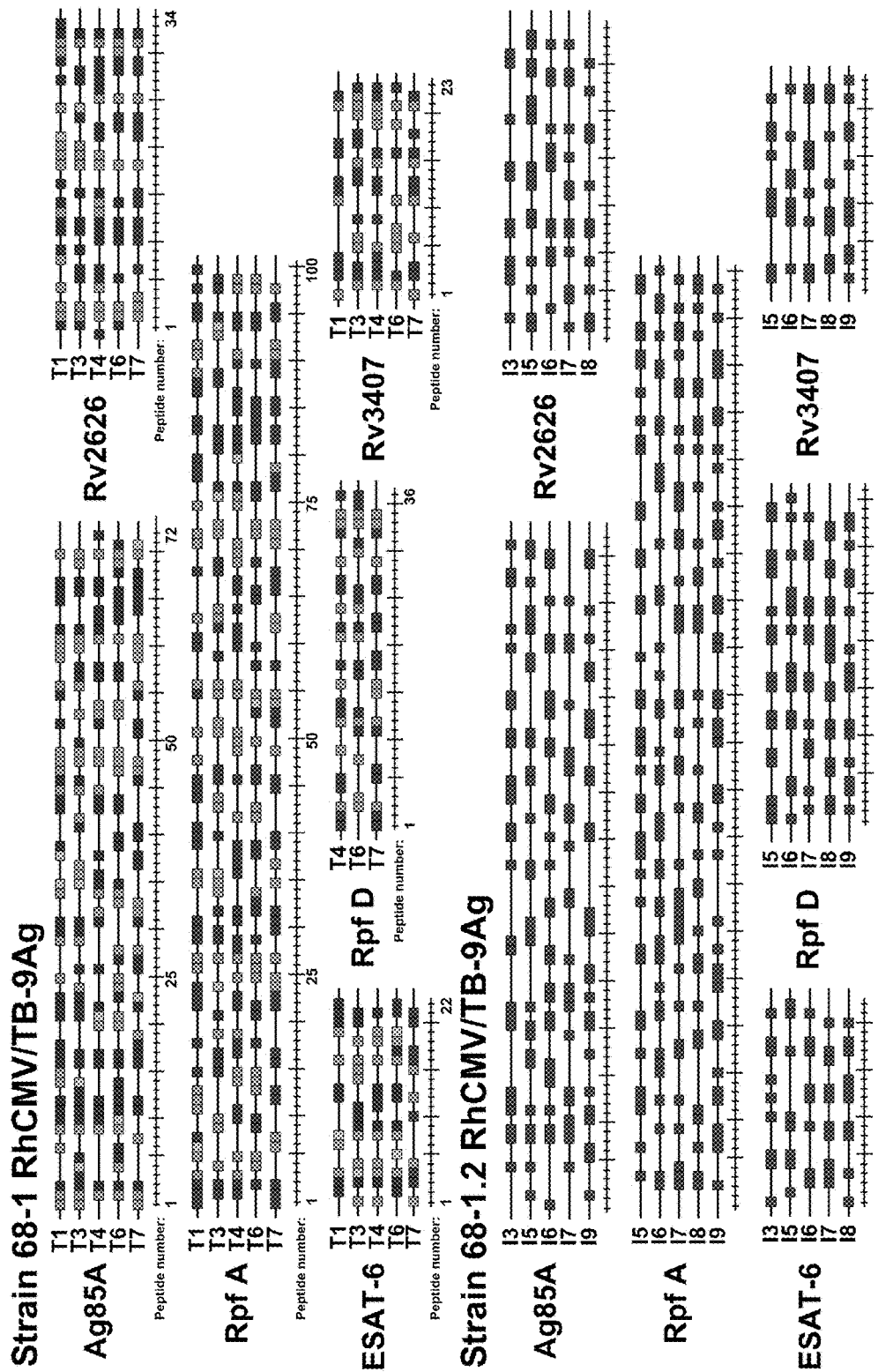
FIG. 52 shows MHC-restriction analysis of RhCMV/TB vector-elicited CD8+ T cell responses in Study 4.
Figure 52:
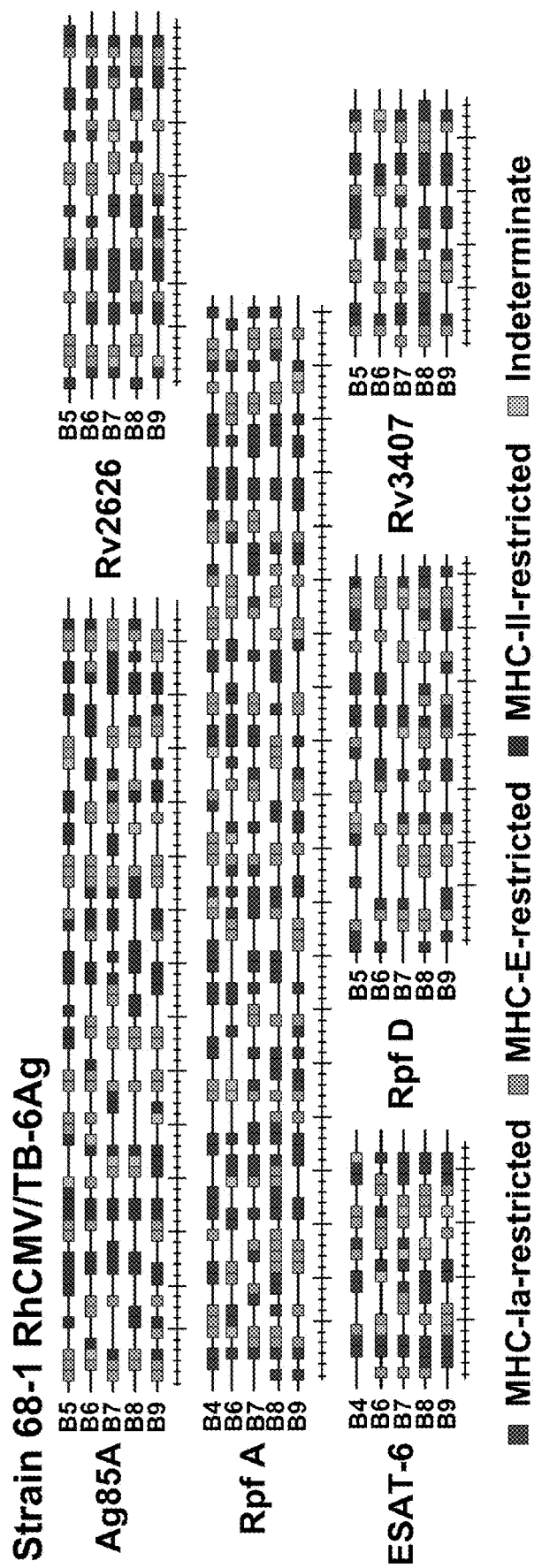

To confirm and further characterize RhCMV/TB efficacy, a second, larger Mtb challenge study (n=9 RM per group; all RhCMV+ at assignment) was performed using a lower dose of Erdman strain and in which we compared the same 68-1 RhCMV/TB-9 Ag vaccine used in Study 3 (group 1) with an analogous RhCMV/TB-9 Ag) vaccine based on the 68-1.2 vector backbone (in which repaired expression of Rh157.5 and Rh157.4 results in distinct CD8+ T cell epitope targeting; group 2), and a single 68-1 RhCMV/TB-6 Ag vector expressing a 6-Ag Mtb polyprotein (Ag85A; ESAT-6; Rv3407; Rv2626; Rpf A; Rpf D) (group 3) (see, FIG. 44, panel a; FIG. 46). 68-1 RhCMV vectors elicit unconventional CD8+ T cell responses that are restricted by MHC-II and MHC-E, whereas the CD8+ T cell responses elicited by 68-1.2 RhCMV vectors are conventionally MHC-Ia restricted; thus, the group 1 vs. group 2 comparison allows determination of the contribution of unconventionally restricted CD8+ T cells to RhCMV/TB efficacy. In the group 1 vs. group 3 comparison, whether the efficacy observed with the 4 RhCMV/TB vector set encoding 9 Mtb Ags (3 each in the acute phase, latency and resuscitation Ag types) can be recapitulated by a single RhCMV/TB vector expressing 6 Mtb Ags (2 each from these Ag types) which is more appropriate for clinical translation was determined. The magnitude of the overall Mtb-specific and individual Mtb insert-specific CD4+ and CD8+ T cell responses elicited by the 68-1 and 68-1.2 RhCMV/TB-9 Ag vectors were comparable in blood throughout the vaccination phase, and in BAL and lymph node at the end of vaccination phase, as was the memory differentiation and functional phenotype of the Mtb-specific response in blood (see, FIG. 44, panels b-g). However, the CD8+ T cells elicited by the 68-1 RhCMV/TB vaccine were unconventionally (MHC-II and MHC-E) restricted, whereas those elicited by 68-1.2 RhCMV/TB vaccine were conventionally (MHC-Ia) restricted (see, FIG. 52). The observed immune responses against the 6 Ags common to both 68-1 RhCMV/TB-6 Ag and RhCMV/TB-9 Ag vaccines are similar between groups 1 and 3 with respect to magnitude, phenotype and (unconventional) MHC restriction, except for slightly different levels of CD8+ T cell responses in LN (see, FIG. 44, panels b-g; FIG. 52).

Figure 3:
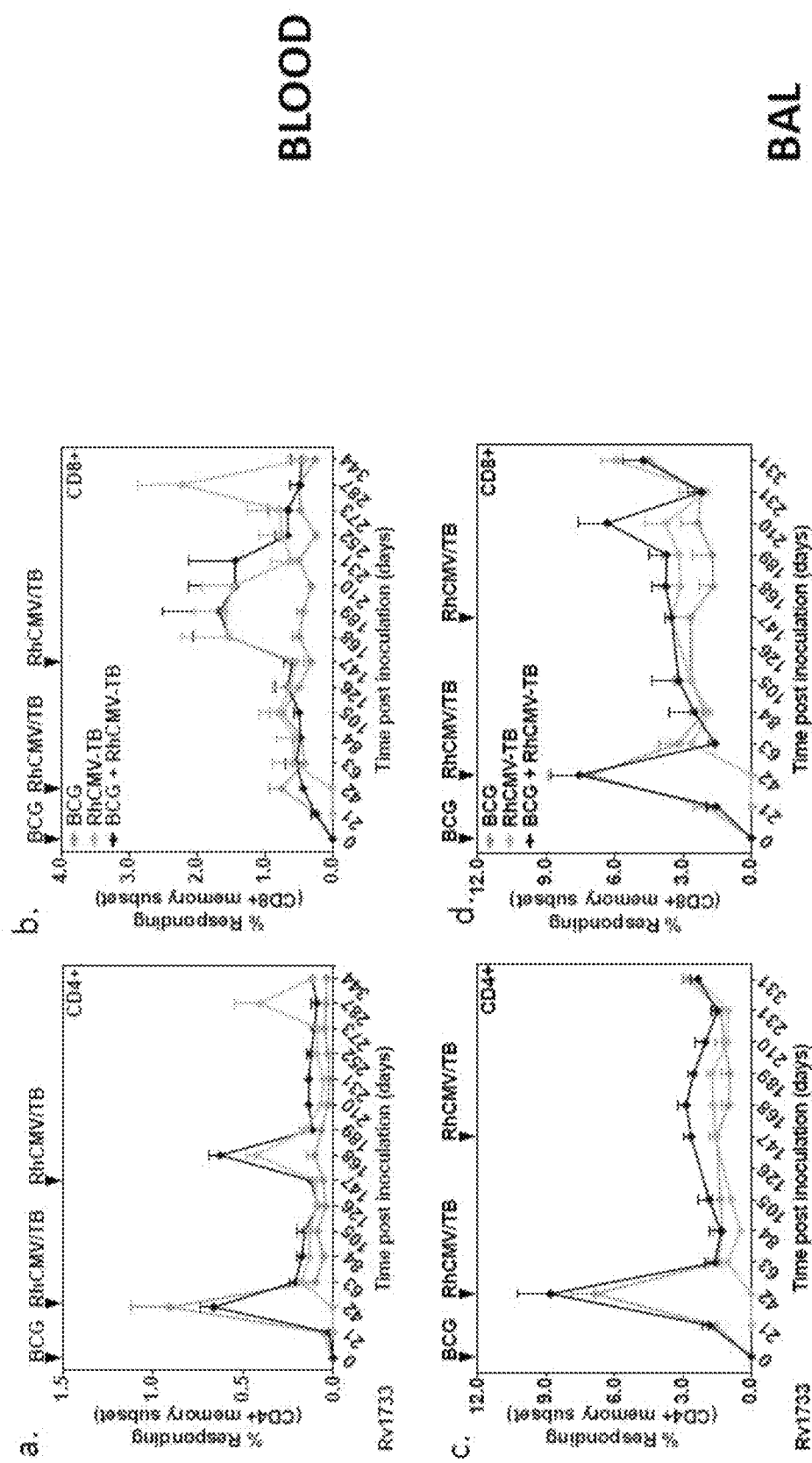
FIG. 3 (panels a, b, c, and d) shows Rv1733-specific responses analyzed by intracellular cytokine staining throughout the vaccination period; shown above are the percentages of memory cells expressing either IFNγ or TNF; included are responses from peripheral blood mononuclear cells (PBMCs; shown in panels a and b) and bronchoalevolar lavage cells (BAL; shown in panels c and d); CD4+ T cells are shown in panels a and c, and CD8+ T cells are shown in panels b and d.
Figure 4:
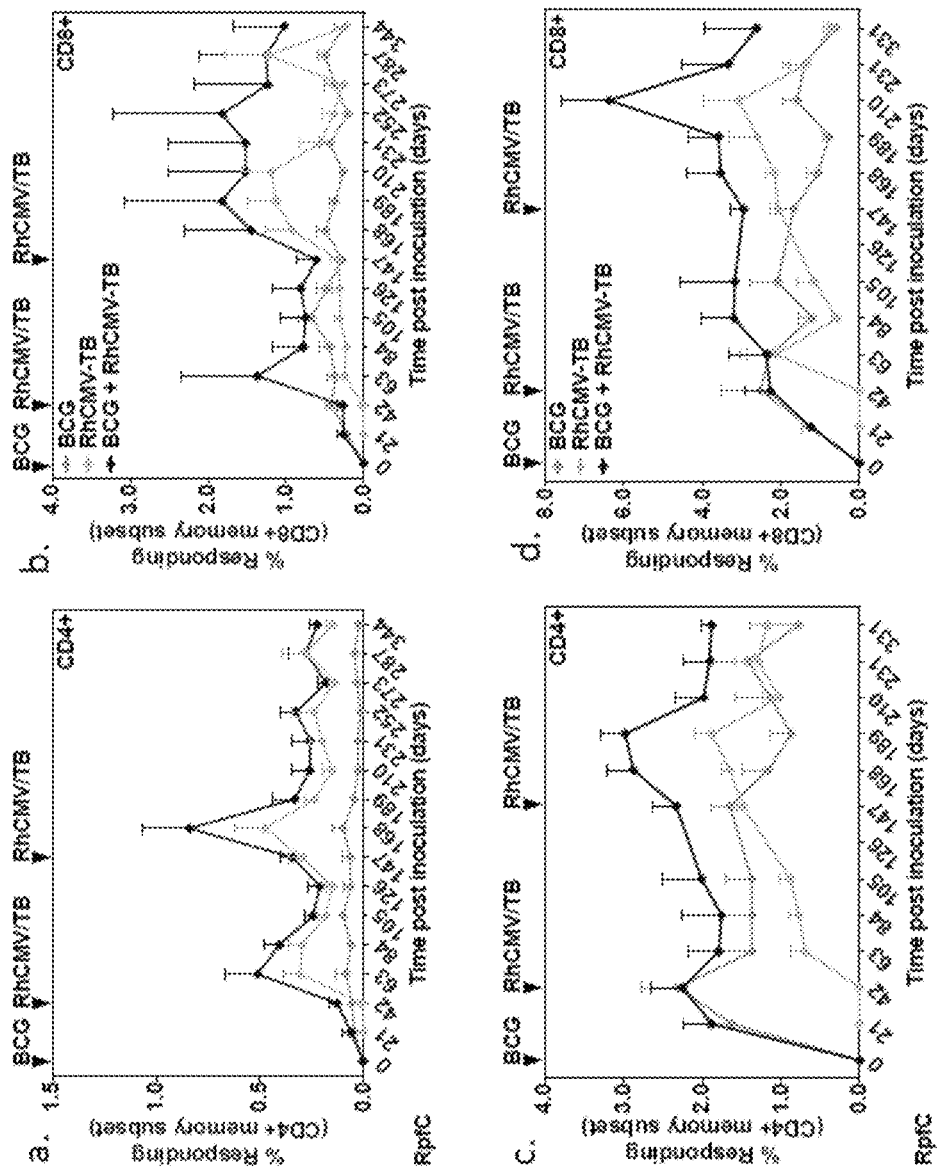
FIG. 4 (panels a, b, c, and d) shows RpfC-specific responses analyzed by intracellular cytokine staining throughout the vaccination period; shown above are the percentages of memory cells expressing either IFNγ or TNF; included are responses from peripheral blood mononuclear cells (PBMCs; shown in panels a and b) and bronchoalevolar lavage cells (BAL; shown in panels c and d); CD4+ T cells are shown in panels a and c, and CD8+ T cells are shown in panels b and d.
Figure 5:
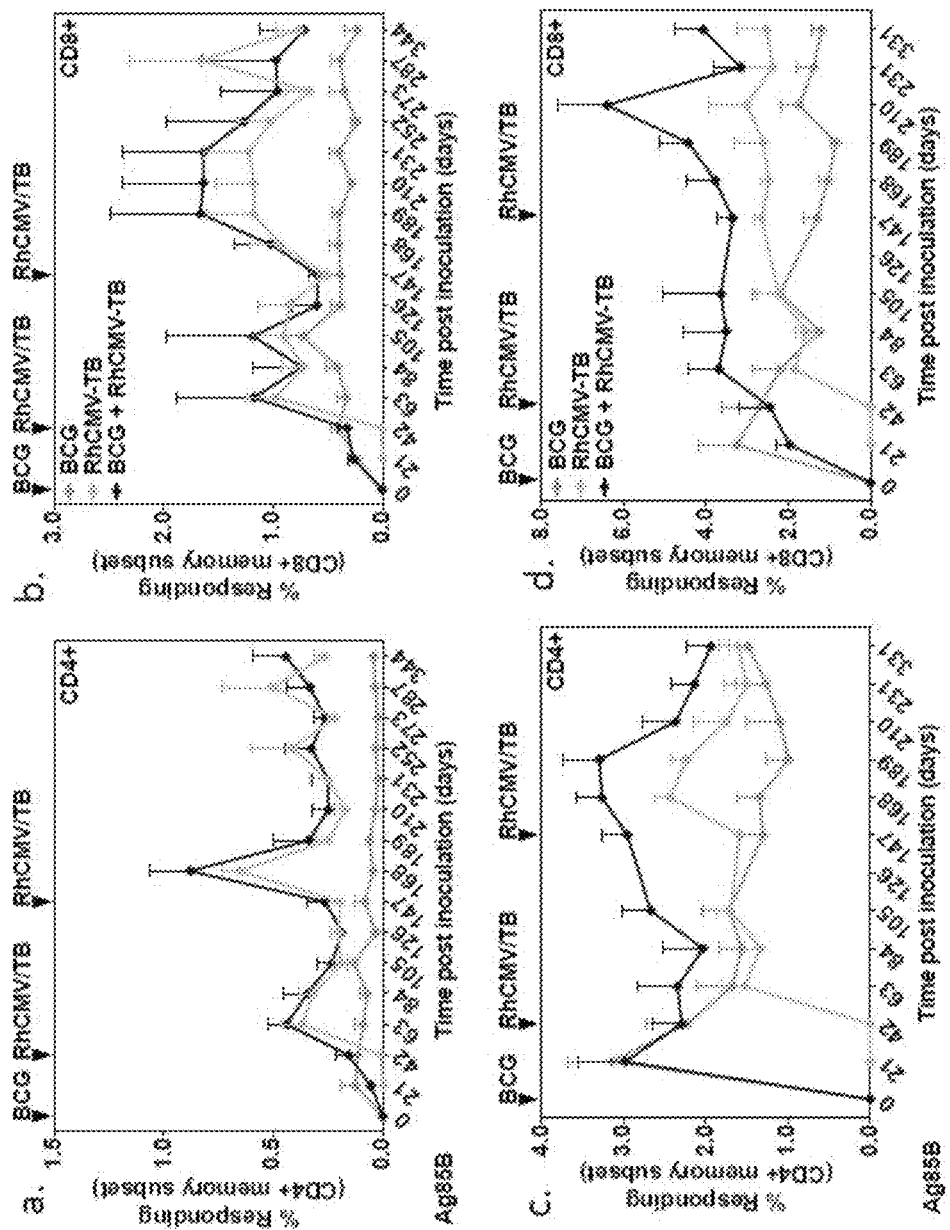
FIG. 5 (panels a, b, c, and d) shows Ag85B-specific responses analyzed by intracellular cytokine staining throughout the vaccination period; shown above are the percentages of memory cells expressing either IFNγ or TNF; included are responses from peripheral blood mononuclear cells (PBMCs; shown in panels a and b) and bronchoalevolar lavage cells (BAL; shown in panels c and d); CD4+ T cells are shown in panels a and c, and CD8+ T cells are shown in panels b and d.

Referring to FIG. 3, the immunogenicity of RhCMV/TB vaccines (Study 4) is shown. Panel a shows a schematic of the vaccination and challenge protocol and RM groups of Study 4. Panel b shows a longitudinal analysis of the overall CD4+ and CD8+ T cell response to the 9 Mtb Ags after vaccination with the designated vaccines, as described in FIG. 42, panel b. Panel c shows boxplots comparing the individual Mtb protein (each of the 9 Mtb inserts plus the non-insert CFP-10)-specific and overall (summed) Mtb-specific CD4+ and CD8+ T cell response frequencies (defined by TNF and/or IFN-γ production) in peripheral blood between the vaccine groups at the end of the vaccine phase (each data point is the mean of response frequencies in 3 separate samples from weeks 49-55; ‡ indicates no response detected). Panel d shows boxplots comparing the memory differentiation (see, FIG. 42, panel d) of the vaccine-elicited CD4+ and CD8+ memory T cells in peripheral blood responding to Ag85A with TNF and/or IFN-γ production at the end of vaccine phase (weeks 51-52). Panel e shows boxplots comparing the frequency of vaccine-elicited CD4+ and CD8+ memory T cells in peripheral blood responding to Ag85A with TNF, IFN-γ and/or IL-2, alone and in all combinations at the end of vaccine phase (weeks 49-50). Panels f and g show boxplots comparing the individual Mtb protein (the 9 Mtb inserts plus the non-insert CFP-10)-specific and overall (summed) Mtb-specific CD4+ and CD8+ T cell response frequencies (defined by TNF and/or IFN-γ production) in BAL (panel f) and in peripheral LN (panel g) between the vaccine groups at the end of vaccine phase (weeks 46-47; ‡ indicates no response detected). In panels c-g, statistics performed as described in FIG. 42 with brackets indicating pair-wise comparisons with Wilcoxon p values ≤0.05.

Referring to FIG. 52, the MHC-restriction analysis of RhCMV/TB vector-elicited CD8+ T cell responses in Study 4 is shown. RhCMV/TB vaccine-elicited CD8+ T cells were epitope-mapped in representative group 1, 2 and 3 RM from Study 4 using flow cytometric ICS to detect recognition of each consecutive, overlapping 15-mer gag peptide comprising the indicated TB proteins. Peptides resulting in specific CD8+ T cell responses are indicated by a box, with the color of the box designating MHC restriction as determined by blocking with the anti-pan-MHC-I mAb W6/32, the MHC-E blocking peptide VL9 and the MHC-II blocking peptide CLIP. The epitope restriction profiles of the strain 68-1 RhCMV/Ag85B/ESAT-6- and RhCMV/Rpf A/Rpf C/Rpf D-elicited CD8+ responses to Rpf A, Ag85B, and ESAT-6 are produced here for comparison with 68-1.2 versions of these vectors and for Rpf A and ESAT-6, with the 68-1 RhCMV/TB-6Ag vector.

After a 56 week vaccination period, all 27 vaccinated RM in groups 1-3 and 9 RhCMV+ unvaccinated control RM (group 4) were intrabronchially challenged with 10 CFUs of Erdman strain Mtb bacteria—the reduction in dose relative to Study 3 intended to slow TB progression in Study 4 RM to more closely resemble the course of human Mtb infection. In addition, post-challenge BAL was not performed in this experiment to prevent procedure-related mortality or enhancement of bacteria spread within the lung. All RM developed de novo CFP-10-specific T cell responses in blood following challenge, and the RhCMV/TB-6 Ag-vaccinated RM (group 3) also developed de novo T cell responses in blood to the Ag85B, Rpf C, and Rv1733 Ags, which were not included in their vaccine (see, FIG. 45, panels a and b; FIG. 47, panels b and c). All 9 unvaccinated (group 4) RM developed TB lesions on CT scans by day 28 pi, but, as anticipated, the disease progression in this study was slower than in Study 3 (see, FIG. 45, panel c), and only 2 unvaccinated (group 4) control RM developed endpoint TB disease over the course of observation (see, FIG. 44, panel a). Remarkably, 13 of the 27 vaccinated RM (5 each in group 1 and group 3; 3 in group 2) did not develop any radiologic signs of pulmonary TB (including no hilar adenopathy) at any time point through to random elective necropsy at >16 weeks pi, and the average CT-determined lesional AUC in lung parenchyma of the overall cohort of vaccinated RM was significantly reduced from the unvaccinated group (see, FIG. 45, panels c and d; FIG. 49, panel c). At necropsy, none of the 13 CT-negative RM from vaccine groups 1-3 manifested any macroscopic granulomatous disease, and 10 of these 13 were culture negative in all tissues (the remaining 3 were Mtb+ in lung-draining lymph nodes; see, FIG. 50, panels c and d; FIG. 54). Despite the development of CD4+ and CD8+ T cell responses to Mtb proteins not in their vaccine in lung, lung-draining and peripheral lymph nodes, and spleen (see, FIG. 53), histopathologic examination of lung and lung-draining lymph node sections in these 13 TB disease-free RM showed no granulomatous inflammation. The overall extent of disease by mycobacterial culture and pathologic score was strongly correlated in this experiment (see, FIG. 50, panel d), and was significantly reduced in the overall (pooled groups 1-3) RhCMV/TB vaccinated group compared to the unvaccinated control group, with no significant difference in efficacy between individual groups 1-3, and similar protection in both lung and non-lung tissues (see, FIG. 45, panels e-g; FIG. 49, panel c; FIG. 54). For the pooled vaccinated group, the overall reduction in disease extent relative to the unvaccinated control group was 74.5% by mycobacterial culture (P=0.0024) and 61.4% by pathologic score (P=0.0011) using Poisson modeling (see, FIG. 51). The finding of efficacy with 68-1.2 RhCMV/TB vaccination indicates that efficacy is not dependent on unconventional MHC-II and MHC-E-restricted CD8+ T cells, indicating that protection can be mediated by either conventional or unconventional CD8+ T cells, or is independent of CD8+ T cells altogether.

Figure 45:
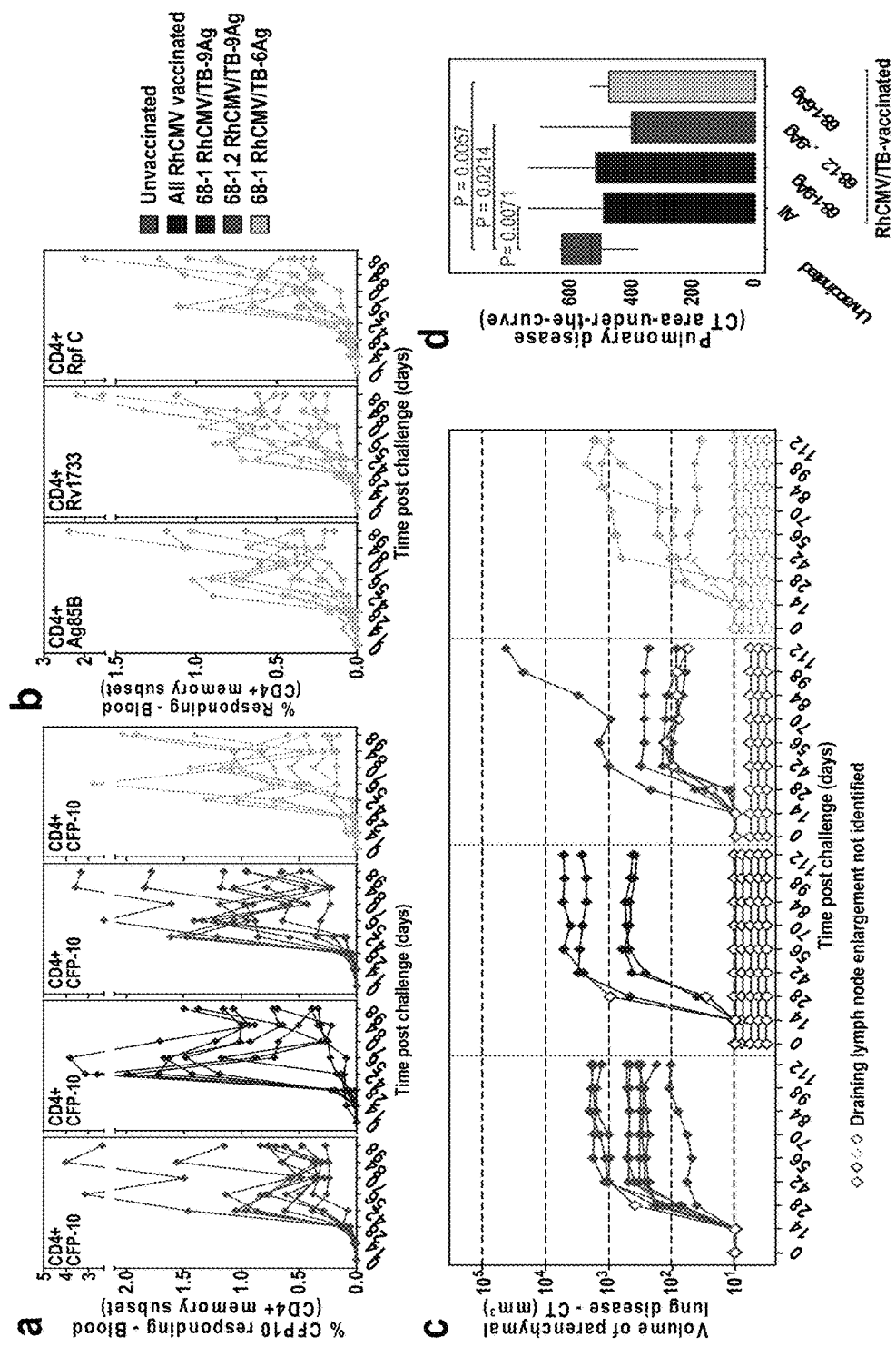
FIG. 45 (panels a, b, c, d, e, f, g, and h) shows the outcome of Mtb challenge for Study 4 and overall.
Figure 45:
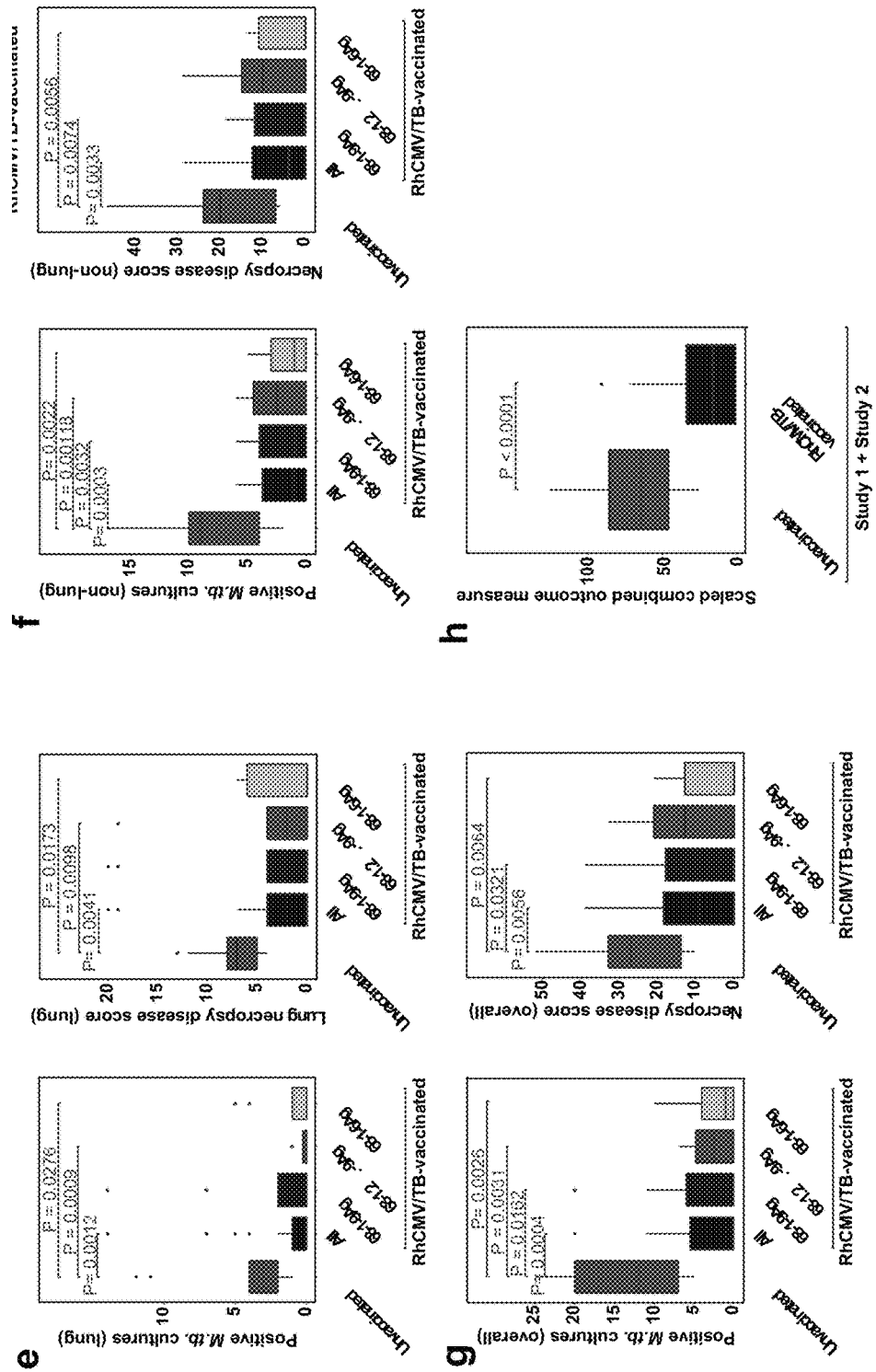

Referring to FIG. 45, the outcome of Mtb challenge (Study 4 and Overall) is shown. Panels a and b show the development of peripheral blood CD4+ T cell responses to the peptide mixes comprising the non-vaccine insert Mtb protein CFP-10 in all Study 4 RM (panel a), and comprising the Ag85B, Rv1733 and Rpf proteins in group 3 RM only (panel b; RM vaccinated with the single 68-1 RhCMV/TB- 6Ag vector lacking these 3 inserts) after Mtb challenge by flow cytometric ICS analysis, as described in FIG. 43, panel a (peripheral blood CD8+ T cell responses and tissue CD4+ and CD8+ T cell responses to these same Ags are shown in FIG. 47, panels b and c and FIG. 53, respectively). Panel c shows CT quantification of disease volume in the pulmonary parenchyma after Mtb challenge (presence or absence of draining LN enlargement indicated by closed vs. open symbols). Panel d shows boxplots comparing the AUC of CT-determined pulmonary lesional volume (day 0-112) of the unvaccinated RM vs. all RhCMV/TB-vaccinated RM vs. RM in each individual RhCMV/TB vaccine group. Panels e-g show boxplots comparing the extent of TB at necropsy measured by Mtb recovery with mycobacterial culture and by pathologic disease score in lung parenchyma (panel e), all non-lung parenchymal tissues (panel f) and all tissues (panel g) in the same RM groups. Panel h shows a boxplot comparing the outcome of Mtb challenge in all unvaccinated RM vs. all RhCMV/TB-only vaccinated RM across both Studies 3 and 4 using a scaled outcome measure that combines both mycobacterial culture and pathologic score data. In panels d-h, unadjusted Wilcoxon p values ≤0.05 are shown (see, FIG. 49, panel c).

Figure 53:
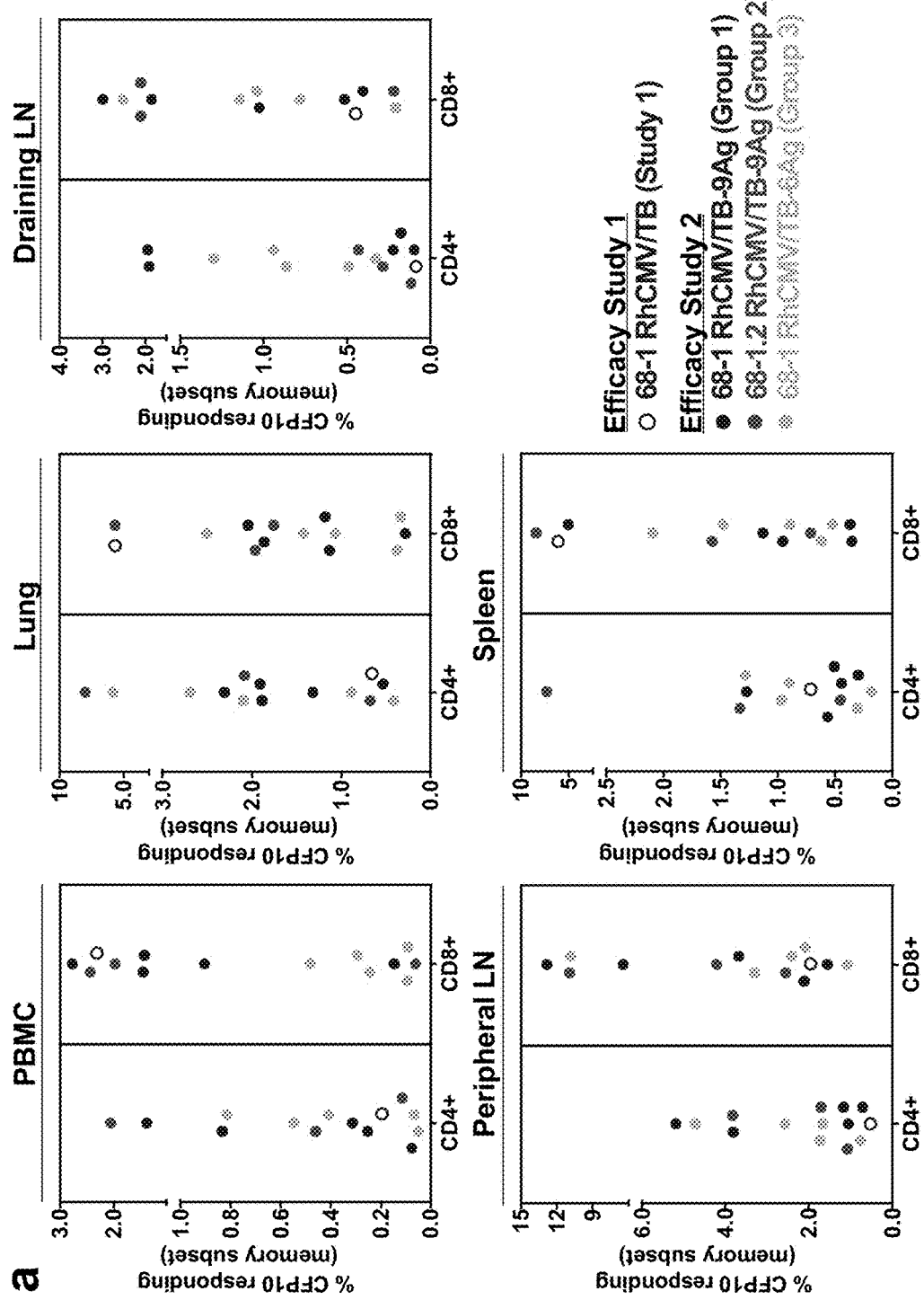
FIG. 53 (panels a and b) shows an analysis of non-vaccine-elicited, Mtb-specific CD4+ and CD8+ T cell responses at necropsy.
Figure 53:
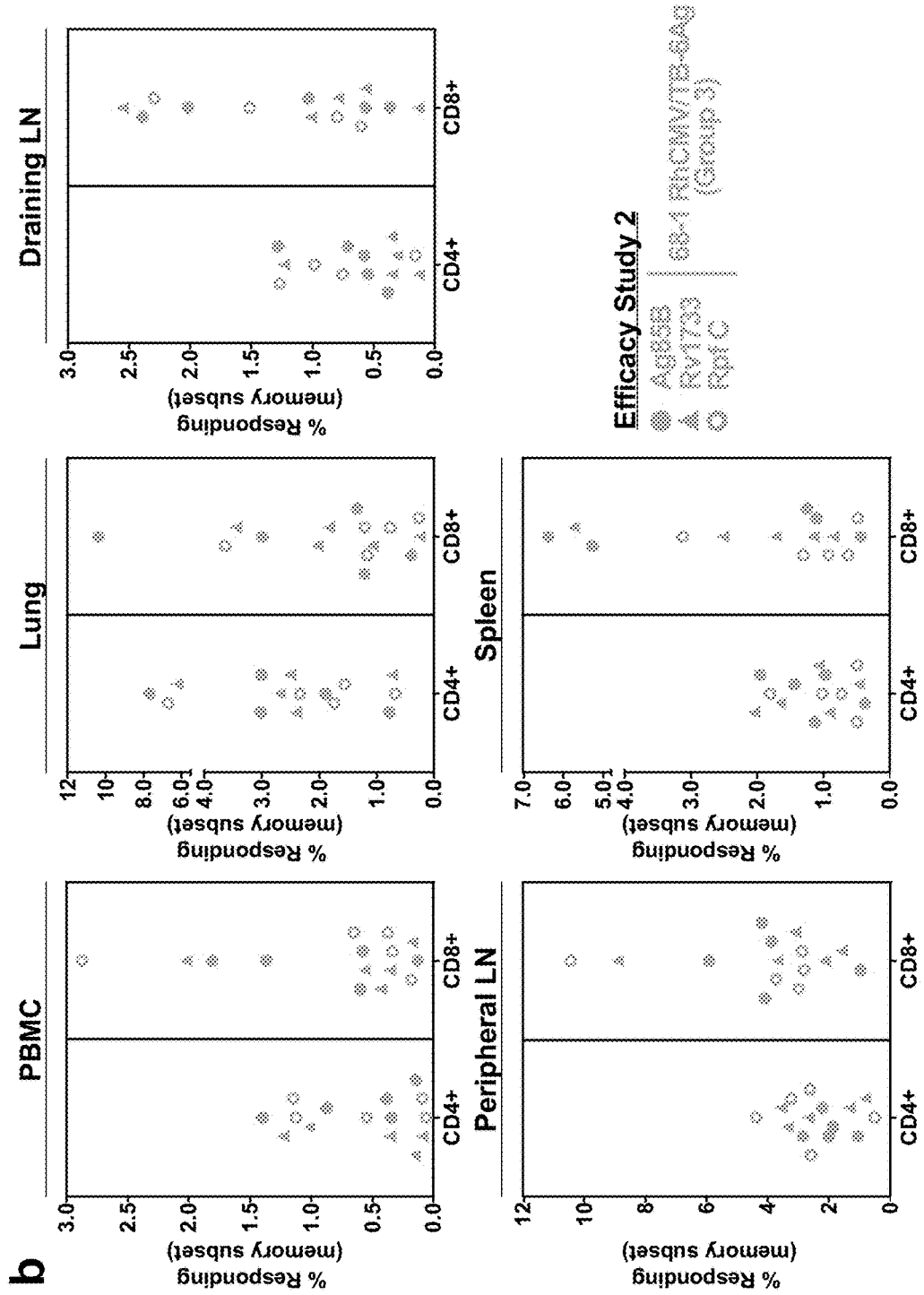
Figure 54:
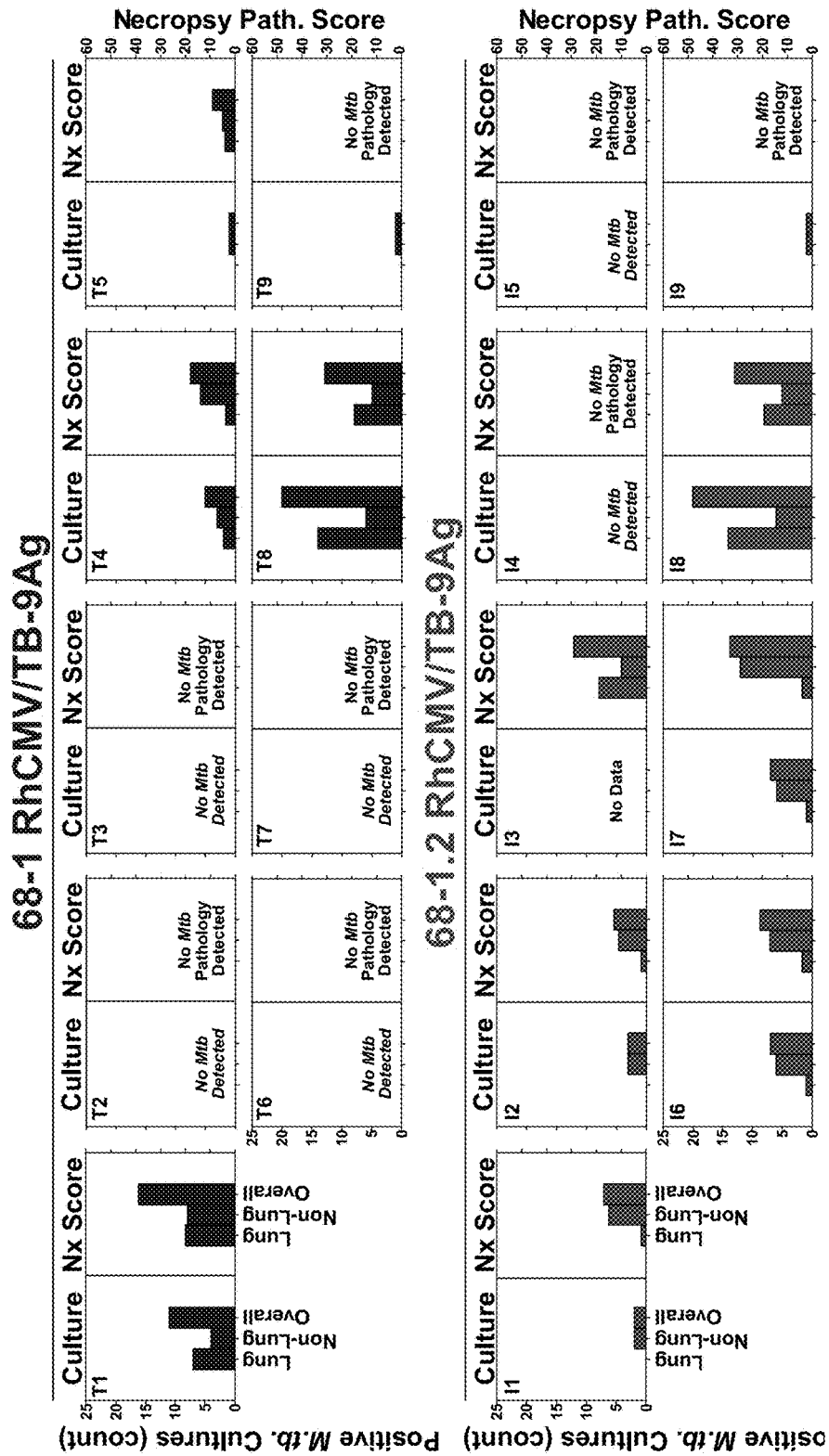
FIG. 54 shows a summary of outcome at necropsy of Study 4.
Figure 54:
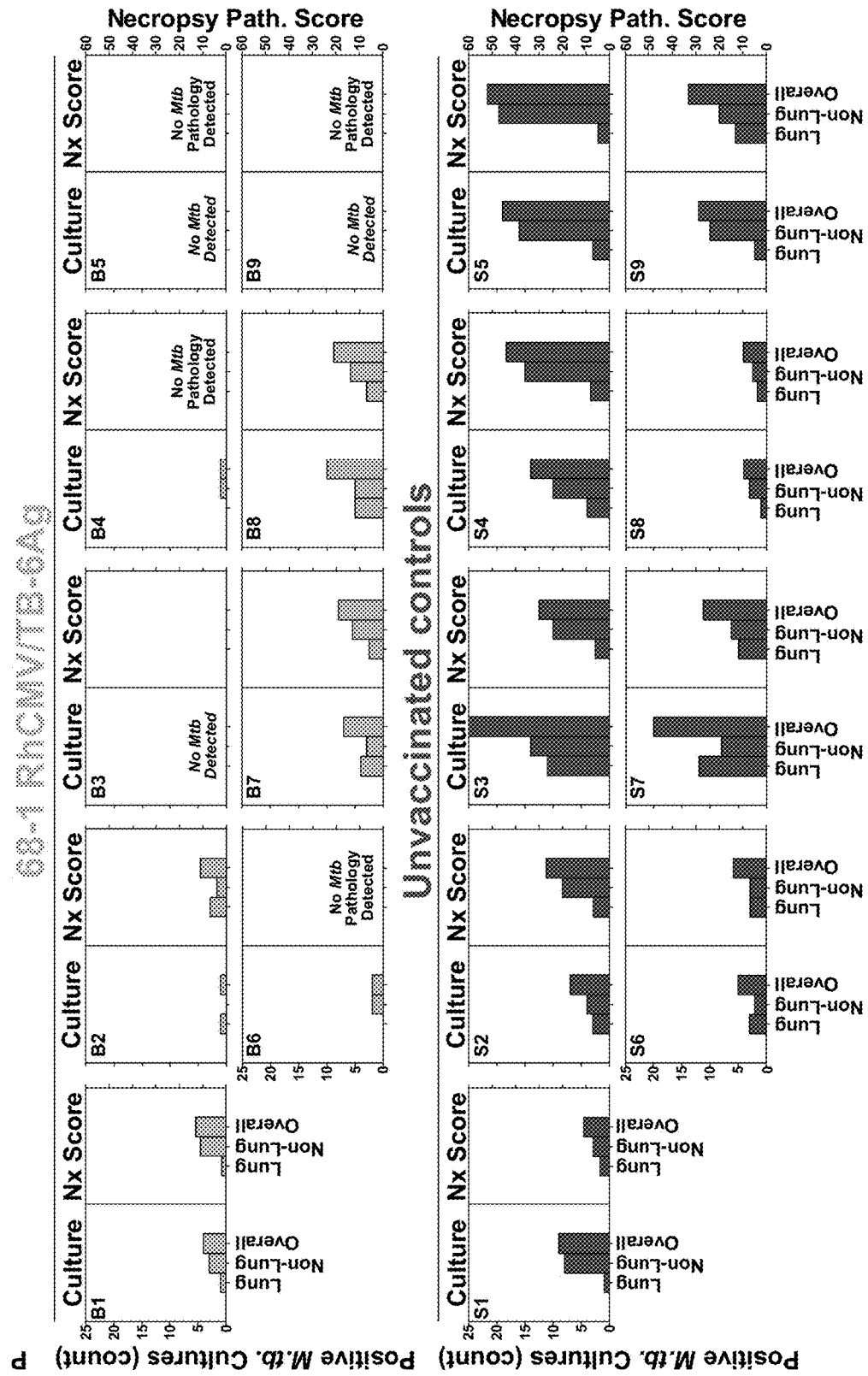

Referring to FIG. 53, an analysis of non-vaccine-elicited, Mtb-specific CD4+ and CD8+ T cell responses at necropsy (response to Mtb challenge) is shown. Panel a shows flow cytometric ICS analysis demonstrating peripheral blood and tissue CD4+ and CD8+ T cell responses to the peptide mixes comprising the non-vaccine insert Mtb protein CFP10 in the 1 Study 3 RM and the 13 Study 4 RM (5, 3, and 5 from Groups 1, 2 and 3, respectively) without pathologic evidence of TB disease at necropsy (see, FIGS. 50 and 54; response defined by TNF and/or IFN-γ production after background subtraction in memory subset). Panel b shows a similar analysis of T cell responses to peptide mixes comprising the Ag85B, Rv1733 and Rpf proteins in the 5 Study 4, group 3 RM (vaccinated with the RhCMV/TB-6 Ag vaccine lacking these inserts) who failed to manifest TB disease after challenge. These data confirm that these protected monkeys were sufficiently exposed to Mtb infection after challenge to develop a robust systemic response to TB proteins that were not present in their vaccine.

Referring to FIG. 54, a summary of outcome at necropsy of Study 4 is shown. The lung, non-lung, and overall extent of Mtb disease by mycobacterial culture (#positive cultures; left y axis) and pathologic scoring (right y-axis; see, FIG. 48) are shown for each individual Study 4 RM.

It is remarkable that despite the fact that the average extent of TB progression in the unvaccinated control monkeys in Studies 3 and 4 was quite different, the reduction in disease with RhCMV/TB vaccination was similar in both studies. Indeed, using a normalized, combination outcome parameter based on both mycobacterial culture and pathologic score, it was estimated that across both studies the extent of disease in the RhCMV/TB-vaccinated RM was reduced 68% relative to unvaccinated controls (P=0.0019) (see, FIG. 45, panel h; FIG. 51). In contrast to the "all or none" efficacy of the RhCMV/SIV vaccine against rapidly progressive SIV infection, the protection afforded by RhCMV/TB against the more slowly progressive Mtb infection appears to be graded, including RM with apparent sterilizing protection, RM with no macroscopic disease but with very focal bacterial persistence, and a higher fraction of RM with reduced progression compared to unvaccinated controls (see, FIGS. 50 and 54). However, there are also vaccinated RM that developed progressive and ultimately fatal TB disease similar to the unvaccinated controls. This outcome heterogeneity was not predicted by the RhCMV/TB-elicited, TNF/IFN-γ-defined, CD4+ or CD8+ T cell response magnitudes in blood, BAL or LN prior to challenge (see, FIG. 55). The observation that BCG vaccination 6 weeks prior to RhCMV/TB vaccination reduces efficacy almost 1 year later supports the concept that mycobacteria-induced immune responses do include an anti-protective component.

Figure 55:
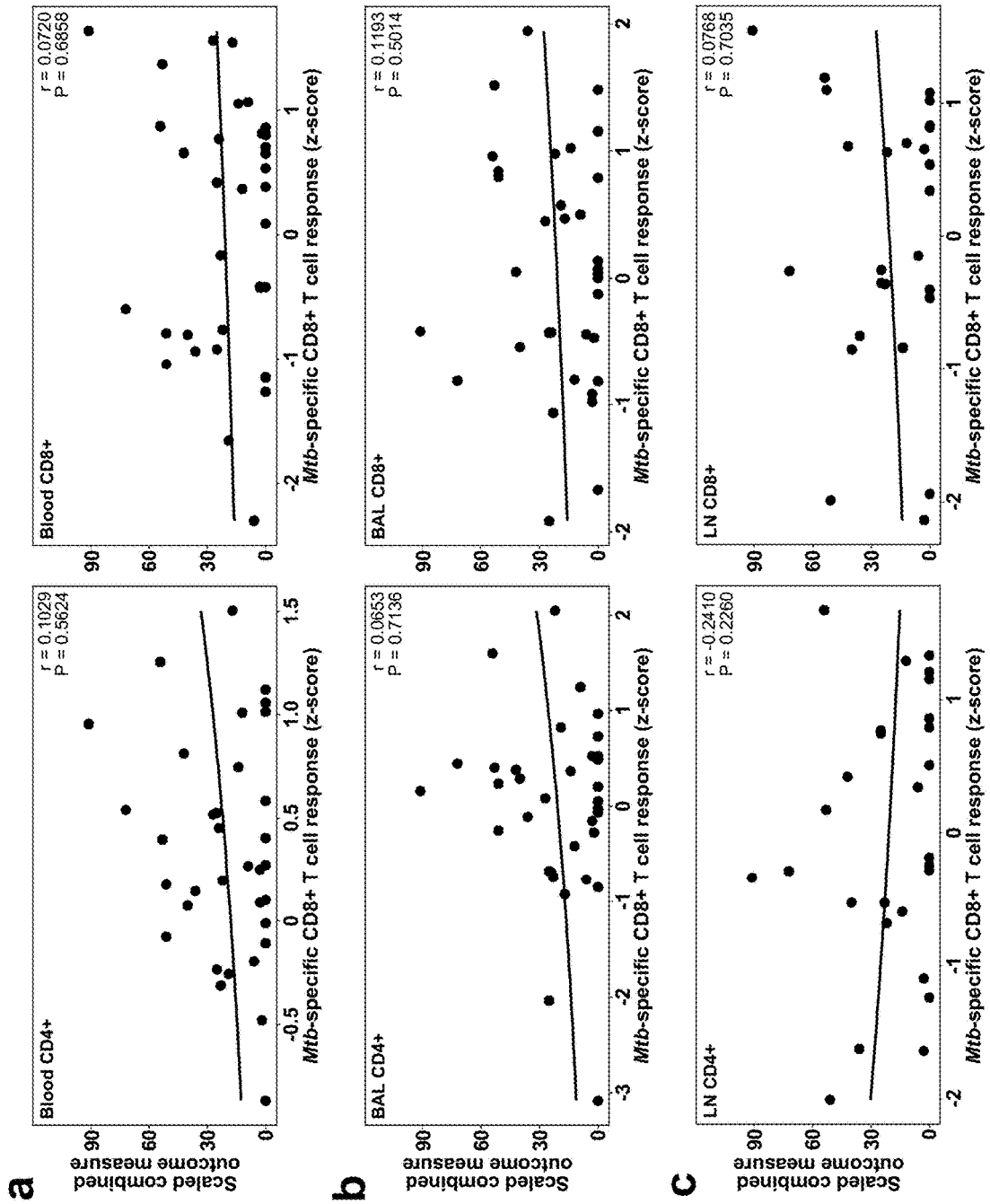
FIG. 55 (panels a, b, and c) shows immune correlates analysis of Studies 3 and 4.

Referring to FIG. 55, immune correlates analysis of Studies 3 and 4 are shown. Panels a and b show the relationship between the end-of-vaccine phase overall TB-specific CD4+ and CD8+ T cell responses in peripheral blood (panel a) and BAL (panel b) to the same scaled outcome measure that combines both mycobacterial culture and pathological score data at necropsy used in FIG. 45, panel h is shown for all Study 3 and 4 RM that received a RhCMV/TB vaccine only. The T cell responses reflect the sum of responses to the ESAT-6, Ag85A, Ag85B, Rv3407, Rv1733, Rv2626, Rpf A, Rpf C, Rpf D Ags and are presented in units of z-score (number of standard deviations that a monkey's normalized total immune response at end of vaccine phase is above the average of the monkeys in that study. Panel c shows the same analysis for overall Mtb-specific CD4+ and CD8+ T cell responses in peripheral lymph node in RhCMV/TB-vaccinated Study 4 RM (lymph node biopsy was not performed in Study 3). Spearman correlation coefficients (r) and associated P values are shown in each plot, with the best-fitting negative binomial curve overlayed Similar results (lack of significant correlation) were observed for total AUC CD4+ or CD8+ T cell responses for the entire vaccine phase in peripheral blood, and for peripheral blood, BAL, and lymph node responses to only the 6 Ags common to all RhCMV/TB-vaccinated RM, or to any individual Mtb Ag prior to challenge.

These studies show that a parenterally administered RhCMV-based vaccine is able to elicit and maintain over the course of at least a year effector responses that can control Mtb at the early stages of infection, and that the protection afforded by this vaccine can be complete, if not sterilizing. To our knowledge, this is the first report of complete prevention of TB in the RM model. Given TEM responses to natural, persistent CMV infection are maintained for life, the protection afforded by this vector platform is likely to be very durable, probably lifelong. The RhCMV/TB vaccine is efficacious against aggressive TB in RM and provides treatment of a human CMV/TB vaccine that would be effective in preventing pulmonary TB in adolescents and adults, and thereby contribute to ending the global TB epidemic.

Over both Studies 3 and 4, RhCMV/TB vaccination reduced the extent of disease at necropsy, as measured by both pathologic score and frequency of mycobacterial culture-positive tissues, by 68% compared to unvaccinated controls (P=0.0019). There was no significant difference in efficacy between cohorts vaccinated with 68-1 vs. 68-1.2 RhCMV vector backbones (which differ in CD8+ T cell epitope recognition) or with 68-1 RhCMV vectors expressing 9 vs. 6 Mtb proteins. In contrast, BCG was not significantly efficacious in this challenge model, and administration of BCG 6 weeks prior to RhCMV/TB vaccination reduced the efficacy of the latter vaccine. Across both studies, 14 of the 34 RhCMV/TB-vaccinated RM (41%) showed no granulomatous disease at necropsy (vs. 0 of 17 unvaccinated controls; P=0.0018), despite immunologic evidence of initial infection after challenge, and 10 of these were mycobacterial culture-negative in all tissues. Thus, the RhCMV/TB vaccine is superior to BCG in the RM model, and is the first vaccine demonstrated to completely prevent progressive TB in primates.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A recombinant rhesus cytomegalovirus (RhCMV) or human cytomegalovirus (HCMV) vector comprising a nucleic acid sequence encoding an expressible Mycobacterium tuberculosis (Mtb) antigen, wherein said Mtb antigen is a fusion protein comprising: a) a tripeptide consisting of the proteins Ag85A, Ag85B, and Rv3407, or fragments thereof, wherein the proteins, or fragments thereof, are joined in the order Ag85A-Ag85B-Rv3407 to form the tripeptide; or b) a dipeptide consisting of the proteins Ag85B and ESAT6, or fragments thereof, wherein the proteins, or fragments thereof, are joined in the order Ag85B-ESAT6 to form the dipeptide.

2. The recombinant RhCMV or HCMV vaccine vector of claim 1, wherein expression of the Mtb antigen is driven by an antigen-coding sequence in operable association with a promoter selected from the group consisting of a constitutive CMV promoter, an immediate early CMV promoter, an early CMV promoter, and a late CMV promoter.

3. The recombinant RhCMV or HCMV vaccine vector of claim 2, wherein the promoter is selected from the group consisting of EF1-alpha, UL82, MIE, pp65, and gH.

4. The recombinant RhCMV or HCMV vaccine vector of claim 1, comprising a deletion or modification of US2, US3, US4, US5, US6, US11, or UL97, or a homolog thereof.

5. The recombinant RhCMV or HCMV vaccine vector of claim 1, comprising a deletion of Rh158-166 or a homolog thereof.

6. The recombinant RhCMV or HCMV vaccine vector of claim 1, wherein the vector lacks genes required for optimal growth in certain cell types or contains targets for tissue-specific micro-RNAs in genes essential for viral replication or wherein the vector has an epithelial, central nervous system (CNS), or macrophage deficient tropism, or a combination thereof.

7. The recombinant RhCMV or HCMV vaccine vector of claim 1, wherein the RhCMV or HCMV vaccine vector has a deletion in a gene region non-essential for growth in vivo.

8. The recombinant RhCMV or HCMV vaccine vector of claim 7, wherein the gene region is selected from the group consisting of the RL11 family, the pp65 family, the US12 family, and the US28 family.

9. The recombinant RhCMV vaccine vector of claim 8, wherein the RhCMV gene region is selected from the group consisting of Rh13-Rh29, Rh111-Rh112, Rh191-Rh202, and Rh214-Rh220, or wherein the RhCMV gene region is selected from the group consisting of Rh13.1, Rh19, Rh20, Rh23, Rh24, Rh112, Rh190, Rh192, Rh196, Rh198, Rh199, Rh200, Rh201, Rh202, and Rh220.

10. The recombinant HCMV vaccine vector of claim 8, wherein the HCMV gene region is selected from the group consisting of RL11, UL6, UL7, UL9, UL11, UL83 (pp65), US12, US13, US14, US17, US18, US19, US20, US21, and UL28.

11. The recombinant RhCMV or HCMV vaccine vector of claim 1, wherein the vector comprises a deletion in a RhCMV or HCMV gene that is essential for replication within a host, dissemination within a host, or spreading from host to host.

12. The recombinant RhCMV or HCMV vaccine vector of claim 11, wherein the essential gene is UL94, UL32, UL99, UL115, or UL44, or a homolog thereof.

13. The recombinant RhCMV or HCMV vaccine vector of claim 1, wherein the vector comprises a deletion in gene UL82 (pp71) or a homolog thereof.

14. The recombinant RhCMV or HCMV vaccine vector of claim 1, wherein the vector encodes US2 protein, US3 protein, or US6 protein, or a homolog thereof, and wherein the vector does not encode a functional US11 protein.

15. The recombinant RhCMV or HCMV vaccine vector of claim 14, wherein the vector does not encode a functional US11 due to deletion of an open reading frame encoding the US11 protein.

16. The recombinant RhCMV or HCMV vaccine vector of claim 14, wherein the vaccine vector comprises a nucleic acid sequence encoding US11 protein, and wherein the nucleic acid sequence encoding the US11 comprises a point mutation, a frameshift mutation, and/or a deletion of one or more nucleotides that renders the encoded US11 protein non-functional.

17. The recombinant RhCMV or HCMV vaccine vector of claim 16, wherein the vector lacks the tegument protein pp65.

18. The recombinant RhCMV or HCMV vaccine vector of claim 1, wherein the vector does not express an active UL130 protein.

19. The recombinant RhCMV or HCMV vaccine vector of claim 1, wherein the RhCMV vaccine vector is Rh68-1 or Rh68-1.2.

20. The recombinant RhCMV or HCMV vaccine vector of claim 1 further comprising a microRNA recognition element (MRE) operably linked to a CMV gene that is essential or augmenting for CMV growth, and wherein the MRE silences expression in the presence of a microRNA that is expressed by a cell of myeloid lineage.

21. A pharmaceutical composition comprising the recombinant RhCMV or HCMV vaccine vector of claim 1, and a pharmaceutically acceptable carrier.

22. A method for treatment of tuberculosis or eliciting an immune response to a Mtb antigen comprising administering to a subject in need thereof at least one recombinant RhCMV or HCMV vaccine vector of claim 1.

23. The method of claim 22, wherein the recombinant RhCMV or HCMV vaccine vector is administered to the subject intravenously, intramuscularly, intraperitoneally, intranasally, orally, or as an aerosol.

* * * * *

SEQUENCE LISTING

<160> NUMBER OF SEQ ID NOS: 31

<210> SEQ ID NO 1
<211> LENGTH: 1017
<212> TYPE: DNA
<213> ORGANISM: Mycobacterium tuberculosis
<220> FEATURE:
<223> OTHER INFORMATION: Ag85A

<400> SEQUENCE: 1
atgcagcttg ttgacagggt tcgtggcgcc gtcacgggta tgtcgcgtcg actcgtggtc 60
ggggccgtcg gcgcggccct agtgtcgggt ctggtcggcg ccgtcggtgg cacggcgacc 120
gcgggggcat tttcccggcc gggcttgccg gtggagtacc tgcaggtgcc gtcgccgtcg 180
atgggccgtg acatcaaggt ccaattccaa agtggtggtg ccaactcgcc cgccctgtac 240
ctgctcgacg gcctgcgcgc gcaggacgac ttcagcggct gggacatcaa caccccggcg 300
ttcgagtggt acgaccagtc gggcctgtcg gtggtcatgc cggtgggtgg ccagtcaagc 360
ttctactccg actggtacca gcccgcctgc ggcaaggccg gttgccagac ttacaagtgg 420
gagaccttcc tgaccagcga gctgccgggg tggctgcagg ccaacaggca cgtcaagccc 480
accggaagcg ccgtcgtcgg tctttcgatg gctgcttctt cggcgctgac gctggcgatc 540
tatcaccccc agcagttcgt ctacgcggga gcgatgtcgg gcctgttgga cccctcccag 600
gcgatgggtc ccaccctgat cggcctggcg atgggtgacg ctggcggcta caaggcctcc 660
gacatgtggg gcccgaagga ggacccggcg tggcagcgca acgacccgct gttgaacgtc 720
gggaagctga tcgccaacaa cacccgcgtc tgggtgtact gcggcaacgg caagccgtcg 780
gatctgggtg gcaacaacct gccggccaag ttcctcgagg gcttcgtgcg gaccagcaac 840
atcaagttcc aagacgccta caacgccggt ggcggccaca acggcgtgtt cgacttcccg 900
gacagcggta cgcacagctg ggagtactgg ggcgcgcagc tcaacgctat gaagcccgac 960
ctgcaacggg cactgggtgc cacgcccaac accgggcccg cgccccaggg cgcctag 1017

<210> SEQ ID NO 2
<211> LENGTH: 338
<212> TYPE: PRT
<213> ORGANISM: Mycobacterium tuberculosis
<220> FEATURE:
<223> OTHER INFORMATION: Ag85A

<400> SEQUENCE: 2

Met Gln Leu Val Asp Arg Val Arg Gly Ala Val Thr Gly Met Ser Arg
1 5 10 15

Arg Leu Val Val Gly Ala Val Gly Ala Ala Leu Val Ser Gly Leu Val
20 25 30

Gly Ala Val Gly Gly Thr Ala Thr Ala Gly Ala Phe Ser Arg Pro Gly
35 40 45

Leu Pro Val Glu Tyr Leu Gln Val Pro Ser Pro Ser Met Gly Arg Asp
50 55 60

Ile Lys Val Gln Phe Gln Ser Gly Gly Ala Asn Ser Pro Ala Leu Tyr
65 70 75 80

```
Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly His Asn Gly Val Phe Asp Phe Pro Asp Ser Gly Thr
    290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala
```

<210> SEQ ID NO 3
<211> LENGTH: 978
<212> TYPE: DNA
<213> ORGANISM: Mycobacterium tuberculosis
<220> FEATURE:
<223> OTHER INFORMATION: Ag85B

<400> SEQUENCE: 3

```
atgacagacg tgagccgaaa gattcgagct tggggacgcc gattgatgat cggcacggca      60
gcggctgtag tccttccggg cctggtgggg cttgccggcg agcggcaac  cgcgggcgcg     120 ttctcccggc cggggctgcc ggtcgagtac ctgcaggtgc cgtcgccgtc gatgggccgc     180
gacatcaagg ttcagttcca gagcggtggg aacaactcac ctgcggttta tctgctcgac     240
ggcctgcgcg cccaagacga ctacaacggc tgggatatca caccccggc  gttcgagtgg     300 tactaccagt cgggactgtc gatagtcatg ccggtcggcg gcagtccag  cttctacagc     360 gactggtaca gcccggcctg cggtaaggct ggctgccaga cttacaagtg gaaaccttc     420 ctgaccagcg agctgccgca atggttgtcc gccaacaggg ccgtgaagcc caccggcagc     480
gctgcaatcg gcttgtcgat ggccggctcg tcggcaatga tcttggccgc ctaccacccc     540
```

-continued

```
cagcagttca tctacgccgg ctcgctgtcg gccctgctgg accccctctca ggggatgggg      600 cctagcctga tcggcctcgc gatgggtgac gccggcggtt acaaggccgc agacatgtgg      660
ggtccctcga gtgacccggc atgggagcgc aacgaccta cgcagcagat ccccaagctg       720
gtcgcaaaca cacccggct atgggtttat tgcgggaacg gcaccccgaa cgagttgggc       780
ggtgccaaca tacccgccga gttcttggag aacttcgttc gtagcagcaa cctgaagttc      840
caggatgcgt acaacgccgc gggcgggcac aacgccgtgt tcaacttccc gcccaacggc      900
acgcacagct gggagtactg gggcgctcag ctcaacgcca tgaagggtga cctgcagagt      960
tcgttaggcg ccggctga                                                    978
```

```
<210> SEQ ID NO 4
<211> LENGTH: 325
<212> TYPE: PRT
<213> ORGANISM: Mycobacterium tuberculosis
<220> FEATURE:
<223> OTHER INFORMATION: Ag85B

<400> SEQUENCE: 4

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
            35                  40                  45

Glu Tyr Leu Gln Val Pro Ser Pro Ser Met Gly Arg Asp Ile Lys Val
        50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285
```

```
Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325

<210> SEQ ID NO 5
<211> LENGTH: 300
<212> TYPE: DNA
<213> ORGANISM: Mycobacterium tuberculosis
<220> FEATURE:
<223> OTHER INFORMATION: Rv3407

<400> SEQUENCE: 5
atgcgtgcta ccgttgggct tgtggaggca atcggaatcc gagaactaag acagcacgca      60
tcgcgatacc tcgcccgggt tgaagccggc gaggaacttg gcgtcaccaa caaaggaaga     120
cttgtgcccc gactcatccc ggtgcaggcc gcggagcgtt ctcgcgaagc cctgattgaa     180
tcaggtgtcc tgattccggc tcgtcgtcca caaaaccttc tcgacgtcac cgccgaaccg     240
gcgcgcggcc gcaagcgcac cctgtccgat gttctcaacg aaatgcgcga cgagcagtga     300

<210> SEQ ID NO 6
<211> LENGTH: 99
<212> TYPE: PRT
<213> ORGANISM: Mycobacterium tuberculosis
<220> FEATURE:
<223> OTHER INFORMATION: Rv3407

<400> SEQUENCE: 6

Met Arg Ala Thr Val Gly Leu Val Glu Ala Ile Gly Ile Arg Glu Leu
1               5                   10                  15

Arg Gln His Ala Ser Arg Tyr Leu Ala Arg Val Glu Ala Gly Glu Glu
            20                  25                  30

Leu Gly Val Thr Asn Lys Gly Arg Leu Val Ala Arg Leu Ile Pro Val
        35                  40                  45

Gln Ala Ala Glu Arg Ser Arg Glu Ala Leu Ile Glu Ser Gly Val Leu
    50                  55                  60

Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
                85                  90                  95

Asp Glu Gln

<210> SEQ ID NO 7
<211> LENGTH: 633
<212> TYPE: DNA
<213> ORGANISM: Mycobacterium tuberculosis
<220> FEATURE:
<223> OTHER INFORMATION: Rv1733

<400> SEQUENCE: 7
atgatcgcca acccgcgca tcgtgaagga gccaccatga tcacgtttag gctgcgcttg      60
ccgtgccgga cgatactgcg ggtgttcagc cgcaatccgc tggtgcgtgg acggatcga     120 ctcgaggcgg tcgtcatgct gctggccgtc acggtctcgc tgctgactat cccgttcgcc     180
gccgcggccg gcaccgcagt ccaggattcc cgcagccacg tctatgccca ccaggcccag     240
acccgccatc ccgcaaccgc gaccgtgatc gatcacgagg gggtgatcga cagcaacacg     300
```

```
accgccacgt cagcgccgcc gcgcacgaag atcaccgtgc ctgcccgatg ggtcgtgaac      360
ggaatagaac gcagcggtga ggtcaacgcg aagccgggaa ccaaatccgg tgaccgcgtc      420
ggcatttggg tcgacagtgc cggtcagctg gtcgatgaac cagctccgcc ggcccgtgcc      480
attgcggatg cggccctggc cgccttggga ctctggttga gcgtcgccgc ggttgcgggc      540
gccctgctgg cgctcactcg ggcgattctg atccgcgttc gcaacgccag ttggcaacac      600
gacatcgaca gcctgttctg cacgcagcgg tga                                   633

<210> SEQ ID NO 8
<211> LENGTH: 210
<212> TYPE: PRT
<213> ORGANISM: Mycobacterium tuberculosis
<220> FEATURE:
<223> OTHER INFORMATION: Rv1733

<400> SEQUENCE: 8

Met Ile Ala Thr Thr Arg Asp Arg Glu Gly Ala Thr Met Ile Thr Phe
1               5                   10                  15

Arg Leu Arg Leu Pro Cys Arg Thr Ile Leu Arg Val Phe Ser Arg Asn
            20                  25                  30

Pro Leu Val Arg Gly Thr Asp Arg Leu Glu Ala Val Val Met Leu Leu
        35                  40                  45

Ala Val Thr Val Ser Leu Leu Thr Ile Pro Phe Ala Ala Ala Ala Gly
    50                  55                  60

Thr Ala Val Gln Asp Ser Arg Ser His Val Tyr Ala His Gln Ala Gln
65                  70                  75                  80

Thr Arg His Pro Ala Thr Ala Thr Val Ile Asp His Glu Gly Val Ile
                85                  90                  95

Asp Ser Asn Thr Thr Ala Thr Ser Ala Pro Pro Arg Thr Lys Ile Thr
            100                 105                 110

Val Pro Ala Arg Trp Val Val Asn Gly Ile Glu Arg Ser Gly Glu Val
        115                 120                 125

Asn Ala Lys Pro Gly Thr Lys Ser Gly Asp Arg Val Gly Ile Trp Val
    130                 135                 140

Asp Ser Ala Gly Gln Leu Val Asp Glu Pro Ala Pro Pro Ala Arg Ala
145                 150                 155                 160

Ile Ala Asp Ala Ala Leu Ala Ala Leu Gly Leu Trp Leu Ser Val Ala
                165                 170                 175

Ala Val Ala Gly Ala Leu Leu Ala Leu Thr Arg Ala Ile Leu Ile Arg
            180                 185                 190

Val Arg Asn Ala Ser Trp Gln His Asp Ile Asp Ser Leu Phe Cys Thr
        195                 200                 205

Gln Arg
    210

<210> SEQ ID NO 9
<211> LENGTH: 432
<212> TYPE: DNA
<213> ORGANISM: Mycobacterium tuberculosis
<220> FEATURE:
<223> OTHER INFORMATION: Rv2626c

<400> SEQUENCE: 9
atgaccaccg cacgcgacat catgaacgca ggtgtgacct gtgttggcga acacgagacg      60
ctaaccgctg ccgctcaata catgcgtgag cacgacatcg gcgcgttgcc gatctgcggg      120
```

-continued

```
gacgacgacc ggctgcacgg catgctcacc gaccgcgaca ttgtgatcaa aggcctggct    180
gcgggcctag acccgaatac cgccacggct ggcgagttgg cccgggacag catctactac    240
gtcgatgcga acgcaagcat ccaggagatg ctcaacgtca tggaagaaca tcaggtccgc    300
cgtgttccgg tcatctcaga gcaccgcttg gtcggaatcg tcaccgaagc cgacatcgcc    360
cgacacctgc ccgagcacgc cattgtgcag ttcgtcaagg caatctgctc gcccatggcc    420
ctcgccagct ag                                                        432
```

<210> SEQ ID NO 10
<211> LENGTH: 143
<212> TYPE: PRT
<213> ORGANISM: Mycobacterium tuberculosis
<220> FEATURE:
<223> OTHER INFORMATION: Rv2626c
<400> SEQUENCE: 10

```
Met Thr Thr Ala Arg Asp Ile Met Asn Ala Gly Val Thr Cys Val Gly
 1               5                  10                  15

Glu His Glu Thr Leu Thr Ala Ala Gln Tyr Met Arg Glu His Asp
            20                  25                  30

Ile Gly Ala Leu Pro Ile Cys Gly Asp Asp Arg Leu His Gly Met
        35                  40                  45

Leu Thr Asp Arg Asp Ile Val Ile Lys Gly Leu Ala Ala Gly Leu Asp
 50                  55                  60

Pro Asn Thr Ala Thr Ala Gly Glu Leu Ala Arg Asp Ser Ile Tyr Tyr
 65                  70                  75                  80

Val Asp Ala Asn Ala Ser Ile Gln Glu Met Leu Asn Val Met Glu Glu
                 85                  90                  95

His Gln Val Arg Arg Val Pro Val Ile Ser Glu His Arg Leu Val Gly
            100                 105                 110

Ile Val Thr Glu Ala Asp Ile Ala Arg His Leu Pro Glu His Ala Ile
        115                 120                 125

Val Gln Phe Val Lys Ala Ile Cys Ser Pro Met Ala Leu Ala Ser
    130                 135                 140
```

<210> SEQ ID NO 11
<211> LENGTH: 1224
<212> TYPE: DNA
<213> ORGANISM: Mycobacterium tuberculosis
<220> FEATURE:
<223> OTHER INFORMATION: RpfA
<400> SEQUENCE: 11

```
atgagtggac gccaccgtaa gcccaccaca tccaacgtca gcgtcgccaa gatcgccttt    60
accggcgcag tactcggtgg cggcggcatc gccatggccg ctcaggcgac gcggccacc    120 gacggggaat gggatcaggt ggcccgctgc gagtcgggcg gcaactggtc gatcaacacc    180
ggcaacggtt acctcggtgg cttgcagttc actcaaagca cctgggccgc acatggtggc    240
ggcgagttcg ccccgtcggc tcagctggcc agccgggagc agcagattgc cgtcggtgag    300
cgggtgctgg ccacccaggg tcgcggcgcc tggccggtgt gcggccgcgg gttatcgaac    360
gcaacacccc gcgaagtgct tcccgcttcg gcagcgatgg acgctccgtt ggacgcggcc    420
gcggtcaacg gcgaaccagc accgctggcc ccgccgcccg ccgacccggc gccaccgtg    480 gaacttgccg ctaacgacct gccgcaccg ctgggtgaac cctcccggc agctcccgcc    540 gacccggcac caccgccgga cctggcacca cccgcgcccg ccgacgtcgc gccacccgtg    600
```

```
gaacttgccg taaacgacct gcccgcaccg ctgggtgaac ccctcccggc agctcccgcc      660
gacccggcac cacccgccga cctggcacca cccgcgcccg ccgacctggc gccaccgcg       720 cccgccgacc tggcgccacc cgcgcccgcc gacctggcac cacccgtgga acttgccgta      780
aacgacctgc ccgcgccgct gggtgaaccc ctcccggcag ctcccgccga actggcgcca      840
cccgccgatc tggcacccgc gtccgccgac ctggcgccac ccgcgcccgc cgacctggcg      900
ccacccgcgc ccgccgaact ggcgccaccc gcgcccgccg aactggcacc acccgctgcg      960
gtgaacgagc aaaccgcgcc gggcgatcag cccgccacag ctccaggcgg cccggttggc     1020
cttgccaccg atttggaact ccccgagccc gaccccaaac cagctgacgc accgccgccc     1080
ggcgacgtca ccgaggcgcc ccgccgaaacg ccccaagtct cgaacatcgc ctatacgaag    1140
aagctgtggc aggcgattcg ggcccaggac gtctgcggca acgatgcgct ggactcgctc     1200
gcacagccgt acgtcatcgg ctga                                            1224
```

<210> SEQ ID NO 12
<211> LENGTH: 407
<212> TYPE: PRT
<213> ORGANISM: Mycobacterium tuberculosis
<220> FEATURE:
<223> OTHER INFORMATION: RpfA

<400> SEQUENCE: 12

```
Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Ile Ala Met
        20                  25                  30

Ala Ala Gln Ala Thr Ala Thr Asp Gly Glu Trp Asp Gln Val Ala
        35                  40                  45

Arg Cys Glu Ser Gly Gly Asn Trp Ser Ile Asn Thr Gly Asn Gly Tyr
    50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Val Asn Gly
    130                 135                 140

Glu Pro Ala Pro Leu Ala Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Ala Leu Ala Pro Ala
            180                 185                 190

Pro Ala Asp Val Ala Pro Pro Val Glu Leu Ala Val Asn Asp Leu Pro
        195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Leu Ala Pro Pro Ala
225                 230                 235                 240

Pro Ala Asp Leu Ala Pro Pro Ala Pro Ala Asp Leu Ala Pro Pro Val
                245                 250                 255
```

```
Glu Leu Ala Val Asn Asp Leu Pro Ala Pro Leu Gly Glu Pro Leu Pro
            260                 265                 270

Ala Ala Pro Ala Glu Leu Ala Pro Ala Asp Leu Ala Pro Ala Ser
        275                 280                 285

Ala Asp Leu Ala Pro Pro Ala Pro Ala Asp Leu Ala Pro Pro Ala Pro
290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

Gln Pro Ala Asp Ala Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405

<210> SEQ ID NO 13
<211> LENGTH: 531
<212> TYPE: DNA
<213> ORGANISM: Mycobacterium tuberculosis
<220> FEATURE:
<223> OTHER INFORMATION: RpfC

<400> SEQUENCE: 13
gtgcatcctt tgccggccga ccacggccgg tcgcggtgca atagacaccc gatctcacca      60
ctctctctaa tcggtaacgc ttcggccact tccggcgata tgtcgagcat gacaagaatc     120
gccaagccgc tcatcaagtc cgccatggcc gcaggactcg tcacggcatc catgtcgctc     180
tccaccgccg ttgcccacgc cggtcccagc ccgaactggg acgccgtcgc gcagtgcgaa     240
tccgggggca actgggcggc caacaccgga acggcaaat acggcggact gcagttcaag      300
ccggccacct gggccgcatt cggcggtgtc ggcaacccag cagctgcctc tcgggaacaa     360
caaatcgcag ttgccaatcg ggttctcgcc gaacagggat tggacgcgtg gccgacgtgc     420
ggcgccgcct ctggccttcc gatcgcactg tggtcgaaac ccgcgcaggg catcaagcaa     480
atcatcaacg agatcatttg gcaggcatt caggcaagta ttccgcgctg a               531

<210> SEQ ID NO 14
<211> LENGTH: 176
<212> TYPE: PRT
<213> ORGANISM: Mycobacterium tuberculosis
<220> FEATURE:
<223> OTHER INFORMATION: RpfC

<400> SEQUENCE: 14

Val His Pro Leu Pro Ala Asp His Gly Arg Ser Arg Cys Asn Arg His
1               5                   10                  15

Pro Ile Ser Pro Leu Ser Leu Ile Gly Asn Ala Ser Ala Thr Ser Gly
            20                  25                  30

Asp Met Ser Ser Met Thr Arg Ile Ala Lys Pro Leu Ile Lys Ser Ala
        35                  40                  45

Met Ala Ala Gly Leu Val Thr Ala Ser Met Ser Leu Ser Thr Ala Val
```

```
                    50                  55                  60

Ala His Ala Gly Pro Ser Pro Asn Trp Asp Ala Val Ala Gln Cys Glu
 65                  70                  75                  80

Ser Gly Gly Asn Trp Ala Ala Asn Thr Gly Asn Gly Lys Tyr Gly Gly
                     85                  90                  95

Leu Gln Phe Lys Pro Ala Thr Trp Ala Ala Phe Gly Gly Val Gly Asn
                100                 105                 110

Pro Ala Ala Ala Ser Arg Glu Gln Gln Ile Ala Val Ala Asn Arg Val
            115                 120                 125

Leu Ala Glu Gln Gly Leu Asp Ala Trp Pro Thr Cys Gly Ala Ala Ser
        130                 135                 140

Gly Leu Pro Ile Ala Leu Trp Ser Lys Pro Ala Gln Gly Ile Lys Gln
145                 150                 155                 160

Ile Ile Asn Glu Ile Ile Trp Ala Gly Ile Gln Ala Ser Ile Pro Arg
                165                 170                 175

<210> SEQ ID NO 15
<211> LENGTH: 465
<212> TYPE: DNA
<213> ORGANISM: Mycobacterium tuberculosis
<220> FEATURE:
<223> OTHER INFORMATION: RpfD

<400> SEQUENCE: 15
atgacaccgg gtttgcttac tactgcgggt gctggccgac cacgtgacag gtgcgccagg      60
atcgtatgca cggtgttcat cgaaaccgcc gttgtcgcga ccatgtttgt cgcgttgttg     120
ggtctgtcca ccatcagctc gaaagccgac gacatcgatt gggacgccat cgcgcaatgc     180
gaatccggcg gcaattgggc ggccaacacc ggtaacgggt tatacggtgg tctgcagatc     240
agccaggcga cgtgggattc aacggtggt gtcgggtcgc cggcggccgc gagtccccag      300
caacagatcg aggtcgcaga caacattatg aaaacccaag gcccgggtgc gtggccgaaa     360
tgtagttctt gtagtcaggg agacgcaccg ctgggctcgc tcacccacat cctgacgttc     420
ctcgcggccg agactggagg ttgttcgggg agcagggacg attga                     465

<210> SEQ ID NO 16
<211> LENGTH: 154
<212> TYPE: PRT
<213> ORGANISM: Mycobacterium tuberculosis
<220> FEATURE:
<223> OTHER INFORMATION: RpfD

<400> SEQUENCE: 16

Met Thr Pro Gly Leu Leu Thr Thr Ala Gly Ala Gly Arg Pro Arg Asp
 1               5                  10                  15

Arg Cys Ala Arg Ile Val Cys Thr Val Phe Ile Glu Thr Ala Val Val
             20                  25                  30

Ala Thr Met Phe Val Ala Leu Leu Gly Leu Ser Thr Ile Ser Ser Lys
         35                  40                  45

Ala Asp Asp Ile Asp Trp Asp Ala Ile Ala Gln Cys Glu Ser Gly Gly
     50                  55                  60

Asn Trp Ala Ala Asn Thr Gly Asn Gly Leu Tyr Gly Gly Leu Gln Ile
 65                  70                  75                  80

Ser Gln Ala Thr Trp Asp Ser Asn Gly Gly Val Gly Ser Pro Ala Ala
                 85                  90                  95

Ala Ser Pro Gln Gln Gln Ile Glu Val Ala Asp Asn Ile Met Lys Thr
            100                 105                 110
```

```
Gln Gly Pro Gly Ala Trp Pro Lys Cys Ser Ser Cys Ser Gln Gly Asp
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150

<210> SEQ ID NO 17
<211> LENGTH: 288
<212> TYPE: DNA
<213> ORGANISM: Mycobacterium tuberculosis
<220> FEATURE:
<223> OTHER INFORMATION: ESAT-6

<400> SEQUENCE: 17
atgacagagc agcagtggaa tttcgcgggt atcgaggccg cggcaagcgc aatccaggga      60
aatgtcacgt ccattcattc cctccttgac gagggaagc agtccctgac caagctcgca     120
gcggcctggg gcggtagcgg ttcggaggcg taccagggtc tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcatag                  288

<210> SEQ ID NO 18
<211> LENGTH: 95
<212> TYPE: PRT
<213> ORGANISM: Mycobacterium tuberculosis
<220> FEATURE:
<223> OTHER INFORMATION: ESAT-6

<400> SEQUENCE: 18

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 19
<211> LENGTH: 2049
<212> TYPE: DNA
<213> ORGANISM: Mycobacterium tuberculosis
<220> FEATURE:
<223> OTHER INFORMATION: Ag85A-Ag85B-Rv3407

<400> SEQUENCE: 19
atggcatttt cccggccggg cttgccggtg gagtacctgc aggtgccgtc gccgtcgatg      60
ggccgtgaca tcaaggtcca attccaaagt ggtggtgcca actcgcccgc cctgtacctg     120
ctcgacggcc tgcgcgcgca ggacgacttc agcggctggg acatcaacac cccggcgttc     180
gagtggtacg accagtcggg cctgtcggtg gtcatgccgg tgggtggcca gtcaagcttc     240
tactccgact ggtaccagcc cgcctgcggc aaggccggtt gccagactta caagtgggag     300
accttcctga ccagcgagct gccggggtgg ctgcaggcca acaggcacgt caagcccacc     360
```

-continued

```
ggaagcgccg tcgtcggtct ttcgatggct gcttcttcgg cgctgacgct ggcgatctat    420
cacccccagc agttcgtcta cgcgggagcg atgtcgggcc tgttggaccc ctcccaggcg    480
atgggtccca ccctgatcgg cctggcgatg ggtgacgctg cggctacaa ggcctccgac     540 atgtggggcc cgaaggagga cccggcgtgg cagcgcaacg acccgctgtt gaacgtcggg    600
aagctgatcg ccaacaacac ccgcgtctgg gtgtactgcg gcaacggcaa gccgtcggat    660
ctgggtggca caacctgcc ggccaagttc ctcgagggct tcgtgcggac cagcaacatc     720
aagttccaag acgcctacaa cgccggtggc ggccacaacg gcgtgttcga cttcccggac    780
agcggtacgc acagctggga gtactggggc gcgcagctca cgctatgaa gcccgacctg     840 caacgggcac tgggtgccac gcccaacacc gggcccgcgc ccagggcgc atgttctcc      900 cggccggggc tgccggtcga gtacctgcag gtgccgtcgc cgtcgatggg ccgcgacatc    960
aaggttcagt tccagagcgg tggaacaaac tcacctgcgg tttatctgct cgacggcctg   1020 cgcgccaag acgactacaa cggctgggat atcaacaccc cggcgttcga gtggtactac    1080
cagtcgggac tgtcgatagt catgccggtc ggcgggcagt ccagcttcta cagcgactgg   1140
tacagcccgg cctgcggtaa ggctggctgc cagacttaca agtgggaaac cttcctgacc   1200
agcgagctgc cgcaatggtt gtccgccaac agggccgtga agcccaccgg cagcgctgca   1260
atcggcttgt cgatggccgg ctcgtcggca atgatcttgg ccgcctacca cccccagcag   1320
ttcatctacg ccggctcgct gtcggccctg ctggaccct ctcaggggat ggggcctagc    1380
ctgatcggcc tcgcgatggg tgacgccggc ggttacaagg ccgcagacat gtggggtccc   1440
tcgagtgacc cggcatggga gcgcaacgac cctacgcagc agatccccaa gctggtcgca   1500
aacaacaccc ggctatgggt ttattgcggg aacggcaccc cgaacgagtt gggcggtgcc   1560
aacatacccg ccgagttctt ggagaacttc gttcgtagca gcaacctgaa gttccaggat   1620
gcgtacaacg ccgcgggcgg gcacaacgcc gtgttcaact tcccgcccaa cggcacgcac   1680
agctgggagt actgggcgc tcagctcaac gccatgaagg gtgacctgca gagttcgtta   1740
ggcgccggca tgcgtgctac cgttgggctt gtggaggcaa tcggaatccg agaactaaga   1800
cagcacgcat cgcgatacct cgcccgggtt gaagccggcg aggaacttgg cgtcaccaac   1860
aaaggaagac ttgtggcccg actcatcccg gtgcaggccg cggagcgttc tcgcgaagcc   1920
ctgattgaat caggtgtcct gattccggct cgtcgtccac aaaaccttct cgacgtcacc   1980
gccgaaccgg cgcgcggccg caagcgcacc ctgtccgatg ttctcaacga aatgcgcgac   2040
gagcagtga                                                          2049
```

<210> SEQ ID NO 20
<211> LENGTH: 683
<212> TYPE: PRT
<213> ORGANISM: Mycobacterium tuberculosis
<220> FEATURE:
<223> OTHER INFORMATION: Ag85A-Ag85B-Rv3407

<400> SEQUENCE: 20

```
Met Ala Phe Ser Arg Pro Gly Leu Pro Val Glu Tyr Leu Gln Val Pro
1               5                  10                  15

Ser Pro Ser Met Gly Arg Asp Ile Lys Val Gln Phe Gln Ser Gly Gly
            20                  25                  30

Ala Asn Ser Pro Ala Leu Tyr Leu Leu Asp Gly Leu Arg Ala Gln Asp
        35                  40                  45

Asp Phe Ser Gly Trp Asp Ile Asn Thr Pro Ala Phe Glu Trp Tyr Asp
```

```
                50                  55                  60
Gln Ser Gly Leu Ser Val Val Met Pro Val Gly Gly Gln Ser Phe
 65                  70                  75                  80

Tyr Ser Asp Trp Tyr Gln Pro Ala Cys Gly Lys Ala Gly Cys Gln Thr
                     85                  90                  95

Tyr Lys Trp Glu Thr Phe Leu Thr Ser Glu Leu Pro Gly Trp Leu Gln
                100                 105                 110

Ala Asn Arg His Val Lys Pro Thr Gly Ser Ala Val Val Gly Leu Ser
            115                 120                 125

Met Ala Ala Ser Ser Ala Leu Thr Leu Ala Ile Tyr His Pro Gln Gln
    130                 135                 140

Phe Val Tyr Ala Gly Ala Met Ser Gly Leu Leu Asp Pro Ser Gln Ala
145                 150                 155                 160

Met Gly Pro Thr Leu Ile Gly Leu Ala Met Gly Asp Ala Gly Gly Tyr
                165                 170                 175

Lys Ala Ser Asp Met Trp Gly Pro Lys Glu Asp Pro Ala Trp Gln Arg
            180                 185                 190

Asn Asp Pro Leu Leu Asn Val Gly Lys Leu Ile Ala Asn Asn Thr Arg
        195                 200                 205

Val Trp Val Tyr Cys Gly Asn Gly Lys Pro Ser Asp Leu Gly Gly Asn
    210                 215                 220

Asn Leu Pro Ala Lys Phe Leu Glu Gly Phe Val Arg Thr Ser Asn Ile
225                 230                 235                 240

Lys Phe Gln Asp Ala Tyr Asn Ala Gly Gly His Asn Gly Val Phe
                245                 250                 255

Asp Phe Pro Asp Ser Gly Thr His Ser Trp Glu Tyr Trp Gly Ala Gln
                260                 265                 270

Leu Asn Ala Met Lys Pro Asp Leu Gln Arg Ala Leu Gly Ala Thr Pro
            275                 280                 285

Asn Thr Gly Pro Ala Pro Gln Gly Ala Phe Ser Arg Pro Gly Leu Pro
        290                 295                 300

Val Glu Tyr Leu Gln Val Pro Ser Pro Ser Met Gly Arg Asp Ile Lys
305                 310                 315                 320

Val Gln Phe Gln Ser Gly Gly Asn Asn Ser Pro Ala Val Tyr Leu Leu
                325                 330                 335

Asp Gly Leu Arg Ala Gln Asp Asp Tyr Asn Gly Trp Asp Ile Asn Thr
            340                 345                 350

Pro Ala Phe Glu Trp Tyr Tyr Gln Ser Gly Leu Ser Ile Val Met Pro
        355                 360                 365

Val Gly Gly Gln Ser Ser Phe Tyr Ser Asp Trp Tyr Ser Pro Ala Cys
370                 375                 380

Gly Lys Ala Gly Cys Gln Thr Tyr Lys Trp Glu Thr Phe Leu Thr Ser
385                 390                 395                 400

Glu Leu Pro Gln Trp Leu Ser Ala Asn Arg Ala Val Lys Pro Thr Gly
                405                 410                 415

Ser Ala Ala Ile Gly Leu Ser Met Ala Gly Ser Ala Met Ile Leu
            420                 425                 430

Ala Ala Tyr His Pro Gln Gln Phe Ile Tyr Ala Gly Ser Leu Ser Ala
            435                 440                 445

Leu Leu Asp Pro Ser Gln Gly Met Gly Pro Ser Leu Ile Gly Leu Ala
        450                 455                 460

Met Gly Asp Ala Gly Gly Tyr Lys Ala Ala Asp Met Trp Gly Pro Ser
465                 470                 475                 480
```

```
Ser Asp Pro Ala Trp Glu Arg Asn Asp Pro Thr Gln Gln Ile Pro Lys
                485                 490                 495

Leu Val Ala Asn Asn Thr Arg Leu Trp Val Tyr Cys Gly Asn Gly Thr
            500                 505                 510

Pro Asn Glu Leu Gly Gly Ala Asn Ile Pro Ala Glu Phe Leu Glu Asn
        515                 520                 525

Phe Val Arg Ser Ser Asn Leu Lys Phe Gln Asp Ala Tyr Asn Ala Ala
    530                 535                 540

Gly Gly His Asn Ala Val Phe Asn Phe Pro Pro Asn Gly Thr His Ser
545                 550                 555                 560

Trp Glu Tyr Trp Gly Ala Gln Leu Asn Ala Met Lys Gly Asp Leu Gln
                565                 570                 575

Ser Ser Leu Gly Ala Gly Ala Ala Ala Arg Ala Thr Val Gly Leu Val
            580                 585                 590

Glu Ala Ile Gly Ile Arg Glu Leu Arg Gln His Ala Ser Arg Tyr Leu
        595                 600                 605

Ala Arg Val Glu Ala Gly Glu Leu Gly Val Thr Asn Lys Gly Arg
    610                 615                 620

Leu Val Ala Arg Leu Ile Pro Val Gln Ala Ala Glu Arg Ser Arg Glu
625                 630                 635                 640

Ala Leu Ile Glu Ser Gly Val Leu Ile Pro Ala Arg Arg Pro Gln Asn
                645                 650                 655

Leu Leu Asp Val Thr Ala Glu Pro Ala Arg Gly Arg Lys Arg Thr Leu
            660                 665                 670

Ser Asp Val Leu Asn Glu Met Arg Asp Glu Gln
        675                 680
```

<210> SEQ ID NO 21
<211> LENGTH: 1062
<212> TYPE: DNA
<213> ORGANISM: Mycobacterium tuberculosis
<220> FEATURE:
<223> OTHER INFORMATION: Rv1733-Rv2626c

<400> SEQUENCE: 21

```
atgaccaccg cacgcgacat catgaacgca ggtgtgacct gtgttggcga acacgagacg      60
ctaaccgctg ccgctcaata catgcgtgag cacgacatcg gcgcgttgcc gatctgcggg     120
gacgacgacc ggctgcacgg catgctcacc gaccgcgaca ttgtgatcaa aggcctggct     180
gcgggcctag acccgaatac cgccacggct ggcgagttgg cccgggacag catctactac     240
gtcgatgcga acgcaagcat ccaggagatg ctcaacgtca tggaagaaca tcaggtccgc     300
cgtgttccgg tcatctcaga gcaccgcttg gtcggaatcg tcaccgaagc cgacatcgcc     360
cgacacctgc ccgagcacgc cattgtgcag ttcgtcaagg caatctgctc gcccatggcc     420
ctcgccagca tgatcgccac aacccgcgat cgtgaaggag ccaccatgat cacgtttagg     480
ctgcgcttgc cgtgccggac gatactgcgg gtgttcagcc gcaatccgct ggtgcgtggg     540
acggatcgac tcgaggcggt cgtcatgctg ctggccgtca cggtctcgct gctgactatc     600
ccgttcgccg ccgcggccgg caccgcagtc caggattccc gcagccacgt ctatgcccac     660
caggcccaga cccgccatcc cgcaaccgcg accgtgatcg atcacgaggg ggtgatcgac     720
agcaacacga ccgccacgtc agcgccgccg cgcacgaaga tcaccgtgcc tgcccgatgg     780
gtcgtgaacg gaatagaacg cagcggtgag gtcaacgcga agccgggaac caaatccggt     840
gaccgcgtcg gcatttgggt cgacagtgcc ggtcagctgg tcgatgaacc agctccgccg     900
```

```
gcccgtgcca ttgcggatgc ggccctggcc gccttgggac tctggttgag cgtcgccgcg    960
gttgcgggcg ccctgctggc gctcactcgg gcgattctga tccgcgttcg caacgccagt   1020
tggcaacacg acatcgacag cctgttctgc acgcagcggt ga                      1062
```

<210> SEQ ID NO 22
<211> LENGTH: 353
<212> TYPE: PRT
<213> ORGANISM: Mycobacterium tuberculosis
<220> FEATURE:
<223> OTHER INFORMATION: Rv1733-Rv2626c

<400> SEQUENCE: 22

```
Met Thr Thr Ala Arg Asp Ile Met Asn Ala Gly Val Thr Cys Val Gly
1               5                   10                  15

Glu His Glu Thr Leu Thr Ala Ala Gln Tyr Met Arg Glu His Asp
            20                  25                  30

Ile Gly Ala Leu Pro Ile Cys Gly Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
            100                 105                 110

Ile Val Thr Glu Ala Asp Ile Ala Arg His Leu Pro Glu His Ala Ile
        115                 120                 125

Val Gln Phe Val Lys Ala Ile Cys Ser Pro Met Ala Leu Ala Ser Met
    130                 135                 140

Ile Ala Thr Thr Arg Asp Arg Glu Gly Ala Thr Met Ile Thr Phe Arg
145                 150                 155                 160

Leu Arg Leu Pro Cys Arg Thr Ile Leu Arg Val Phe Ser Arg Asn Pro
                165                 170                 175

Leu Val Arg Gly Thr Asp Arg Leu Glu Ala Val Val Met Leu Leu Ala
            180                 185                 190

Val Thr Val Ser Leu Leu Thr Ile Pro Phe Ala Ala Ala Gly Thr
        195                 200                 205

Ala Val Gln Asp Ser Arg Ser His Val Tyr Ala His Gln Ala Gln Thr
    210                 215                 220

Arg His Pro Ala Thr Ala Thr Val Ile Asp His Glu Gly Val Ile Asp
225                 230                 235                 240

Ser Asn Thr Thr Ala Thr Ser Ala Pro Pro Arg Thr Lys Ile Thr Val
                245                 250                 255

Pro Ala Arg Trp Val Val Asn Gly Ile Glu Arg Ser Gly Glu Val Asn
            260                 265                 270

Ala Lys Pro Gly Thr Lys Ser Gly Asp Arg Val Gly Ile Trp Val Asp
        275                 280                 285

Ser Ala Gly Gln Leu Val Asp Glu Pro Ala Pro Ala Arg Ala Ile
    290                 295                 300

Ala Asp Ala Ala Leu Ala Ala Leu Gly Leu Trp Leu Ser Val Ala Ala
305                 310                 315                 320

Val Ala Gly Ala Leu Leu Ala Leu Thr Arg Ala Ile Leu Ile Arg Val
                325                 330                 335
```

Arg Asn Ala Ser Trp Gln His Asp Ile Asp Ser Leu Phe Cys Thr Gln
            340                 345                 350

Arg

<210> SEQ ID NO 23
<211> LENGTH: 2217
<212> TYPE: DNA
<213> ORGANISM: Mycobacterium tuberculosis
<220> FEATURE:
<223> OTHER INFORMATION: RpfA-RpfC-RpfD

<400> SEQUENCE: 23

| | | | | | |
|---|---|---|---|---|---|
| atggcgtcag | ggaggcatcg | gaaaccaact | acaagcaatg | tatctgttgc | caagattgct | 60 |
| ttcaccggcg | cagttcttgg | aggtggcgga | attgccatgg | ctgcccaggc | aacagccgct | 120 |
| acagatggag | agtgggatca | ggtggctcga | tgtgagtctg | gtggcaactg | gtctatcaac | 180 |
| actgggaacg | ggtatcttgg | cggcttgcaa | tttactcaga | gcacttgggc | tgcccacgga | 240 |
| gggggtgaat | ttgctcctag | cgcgcagctg | gcctcccgcg | agcagcagat | cgctgtggga | 300 |
| gagagggtgt | tggccacaca | gggaagaggt | gcctggcctg | tctgtggccg | cggactcagt | 360 |
| aatgctaccc | ctagggaggt | gctgcccgcc | tcagccgcta | tggacgctcc | actggatgct | 420 |
| gccgccgtga | atggcgagcc | agctccgctg | caccccccac | ctgcagaccc | cgctccccca | 480 |
| gtcgagctgg | cggcaaacga | cctgcccgca | cctctcggag | aaccacttcc | tgcagcgcct | 540 |
| gccgatccag | ctccacctgc | tgatttggct | cccccgctc | ccgccgatgt | agcccctccg | 600 |
| gtcgagttgg | ctgtgaatga | cctgccggca | cctctgggcg | agcccctccc | agccgctccg | 660 |
| gccgaccctg | cccctcctgc | tgatctggca | ccaccgctc | ctgccgacct | cgccccaccc | 720 |
| gccccagcag | acctggctcc | accagcgcct | gcggatcttg | cccgcctgt | tgagctggct | 780 |
| gtcaacgatc | ttcctgcgcc | tcttggagag | ccctgcccg | ctgctccagc | cgaactcgca | 840 |
| ccaccggcag | atctggctcc | cgcctctgcc | gatcttgcac | ctcccgcacc | ggcggacttg | 900 |
| gcacctccag | caccagcaga | actggctccc | cctgcgccgg | ctgacctggc | cctccagca | 960 |
| gccgttaatg | agcaaaccgc | accaggggac | cagccggcta | cggcaccagg | tggaccggtg | 1020 |
| gggctggcca | ccgacctgga | gctgcctgag | ccggatcccc | aaccagctga | tgctccccca | 1080 |
| cctggcgacg | taactgaggc | cccagctgaa | acgcccagg | tcagtaacat | cgcttacaca | 1140 |
| aagaaactgt | ggcaggcaat | tagggctcag | gacgtgtgtg | ggaacgacgc | cctggacagc | 1200 |
| ttggcccaac | cgtacgtgat | cggtatgcac | cccctcccg | ctgatcatgg | tcgcagtcgc | 1260 |
| tgtaaccgcc | accccatttc | acctctcagc | cttattggga | atgcgtctgc | tacaagtggc | 1320 |
| gacatgtcta | gtatgacaag | gattgctaag | cccctcatca | aaagtgcgat | ggctgccggt | 1380 |
| ctggtaacag | catccatgag | cttgtccacc | gcagtggctc | acgctgggcc | ttccccgaac | 1440 |
| tgggatgccg | tcgcccagtg | cgagtcaggc | ggcaattggg | ccgcaaatac | cggtaacggt | 1500 |
| aagtatggag | gactgcagtt | taaacctgca | acttgggccg | cctttggagg | agtgggtaat | 1560 |
| cctgcagctg | cttctagaga | acagcagatt | gccgtggcta | accgcgttct | cgcggagcag | 1620 |
| ggtctgacg | cctggccgac | ctgtggcgcc | gcatcaggtt | tgccgatcgc | gttgtggtca | 1680 |
| aagcccgccc | agggaatcaa | gcagattatc | aatgagatca | tctgggccgg | aatacaggca | 1740 |
| agcatcccta | gaatgactcc | tgggcttctg | caaccgctg | gcgctgggag | gcccagggat | 1800 |
| aggtgcgccc | ggatcgtttg | taccgtattc | atagagaccg | ccgtggtcgc | gacaatgttc | 1860 |
| gtggctctct | tgggcttgag | caccattagc | tctaaggccg | atgatataga | ttgggatgct | 1920 |

```
attgctcaat gcgaatccgg tgggaactgg gccgctaata ccggaaatgg gctctacggc    1980
ggactgcaga tcagccaggc tacatgggat agcaacggag gagtcgggtc ccctgccgct    2040
gcatccccgc aacagcaaat cgaggtggcc gataacatca tgaaaaccca gggacccgga    2100
gcctggccca atgtagctc atgtagccaa ggagatgcgc ccctcggttc actgacgcac    2160
atcctcacct tcctcgccgc ggaaaccgga gggtgctctg gcagccggga cgactga       2217
```

<210> SEQ ID NO 24
<211> LENGTH: 737
<212> TYPE: PRT
<213> ORGANISM: Mycobacterium tuberculosis
<220> FEATURE:
<223> OTHER INFORMATION: RpfA-RpfC-RpfD

<400> SEQUENCE: 24

```
Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Ile Ala Met
            20                  25                  30

Ala Ala Gln Ala Thr Ala Thr Asp Gly Glu Trp Asp Gln Val Ala
        35                  40                  45

Arg Cys Glu Ser Gly Gly Asn Trp Ser Ile Asn Thr Gly Asn Gly Tyr
    50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Val Asn Gly
    130                 135                 140

Glu Pro Ala Pro Leu Ala Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Ala Asp Leu Ala Pro Pro Ala
            180                 185                 190

Pro Ala Asp Val Ala Pro Pro Val Glu Leu Ala Val Asn Asp Leu Pro
        195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
            260                 265                 270

Ala Ala Pro Ala Glu Leu Ala Pro Pro Ala Asp Leu Ala Pro Ala Ser
        275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
```

```
          305                 310                 315                 320
Val Asn Glu Gln Thr Ala Pro Gly Asp Gln Pro Ala Thr Ala Pro Gly
                    325                 330                 335

Gly Pro Val Gly Leu Ala Thr Asp Leu Glu Leu Pro Glu Pro Asp Pro
                340                 345                 350

Gln Pro Ala Asp Ala Pro Pro Gly Asp Val Thr Glu Ala Pro Ala
                355                 360                 365

Glu Thr Pro Gln Val Ser Asn Ile Ala Tyr Thr Lys Lys Leu Trp Gln
                370                 375                 380

Ala Ile Arg Ala Gln Asp Val Cys Gly Asn Asp Ala Leu Asp Ser Leu
385                 390                 395                 400

Ala Gln Pro Tyr Val Ile Gly Val His Pro Leu Pro Ala Asp His Gly
                405                 410                 415

Arg Ser Arg Cys Asn Arg His Pro Ile Ser Pro Leu Ser Leu Ile Gly
                420                 425                 430

Asn Ala Ser Ala Thr Ser Gly Asp Met Ser Ser Met Thr Arg Ile Ala
                435                 440                 445

Lys Pro Leu Ile Lys Ser Ala Met Ala Ala Gly Leu Val Thr Ala Ser
                450                 455                 460

Met Ser Leu Ser Thr Ala Val Ala His Ala Gly Pro Ser Pro Asn Trp
465                 470                 475                 480

Asp Ala Val Ala Gln Cys Glu Ser Gly Gly Asn Trp Ala Ala Asn Thr
                485                 490                 495

Gly Asn Gly Lys Tyr Gly Gly Leu Gln Phe Lys Pro Ala Thr Trp Ala
                500                 505                 510

Ala Phe Gly Gly Val Gly Asn Pro Ala Ala Ser Arg Glu Gln Gln
                515                 520                 525

Ile Ala Val Ala Asn Arg Val Leu Ala Glu Gln Gly Leu Asp Ala Trp
                530                 535                 540

Pro Thr Cys Gly Ala Ala Ser Gly Leu Pro Ile Ala Leu Trp Ser Lys
545                 550                 555                 560

Pro Ala Gln Gly Ile Lys Gln Ile Ile Asn Glu Ile Ile Trp Ala Gly
                565                 570                 575

Ile Gln Ala Ser Ile Pro Arg Met Thr Pro Gly Leu Leu Thr Thr Ala
                580                 585                 590

Gly Ala Gly Arg Pro Arg Asp Arg Cys Ala Arg Ile Val Cys Thr Val
                595                 600                 605

Phe Ile Glu Thr Ala Val Val Ala Thr Met Phe Val Ala Leu Leu Gly
                610                 615                 620

Leu Ser Thr Ile Ser Ser Lys Ala Asp Asp Ile Asp Trp Asp Ala Ile
625                 630                 635                 640

Ala Gln Cys Glu Ser Gly Gly Asn Trp Ala Ala Asn Thr Gly Asn Gly
                645                 650                 655

Leu Tyr Gly Gly Leu Gln Ile Ser Gln Ala Thr Trp Asp Ser Asn Gly
                660                 665                 670

Gly Val Gly Ser Pro Ala Ala Ser Pro Gln Gln Ile Glu Val
                675                 680                 685

Ala Asp Asn Ile Met Lys Thr Gln Gly Pro Gly Ala Trp Pro Lys Cys
                690                 695                 700

Ser Ser Cys Ser Gln Gly Asp Ala Pro Leu Gly Ser Leu Thr His Ile
705                 710                 715                 720

Leu Thr Phe Leu Ala Ala Glu Thr Gly Gly Cys Ser Gly Ser Arg Asp
                725                 730                 735
```

Asp

<210> SEQ ID NO 25
<211> LENGTH: 1146
<212> TYPE: DNA
<213> ORGANISM: Mycobacterium tuberculosis
<220> FEATURE:
<223> OTHER INFORMATION: Ag85B-ESAT6

<400> SEQUENCE: 25
atgttctccc ggccggggct gccggtcgag tacctgcagg tgccgtcgcc gtcgatgggc 60
cgcgacatca aggttcagtt ccagagcggt gggaacaact cacctgcggt ttatctgctc 120
gacggcctgc gcgcccaaga cgactacaac ggctgggata tcaacacccc ggcgttcgag 180
tggtactacc agtcgggact gtcgatagtc atgccggtcg gcgggcagtc cagcttctac 240
agcgactggt acagcccggc ctgcggtaag gctggctgcc agacttacaa gtgggaaacc 300
ttcctgacca gcgagctgcc gcaatggttg tccgccaaca gggccgtgaa gcccaccggc 360
agcgctgcaa tcggcttgtc gatggccggc tcgtcggcaa tgatcttggc cgcctaccac 420
ccccagcagt tcatctacgc cggctcgctg tcggccctgc tggacccctc tcaggggatg 480
gggcctagcc tgatcggcct cgcgatgggt gacgccggcg gttacaaggc cgcagacatg 540
tggggtccct cgagtgaccc ggcatgggag cgcaacgacc ctacgcagca gatccccaag 600
ctggtcgcaa acaacacccg gctatgggtt tattgcggga acggcacccc gaacgagttg 660
ggcggtgcca acatacccgc cgagttcttg gagaacttcg ttcgtagcag caacctgaag 720
ttccaggatg cgtacaacgc cgcgggcggg cacaacgccg tgttcaactt cccgcccaac 780
ggcacgcaca gctgggagta ctggggcgct cagctcaacg ccatgaaggg tgacctgcag 840
agttcgttag gcgccggcat gacagagcag cagtggaatt tcgcgggtat cgaggccgcg 900
gcaagcgcaa tccagggaaa tgtcacgtcc attcattccc tccttgacga ggggaagcag 960
tccctgacca agctcgcagc ggcctggggc ggtagcggtt cggaggcgta ccagggtgtc 1020
cagcaaaaat gggacgccac ggctaccgag ctgaacaacg cgctgcagaa cctggcgcgg 1080
acgatcagcg aagccggtca ggcaatggct tcgaccgaag gcaacgtcac tgggatgttc 1140
gcatag 1146

<210> SEQ ID NO 26
<211> LENGTH: 381
<212> TYPE: PRT
<213> ORGANISM: Mycobacterium tuberculosis
<220> FEATURE:
<223> OTHER INFORMATION: Ag85B-ESAT6

<400> SEQUENCE: 26

Met Phe Ser Arg Pro Gly Leu Pro Val Glu Tyr Leu Gln Val Pro Ser
1 5 10 15

Pro Ser Met Gly Arg Asp Ile Lys Val Gln Phe Gln Ser Gly Gly Asn
20 25 30

Asn Ser Pro Ala Val Tyr Leu Leu Asp Gly Leu Arg Ala Gln Asp Asp
35 40 45

Tyr Asn Gly Trp Asp Ile Asn Thr Pro Ala Phe Glu Trp Tyr Tyr Gln
50 55 60

Ser Gly Leu Ser Ile Val Met Pro Val Gly Gly Gln Ser Ser Phe Tyr
65 70 75 80

Ser Asp Trp Tyr Ser Pro Ala Cys Gly Lys Ala Gly Cys Gln Thr Tyr

-continued

```
                85                  90                  95

Lys Trp Glu Thr Phe Leu Thr Ser Glu Leu Pro Gln Trp Leu Ser Ala
            100                 105                 110

Asn Arg Ala Val Lys Pro Thr Gly Ser Ala Ala Ile Gly Leu Ser Met
        115                 120                 125

Ala Gly Ser Ser Ala Met Ile Leu Ala Ala Tyr His Pro Gln Gln Phe
    130                 135                 140

Ile Tyr Ala Gly Ser Leu Ser Ala Leu Leu Asp Pro Ser Gln Gly Met
145                 150                 155                 160

Gly Pro Ser Leu Ile Gly Leu Ala Met Gly Asp Ala Gly Gly Tyr Lys
                165                 170                 175

Ala Ala Asp Met Trp Gly Pro Ser Ser Asp Pro Ala Trp Glu Arg Asn
            180                 185                 190

Asp Pro Thr Gln Gln Ile Pro Lys Leu Val Ala Asn Asn Thr Arg Leu
        195                 200                 205

Trp Val Tyr Cys Gly Asn Gly Thr Pro Asn Glu Leu Gly Gly Ala Asn
    210                 215                 220

Ile Pro Ala Glu Phe Leu Glu Asn Phe Val Arg Ser Ser Asn Leu Lys
225                 230                 235                 240

Phe Gln Asp Ala Tyr Asn Ala Ala Gly Gly His Asn Ala Val Phe Asn
                245                 250                 255

Phe Pro Pro Asn Gly Thr His Ser Trp Glu Tyr Trp Gly Ala Gln Leu
            260                 265                 270

Asn Ala Met Lys Gly Asp Leu Gln Ser Ser Leu Gly Ala Gly Met Thr
        275                 280                 285

Glu Gln Gln Trp Asn Phe Ala Gly Ile Glu Ala Ala Ala Ser Ala Ile
    290                 295                 300

Gln Gly Asn Val Thr Ser Ile His Ser Leu Leu Asp Glu Gly Lys Gln
305                 310                 315                 320

Ser Leu Thr Lys Leu Ala Ala Ala Trp Gly Gly Ser Gly Ser Glu Ala
                325                 330                 335

Tyr Gln Gly Val Gln Gln Lys Trp Asp Ala Thr Ala Thr Glu Leu Asn
            340                 345                 350

Asn Ala Leu Gln Asn Leu Ala Arg Thr Ile Ser Glu Ala Gly Gln Ala
        355                 360                 365

Met Ala Ser Thr Glu Gly Asn Val Thr Gly Met Phe Ala
    370                 375                 380
```

<210> SEQ ID NO 27
<211> LENGTH: 3570
<212> TYPE: DNA
<213> ORGANISM: Mycobacterium tuberculosis
<220> FEATURE:
<223> OTHER INFORMATION: Ag85A-ESAT6-Rv3407-Rv2626c-RpfA-RpfD

<400> SEQUENCE: 27

```
atggcgttca gcagacccgg cctgcccgtg gagtacctgc aggtgcccag ccccagcatg     60
ggccgggaca tcaaagtgca gttccagagc ggcggagcca acagccctgc cctgtacctg    120
ctggacggcc tgcgggccca ggacgacttc agcggctggg acatcaacac ccccgccttc    180
gagtggtacg accagagcgg cctgagcgtg gtgatgcccg tgggcggcca gagcagcttc    240
tacagcgact ggtatcagcc cgcctgcggc aaggccggct gccagaccta caagtgggag    300
accttcctga ccagcgagct gcccggctgg ctgcaggcca accggcacgt gaagcccacc    360
ggcagcgccg tggtgggcct gagcatggcc gccagcagcg ccctgaccct ggccatctac    420
```

```
cacccccagc agttcgtgta cgccggagcc atgagcggcc tgctggaccc cagccaggcc    480
atgggcccca ccctgatcgg cctggccatg ggcgacgccg gaggctacaa ggccagcgac    540
atgtggggcc ccaaggagga ccccgcctgg cagcggaacg acccccctgct gaacgtgggc   600 aagctgatcg ccaacaacac ccgcgtgtgg gtgtactgcg gcaacggcaa gcccagcgac   660
ctgggcggca caacctgcc cgccaagttc ctggagggct cgtgcggac cagcaacatc     720 aagttccagg acgcctacaa cgccggaggc ggccacaacg gcgtgttcga cttccccgac   780
agcggcaccc acagctggga gtactgggga gcccagctga cgccatgaa gcccgacctg    840 cagcgggccc tggcgccac ccccaacacc ggccctgccc ccagggcgc taccgagcag    900 cagtggaact cgccggcat cgaagctgcc gcgagcgcca tccaaggcaa cgtgaccagc    960
atccacagcg tgctggacga gggcaagcag agcctgacca gctggctgc tgcttggggc    1020 ggatccggaa gcgaagccta ccagggcgtg cagcagaagt gggacgccac agccaccgag   1080
ctgaacaacg ccctgcagaa cctcgccaga accatcagcg aggccggaca ggctatggcc   1140
agcacagagg gcaatgtgac cggcatgttc gccagggcca cagtgggcct ggtggaggcc   1200
attggcatca gggagctgag gcagcacgcc agcaggtacc tggccagagt ggaggctgga   1260
gaggagctgg gcgtgaccaa caagggcagg ctggtggcca gactgatccc cgtgcaggct   1320
gccgagagga gcagagaggc cctgatcgag agcggcgtgc tgatccctgc cagaaggcct   1380
cagaacctgc tggacgtgac cgctgagcct gccagaggca ggaagaggac cctgagcgac   1440
gtgctgaacg agatgaggga cgagcagaca cagccaggg acatcatgaa cgccggcgtg   1500
acctgcgtgg gagagcatga accctcacc gccgccgccc aatacatgag ggagcacgac   1560
atcggcgccc tgcccatctg tggagacgac gacaggctgc acggcatgct gaccgacagg   1620
gacatcgtga tcaagggcct ggctgccggc ctcgatccta acaccgctac agccggcgag   1680
ctggccagag acagcatcta ctacgtggac gccaacgcca gcatccagga gatgctcaac   1740
gtgatggagg agcaccaggt gagaaggggtg cctgtgatca gcgagcacag gctggtgggc   1800
atcgtgaccg aggccgatat cgctaggcac ctgcccgagc acgccatcgt gcagttcgtg   1860
aaggccatct gcagccccat ggctctggcc agctcaggga ggcatcggaa ccaactaca    1920 agcaatgtat ctgttgccaa gattgctttc accggcgcag ttcttggagg tggcggaatt   1980
gccatggctg cccaggcaac agccgctaca gatggagagt gggatcaggt ggctcgatgt   2040
gagtctggtg gcaactggtc tatcaacact gggaacgggt atcttggcgg cttgcaattt   2100
actcagagca cttgggctgc ccacggaggg ggtgaatttg ctcctagcgc gcagctggcc   2160
tcccgcgagc agcagatcgc tgtgggagag agggtgttgg ccacacaggg aagaggtgcc   2220
tggcctgtct gtggccgcgg actcagtaat gctacccct ggggaggtgct gcccgcctca   2280 gccgctatgg acgctccact ggatgctgcc gccgtgaatg gcgagccagc tccgctggca   2340
cccccacctg cagaccccgc tcccccagtc gagctggcgg caaacgacct gcccgcacct   2400
ctcggagaac cacttcctgc agcgcctgcc gatccagctc cacctgctga tttggctccc   2460
cccgctcccg ccgatgtagc ccctccggtc gagttggctg tgaatgacct gccggcacct   2520
ctgggcgagc cctcccagc cgctccggcc gaccctgccc tcctgctga tctgcaccac   2580 cccgctcctg ccgacctcgc cccacccgcc ccagcagacc tggctccacc agcgcctgcg   2640
gatcttgccc cgcctgttga gctggctgtc aacgatcttc ctgcgcctct ggagagccc    2700 ctgcccgctg ctccagccga actcgcacca ccggcagatc tggctcccgc ctctgccgat   2760
```

-continued

```
cttgcacctc ccgcaccggc ggacttggca cctccagcac cagcagaact ggctccccct   2820
gcgccggctg acctggcccc tccagcagcc gttaatgagc aaaccgcacc aggggaccag   2880
ccggctacgg caccaggtgg accggtgggg ctggccaccg acctggagct gcctgagccg   2940
gatccccaac cagctgatgc tcccccacct ggcgacgtaa ctgaggcccc agctgaaacg   3000
ccccaggtca gtaacatcgc ttacacaaag aaactgtggc aggcaattag ggctcaggac   3060
gtgtgtggga acgacgccct ggacagcttg gcccaaccgt acgtgatcgg tacccccgga   3120
ctcctcacca cagctggagc tggcaggccc agagacagat gcgccaggat cgtgtgcacc   3180
gtgttcatcg agaccgccgt ggtggctacc atgttcgtgg ccctgctggg cctgagcacc   3240
atcagcagca aggccgacga catcgactgg gacgccatcg cccagtgtga atccggcgga   3300
aactgggccg ccaataccgg caatggcctg tacggcggcc tgcagatcag ccaggctacc   3360
tgggactcca acggaggagt gggaagccct gccgctgctt cccctcagca gcagatcgag   3420
gtggccgaca acatcatgaa gacccaaggc cctggcgcct ggcctaagtg ttccagctgt   3480
agccagggcg atgctcctct gggcagcctg acccacatcc tgacctttct cgccgccgag   3540
acaggcggat gtagcggaag cagggacgac                                   3570
```

<210> SEQ ID NO 28
<211> LENGTH: 3618
<212> TYPE: DNA
<213> ORGANISM: Mycobacterium tuberculosis
<220> FEATURE:
<223> OTHER INFORMATION: Ag85A-ESAT6-Rv3407-Rv2626c-RpfA-RpfD

<400> SEQUENCE: 28

```
gctagcacca tggcgttcag cagacccggc ctgcccgtgg agtacctgca ggtgcccagc     60
cccagcatgg gccgggacat caaagtgcag ttccagagcg gcggagccaa cagccctgcc    120
ctgtacctgc tggacggcct gcgggcccag gacgacttca gcggctggga catcaacacc    180
cccgccttcg agtggtacga ccagagcggc ctgagcgtgg tgatgcccgt gggcggccag    240
agcagcttct acagcgactg gtatcagccc gcctgcggca aggccggctg ccagacctac    300
aagtgggaga ccttcctgac cagcgagctg cccggctggc tgcaggccaa ccggcacgtg    360
aagcccaccg gcagcgccgt ggtgggcctg agcatggccg ccagcagcgc cctgaccctg    420
gccatctacc acccccagca gttcgtgtac gccggagcca tgagcggcct gctggacccc    480
agccaggcca tgggccccac cctgatcggc ctggccatgg gcgacgccgg aggctacaag    540
gccagcgaca tgtggggccc caaggaggac cccgcctggc agcggaacga cccccctgctg    600 aacgtgggca agctgatcgc caacaacacc cgcgtgtggg tgtactgcgg caacggcaag    660
cccagcgacc tgggcggcaa caacctgccc gccaagttcc tggagggctt cgtgcggacc    720
agcaacatca agttccagga cgcctacaac gccggaggcg gccacaacgg cgtgttcgac    780
ttccccgaca gcggcaccca cagctgggag tactggggag cccagctgaa cgccatgaag    840
cccgacctgc agcgggccct gggcgccacc cccaacaccg gccctgcccc ccagggcgct    900
accgagcagc agtggaactt cgccggcatc gaagctgccg cgagcgccat ccaaggcaac    960
gtgaccagca tccacagcct gctggacgag ggcaagcaga gcctgaccaa gctggctgct   1020
gcttggggcg gatccggaag cgaagcctac cagggcgtgc agcagaagtg ggacgccaca   1080
gccaccgagc tgaacaacgc cctgcagaac ctcgccagaa ccatcagcga ggccggacag   1140
gctatggcca gcacagaggg caatgtgacc ggcatgttcg ccagggccac agtgggcctg   1200
gtggaggcca ttggcatcag ggagctgagg cagcacgcca gcaggtacct ggccagagtg   1260
```

```
gaggctggag aggagctggg cgtgaccaac aagggcaggc tggtggccag actgatcccc   1320
gtgcaggctg ccgagaggag cagagaggcc ctgatcgaga gcggcgtgct gatccctgcc   1380
agaaggcctc agaacctgct ggacgtgacc gctgagcctg ccagaggcag gaagaggacc   1440
ctgagcgacg tgctgaacga gatgaggggac gagcagacaa cagccaggga catcatgaac   1500
gccggcgtga cctgcgtggg agagcatgaa accctcaccg ccgccgccca atacatgagg   1560
gagcacgaca tcggcgccct gcccatctgt ggagacgacg acaggctgca cggcatgctg   1620
accgacaggg acatcgtgat caagggcctg gctgccggcc tcgatcctaa caccgctaca   1680
gccggcgagc tggccagaga cagcatctac tacgtggacg ccaacgccag catccaggag   1740
atgctcaacg tgatggagga gcaccaggtg agaagggtgc ctgtgatcag cgagcacagg   1800
ctggtgggca tcgtgaccga ggccgatatc gctaggcacc tgcccgagca cgccatcgtg   1860
cagttcgtga aggccatctg cagccccatg gctctggcca gctcagggag catcggaaaa   1920
ccaactacaa gcaatgtatc tgttgccaag attgctttca ccggcgcagt tcttggaggt   1980
ggcggaattg ccatggctgc ccaggcaaca gccgctacag atggagagtg ggatcaggtg   2040
gctcgatgtg agtctggtgg caactggtct atcaacactg gaacgggta tcttggcggc   2100
ttgcaattta ctcagagcac ttgggctgcc cacggagggg gtgaatttgc tcctagcgcg   2160
cagctggcct cccgcgagca gcagatcgct gtgggagaga gggtgttggc cacacaggga   2220
agaggtgcct ggcctgtctg tggccgcgga ctcagtaatg ctacccctag ggaggtgctg   2280
cccgcctcag ccgctatgga cgctccactg gatgctgccg ccgtgaatgg cgagccagct   2340
ccgctggcac ccccacctgc agacccgct ccccagtcg agctggcggc aaacgacctg   2400
cccgcacctc tcggagaacc acttcctgca gcgcctgccg atccagctcc acctgctgat   2460
ttggctcccc ccgctcccgc cgatgtagcc cctccggtcg agttggctgt gaatgacctg   2520
ccggcacctc tgggcgagcc cctcccagcc gctccggccg accctgcccc tcctgctgat   2580
ctggcaccac ccgctcctgc cgacctcgcc ccacccgccc cagcagacct ggctccacca   2640
gcgcctgcgg atcttgcccc gcctgttgag ctggctgtca acgatcttcc tgcgcctctt   2700
ggagagcccc tgcccgctgc tccagccgaa ctcgcaccac cggcagatct ggctcccgcc   2760
tctgccgatc ttgcacctcc cgcaccggcg gacttggcac ctccagcacc agcagaactg   2820
gctccccctg cgcggctga cctggcccct ccagcagccg ttaatgagca aaccgcacca   2880
ggggaccagc cggctacggc accaggtgga ccggtgggc tggccaccga cctggagctg   2940
cctgagccgg atccccaacc agctgatgct cccccacctg cgacgtaac tgaggcccca   3000
gctgaaacgc cccaggtcag taacatcgct tacacaaaga aactgtggca ggcaattagg   3060
gctcaggacg tgtgtgggaa cgacgccctg gacagcttgg cccaaccgta cgtgatcggt   3120
accccccggac tcctcaccac agctggagct ggcaggccca gagacagatg cgccaggatc   3180
gtgtgcaccg tgttcatcga gaccgccgtg gtggctacca tgttcgtggc cctgctgggc   3240
ctgagcacca tcagcagcaa ggccgacgac atcgactggg acgccatcgc ccagtgtgaa   3300
tccggcggaa actgggccgc caataccggc aatggcctgt acggcggcct gcagatcagc   3360
caggctacct gggactccaa cggaggagtg ggaagccctg ccgctgcttc ccctcagcag   3420
cagatcgagg tggccgacaa catcatgaag acccaaggcc ctggcgcctg gctaagtgt   3480
tccagctgta gccagggcga tgctcctctg ggcagcctga cccacatcct gacctttctc   3540
gccgccgaga caggcggatg tagcggaagc agggacgact accctacga cgtgcccgac   3600
```
tacgccgatt agtctaga                                              3618

<210> SEQ ID NO 29
<211> LENGTH: 1190
<212> TYPE: PRT
<213> ORGANISM: Mycobacterium tuberculosis
<220> FEATURE:
<223> OTHER INFORMATION: Ag85A-ESAT6-Rv3407-Rv2626c-RpfA-RpfD

<400> SEQUENCE: 29

```
Met Ala Phe Ser Arg Pro Gly Leu Pro Val Glu Tyr Leu Gln Val Pro
1               5                   10                  15

Ser Pro Ser Met Gly Arg Asp Ile Lys Val Gln Phe Gln Ser Gly Gly
            20                  25                  30

Ala Asn Ser Pro Ala Leu Tyr Leu Leu Asp Gly Leu Arg Ala Gln Asp
        35                  40                  45

Asp Phe Ser Gly Trp Asp Ile Asn Thr Pro Ala Phe Glu Trp Tyr Asp
    50                  55                  60

Gln Ser Gly Leu Ser Val Val Met Pro Val Gly Gly Gln Ser Ser Phe
65                  70                  75                  80

Tyr Ser Asp Trp Tyr Gln Pro Ala Cys Gly Lys Ala Gly Cys Gln Thr
                85                  90                  95

Tyr Lys Trp Glu Thr Phe Leu Thr Ser Glu Leu Pro Gly Trp Leu Gln
            100                 105                 110

Ala Asn Arg His Val Lys Pro Thr Gly Ser Ala Val Val Gly Leu Ser
        115                 120                 125

Met Ala Ala Ser Ser Ala Leu Thr Leu Ala Ile Tyr His Pro Gln Gln
130                 135                 140

Phe Val Tyr Ala Gly Ala Met Ser Gly Leu Leu Asp Pro Ser Gln Ala
145                 150                 155                 160

Met Gly Pro Thr Leu Ile Gly Leu Ala Met Gly Asp Ala Gly Gly Tyr
                165                 170                 175

Lys Ala Ser Asp Met Trp Gly Pro Lys Glu Asp Pro Ala Trp Gln Arg
            180                 185                 190

Asn Asp Pro Leu Leu Asn Val Gly Lys Leu Ile Ala Asn Asn Thr Arg
        195                 200                 205

Val Trp Val Tyr Cys Gly Asn Gly Lys Pro Ser Asp Leu Gly Gly Asn
    210                 215                 220

Asn Leu Pro Ala Lys Phe Leu Glu Gly Phe Val Arg Thr Ser Asn Ile
225                 230                 235                 240

Lys Phe Gln Asp Ala Tyr Asn Ala Gly Gly Gly His Asn Gly Val Phe
                245                 250                 255

Asp Phe Pro Asp Ser Gly Thr His Ser Trp Glu Tyr Trp Gly Ala Gln
            260                 265                 270

Leu Asn Ala Met Lys Pro Asp Leu Gln Arg Ala Leu Gly Ala Thr Pro
        275                 280                 285

Asn Thr Gly Pro Ala Pro Gln Gly Ala Thr Gln Gln Trp Asn Phe
        290                 295                 300

Ala Gly Ile Glu Ala Ala Ala Ser Ala Ile Gln Gly Asn Val Thr Ser
305                 310                 315                 320

Ile His Ser Leu Leu Asp Glu Gly Lys Gln Ser Leu Thr Lys Leu Ala
                325                 330                 335

Ala Ala Trp Gly Gly Ser Gly Ser Glu Ala Tyr Gln Gly Val Gln Gln
            340                 345                 350

Lys Trp Asp Ala Thr Ala Thr Glu Leu Asn Asn Ala Leu Gln Asn Leu
```

-continued

```
            355                 360                 365
Ala Arg Thr Ile Ser Glu Ala Gly Gln Ala Met Ala Ser Thr Glu Gly
    370                 375                 380

Asn Val Thr Gly Met Phe Ala Arg Ala Thr Val Gly Leu Val Glu Ala
385                 390                 395                 400

Ile Gly Ile Arg Glu Leu Arg Gln His Ala Ser Arg Tyr Leu Ala Arg
                405                 410                 415

Val Glu Ala Gly Glu Glu Leu Gly Val Thr Asn Lys Gly Arg Leu Val
            420                 425                 430

Ala Arg Leu Ile Pro Val Gln Ala Ala Glu Arg Ser Arg Glu Ala Leu
        435                 440                 445

Ile Glu Ser Gly Val Leu Ile Pro Ala Arg Arg Pro Gln Asn Leu Leu
    450                 455                 460

Asp Val Thr Ala Glu Pro Ala Arg Gly Arg Lys Arg Thr Leu Ser Asp
465                 470                 475                 480

Val Leu Asn Glu Met Arg Asp Glu Gln Thr Thr Ala Arg Asp Ile Met
                485                 490                 495

Asn Ala Gly Val Thr Cys Val Gly Glu His Glu Thr Leu Thr Ala Ala
            500                 505                 510

Ala Gln Tyr Met Arg Glu His Asp Ile Gly Ala Leu Pro Ile Cys Gly
        515                 520                 525

Asp Asp Asp Arg Leu His Gly Met Leu Thr Asp Arg Asp Ile Val Ile
    530                 535                 540

Lys Gly Leu Ala Ala Gly Leu Asp Pro Asn Thr Ala Thr Ala Gly Glu
545                 550                 555                 560

Leu Ala Arg Asp Ser Ile Tyr Tyr Val Asp Ala Asn Ala Ser Ile Gln
                565                 570                 575

Glu Met Leu Asn Val Met Glu Glu His Gln Val Arg Arg Val Pro Val
            580                 585                 590

Ile Ser Glu His Arg Leu Val Gly Ile Val Thr Glu Ala Asp Ile Ala
        595                 600                 605

Arg His Leu Pro Glu His Ala Ile Val Gln Phe Val Lys Ala Ile Cys
    610                 615                 620

Ser Pro Met Ala Leu Ala Ser Ser Gly Arg His Arg Lys Pro Thr Thr
625                 630                 635                 640

Ser Asn Val Ser Val Ala Lys Ile Ala Phe Thr Gly Ala Val Leu Gly
                645                 650                 655

Gly Gly Gly Ile Ala Met Ala Ala Gln Ala Thr Ala Ala Thr Asp Gly
            660                 665                 670

Glu Trp Asp Gln Val Ala Arg Cys Glu Ser Gly Gly Asn Trp Ser Ile
        675                 680                 685

Asn Thr Gly Asn Gly Tyr Leu Gly Gly Leu Gln Phe Thr Gln Ser Thr
    690                 695                 700

Trp Ala Ala His Gly Gly Gly Glu Phe Ala Pro Ser Ala Gln Leu Ala
705                 710                 715                 720

Ser Arg Glu Gln Gln Ile Ala Val Gly Glu Arg Val Leu Ala Thr Gln
                725                 730                 735

Gly Arg Gly Ala Trp Pro Val Cys Gly Arg Gly Leu Ser Asn Ala Thr
            740                 745                 750

Pro Arg Glu Val Leu Pro Ala Ser Ala Met Asp Ala Pro Leu Asp
        755                 760                 765

Ala Ala Ala Val Asn Gly Glu Pro Ala Pro Leu Ala Pro Pro Ala
    770                 775                 780
```

```
Asp Pro Ala Pro Pro Val Glu Leu Ala Ala Asn Asp Leu Pro Ala Pro
785                 790                 795                 800

Leu Gly Glu Pro Leu Pro Ala Ala Pro Ala Asp Pro Ala Pro Pro Ala
            805                 810                 815

Asp Leu Ala Pro Pro Ala Pro Ala Asp Val Ala Pro Val Glu Leu
        820                 825                 830

Ala Val Asn Asp Leu Pro Ala Pro Leu Gly Glu Pro Leu Pro Ala Ala
            835                 840                 845

Pro Ala Asp Pro Ala Pro Pro Ala Asp Leu Ala Pro Pro Ala Pro Ala
    850                 855                 860

Asp Leu Ala Pro Pro Ala Pro Ala Asp Leu Ala Pro Pro Ala Pro Ala
865                 870                 875                 880

Asp Leu Ala Pro Pro Val Glu Leu Ala Val Asn Asp Leu Pro Ala Pro
                885                 890                 895

Leu Gly Glu Pro Leu Pro Ala Ala Pro Ala Glu Leu Ala Pro Pro Ala
            900                 905                 910

Asp Leu Ala Pro Ala Ser Ala Asp Leu Ala Pro Pro Ala Pro Ala Asp
            915                 920                 925

Leu Ala Pro Pro Ala Pro Ala Glu Leu Ala Pro Pro Ala Pro Ala Asp
        930                 935                 940

Leu Ala Pro Pro Ala Ala Val Asn Glu Gln Thr Ala Pro Gly Asp Gln
945                 950                 955                 960

Pro Ala Thr Ala Pro Gly Gly Pro Val Gly Leu Ala Thr Asp Leu Glu
                965                 970                 975

Leu Pro Glu Pro Asp Pro Gln Pro Ala Asp Ala Pro Pro Gly Asp
            980                 985                 990

Val Thr Glu Ala Pro Ala Glu Thr Pro Gln Val Ser Asn Ile Ala Tyr
        995                 1000                1005

Thr Lys Lys Leu Trp Gln Ala Ile Arg Ala Gln Asp Val Cys Gly
        1010                1015                1020

Asn Asp Ala Leu Asp Ser Leu Ala Gln Pro Tyr Val Ile Gly Thr
        1025                1030                1035

Pro Gly Leu Leu Thr Thr Ala Gly Ala Gly Arg Pro Arg Asp Arg
        1040                1045                1050

Cys Ala Arg Ile Val Cys Thr Val Phe Ile Glu Thr Ala Val Val
        1055                1060                1065

Ala Thr Met Phe Val Ala Leu Leu Gly Leu Ser Thr Ile Ser Ser
        1070                1075                1080

Lys Ala Asp Asp Ile Asp Trp Asp Ala Ile Ala Gln Cys Glu Ser
        1085                1090                1095

Gly Gly Asn Trp Ala Ala Asn Thr Gly Asn Gly Leu Tyr Gly Gly
        1100                1105                1110

Leu Gln Ile Ser Gln Ala Thr Trp Asp Ser Asn Gly Gly Val Gly
        1115                1120                1125

Ser Pro Ala Ala Ala Ser Pro Gln Gln Gln Ile Glu Val Ala Asp
        1130                1135                1140

Asn Ile Met Lys Thr Gln Gly Pro Gly Ala Trp Pro Lys Cys Ser
        1145                1150                1155

Ser Cys Ser Gln Gly Asp Ala Pro Leu Gly Ser Leu Thr His Ile
        1160                1165                1170

Leu Thr Phe Leu Ala Ala Glu Thr Gly Gly Cys Ser Gly Ser Arg
        1175                1180                1185
```

Asp Asp
   1190

<210> SEQ ID NO 30
<211> LENGTH: 1200
<212> TYPE: PRT
<213> ORGANISM: Mycobacterium tuberculosis
<220> FEATURE:
<223> OTHER INFORMATION: Ag85A-ESAT6-Rv3407-Rv2626c-RpfA-RpfD

<400> SEQUENCE: 30

Met Ala Phe Ser Arg Pro Gly Leu Pro Val Glu Tyr Leu Gln Val Pro
1               5                   10                  15

Ser Pro Ser Met Gly Arg Asp Ile Lys Val Gln Phe Gln Ser Gly Gly
            20                  25                  30

Ala Asn Ser Pro Ala Leu Tyr Leu Leu Asp Gly Leu Arg Ala Gln Asp
        35                  40                  45

Asp Phe Ser Gly Trp Asp Ile Asn Thr Pro Ala Phe Glu Trp Tyr Asp
    50                  55                  60

Gln Ser Gly Leu Ser Val Val Met Pro Val Gly Gly Gln Ser Ser Phe
65                  70                  75                  80

Tyr Ser Asp Trp Tyr Gln Pro Ala Cys Gly Lys Ala Gly Cys Gln Thr
                85                  90                  95

Tyr Lys Trp Glu Thr Phe Leu Thr Ser Glu Leu Pro Gly Trp Leu Gln
            100                 105                 110

Ala Asn Arg His Val Lys Pro Thr Gly Ser Ala Val Val Gly Leu Ser
        115                 120                 125

Met Ala Ala Ser Ser Ala Leu Thr Leu Ala Ile Tyr His Pro Gln Gln
    130                 135                 140

Phe Val Tyr Ala Gly Ala Met Ser Gly Leu Leu Asp Pro Ser Gln Ala
145                 150                 155                 160

Met Gly Pro Thr Leu Ile Gly Leu Ala Met Gly Asp Ala Gly Gly Tyr
                165                 170                 175

Lys Ala Ser Asp Met Trp Gly Pro Lys Glu Asp Pro Ala Trp Gln Arg
            180                 185                 190

Asn Asp Pro Leu Leu Asn Val Gly Lys Leu Ile Ala Asn Asn Thr Arg
        195                 200                 205

Val Trp Val Tyr Cys Gly Asn Gly Lys Pro Ser Asp Leu Gly Gly Asn
    210                 215                 220

Asn Leu Pro Ala Lys Phe Leu Glu Gly Phe Val Arg Thr Ser Asn Ile
225                 230                 235                 240

Lys Phe Gln Asp Ala Tyr Asn Ala Gly Gly His Asn Gly Val Phe
                245                 250                 255

Asp Phe Pro Asp Ser Gly Thr His Ser Trp Glu Tyr Trp Gly Ala Gln
            260                 265                 270

Leu Asn Ala Met Lys Pro Asp Leu Gln Arg Ala Leu Gly Ala Thr Pro
        275                 280                 285

Asn Thr Gly Pro Ala Pro Gln Gly Ala Thr Glu Gln Gln Trp Asn Phe
    290                 295                 300

Ala Gly Ile Glu Ala Ala Ala Ser Ala Ile Gln Gly Asn Val Thr Ser
305                 310                 315                 320

Ile His Ser Leu Leu Asp Glu Gly Lys Gln Ser Leu Thr Lys Leu Ala
                325                 330                 335

Ala Ala Trp Gly Gly Ser Gly Ser Glu Ala Tyr Gln Gly Val Gln Gln
            340                 345                 350

```
Lys Trp Asp Ala Thr Ala Thr Glu Leu Asn Asn Ala Leu Gln Asn Leu
            355                 360                 365

Ala Arg Thr Ile Ser Glu Ala Gly Gln Ala Met Ala Ser Thr Glu Gly
    370                 375                 380

Asn Val Thr Gly Met Phe Ala Arg Ala Thr Val Gly Leu Val Glu Ala
385                 390                 395                 400

Ile Gly Ile Arg Glu Leu Arg Gln His Ala Ser Arg Tyr Leu Ala Arg
                405                 410                 415

Val Glu Ala Gly Glu Leu Gly Val Thr Asn Lys Gly Arg Leu Val
        420                 425                 430

Ala Arg Leu Ile Pro Val Gln Ala Ala Glu Arg Ser Arg Glu Ala Leu
    435                 440                 445

Ile Glu Ser Gly Val Leu Ile Pro Ala Arg Arg Pro Gln Asn Leu Leu
    450                 455                 460

Asp Val Thr Ala Glu Pro Ala Arg Gly Arg Lys Arg Thr Leu Ser Asp
465                 470                 475                 480

Val Leu Asn Glu Met Arg Asp Glu Gln Thr Thr Ala Arg Asp Ile Met
                485                 490                 495

Asn Ala Gly Val Thr Cys Val Gly Glu His Glu Thr Leu Thr Ala Ala
                500                 505                 510

Ala Gln Tyr Met Arg Glu His Asp Ile Gly Ala Leu Pro Ile Cys Gly
    515                 520                 525

Asp Asp Asp Arg Leu His Gly Met Leu Thr Asp Arg Asp Ile Val Ile
    530                 535                 540

Lys Gly Leu Ala Ala Gly Leu Asp Pro Asn Thr Ala Thr Ala Gly Glu
545                 550                 555                 560

Leu Ala Arg Asp Ser Ile Tyr Tyr Val Asp Ala Asn Ala Ser Ile Gln
                565                 570                 575

Glu Met Leu Asn Val Met Glu Glu His Gln Val Arg Arg Val Pro Val
            580                 585                 590

Ile Ser Glu His Arg Leu Val Gly Ile Val Thr Glu Ala Asp Ile Ala
        595                 600                 605

Arg His Leu Pro Glu His Ala Ile Val Gln Phe Val Lys Ala Ile Cys
    610                 615                 620

Ser Pro Met Ala Leu Ala Ser Ser Gly Arg His Arg Lys Pro Thr Thr
625                 630                 635                 640

Ser Asn Val Ser Val Ala Lys Ile Ala Phe Thr Gly Ala Val Leu Gly
                645                 650                 655

Gly Gly Gly Ile Ala Met Ala Ala Gln Ala Thr Ala Ala Thr Asp Gly
                660                 665                 670

Glu Trp Asp Gln Val Ala Arg Cys Glu Ser Gly Gly Asn Trp Ser Ile
            675                 680                 685

Asn Thr Gly Asn Gly Tyr Leu Gly Gly Leu Gln Phe Thr Gln Ser Thr
    690                 695                 700

Trp Ala Ala His Gly Gly Gly Glu Phe Ala Pro Ser Ala Gln Leu Ala
705                 710                 715                 720

Ser Arg Glu Gln Gln Ile Ala Val Gly Glu Arg Val Leu Ala Thr Gln
                725                 730                 735

Gly Arg Gly Ala Trp Pro Val Cys Gly Arg Gly Leu Ser Asn Ala Thr
            740                 745                 750

Pro Arg Glu Val Leu Pro Ala Ser Ala Met Asp Ala Pro Leu Asp
    755                 760                 765

Ala Ala Ala Val Asn Gly Glu Pro Ala Pro Leu Ala Pro Pro Ala
```

```
                770             775             780
Asp Pro Ala Pro Pro Val Glu Leu Ala Ala Asn Asp Leu Pro Ala Pro
785             790             795             800

Leu Gly Glu Pro Leu Pro Ala Ala Pro Ala Asp Pro Ala Pro Pro Ala
            805             810             815

Asp Leu Ala Pro Pro Ala Pro Ala Asp Val Ala Pro Val Glu Leu
            820             825             830

Ala Val Asn Asp Leu Pro Ala Pro Leu Gly Glu Pro Leu Pro Ala Ala
            835             840             845

Pro Ala Asp Pro Ala Pro Pro Ala Asp Leu Ala Pro Pro Ala Pro Ala
850             855             860

Asp Leu Ala Pro Pro Ala Pro Ala Asp Leu Ala Pro Pro Ala Pro Ala
865             870             875             880

Asp Leu Ala Pro Pro Val Glu Leu Ala Val Asn Asp Leu Pro Ala Pro
                885             890             895

Leu Gly Glu Pro Leu Pro Ala Ala Pro Ala Glu Leu Ala Pro Pro Ala
            900             905             910

Asp Leu Ala Pro Ala Ser Ala Asp Leu Ala Pro Pro Ala Pro Ala Asp
            915             920             925

Leu Ala Pro Pro Ala Pro Ala Glu Leu Ala Pro Pro Ala Pro Ala Asp
930             935             940

Leu Ala Pro Pro Ala Ala Val Asn Glu Gln Thr Ala Pro Gly Asp Gln
945             950             955             960

Pro Ala Thr Ala Pro Gly Gly Pro Val Gly Leu Ala Thr Asp Leu Glu
            965             970             975

Leu Pro Glu Pro Asp Pro Gln Pro Ala Asp Ala Pro Pro Gly Asp
            980             985             990

Val Thr Glu Ala Pro Ala Glu Thr Pro Gln Val Ser Asn Ile Ala Tyr
            995             1000            1005

Thr Lys Lys Leu Trp Gln Ala Ile Arg Ala Gln Asp Val Cys Gly
        1010            1015            1020

Asn Asp Ala Leu Asp Ser Leu Ala Gln Pro Tyr Val Ile Gly Thr
        1025            1030            1035

Pro Gly Leu Leu Thr Thr Ala Gly Ala Gly Arg Pro Arg Asp Arg
        1040            1045            1050

Cys Ala Arg Ile Val Cys Thr Val Phe Ile Glu Thr Ala Val Val
        1055            1060            1065

Ala Thr Met Phe Val Ala Leu Leu Gly Leu Ser Thr Ile Ser Ser
        1070            1075            1080

Lys Ala Asp Asp Ile Asp Trp Asp Ala Ile Ala Gln Cys Glu Ser
        1085            1090            1095

Gly Gly Asn Trp Ala Ala Asn Thr Gly Asn Gly Leu Tyr Gly Gly
        1100            1105            1110

Leu Gln Ile Ser Gln Ala Thr Trp Asp Ser Asn Gly Gly Val Gly
        1115            1120            1125

Ser Pro Ala Ala Ala Ser Pro Gln Gln Gln Ile Glu Val Ala Asp
        1130            1135            1140

Asn Ile Met Lys Thr Gln Gly Pro Gly Ala Trp Pro Lys Cys Ser
        1145            1150            1155

Ser Cys Ser Gln Gly Asp Ala Pro Leu Gly Ser Leu Thr His Ile
        1160            1165            1170

Leu Thr Phe Leu Ala Ala Glu Thr Gly Gly Cys Ser Gly Ser Arg
        1175            1180            1185
```

```
Asp Asp  Tyr Pro Tyr Asp Val  Pro Asp Tyr Ala Asp
    1190             1195             1200

<210> SEQ ID NO 31
<211> LENGTH: 9
<212> TYPE: PRT
<213> ORGANISM: Mycobacterium tuberculosis
<220> FEATURE:
<223> OTHER INFORMATION: VL9 peptide

<400> SEQUENCE: 31

Val Met Ala Pro Arg Thr Leu Leu Leu
1               5
```